US009562033B2

(12) United States Patent
Benarous et al.

(10) Patent No.: US 9,562,033 B2
(45) Date of Patent: *Feb. 7, 2017

(54) INHIBITORS OF VIRAL REPLICATION, THEIR PROCESS OF PREPARATION AND THEIR THERAPEUTICAL USES

(71) Applicant: LABORATOIRE BIODIM, Paris (FR)

(72) Inventors: Richard Benarous, Paris (FR); Francis Chevreuil, Chantilly (FR); Benoit Ledoussal, Pommerit Jaudy (FR); Sophie Chasset, Nandy (FR); Frédéric Le Strat, Combs-la-Ville (FR)

(73) Assignee: LABORATOIRE BIODIM, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/433,095

(22) PCT Filed: Oct. 7, 2013

(86) PCT No.: PCT/EP2013/070862
§ 371 (c)(1),
(2) Date: Apr. 2, 2015

(87) PCT Pub. No.: WO2014/053666
PCT Pub. Date: Apr. 10, 2014

(65) Prior Publication Data
US 2016/0039783 A1 Feb. 11, 2016

Related U.S. Application Data

(60) Provisional application No. 61/710,358, filed on Oct. 5, 2012.

(30) Foreign Application Priority Data

Oct. 5, 2012 (EP) .................................. 12187528

(51) Int. Cl.
| | |
|---|---|
| *C07D 409/04* | (2006.01) |
| *C07D 409/14* | (2006.01) |
| *C07D 491/04* | (2006.01) |
| *C07D 491/052* | (2006.01) |
| *C07D 491/06* | (2006.01) |
| *C07D 417/04* | (2006.01) |
| *C07D 333/24* | (2006.01) |
| *A61K 31/381* | (2006.01) |
| *A61K 31/4155* | (2006.01) |
| *A61K 31/427* | (2006.01) |
| *A61K 31/436* | (2006.01) |
| *A61K 31/4436* | (2006.01) |
| *A61K 31/4709* | (2006.01) |
| *A61K 31/506* | (2006.01) |
| *A61K 45/06* | (2006.01) |

(52) U.S. Cl.
CPC ........... *C07D 333/24* (2013.01); *A61K 31/381* (2013.01); *A61K 31/4155* (2013.01); *A61K 31/427* (2013.01); *A61K 31/436* (2013.01); *A61K 31/4436* (2013.01); *A61K 31/4709* (2013.01); *A61K 31/506* (2013.01); *A61K 45/06* (2013.01); *C07D 409/04* (2013.01); *C07D 409/14* (2013.01); *C07D 417/04* (2013.01); *C07D 491/04* (2013.01); *C07D 491/052* (2013.01); *C07D 491/06* (2013.01)

(58) Field of Classification Search
CPC ... C07D 409/04; C07D 409/14; C07D 491/04; C07D 491/052; C07D 491/06; C07D 417/04; C07D 333/24
See application file for complete search history.

(56) References Cited

U.S. PATENT DOCUMENTS

| | | |
|---|---|---|
| 5,910,506 A | 6/1999 | Sugimoto et al. |
| 2008/0221159 A1 | 9/2008 | Tsantrizos et al. |
| 2010/0292227 A1 | 11/2010 | Yoakim et al. |
| 2010/0305115 A1 | 12/2010 | Carson et al. |
| 2010/0311735 A1 | 12/2010 | Tsantrizos et al. |
| 2011/0028464 A1 | 2/2011 | Tsantrizos et al. |
| 2011/0118249 A1 | 5/2011 | Tsantrizos et al. |
| 2012/0059028 A1 | 3/2012 | Bardiot et al. |
| 2012/0129840 A1 | 5/2012 | Chaltin et al. |
| 2013/0190491 A1 | 7/2013 | Tsantrizos et al. |
| 2013/0197231 A1 | 8/2013 | Tsantrizos et al. |
| 2013/0203747 A1 | 8/2013 | Yoakim et al. |
| 2014/0296272 A1 | 10/2014 | Bardiot et al. |

OTHER PUBLICATIONS

International Search Report for PCT/EP2013/070862 dated Oct. 23, 2013.
Cervia et al: "Enfuvirtide (T-20): A Novel Human Immunodeficiency Virus Type 1 Fusion Inhibitor", Clinical Infectious Diseases (Oct. 15, 2003), vol. 37, No. 8, pp. 1102-1106.
Hughes et al: "New Treatment Options for HIV Salvage Patients: An Overview of Second Generation PIs, NNRTIs, Integrase Inhibitors and CCR5 Antagonists", Journal of Infection, The British Infection Society, 2008, vol. 57, pp. 1-10.
Daar Es: "Emerging Resistance Profiles of Newly Approved Antiretroviral Drugs" Topics in HIV Medicine, (Oct. 11, 2008), vol. 16, No. 4, pp. 110-116.
De Clercq E: "Emerging antiviral drugs" Expert Opinion Emerging Drugs, Informa UK Ltd., (2008), vol. 13, No. 3, pp. 393-416.
Christ et al: "Rational design of small-molecule inhibitors of the LEDGF/p75-integrase interaction and HIV replication"; Nature Chemical Biology, (May 16, 2010), pp. 1-7.
Gregg S. Jones et al: "Preclinical Evaluation of GS-9160, a Novel Inhibitor of Human Immunodificiency Virus Type 1 Integrase" Antimicrobial Agents and Chemotherapy, (Mar. 2009), vol. 53, No. 3, pp. 1194-1203.
Adachi et al: "Production of acquired immunodeficiency syndrome-associated retrovirus in human and nonhuman cells transfected with an infectious molecular clone", Journal of Virology, American Society for Microbiology, (Aug. 1986), vol. 59, No. 2, pp. 284-291.
Lopez-Verges et al: "Tail-interacting protein TIP47 is a connector between Gag and Env and is required for Env incorporation into HIV-1 virions", PNAS, U S A., (Oct. 3, 2006), vol. 103, No. 40, pp. 14947-14952.

*Primary Examiner* — Bruck Kifle
(74) *Attorney, Agent, or Firm* — B. Aaron Schulman, Esq.; Stites & Harbison, PLLC.

(57) ABSTRACT

The present invention relates to compounds, their use in the treatment or the prevention of viral disorders, including HIV.

14 Claims, No Drawings

INHIBITORS OF VIRAL REPLICATION, THEIR PROCESS OF PREPARATION AND THEIR THERAPEUTICAL USES

The present invention relates to compounds, their use in the treatment or the prevention of viral disorders, including HIV. The present invention also relates to methods for the preparation of such compounds. The present invention also relates to pharmaceutical compositions comprising such compounds. The present invention also relates to the treatment of viral infections by the administration of a therapeutically efficient amount of such compounds.

The Acquired Immuno Deficiency Syndrome (AIDS) is a disease due to infection by the Human Immunodeficiency Virus (HIV). HIV is a retrovirus, belonging to the subclass of primate lentiviruses. Two types of HIV have been identified, HIV-1 and HIV-2. HIV-1 is responsible for the larger part of the AIDS global epidemic in the world, with virtually every country reporting cases.

Currently HIV infected patients are treated with Highly Active Anti Retroviral Therapies (HAART) that rely on a combination of several drugs belonging to different classes. Up to 2003, all approved anti-HIV drugs were inhibitors of the catalytic activity of two viral enzymes, Reverse Transcriptase (RT) inhibitors and Protease (PR) inhibitors. Reverse Transcriptase inhibitors include two different classes, Nucleoside/Nucleotide RT Inhibitors (NRTI) and Non Nucleoside RT Inhibitors (NNRTI). In 2003, a new class of Anti-retroviral drug (ARV), Fusion inhibitor (Enfuvirtide) was introduced (Cervia and al., Clin Infect Dis., 2003, 37(8):1102-6). And lately, in 2007, two other classes of ARV were approved, Entry inhibitors (Maraviroc (Pfizer)) targeting the CCR5 co-receptor, and Integrase inhibitors (Raltegravir (Merck)) (Hughes and al., J Infect., 2008, 57(1):1-10). Although these three novel drugs were very useful to treat patients in therapeutic failure due to multiresistance to RT and PR inhibitors, resistance mutations against these drugs have already been reported.

Although the development of these potent anti-HIV drugs, has allowed HIV-infected people to live longer and to benefit of a higher quality of life, it is clear that these drugs do not cure the HIV infection. Moreover, their prolonged use often results in significant toxicity and in the emergence of drug-resistant viruses. Importantly, the ability of HIV to establish latent reservoirs early in the course of infection ensures the persistence of the virus even in the face of intensive drug therapy and vigorous antiviral immune response.

Thus, there is a continuous need for the development of novel anti-HIV therapies or agents to overcome the problems of resistance to the existing drugs and to improve treatment efficiency (Daar E S, Top HIV Med, 2008, 16(4):110-6; De Clercq E, Expert Opin Emerg Drugs. 2008, 13(3):393-416).

Document of Christ and al. (Christ and al., Nat. Chem. Biol., 2010, 6: 442) and documents WO 2007/131350, WO 2009/062285, WO 2009/062288, WO 2009/062289, WO 2009/062308, WO 2010/130034, WO 2010/130842 or WO 2011/015641 describe partially or totally unsaturated 6-membered heterocyclic derivatives as anti-HIV agents.

Document U.S. Pat. No. 5,910,506 describes imidazole derivatives as anti-HIV agents.

It is also known 5-membered carbo- or heterocyclic derivatives as anti-HIV agents.

Suprisingly, the inventors have identified and prepared compounds having an improved antiviral activity, especially against HIV in comparison with prior art compounds.

SUMMARY OF THE INVENTION

The present invention relates to compounds that are able to totally or partially solve the above-mentioned problems and drawbacks.

The present invention provides antiviral agents, especially anti-retroviral agents, and more particularly anti-HIV compounds.

The compounds according the invention are inhibitors of HIV replication as assessed by HIV-1 replication assay as herein-detailed. These compounds are thus useful agents for treating or preventing virus infection, in particular retroviral infection such as HIV infection, or other viral pathogenic diseases or disorders, by inhibiting replication of the virus into the host infected cells.

Therefore, the compounds according to the invention constitute a useful class of new potent antiviral compounds that can be used for the treatment and/or prevention of viral infections in animals, mammals and humans, more specifically for the treatment and/or prevention of HIV in humans.

The present invention further relates to such compounds for their use as a medicament (medicine), to the use of such compounds as medicaments (medicines), more specifically as antiviral agents, and to their use for the manufacture of medicaments for treating and/or preventing viral infections, in particular retroviral infections such as, but not limited to, HIV in humans.

The invention also relates to pharmaceutical composition comprising such compound as an active ingredient and at least a pharmaceutically acceptable carrier. This pharmaceutical composition further comprises at least a further antiviral agent.

The invention also relates to pharmaceutical compositions comprising such compounds in an antiviral effective amount, optionally in combination with at least one further antiviral agent.

The present invention further relates to such pharmaceutical composition for use for the prevention and/or the treatment of viral infection, preferably for the prevention and/or the treatment of retroviral infection, more preferably for the prevention and/or the treatment of an HIV infection.

The present invention further relates to such pharmaceutical composition for its use for the treatment of an HIV infection in a mammal being infected or having a risk to be infected by the HIV.

The present invention also relates to a method of treatment or prevention of viral infections, in particular retroviral infections such as, but not limited to HIV in humans by the administration of one or more such compounds, optionally in combination with one or more other antiviral agents, to a patient in need thereof.

The present invention also relates to a method of inhibiting the replication of HIV comprising exposing the virus to an effective amount of one or more such compounds under conditions where replication of HIV is inhibited.

The invention provides compounds comprising a five membered heterocycle, said compounds having a structure according to formula (I):

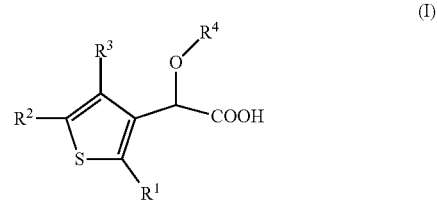

wherein:
R$^1$, identical or different, independently represent a halogen atom; —CF$_3$; a linear or branched C$_1$-C$_6$ alkyl; a linear or branched C$_2$-C$_6$ alkenyl; a linear or branched C$_2$-C$_6$ alkynyl; a linear or branched fluoroalkyl; a C$_3$-C$_6$ cycloalkyl, CH$_2$OH; or —CH$_2$—O—CH$_3$;

R$^2$, non-substituted or substituted by at least one T$^1$, represents a linear or branched C$_2$-C$_8$ alkyl; a linear or branched C$_2$-C$_8$ alkenyl; a linear or branched C$_2$-C$_8$ alkynyl; a linear or branched C$_1$-C$_8$ heteroalkyl; a linear or branched C$_2$-C$_8$ heteroalkenyl; a linear or branched C$_2$-C$_8$ heteroalkynyl; a saturated, partially or totally unsaturated or aromatic 3-, 4-, 5-, 6- or 7-membered carbocycle; a saturated, partially or totally unsaturated or aromatic 4-, 5-, 6- or 7-membered heterocycle; a saturated, partially or totally unsaturated or aromatic 3-, 4-, 5-, 6- or 7-membered carbocycle fused with a saturated, partially or totally unsaturated 3-, 4-, 5-, 6- or 7-membered carbocycle; a saturated, partially or totally unsaturated or aromatic 3-, 4-, 5-, 6- or 7-membered carbocycle fused with a saturated, partially or totally unsaturated 4-, 5-, 6- or 7-membered heterocycle; a saturated, partially or totally unsaturated or aromatic 4-, 5-, 6- or 7-membered heterocycle fused with a saturated, partially or totally unsaturated 3-, 4-, 5-, 6- or 7-membered carbocycle; a saturated, partially or totally unsaturated or aromatic 4-, 5-, 6- or 7-membered heterocycle fused with a saturated, partially or totally unsaturated 4-, 5-, 6- or 7-membered heterocycle; a C$_1$-C$_8$ alkyl-(saturated, partially or totally unsaturated or aromatic C$_3$-C$_7$ carbocycle); a C$_1$-C$_8$ heteroalkyl-(saturated, partially or totally unsaturated or aromatic C$_3$-C$_7$ carbocycle); a C$_1$-C$_8$ alkyl-(saturated, partially or totally unsaturated or aromatic C$_4$-C$_7$ heterocycle); a C$_1$-C$_8$ heteroalkyl-(saturated, partially or totally unsaturated or aromatic C$_4$-C$_7$ heterocycle); a bicyclo[2.2.1]heptane; a bicyclo[2.2.1]heptene; a bicyclo[2.2.2]octane; or a bicyclo[2.2.1]octene;

R$^3$, non-substituted or substituted by at least one T$^2$, represents an aryl; an aryl fused with a saturated, partially or totally unsaturated or aromatic 3-, 4-, 5-, 6- or 7-membered carbocycle; an aryl fused with a saturated, partially or totally unsaturated or aromatic 4-, 5-, 6- or 7-membered heterocycle; an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a heteroaryl; a heteroaryl fused with a saturated, partially or totally unsaturated or aromatic 3-, 4-, 5-, 6- or 7-membered carbocycle; a heteroaryl fused with a saturated, partially or totally unsaturated or aromatic 4-, 5-, 6- or 7-membered heterocycle; a C$_6$-C$_7$ cycloalkenyl; a C$_6$-C$_7$ cycloalkenyl fused with a saturated, partially or totally unsaturated or aromatic 4-, 5-, 6- or 7-membered heterocycle; or a saturated, partially or totally unsaturated or aromatic 5-, 6- or 7-membered heterocycle;

R$^4$, substituted or non-substituted by at least one T$^5$, represents a linear or branched C$_2$-C$_6$ alkyl; a linear or branched C$_1$-C$_6$ fluoroalkyl; or a C$_3$-C$_6$ cycloalkyl;

T$^1$ independently represents a hydrogen atom, a halogen atom; an alkyl; —(X)$_a$—C$_1$-C$_6$ alkyl; a linear or branched fluoroalkyl; a linear or branched —O—C$_1$-C$_3$ fluoroalkyl; —(X)$_a$—C$_3$-C$_6$ cycloalkyl; —(X)$_a$—(CT$^5$T$^6$)$_b$-C$_3$-C$_6$ cycloalkyl; —(X)$_a$—(CT$^5$T$^6$)$_b$-aryl; —(X)$_a$(CT$^5$T$^6$)$_b$CN; —(X)$_a$—(CT$^5$T$^6$)$_b$OT$^3$; —(X)$_a$—(CT$^5$T$^6$)$_b$ST$^3$; —(X)$_a$—(CT$^5$T$^6$)$_b$S(O)T$^3$; —(X)$_a$—(CT$^5$T$^6$)$_b$S(O)$_2$T$^3$; —(X)$_a$—(CT$^5$T$^6$)$_b$NT$^3$T$^4$; —(X)$_a$—(CT$^5$T$^6$)$_b$C(O)T$^3$; —(X)$_a$—(CT$^5$T$^6$)$_b$C(O)OT$^3$; —(X)$_a$—(CT$^5$T$^6$)$_b$C(O)NT$^3$T$^4$; —(X)$_a$—(CT$^5$T$^6$)$_b$NT$^3$C(O)NT$^3$T$^4$; —(X)$_a$—(CT$^5$T$^6$)$_b$NT$^3$C(O)T$^4$; —(X)$_a$—(CT$^5$T$^6$)$_b$NT$^3$C(O)OT$^4$; —(X)$_a$—(CT$^5$T$^6$)$_b$OC(O)NT$^3$T$^4$; —(X)$_a$—(CT$^5$T$^6$)$_b$S(O)$_2$NT$^3$T$^4$ or —(X)$_a$—(CT$^5$T$^6$)$_b$NT$^3$S(O)$_2$T$^4$;

T$^2$ independently represents a hydrogen atom; a halogen atom; a linear or branched —O—C$_1$-C$_3$ alkyl; a linear or branched C$_1$-C$_3$ fluoroalkyl; a linear or branched —O—C$_1$-C$_3$ fluoroalkyl; a linear or branched C$_1$-C$_3$ alkyl; or —CN; optionally two geminal T$^2$ form with the carbon atom to which they are bonded, a C$_3$-C$_7$ cycloalkyl;

X independently represents an oxygen atom; a sulphur atom; NT$^3$; S=O or S(O)$_2$;

T$^3$ and T$^4$, identical or different, independently represent a hydrogen atom; a branched or linear C$_1$-C$_6$ alkyl or a C$_3$-C$_6$ cycloalkyl; optionally T$^3$, T$^4$ and the nitrogen atom to which they are bonded form a C$_4$-C$_6$ heterocycloalkyl;

T$^5$ and T$^6$, identical or different, independently represent a hydrogen atom; a fluorine atom or a linear or branched C$_1$-C$_3$ alkyl or a C$_3$-C$_6$ cycloalkyl; optionally T$^5$, T$^6$ and the carbon atom to which they are bonded form a cyclopropyl;

a independently represents 0 or 1;

b independently represents 0, 1, 2 or 3;

and a racemate, enantiomer, tautomer, atropisomer, diastereoisomer or a pharmaceutically acceptable salt thereof.

The invention also provides compounds of formula (I), wherein:

R$^1$ represents —CF$_3$; a linear or branched C$_1$-C$_6$ alkyl; a linear or branched fluoroalkyl, a C$_3$-C$_6$ cycloalkyl; or —CH$_2$OH;

R$^2$, non-substituted or substituted by at least one T$^1$, represents a linear or branched C$_2$-C$_8$ alkyl; a linear or branched C$_2$-C$_8$ alkenyl; a linear or branched C$_2$-C$_8$ alkynyl; a linear or branched C$_1$-C$_8$ heteroalkyl; a linear or branched C$_2$-C$_8$ heteroalkenyl; a linear or branched C$_2$-C$_8$ heteroalkynyl; a saturated, partially or totally unsaturated or aromatic 3-, 4-, 5-, 6- or 7-membered carbocycle; a saturated, partially or totally unsaturated or aromatic 4-, 5-, 6- or 7-membered heterocycle; a saturated, partially or totally unsaturated or aromatic 3-, 4-, 5-, 6- or 7-membered carbocycle fused with a saturated, partially or totally unsaturated 3-, 4-, 5-, 6- or 7-membered carbocycle; a saturated, partially or totally unsaturated or aromatic 3-, 4-, 5-, 6- or 7-membered carbocycle fused with a saturated, partially or totally unsaturated 4-, 5-, 6- or 7-membered heterocycle; a saturated, partially or totally unsaturated or aromatic 4-, 5-, 6- or 7-membered heterocycle fused with a saturated, partially or totally unsaturated 3-, 4-, 5-, 6- or 7-membered carbocycle; a saturated, partially or totally unsaturated or aromatic 4-, 5-, 6- or 7-membered heterocycle fused with a saturated, partially or totally unsaturated 4-, 5-, 6- or 7-membered heterocycle; a C$_1$-C$_8$ alkyl-(saturated, partially or totally unsaturated or aromatic C$_3$-C$_7$ carbocycle); a C$_1$-C$_8$ heteroalkyl-(saturated, partially or totally unsaturated or aromatic C$_3$-C$_7$ carbocycle); a C$_1$-C$_8$ alkyl-(saturated, partially or totally unsaturated or aromatic C$_4$-C$_7$ heterocycle); a C$_1$-C$_8$ heteroalkyl-(saturated, partially or totally unsaturated or aromatic C$_4$-C$_7$ heterocycle);

R$^3$, non-substituted or substituted by at least one T$^2$, represents an aryl; an aryl fused with a saturated, partially or totally unsaturated or aromatic 3-, 4-, 5-, 6- or 7-membered carbocycle; an aryl fused with a saturated, partially or totally unsaturated or aromatic 4-, 5-, 6- or 7-membered heterocycle; an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a heteroaryl; a heteroaryl fused with a saturated, partially or totally unsaturated or aromatic 3-, 4-, 5-, 6- or 7-membered carbocycle; a heteroaryl fused with a saturated, partially or totally unsaturated or aromatic 4-, 5-, 6- or 7-membered heterocycle; a $C_5$-$C_7$ cycloalkenyl; or a $C_5$-$C_7$ cycloalkenyl fused with a saturated, partially or totally unsaturated or aromatic 4-, 5-, 6- or 7-membered heterocycle;

$R^4$, non-substituted or substituted by at least one $T^5$, represents a linear or branched $C_1$-$C_6$-alkyl; a linear or branched $C_1$-$C_6$ fluoroalkyl; or a $C_3$-$C_6$ cycloalkyl;

$T^1$ independently represents a hydrogen atom, a halogen atom; an alkyl; —$(X)_a$—$C_1$-$C_6$ alkyl; a linear or branched fluoroalkyl; a linear or branched —O—$C_1$-$C_3$ fluoroalkyl; —$(X)_a$—$C_3$-$C_6$ cycloalkyl; —$(X)_a$—$(CT^5T^6)_b$-$C_3$-$C_6$ cycloalkyl; —$(X)_a$—$(CT^5T^6)_b$-aryl; —$(X)_a$—$(CT^5T^6)_b$CN; —$(X)_a$—$(CT^5T^6)_b$OT$^3$; —$(X)_a$—$(CT^5T^6)_b$ST$^3$; —$(X)_a$—$(CT^5T^6)_b$S(O)T$^3$; —$(X)_a$—$(CT^5T^6)_b$S(O)$_2$T$^3$; —$(X)_a$—$(CT^5T^6)_b$NT$^3$T$^4$; —$(X)_a$—$(CT^5T^6)_b$C(O)T$^3$; —$(X)_a$—$(CT^5T^6)_b$C(O)OT$^3$; —$(X)_a$—$(CT^5T^6)_b$C(O)NT$^3$T$^4$; —$(X)_a$—$(CT^5T^6)_b$NT$^3$C(O)NT$^3$T$^4$; —$(X)_a$—$(CT^5T^6)_b$NT$^3$C(O)T$^4$; —$(X)_a$—$(CT^5T^6)_b$NT$^3$C(O)OT$^4$; —$(X)_a$—$(CT^5T^6)_b$OC(O)NT$^3$T$^4$; —$(X)_a$—$(CT^5T^6)_b$S(O)$_2$NT$^3$T$^4$ or —$(X)_a$—$(CT^5T^6)_b$NT$^3$S(O)$_2$T$^4$;

$T^2$ independently represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; or —CN; optionally two geminal $T^2$ form with the carbon atom to which they are bonded, a $C_3$-$C_7$ cycloalkyl;

X independently represents an oxygen atom; a sulphur atom; NT$^3$; S=O or S(O)$_2$;

$T^3$ and $T^4$, identical or different, independently represent a hydrogen atom; a branched or linear $C_1$-$C_6$ alkyl; or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom; a linear or branched $C_1$-$C_3$ alkyl; or a $C_3$-$C_6$ cycloalkyl; optionally $T^5$, $T^6$ and the carbon atom to which they are bonded form a cyclopropyl;

a independently represents 0 or 1;

b independently represents 0, 1, 2 or 3;

and a racemate, enantiomer, tautomer, atropisomer, diastereoisomer or a pharmaceutically acceptable salt thereof.

The invention also provides compounds comprising a five membered heterocycle, said compounds having a structure according to formula (I) wherein:

$R^1$ represents a linear or branched $C_1$-$C_6$ alkyl; a linear or branched fluoroalkyl, a $C_3$-$C_6$ cycloalkyl or CH$_2$OH;

$R^2$, non-substituted or substituted by at least one $T^1$, represents a partially or totally unsaturated or aromatic 5-, 6- or 7-membered carbocycle; a partially or totally unsaturated or aromatic 5-, 6- or 7-membered heterocycle; a partially or totally unsaturated 5-, 6- or 7-membered carbocycle fused with a saturated, partially or totally unsaturated 5-, 6- or 7-membered carbocycle; a partially or totally unsaturated or aromatic 5-, 6- or 7-membered carbocycle fused with a saturated, partially or totally unsaturated 5-, 6- or 7-membered heterocycle; a partially or totally unsaturated or aromatic 5-, 6- or 7-membered heterocycle fused with a saturated, partially or totally unsaturated 5-, 6- or 7-membered carbocycle; a partially or totally unsaturated or aromatic 5-, 6- or 7-membered heterocycle fused with a saturated, partially or totally unsaturated 5-, 6- or 7-membered heterocycle;

$R^3$, non-substituted or substituted by at least one $T^2$, represents an aryl; an aryl fused with a saturated, partially or totally unsaturated or aromatic 5-, 6- or 7-membered carbocycle; an aryl fused with a saturated, partially or totally unsaturated or aromatic 5-, 6- or 7-membered heterocycle; a heteroaryl; a heteroaryl fused with a saturated, partially or totally unsaturated or aromatic 5-, 6- or 7-membered carbocycle; a heteroaryl fused with a saturated, partially or totally unsaturated or aromatic 5-, 6- or 7-membered heterocycle or a $C_3$-$C_7$ cycloalkenyl;

$R^4$ represents a linear or branched $C_1$-$C_6$-alkyl; a linear or branched $C_1$-$C_6$ fluoroalkyl or a $C_3$-$C_6$ cycloalkyl;

$T^1$ represents a hydrogen atom, a halogen atom; an alkyl; —$(X)_a$—$C_1$-$C_6$ alkyl; a linear or branched fluoroalkyl; a linear or branched —O—$C_1$-$C_3$ fluorooalkyl; —$(X)_a$—$C_3$-$C_6$ cycloalkyl; —$(X)_a$—$(CT^5T^6)_b$-aryl; —$(X)_a$—$(CT^5T^6)_b$CN; —$(X)_a$—$(CT^5T^6)_b$OT$^3$; —$(X)_a$—$(CT^5T^6)_b$ST$^3$; —$(X)_a$—$(CT^5T^6)_b$S(O)T$^3$; —$(X)_a$—$(CT^5T^6)_b$S(O)$_2$T$^3$; —$(X)_a$—$(CT^5T^6)_b$NT$^3$T$^4$; —$(X)_a$—$(CT^5T^6)_b$C(O)T$^3$; —$(X)_a$—$(CT^5T^6)_b$C(O)OT$^3$; —$(X)_a$—$(CT^5T^6)_b$C(O)NT$^3$T$^4$; —$(X)_a$—$(CT^5T^6)_b$NT$^3$C(O)NT$^3$T$^4$; —$(X)_a$—$(CT^5T^6)_b$NT$^3$C(O)T$^4$; —$(X)_a$—$(CT^5T^6)_b$NT$^3$C(O)OT$^4$; —$(X)_a$—$(CT^5T^6)_b$OC(O)NT$^3$T$^4$; —$(X)_a$—$(CT^5T^6)_b$S(O)$_2$NT$^3$T$^4$ or —$(X)_a$—$(CT^5T^6)_b$NT$^3$S(O)$_2$T$^4$;

$T^2$ represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; cyclopropyl or —CN;

X represents an oxygen atom; a sulphur atom; NT$^3$; S=O or S(O)$_2$;

$T^3$ and $T^4$, identical or different, independently represent a hydrogen atom; a branched or linear $C_1$-$C_6$ alkyl or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom or a linear or branched $C_1$-$C_3$ alkyl or a $C_3$-$C_6$ cycloalkyl; optionally $T^5$, $T^6$ and the carbon atom to which they are bonded form a cyclopropyl;

a represents 0 or 1;

b represents 0, 1, 2 or 3;

and a racemate, enantiomer, isomer, tautomer, atropisomer, diastereoisomer or a pharmaceutically acceptable salt thereof.

DETAILED DESCRIPTION OF THE INVENTION

Even if described in particular or preferred embodiments, the present invention is not to be understood as being limited to such particular or preferred embodiments.

The term "alkyl" as used herein, either alone or in combination with another radical, refers to acyclic, linear or branched chain alkyl radicals.

The term "cycloalkyl", as used herein, either alone or in combination with another radical, refers to a monocyclic or polycyclic saturated hydrocarbon radical.

The term "aryl", as used herein, either alone or in combination with another radical, refers to a carbocyclic aromatic monocyclic group containing 6 carbon atoms which can be fused with at least another saturated, unsaturated or aromatic carbocycle.

The term "carbocycle", as used herein and unless specified otherwise, either alone or in combination with another radical, refers in particular to a 3- to 8 membered saturated, unsaturated or aromatic cyclic radical in which all of the ring members are carbon atoms and which can be fused with at least another carbocycle.

The term "heterocycle" as used herein means a saturated, unsaturated or aromatic ring system in particular, of 3 to 18 atoms including at least one N, O or S and which can be fused with at least another carbocycle or heterocycle.

The terms "alkyl-(saturated, partially or totally unsaturated or aromatic carbocycle)" or "alkyl-(saturated, partially or totally unsaturated or aromatic heterocycle)" as used herein, alone or in combination with another radical, refer to an alkyl radical in which one of the hydrogen atoms bonded to a carbon atom of the alkyl moiety, is replaced respectively by a saturated, partially or totally unsaturated or aromatic carbocycle radical or a saturated, partially or totally unsaturated or aromatic heterocycle radical.

The term "alkyl-(saturated, partially or totally unsaturated or aromatic carbocycle)" as used herein, means an alkyl-(saturated carbocycle), an alkyl-(partially unsaturated carbocycle), an alkyl-(totally unsaturated carbocycle) or an alkyl-(aromatic carbocycle).

The term "alkyl-(saturated, partially or totally unsaturated or aromatic heterocycle)" as used herein, means an alkyl-(saturated heterocycle), an alkyl-(partially unsaturated heterocycle), an alkyl-(totally unsaturated heterocycle) or an alkyl-(aromatic heterocycle).

The terms "heteroalkyl-(saturated, partially or totally unsaturated or aromatic carbocycle)" or "heteroalkyl-(saturated, partially or totally unsaturated or aromatic heterocycle)" as used herein, alone or in combination with another radical, refer to a heteroalkyl radical in which one of the hydrogen atoms bonded to a carbon atom or a heteroatom of the heteroalkyl moiety, is replaced respectively by a saturated, partially or totally unsaturated or aromatic carbocycle radical or a saturated, partially or totally unsaturated or aromatic heterocycle radical.

The term "heteroalkyl-(saturated, partially or totally unsaturated or aromatic carbocycle)" as used herein, means a heteroalkyl-(saturated carbocycle), a heteroalkyl-(partially unsaturated carbocycle), a heteroalkyl-(totally unsaturated carbocycle) or a heteroalkyl-(aromatic carbocycle).

The term "heteroalkyl—(saturated, partially or totally unsaturated or aromatic heterocycle)" as used herein, means a heteroalkyl—(saturated heterocycle), a heteroalkyl—(partially unsaturated heterocycle), a heteroalkyl—(totally unsaturated heterocycle) or a heteroalkyl—(aromatic heterocycle).

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods.

The term "enantiomer" is employed herein to refer to one of the two specific stereoisomers which is a non-superimposable mirror image with one other but is related to one other by reflection.

The term "diastereoisomer" is employed herein to refer to one of the stereoisomers which is a non-superimposable mirror image with one other but is not related to one other by reflection.

The term "racemate" is employed herein to refer to an equal amount of two specific enantiomers.

The term "atropisomer" is employed herein to refer to stereoisomer obtained by a sterically hindered single bond whereby the free rotation of functional groups on either side of this bond is not allowed.

The term "tautomer" is employed herein to refer to constitutional isomer obtained by a formal migration of a hydrogen atom or a proton accompanied by a switch of a single bond and adjacent double bond.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

The expression "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient Such a therapeutically effective amount can be determined routinely by one of ordinary skill in the art having regard to their own knowledge, the state of the art, and this disclosure The term "mammal" as used herein is intended to encompass humans, as well as non-human mammals which are susceptible to infection by HIV or non human equivalents of HIV. Non-human mammals include but are not limited to domestic animals, such as cows, pigs, dogs, cats, rabbits, rats and mice, and non domestic animals.

The compounds according to the invention are compounds of formula (I) as defined and including the embodiments described in the summary of the invention.

Particularly, according to a feature (a), the compounds according to the invention are compounds of formula (I) wherein $R^4$ represents tBu.

Particularly, according to a feature (b), the compounds according to the invention are compounds of formula (I) wherein $R^2$, non-substituted or substituted by at least one $T^1$, represents a partially or totally unsaturated or aromatic 5-, 6- or 7-membered carbocycle; a partially or totally unsaturated or aromatic 5-, 6- or 7-membered heterocycle; a partially or totally unsaturated or aromatic 5-, 6- or 7-membered heterocycle fused with a saturated, partially or totally unsaturated 5-, 6- or 7-membered carbocycle; or a partially or totally unsaturated or aromatic 5-, 6- or 7-membered heterocycle fused with a saturated, partially or totally unsaturated 5-, 6- or 7-membered heterocycle;

$T^1$ represents a hydrogen atom; a halogen atom; —$CH_3$; —$CH_2F$; —$CHF_2$; —$CF_3$; —OMe; —$OCH_2F$; —$OCHF_2$; —$OCF_3$, —$(X)_a$—$C_1$-$C_6$ cycloalkyl; —$(X)_a$—$(CT^5T^6)_b$-aryl; —$(X)_a$—$(CT^5T^6)_b$CN; —$(X)_a$—$(CT^5T^6)_b$OT$^3$; —$(X)_a$—$(CT^5T^6)_b$ST$^3$; —$(X)_a$—$(CT^5T^6)_b$S(O)T$^3$; —$(X)_a$—$(CT^5T^6)_b$S(O)$_2$T$^3$; —$(X)_a$—$(CT^5T^6)_b$NT$^3$T$^4$; —$(X)_a$—$(CT^5T^6)_b$C(O)T$^3$; —$(X)_a$—$(CT^5T^6)_b$C(O)OT$^3$; —$(X)_a$—$(CT^5T^6)_b$C(O)NT$^3$T$^4$; —$(X)_a$($CT^5T^6)_b$NT$^3$C(O)NT$^3$T$^4$; —$(X)_a$($CT^5T^6)_b$NT$^3$C(O)T$^4$; —$(X)_a$—$(CT^5T^6)_b$NT$^3$C(O)OT$^4$; —$(X)_a$($CT^5T^6)_b$OC(O)NT$^3$T$^4$; —$(X)_a$—$(CT^5T^6)_b$S(O)$_2$NT$^3$T$^4$ or —$(X)_a$ $(CT^5T^6)_b$NT$^3$S(O)$_2$T$^4$;

X independently represents an oxygen atom; a sulphur atom; NT$^3$; S=O or S(O)$_2$;

$T^3$ and $T^4$, identical or different, independently represent a hydrogen atom; a branched or linear $C_1$-$C_6$ alkyl; or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom or methyl;

a independently represents 0 or 1;

b independently represents 0, 1, 2 or 3.

Particularly, according to feature (c), the compounds according to the invention are compounds of formula (I) wherein $R^2$, non-substituted or substituted by at least one $T^1$, represents a linear or branched $C_2$-$C_8$ alkyl; a linear or branched $C_2$-$C_8$ alkenyl; a linear or branched $C_2$-$C_8$ alkynyl; a $C_1$-$C_8$ alkyl-(saturated, partially or totally unsaturated or aromatic $C_3$-$C_7$ carbocycle); a saturated, partially or totally unsaturated or aromatic 3-, 4-, 5-, 6- or 7-membered carbocycle; a saturated, partially or totally unsaturated or aromatic 3-, 4-, 5-, 6- or 7-membered carbocycle fused with a saturated, partially or totally unsaturated or aromatic 4-, 5-, 6- or 7-membered heterocycle; a saturated, partially or totally unsaturated or aromatic 4-, 5-, 6- or 7-membered heterocycle; a saturated, partially or totally unsaturated or aromatic 4-, 5-, 6- or 7-membered heterocycle fused with a saturated, partially or totally unsaturated 3-, 4-, 5-, 6- or 7-membered carbocycle; or a saturated, partially or totally unsaturated or aromatic 4-, 5-, 6- or 7-membered heterocycle fused with a saturated, partially or totally unsaturated 4-, 5-, 6- or 7-membered heterocycle;

$T^1$ represents a hydrogen atom; a halogen atom; —$CH_3$; —$CH_2$—$CH_3$; —CH—$(CH_3)_2$; —$CH_2$—$CH_2$—$CH_3$; —$CH_2F$; —$CHF_2$; —$CF_3$; —$OCH_3$; —$OCH_2F$; —$OCHF_2$; —$OCF_3$; —$(X)_a$—$C_1$-$C_6$ cycloalkyl; —$(X)_a$—$(CT^5T^6)_b$-(C1-$C_6$cycloalkyl); —$(X)_a$—$(CT^5T^6)_b$-aryl; —$(X)_a$—$(CT^5T^6)_b$CN; —$(X)_a$—$(CT^5T^6)_b$OT$^3$; —$(X)_a$—$(CT^5T^6)_b$ST$^3$; —$(X)_a$—$(CT^5T^6)_b$S(O)T$^3$; —$(X)_a$—$(CT^5T^6)_b$S(O)$_2$T$^3$; —$(X)_a$—$(CT^5T^6)_b$NT$^3$T$^4$; —$(X)_a$—$(CT^5T^6)_b$C(O)T$^3$; —$(X)_a$—$(CT^5T^6)_b$C(O)OT$^3$; —$(X)_a$—$(CT^5T^6)_b$C(O) NT$^3$T$^4$; —$(X)_a$—$(CT^5T^6)_b$NT$^3$C(O)NT$^3$T$^4$; —$(X)_a$—$(CT^5T^6)_b$NT$^3$C(O)T$^4$; —$(X)_a$—$(CT^5T^6)_b$NT$^3$C(O) OT$^4$; —$(X)_a$—$(CT^5T^6)_b$OC(O)NT$^3$T$^4$; —$(X)_a$—$(CT^5T^6)_b$-S(O)$_2$NT$^3$T$^4$ or —$(X)_a$—$(CT^5T^6)_b$NT$^3$ S(O)$_2$T$^4$;

X independently represents an oxygen atom; a sulphur atom; NT$^3$; S=O; or S(O)$_2$;

$T^3$ and $T^4$, identical or different, independently represent a hydrogen atom; a branched or linear $C_1$-$C_6$ alkyl; or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom; or methyl;

a independently represents 0 or 1;

b independently represents 0, 1, 2 or 3.

Preferably, according to a feature (d), the invention provides compounds of formula (I), wherein $R^1$ represents:
a linear or branched $C_1$-$C_3$ alkyl;
a linear or branched fluoroalkyl;
a $C_3$-$C_6$ cycloalkyl; or
—$CH_2OH$.

Preferably, according to a feature (e), the invention provides compounds of formula (I), wherein $R^1$ represents:
a linear or branched $C_1$-$C_3$ alkyl;
a linear or branched $C_1$-$C_3$ fluoroalkyl;
a $C_3$-$C_6$ cycloalkyl; or
—$CH_2OH$.

Advantageously, according to a feature (f), the invention provides compounds of formula (I), wherein $R^1$ represents:
methyl;
ethyl;
—$CH_2F$;
—$CHF_2$;
—$CF_3$;
—$CH_2CH_2F$;
—$CH_2CHF_2$;
—$CH_2CF_3$; or
—$CH_2OH$.

More advantageously, according to a feature (g), the invention provides compounds of formula (I), wherein $R^1$ represents $CH_3$; —$CF_3$ or —$CH_2OH$.

Preferably, according to a feature (h), the invention provides compounds of formula (I), wherein $R^2$, non-substituted or substituted by at least one $T^1$, represents a linear or branched $C_2$-$C_8$ alkyl; a linear or branched $C_2$-$C_8$ alkenyl; a linear or branched $C_2$-$C_8$ alkynyl; a saturated, partially or totally unsaturated or aromatic 3-, 4-, 5- or 6-membered carbocycle; a saturated, partially or totally unsaturated or aromatic 5- or 6-membered heterocycle; an aromatic 6-membered heterocycle fused with a totally unsaturated 6-membered carbocycle; an aromatic 6-membered heterocycle fused with a partially or totally unsaturated 6-membered heterocycle; an aromatic 6-membered carbocycle fused with a partially or totally unsaturated 6-membered heterocycle; or a $C_1$-$C_8$ alkyl-(aromatic $C_6$ carbocycle).

Advantageously, according to a feature (i), the invention provides compounds of formula (I), wherein $R^2$, non-substituted or substituted by at least one $T^1$, represents a propyl, a propenyl; a cyclopropyl, a phenyl, an ethylphenyl, a pyridinyl, a cyclohexenyl, a dihydropyranyl, a pyrimidinyl, a pyridinonyl, a cyclopentenyl, a thiophenyl, a furanyl, a pyrazolyl, a pyrrolyl, a thiazolyl, an isothiazolyl, a dihydropyrrolonyl, a pyrrolidinonyl, a quinolinyl, a dihydropyranopyridinyl or a 5,6-dihydroquinolinyl.

Preferably, according to a feature (j), the invention provides compounds of formula (I), wherein $R^3$, non-substituted or substituted by at least one $T^2$, represents an aryl; an aryl fused with a saturated, partially or totally unsaturated or aromatic 5-, 6- or 7-membered heterocycle; an aryl fused with a saturated, partially or totally unsaturated or aromatic 5-, 6- or 7-membered heterocycle and further fused with a saturated, partially or totally unsaturated or aromatic 5-, 6- or 7-membered heterocycle; a $C_5$-$C_7$ cycloalkenyl; or a $C_5$-$C_7$ cycloalkenyl fused with a saturated, partially or totally unsaturated or aromatic 5-, 6- or 7-membered heterocycle.

Advantageously, according to a feature (k), the invention provides compounds of formula (I), wherein $R^3$, non-substituted or substituted by at least one $T^2$, represents a cyclohexenyl, a dihydrobenzopyranyl, a 5,6-dihydroquinoline or a

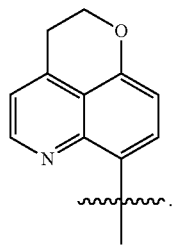

Preferably, according to a feature (l), the invention provides compounds of formula (I), wherein $T^1$ independently represents a hydrogen atom; a halogen atom; an alkyl; a linear or branched fluoroalkyl; —$(X)_a$—$C_1$-$C_6$ alkyl; —$(X)_a$—$C_1$-$C_6$ cycloalkyl; —$(X)_a$—$(CT^5T^6)_b$-($C_1$-$C_6$cycloalkyl); —$(X)_a$—$(CT^5T^6)_b$-aryl; —$(X)_a$—$(CT^5T^6)_b$$NT^3T^4$; —$(X)_a$—$(CT^5T^6)_b$$NT^3C(O)T^4$; —$(X)_a$—$(CT^5T^6)_b$$C(O)NT^3T^4$; —$(X)_a$—$(CT^5T^6)_b$ $S(O)_2NT^3T^4$;

$T^2$ independently represents a hydrogen atom; a halogen atom; a linear or branched —O—$C_1$-$C_3$ alkyl; a linear or branched $C_1$-$C_3$ fluoroalkyl; a linear or branched $C_1$-$C_3$ alkyl; or; optionally two geminal $T^2$ form with the carbon atom to which they are bonded, a cyclopropyl;

X independently represents an oxygen atom;

$T^3$ and $T^4$, identical or different, independently represent a hydrogen atom; or a branched or linear $C_1$-$C_6$ alkyl; optionally $T^5$ and $T^6$, identical or different, independently represent a hydrogen atom; a fluorine atom; or a linear or branched $C_1$-$C_3$ alkyl;

a independently represents 0 or 1;

b independently represents 0, 1 or 3.

Advantageously, according to a feature (m), the invention provides compounds of formula (I), wherein $T^1$ independently represents a hydrogen atom, a methyl, a propyl, a methoxy, a fluorine atom, a trifluoromethyl, an amino, a cyclopropyl, —$(X)_a$—$(CT^5T^6)_b$-(cyclopropyl); a —$(X)_a$—$(CT^5T^6)_b$-aryl, a —$(CT^5T^6)_b$NHC(O)$T^4$; a —$(CT^5T^6)_b$C(O)$NT^3T^4$; or —$(X)_a$—$(CT^5T^6)_b$$S(O)_2NT^3T^4$;

$T^2$ independently represents a hydrogen atom; a fluorine atom; a methoxy; a fluoromethyl; a methyl; or an isopropyl; optionally; two geminal $T^2$ form with the carbon atom to which they are bonded, a cyclopropyl;

X represents an oxygen atom;

$T^3$ and $T^4$, identical or different, independently represent a hydrogen atom; a methyl; or a propyl;

$T^5$ and $T^6$ represent a hydrogen atom;

a independently represents 0 or 1;

b independently represents 0, 1, 2 or 3.

Preferably, the invention provides compounds of formula (I) comprising the two features: (a) and (b); (a) and (c); (a) and (d); (a) and (e); (a) and (f); (a) and (g); (a) and (h); (a) and (i); (a) and (j); (a) and (k); (a) and (l); (a) and (m); (b) and (d); (b) and (e); (b) and (f); (b) and (g); (b) and (j); (b) and (k); (c) and (d); (c) and (e); (c) and (f); (c) and (g); (c) and (j); (c) and (k); (d) and (h); (d) and (i); (d) and (j); (d) and (k); (d) and (l); (d) and (m); (d) and (h); (e) and (i); (e) and (j); (e) and (k); (e) and (l); (e) and (m); (f) and (h); (f) and (i); (f) and (j); (f) and (k); (f) and (l); (f) and (m); (g) and (h); (g) and (i); (g) and (j); (g) and (k); (g) and (l); (g) and (m); (h) and (j); (h) and (k); (h) and (l); (h) and (m); (i) and (j); (i) and (k); (i) and (l); (i) and (m); (j) and (l); (j) and (m); (k) and (l); or (k) and (m).

Preferably, the invention provides compounds of formula (I) comprising the three features: (a), (b) and (d); (a), (b) and (e); (a), (b) and (f); (a), (b) and (g); (a), (b) and (j); (a), (b) and (k); (a), (c) and (d); (a), (c) and (e); (a), (c) and (f); (a), (c) and (g); (a), (c) and (j); (a), (c) and (k); (a), (d) and (h); (a), (d) and (i); (a), (d) and (j); (a), (d) and (k); (a), (d) and (l); (a), (d) and (m); (a), (e) and (h); (a), (e) and (i); (a), (e) and (j); (a), (e) and (k); (a), (e) and (l); (a), (e) and (m); (a), (f) and (h); (a), (f) and (i); (a), (f) and a); (a), (f) and (k); (a), (f) and (l); (a), (f) and (m); (a), (g) and (h); (a), (g) and (i); (a), (g) and (j); (a), (g) and (k); (a), (g) and (l); (a), (g) and (m); (a), (h) and (j); (a), (h) and (k); (a), (h) and (l); (a), (h) and (m); (a), (i) and (j); (a), (i) and (k); (a), (i) and (l); (a), (i) and (m); (a), (j) and (l); (a), (j) and (m); (a), (k) and (l); or (a), (k) and (m).

Preferably, the invention provides compounds of formula (I) comprising the four features: (a), (b), (d) and (j); (a), (b), (d) and (k); (a), (c), (d) and (j); (a), (c), (d) and (k); (a), (d), (h) and (j); (a), (d), (h) and (k); (a), (d), (h) and (l); (a), (d), (h) and (m); (a), (e), (h) and (j); (a), (e), (h) and (k); (a), (e), (h) and (l); (a), (e), (h) and (m); (a), (f), (h) and (j); (a), (f), (h) and (k); (a), (f), (h) and (l); (a), (f), (h) and (m); (a), (g), (h) and (j); (a), (g), (h) and (k); (a), (g), (h) and (l); (a), (g), (h) and (m); (a), (h), (j) and (l); or (a), (h), (j) and (m).

Preferably, the invention provides compounds of formula (I) comprising the five features: (a), (d), (h), (j) and (l); (a), (d), (h), (j) and (m); (a), (e), (h), (j) and (l); (a), (f), (h), (j) and (l); (a), (g), (h), (j) and (l); (a), (e), (h), (j) and (m); (a), (f), (h), (j) and (m); (a), (g), (h), (j) and (m); (a), (d), (i), (j) and (l); (a), (d), (i), (j) and (m); (a), (e), (i), (j) and (l); (a), (f), (i), (j) and (l); (a), (g), (i), (j) and (l); (a), (e), (i), (j) and (m); (a), (f), (i), (j) and (m); (a), (g), (i), (j) and (m); (a), (d), (h), (k) and (l); (a), (d), (h), (k) and (m); (a), (e), (h), (k) and (l); (a), (f), (h), (k) and (l); (a), (g), (h), (k) and (l); (a), (e), (h), (k) and (m); (a), (f), (h), (k) and (m); (a), (g), (h), (k) and (m); (a), (d), (i), (k) and (l); (a), (d), (i), (k) and (m); (a), (e), (i), (k) and (l); (a), (f), (i), (k) and (l); (a), (g), (i), (k) and (l); (a), (e), (i), (k) and (m); (a), (f), (i), (k) and (m); or (a), (g), (i), (k) and (m).

Advantageously, the invention provides a compound of formula (A), (B), (C) or (D):

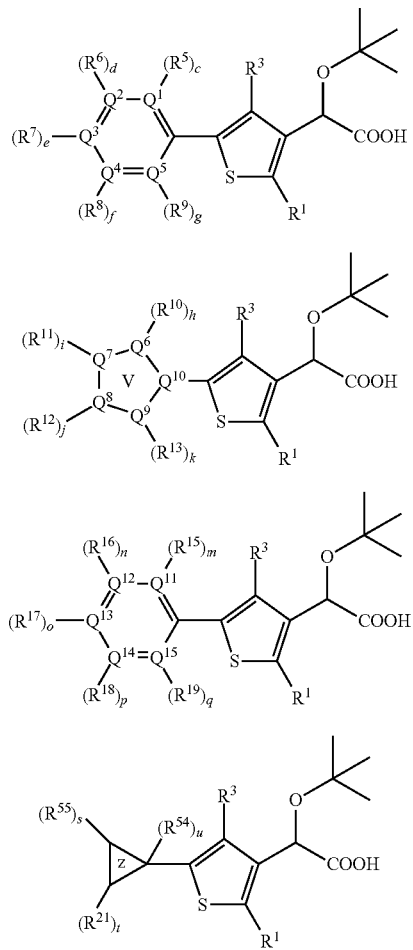

wherein
- h, i, j, k, m, n, o, p, q, s and t independently represent 0, 1 or 2;
- c, d, e, f, g, l, r and u independently represents 0 or 1;
- V represents a substituted or non-substituted, saturated, partially or totally unsaturated carbocycle or a saturated, partially or totally unsaturated or aromatic heterocycle;
- W represents a substituted or non-substituted, saturated, partially unsaturated carbocycle or a saturated, partially unsaturated heterocycle;
- Z represents a substituted or non-substituted, cyclopropyl;
- $Q^1$ represents $CR^5$ or N;
- $Q^2$ represents $CR^6$ or N;
- $Q^3$ represents $CR^7$ or N;
- $Q^4$ represents $CR^8$ or N;
- $Q^5$ represents $CR^9$ or N;
- $Q^6$ represents $CR^{10}$, C=O, N, $NR^{10}$, O, S, S=O or $S(O)_2$;
- $Q^7$ represents $CR^{11}$, C=O, N, $NR^{11}$, O, S, S=O or $S(O)_2$;
- $Q^8$ represents $CR^{12}$, C=O, N, $NR^{12}$, O, S, S=O or $S(O)_2$;
- $Q^9$ represents $CR^{13}$, C=O, N, $NR^{13}$, O, S, S=O or $S(O)_2$;
- $Q^{10}$ represents C, $CR^{14}$ or N;
- $Q^{11}$ represents C, $CR^{15}$, C=O, N, $NR^{15}$, O, S, S=O or $S(O)_2$;
- $Q^{12}$ represents C, $CR^{16}$, C=O, N, $NR^{16}$, O, S, S=O or $S(O)_2$;
- $Q^{13}$ represents C, $CR^{17}$, C=O, N, $NR^{17}$, O, S, S=O or $S(O)_2$;
- $Q^{14}$ represents C, $CR^{18}$, C=O, N, $NR^{18}$, O, S, S=O or $S(O)_2$;
- $Q^{15}$ represents C, $CR^{19}$, C=O, N, $NR^{19}$, O, S, S=O or $S(O)_2$;
- $Q^{16}$ represents C, CR or N;
- $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{54}$, $R^{55}$, $R^{56}$ and R identical or different, independently represent a hydrogen atom; a halogen atom; —$CH_3$; —$CH_2$—$CH_3$; —CH—$(CH_3)_2$; —$CH_2$—$CH_2$—$CH_3$; —$CH_2F$; —$CHF_2$; —$CF_3$; —$OCH_3$; —$OCH_2F$; —$OCHF_2$, —$OCF_3$, —$(X)_a$—$C_1$-$C_6$ cycloalkyl; —$(X)_a$—$(CT^5T^6)_b$-$(C_3$-$C_6$ cycloalkyl); —$(X)_a$—$(CT^5T^6)_b$-aryl; —$(X)_a$—$(CT^5T^6)_b$CN; —$(X)_a$—$(CT^5T^6)_b OT^3$; —$(X)_a$—$(CT^5T^6)_b ST^3$; —$(X)_a$—$(CT^5T^6)_b S(O)T^3$; —$(X)_a$—$(CT^5T^6)_b S(O)_2T^3$; —$(X)_a$—$(CT^5T^6)_b NT^3T^4$; —$(X)_a$—$(CT^5T^6)_b C(O)T^3$; —$(X)_a$—$(CT^5T^6)_b C(O)OT^3$; —$(X)_a$—$(CT^5T^6)_b C(O)NT^3T^4$; —$(X)_a$—$(CT^5T^6)_b NT^3C(O)NT^3T^4$; —$(X)_a$—$(CT^5T^6)_b NT^3C(O)T^4$; —$(X)_a$—$(CT^5T^6)_b NT^3C(O)OT^4$; —$(X)_a$—$(CT^5T^6)_b OC(O)NT^3T^4$; —$(X)_a$—$(CT^5T^6)_b S(O)_2NT^3T^4$ or —$(X)_a$—$(CT^5T^6)_b NT^3S(O)_2T^4$;
- $T^2$ independently represents a hydrogen atom; a halogen atom; methyl; —$CH_2F$; —$CHF_2$, —$CF_3$, —OMe; —$OCH_2F$; —$OCHF_2$; —$OCF_3$; or —CN; optionally two geminal $T^2$ form with the carbon atom to which they are bonded, a cyclopropyl;
- $R^1$, $R^3$, X, a, b and $T^3$ to $T^6$ are independently defined as for the compounds of formula (I).

Advantageously, the invention provides a compound of formula (A), (B), (C) or (D) wherein:
- $R^5$, $Q^1$, $Q^2$ and $R^6$ form a saturated, partially or totally unsaturated or aromatic 6-membered carbo- or heterocycle;
- $R^6$, $Q^2$, $Q^3$ and $R^7$ form a saturated, partially or totally unsaturated or aromatic 6-membered carbo- or heterocycle;
- $R^7$, $Q^3$, $Q^4$ and $R^8$ form a saturated, partially or totally unsaturated or aromatic 6-membered carbo- or heterocycle; or
- $R^8$, $Q^4$, $Q^5$ and $R^9$ form a saturated, partially or totally unsaturated or aromatic 6-membered carbo- or heterocycle.

More advantageously, in compounds of formula (A), (B), (C) or (D), $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{54}$, $R^{55}$, $R^{56}$ and R, identical or different, independently represent a hydrogen atom; a halogen atom; a linear or branched $C_1$-$C_6$ alkyl; a linear or branched fluoroalkyl; a linear or branched —O—$C_1$-$C_6$ alkyl; a linear or branched —O—$C_1$-$C_{10}$ alkylaryl; a linear or branched $C_1$-$C_{10}$ alkylaryl; a cyclopropyl; a linear or branched $C_1$-$C_{10}$ alkylcyclopropyl; —C(O)$NH_2$; —C(O)$NHCH_3$; —C(O)N$(CH_3)_2$; —C(O)NH$(CH_2)_2CH_3$; $CH_2$NHC(O)$CH_3$; —$S(O)_2NH_2$; or —$S(O)_2N(CH_3)_2$.

Preferably, the invention provides compounds of formulae (A1) to (A10), (B1) to (B16) or (C1) to (C10) or (D1):

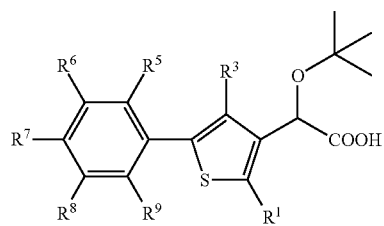
(A1)
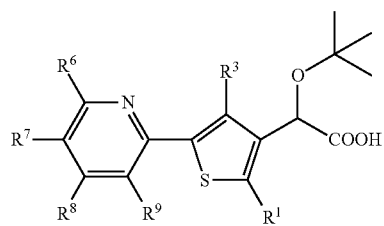
(A2)
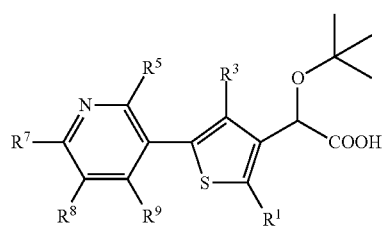
(A3)
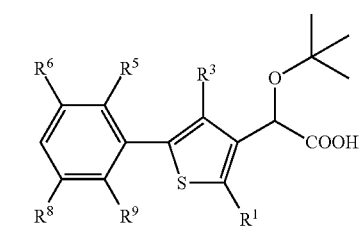
(A4)
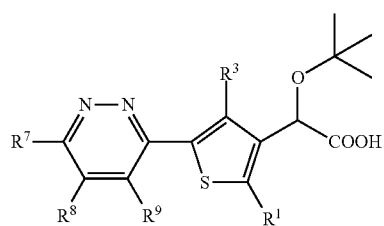
(A5)
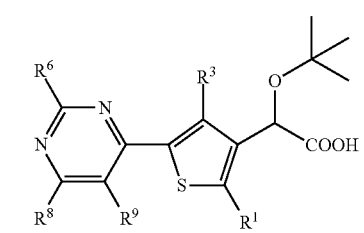
(A6)
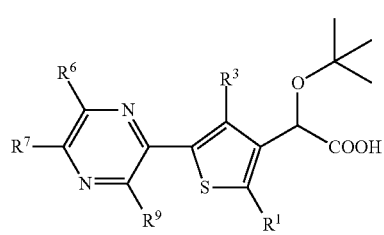
(A7)
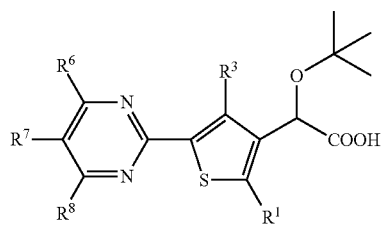
(A8)
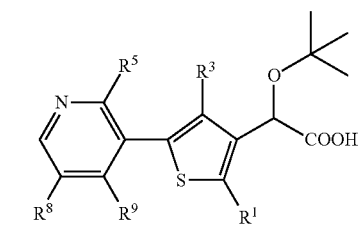
(A9)
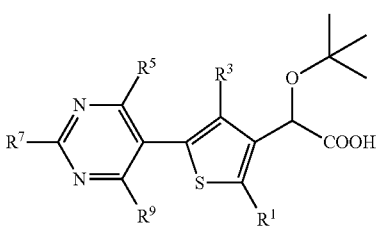
(A10)
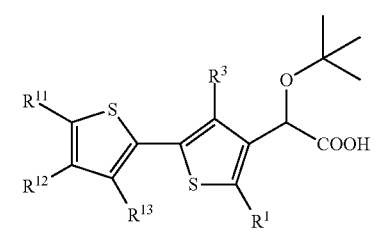
(B1)
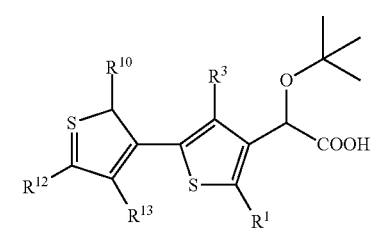
(B2)
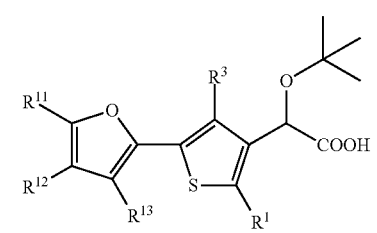
(B3)
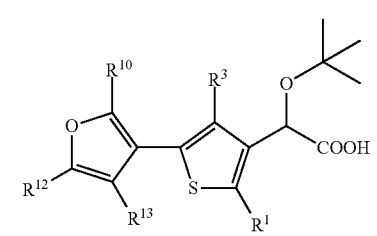
(B4)

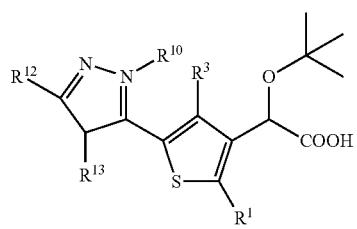 (B5)
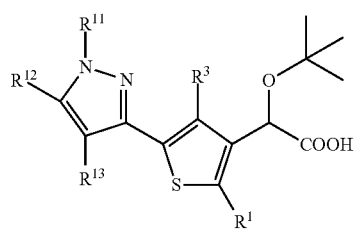 (B6)
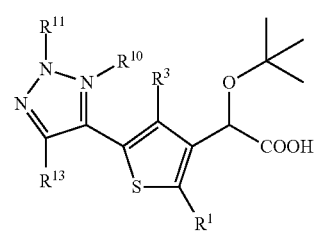 (B7)
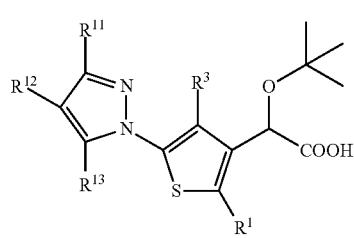 (B8)
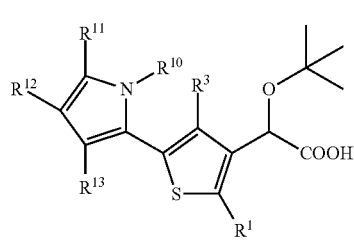 (B9)
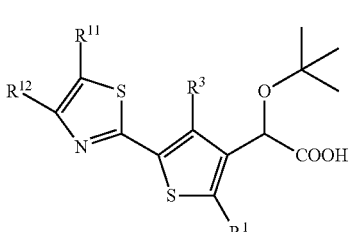 (B10)
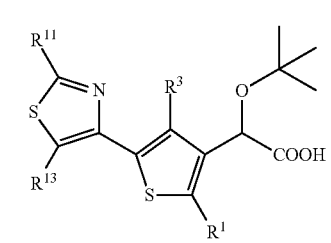 (B11)
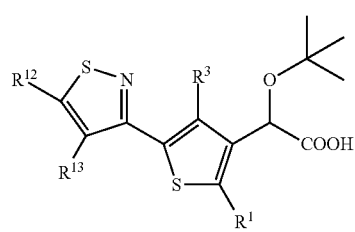 (B12)
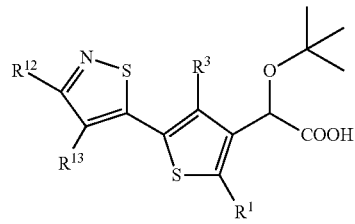 (B13)
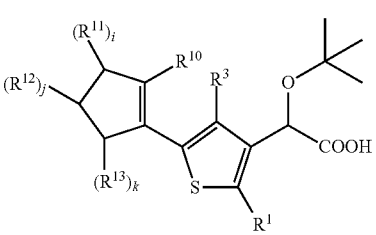 (B14)
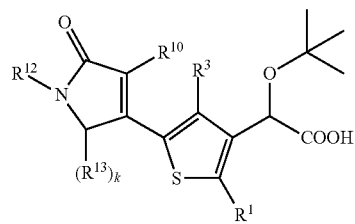 (B15)
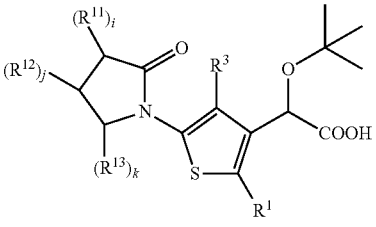 (B16)
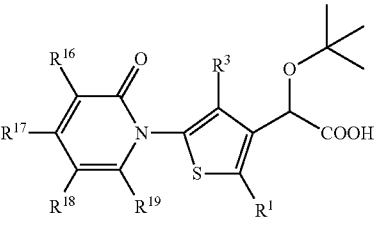 (C1)
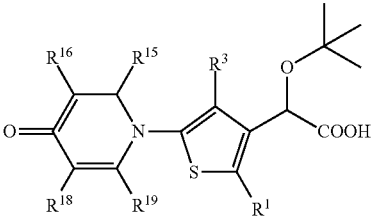 (C2)

-continued (C3)
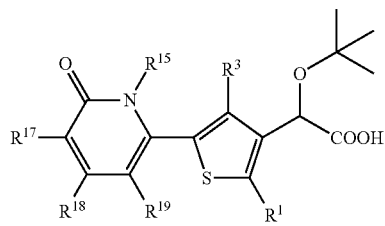

(C4)
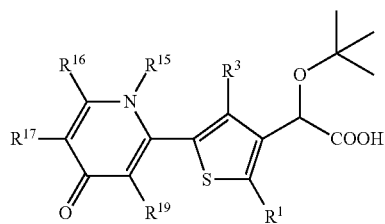

(C5)
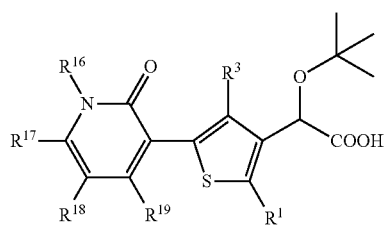

(C6)
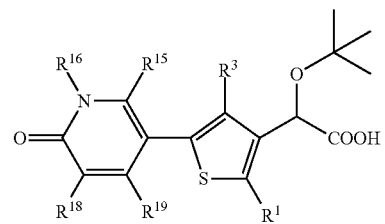

(C7)
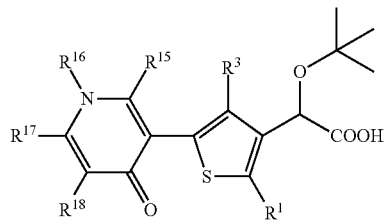

(C8)
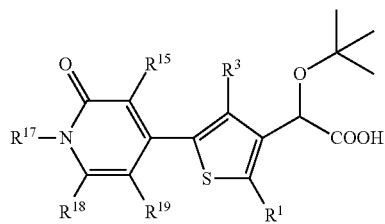

(C9)
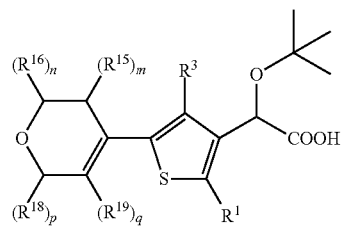

-continued (C10)
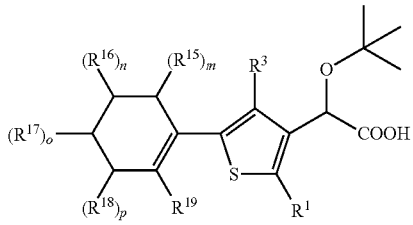

(D1)
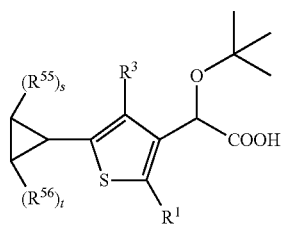

wherein:
$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{55}$, $R^{56}$ and R, identical or different, independently represent a hydrogen atom; a halogen atom; —$CH_3$; —$CH_2F$; —$CHF_2$; —$CF_3$; —OMe; —$OCH_2F$; —$OCHF_2$; —$OCF_3$; —$(X)_a$—$C_1$-$C_6$ cycloalkyl; —$(X)_a$—$(CT^5T^6)_b$-$(C_3$-$C_6$ cycloalkyl); —$(X)_a$—$(CT^5T^6)_b$-aryl; —$(X)_a$—$(CT^5T^6)_b$CN; —$(X)_a$—$(CT^5T^6)_b$OT$^3$; —$(X)_a$—$(CT^5T^6)_b$ST$^3$; —$(X)_a$—$(CT^5T^6)_b$S(O)T$^3$; —$(X)_a$—$(CT^5T^6)_b$S(O)$_2$T$^3$; —$(X)_a$—$(CT^5T^6)_b$NT$^3$T$^4$; —$(X)_a$—$(CT^5T^6)_b$C(O)T$^3$; —$(X)_a$—$(CT^5T^6)_b$C(O)OT$^3$; —$(X)_a$—$(CT^5T^6)_b$C(O)NT$^3$T$^4$; —$(X)_a$—$(CT^5T^6)_b$NT$^3$C(O)NT$^3$T$^4$; —$(X)_a$—$(CT^5T^6)_b$NT$^3$C(O)T$^4$; —$(X)_a$—$(CT^5T^6)_b$NT$^3$C(O)OT$^4$; —$(X)_a$—$(CT^5T^6)_b$OC(O)NT$^3$T$^4$; —$(X)_a$—$(CT^5T^6)_b$ S(O)$_2$NT$^3$T$^4$ or —$(X)_a$ $(CT^5T^6)_b$NT$^3$S(O)$_2$T$^4$;

i, j, k, m, n, o, p, q, s and t independently represent 0, 1 or 2;

$T^2$ independently represents a hydrogen atom; a halogen atom; methyl; —$CH_2F$; —$CHF_2$; —$CF_3$; —OMe; —$OCH_2F$; —$OCHF_2$; —$OCF_3$; or CN; optionally two geminal $T^2$ form with the carbon atom to which they are bonded, a cyclopropyl;

$R^1$, $R^3$, X, a, b and $T^3$ to $T^6$ are independently defined as for the compounds of formulae (I), (A), (B), (C) or (D).

Advantageously, in compound of formula (A1) to (A10), (B1) to (B16) or (C1) to (C10) or (D1):
$R^5$, $R^6$ and the carbon atoms to which they are bonded form a saturated, partially or totally unsaturated or aromatic 6-membered carbo- or heterocycle;
$R^6$, $R^7$ and the carbon atoms to which they are bonded form a saturated, partially or totally unsaturated or aromatic 6-membered carbo- or heterocycle;
$R^7$, $R^8$ and the carbon atoms to which they are bonded form a saturated, partially or totally unsaturated or aromatic 6-membered carbo- or heterocycle; or
$R^8$, $R^9$ and the carbon atoms to which they are bonded form a saturated, partially or totally unsaturated or aromatic 6-membered carbo- or heterocycle.

More advantageously, in compounds of formulae (A1) to (A10), (B1) to (B16) or (C1) to (C10) or (D1), $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{55}$, $R^{56}$ and R, identical or different, independently represent a hydrogen atom; a halogen atom; a linear or branched $C_1$-$C_6$ alkyl; a linear or branched $C_1$-$C_6$ fluoroalkyl; a linear or branched —O—$C_1$-$C_6$ alkyl; a linear or branched —O—$C_1$-$C_{10}$ alkylaryl; a linear or branched —$C_1$-$C_{10}$ alkylaryl; a cyclopropyl; a linear or branched —$C_1$-$C_{10}$ alkylcyclopropyl; —C(O)NH$_2$; —C(O)NHCH$_3$; C(O)N(CH$_3$)$_2$; C(O)N(CH$_2$)$_2$CH$_3$; CH$_2$NHC(O)Me; —NHC(O)CH$_3$; or —S(O)$_2$N(CH$_3$)$_2$.

Advantageously, the invention provides compounds of formulae (A1a) to (A10a), (A1b) to (A10b), (A1c) to (A10c), (A1d) to (A10d), (A1e) to (A10e), (B1a) to (B16a), (B1b) to (B16b), (B1c) to (B16c), (B1d) to (B16d), (B1e) to (B10e), (C1a) to (C10a), (C1b) to (C10b), (C1c) to (C10c), (C1d) to (C10d), (C1e) to (C10e), (D1a), (D1b), (D1c), (D1d) or (D1e),

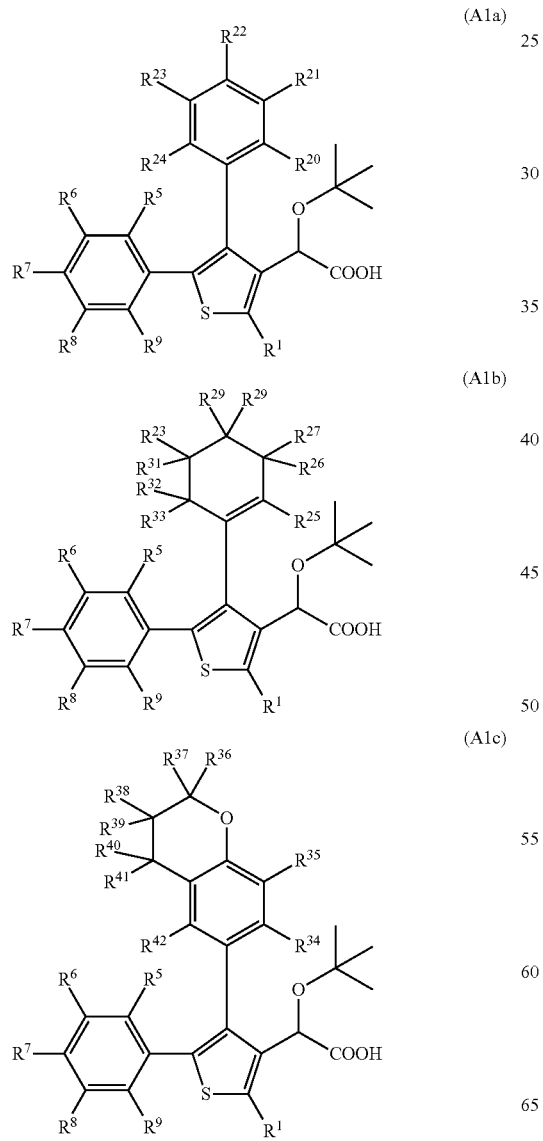

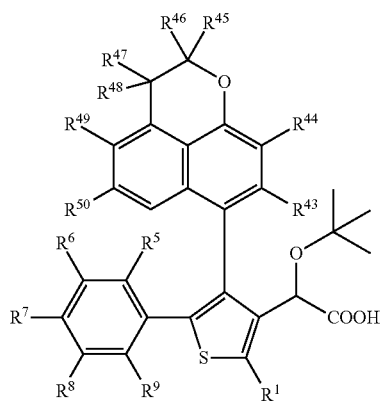

(A1d)

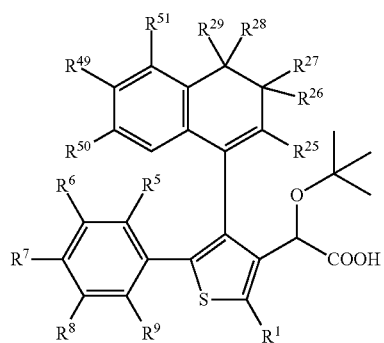

(A1e)

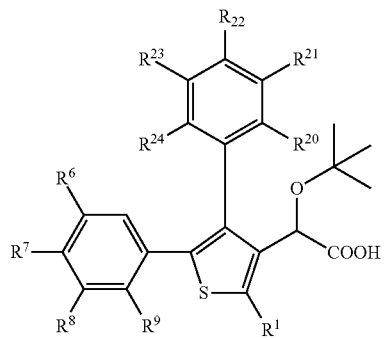

(A2a)

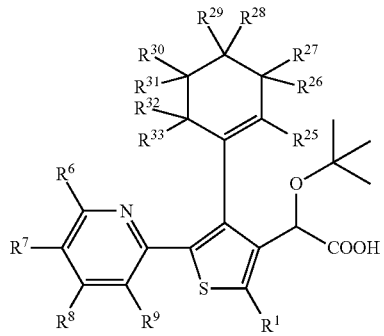

(A2b)

(A2c) 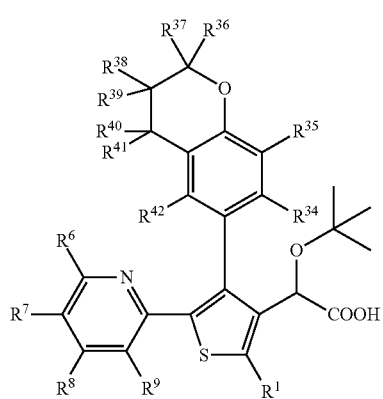
(A2d) 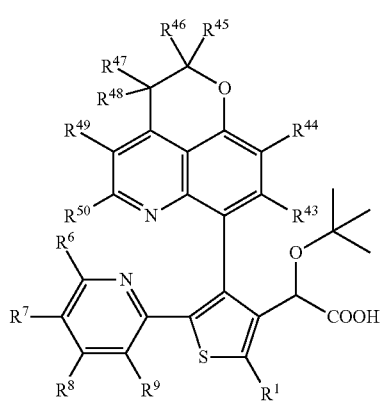
(A2e) 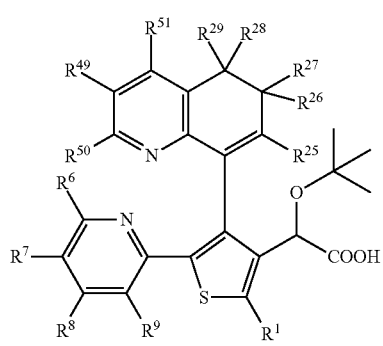
(A3a) 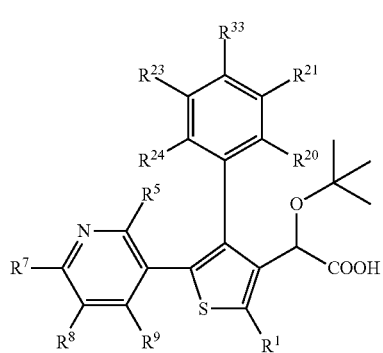
(A3b) 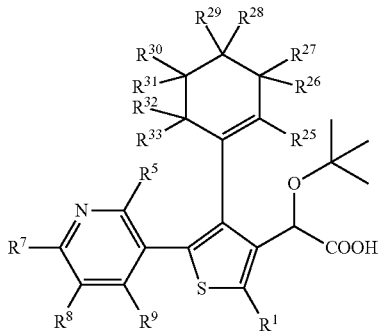
(Ac) 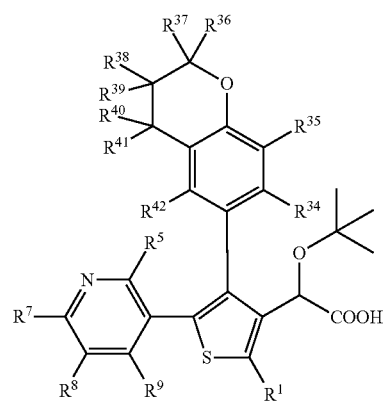
(A3d) 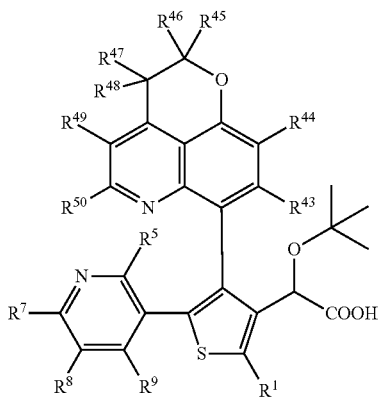
(A3e) 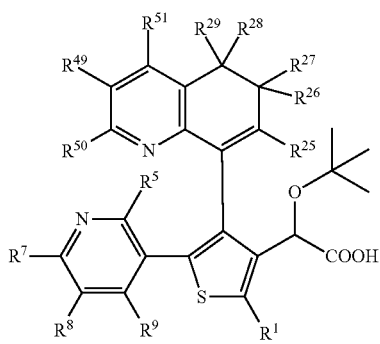

(A4a)
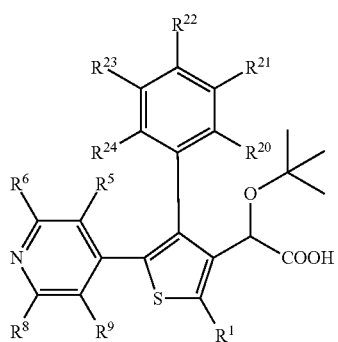
(A4b)
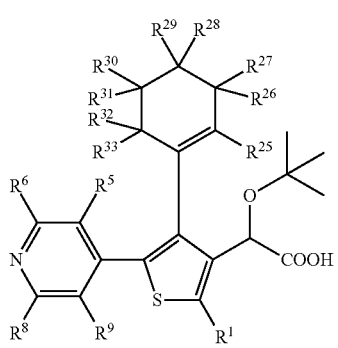
(A4c)
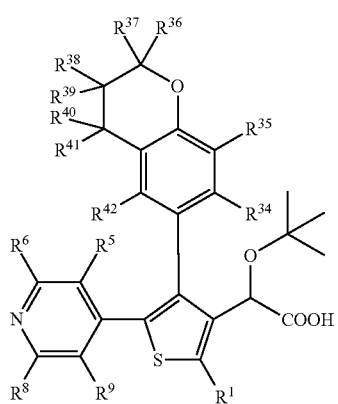
(A4d)
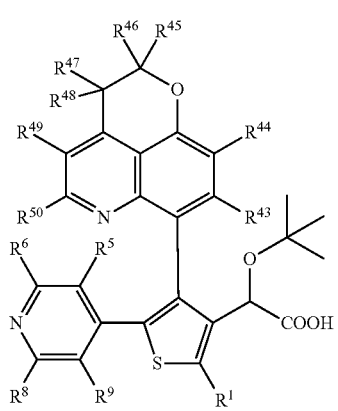
(A4e)
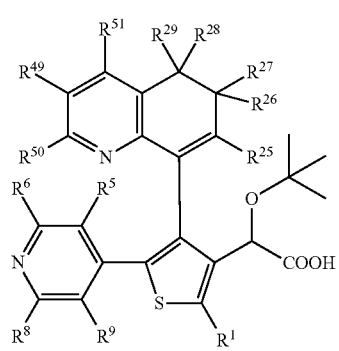
(A5a)
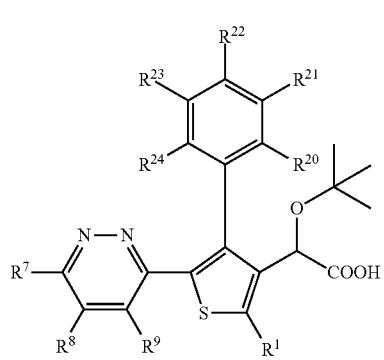
(A5b)
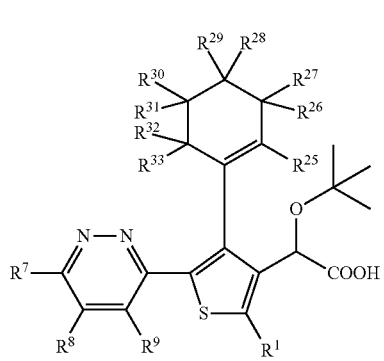
(A5c)
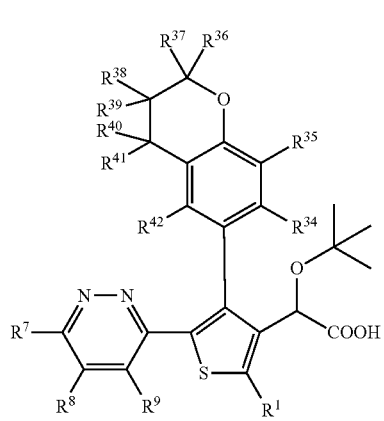

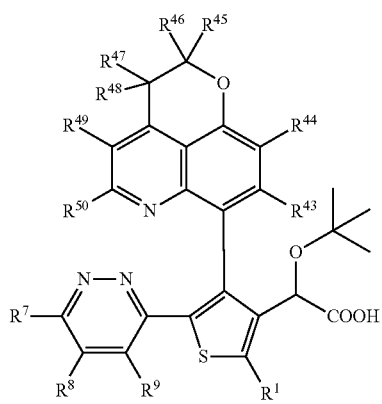
(A5d)
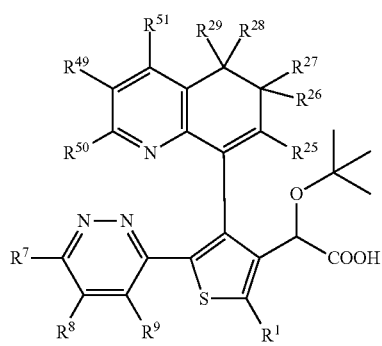
(A5e)
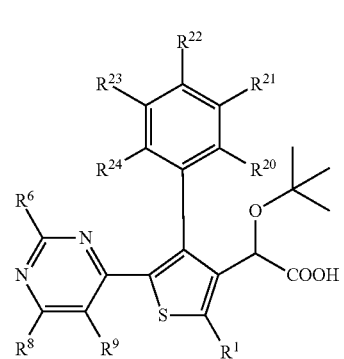
(A6a)
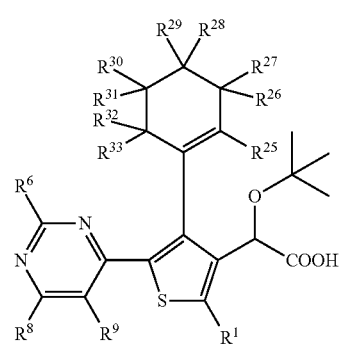
(A6b)
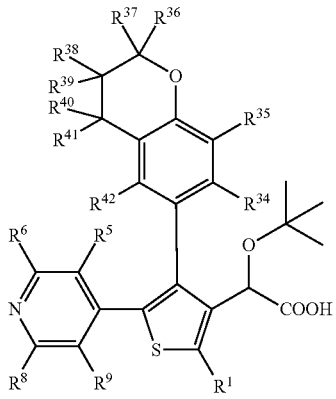
(A6c)
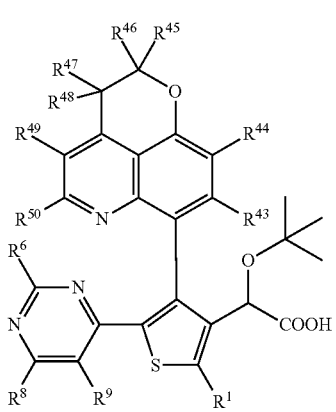
(A6d)
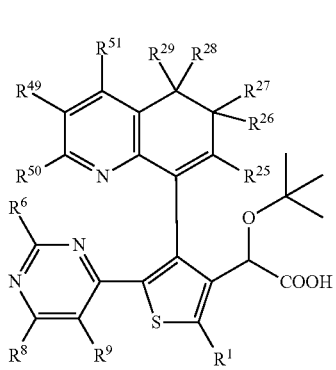
(A6e)
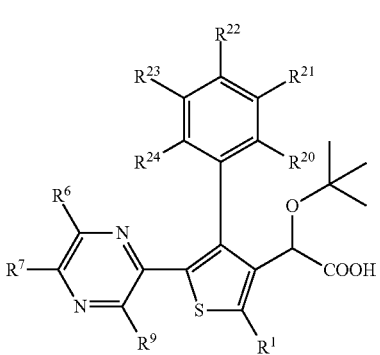
(Aa)

-continued
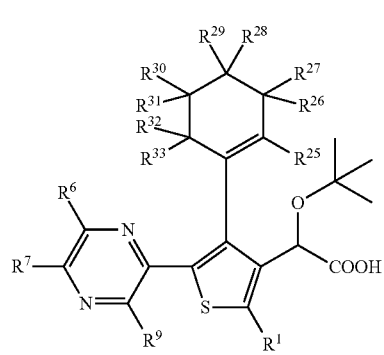
(A7b)
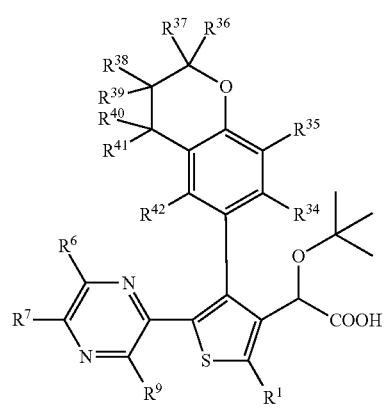
(A7c)
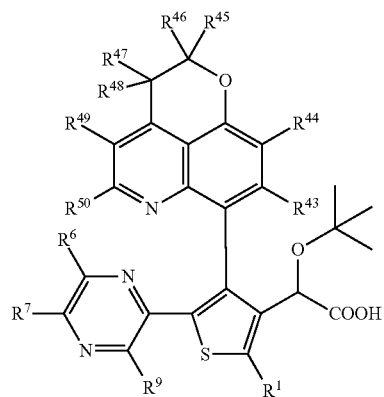
(A7d)
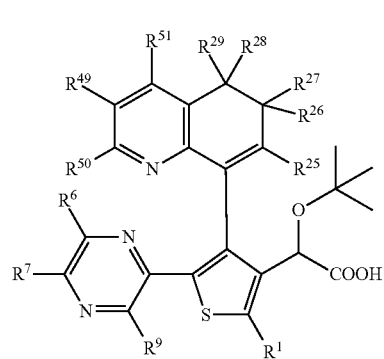
(A7e)
-continued
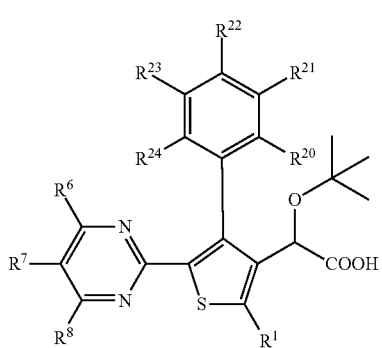
(A8a)
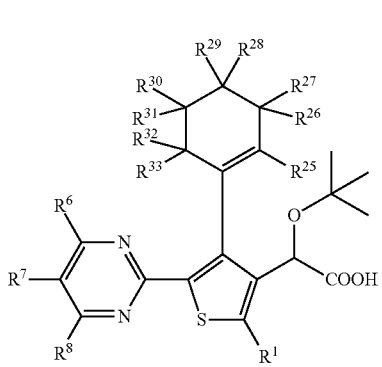
(A8b)
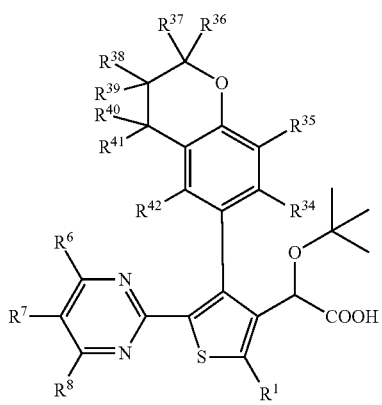
(A8c)
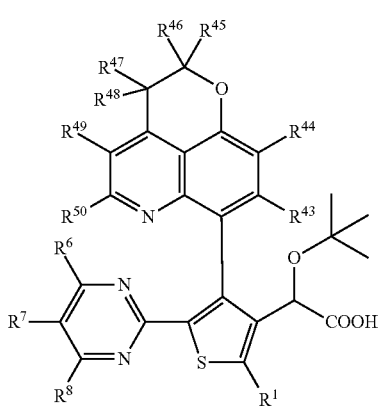
(A8d)

-continued
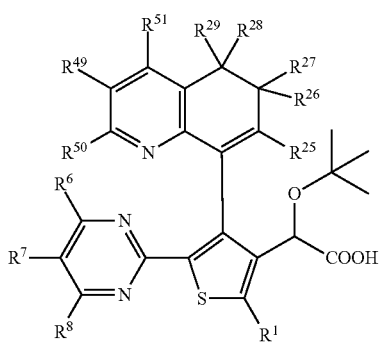
(A8e)
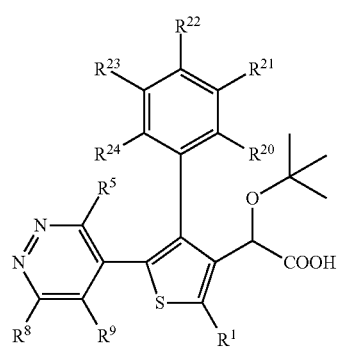
(A9a)
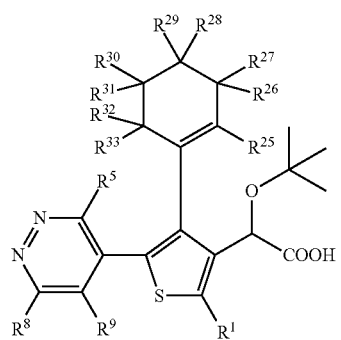
(A9b)
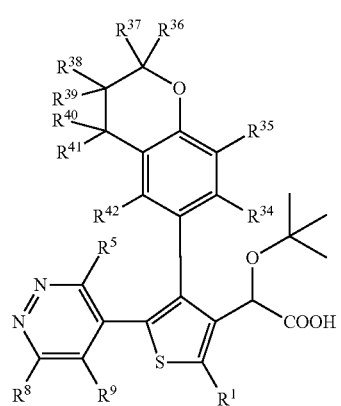
(A9c)
-continued
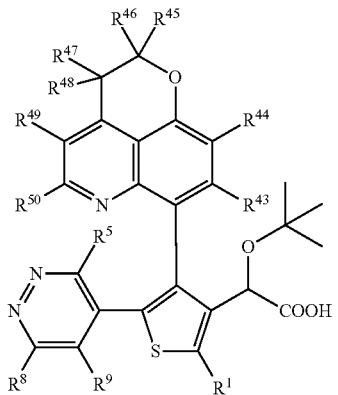
(A9d)
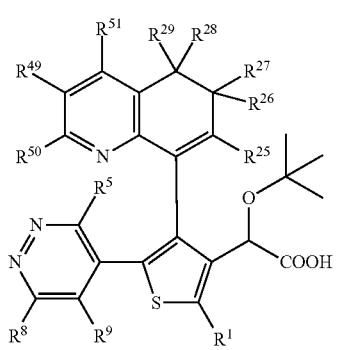
(A9e)
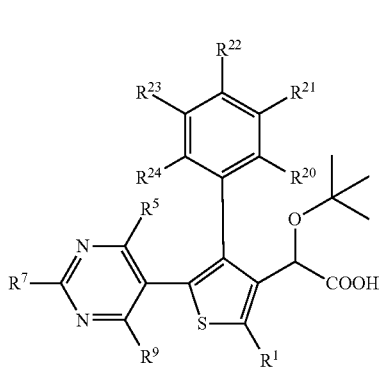
(A10a)
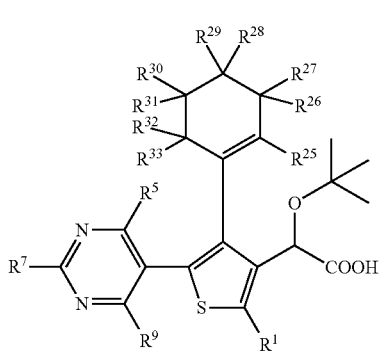
(A10b)

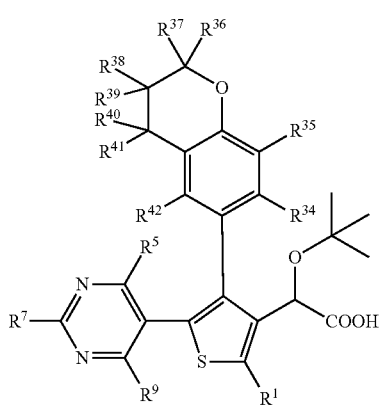 (A10c)
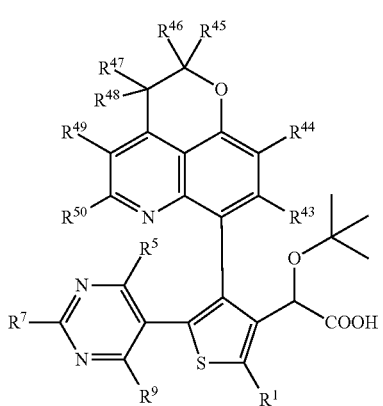 (A10d)
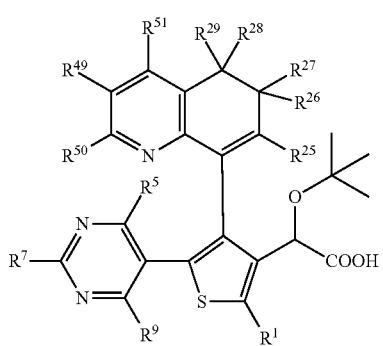 (A10e)
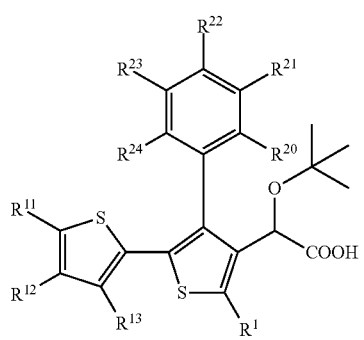 (B1a)
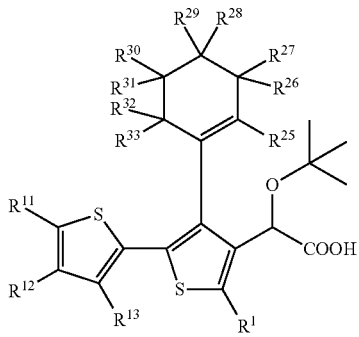 (B1b)
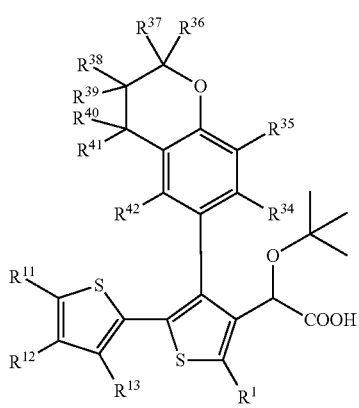 (B1c)
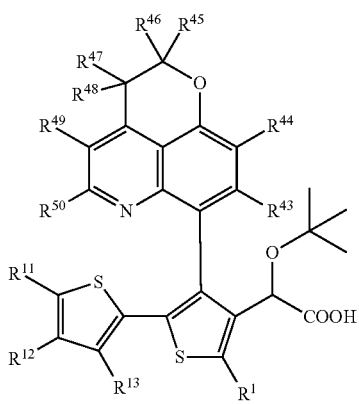 (B1d)
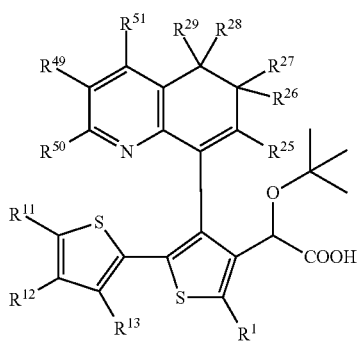 (B1e)

(B2a) 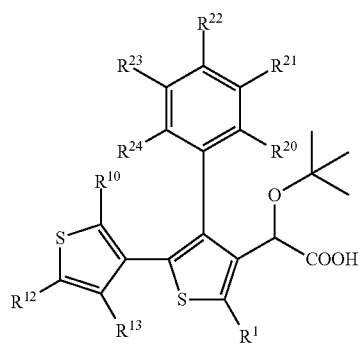
(B2b) 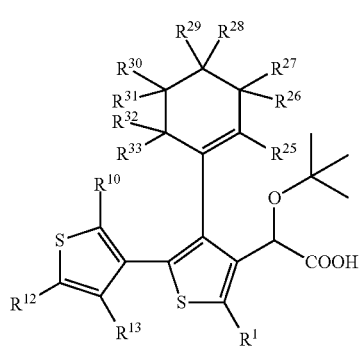
(B2c) 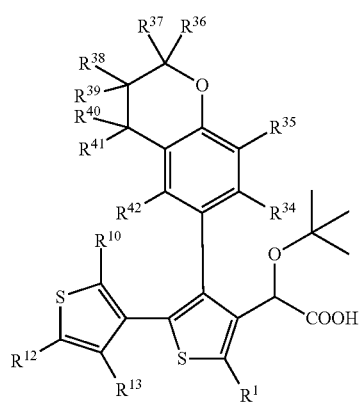
(B2d) 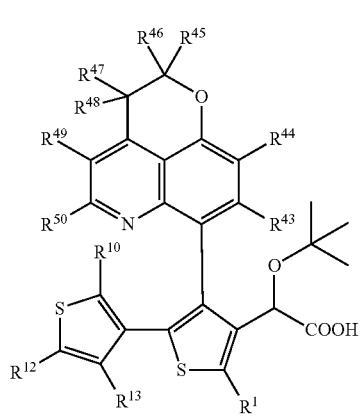
(B2e) 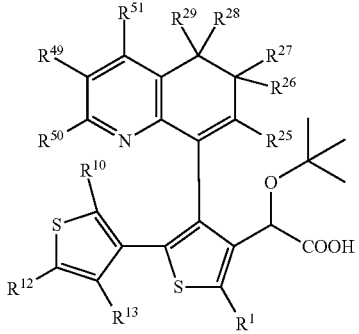
(B3a) 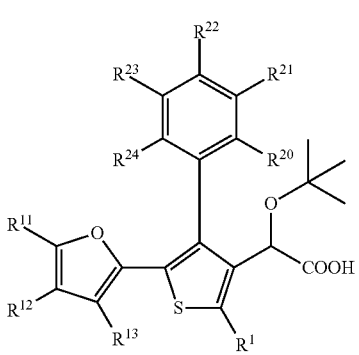
(B3b) 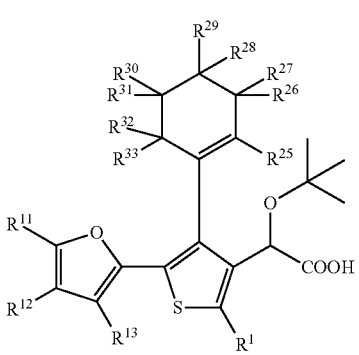
(B3c)

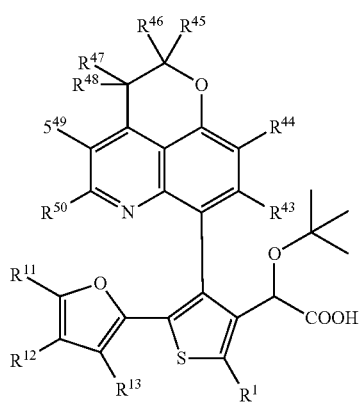
(B3d)
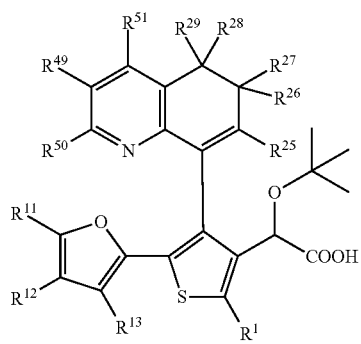
(B3e)
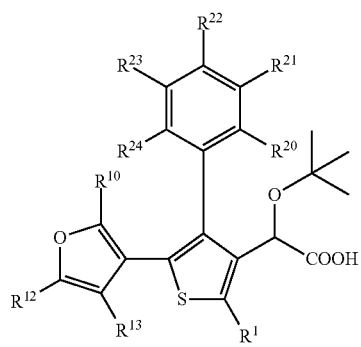
(B4a)
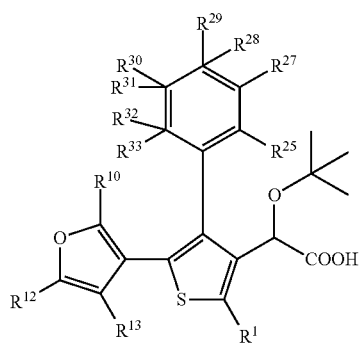
(B4b)
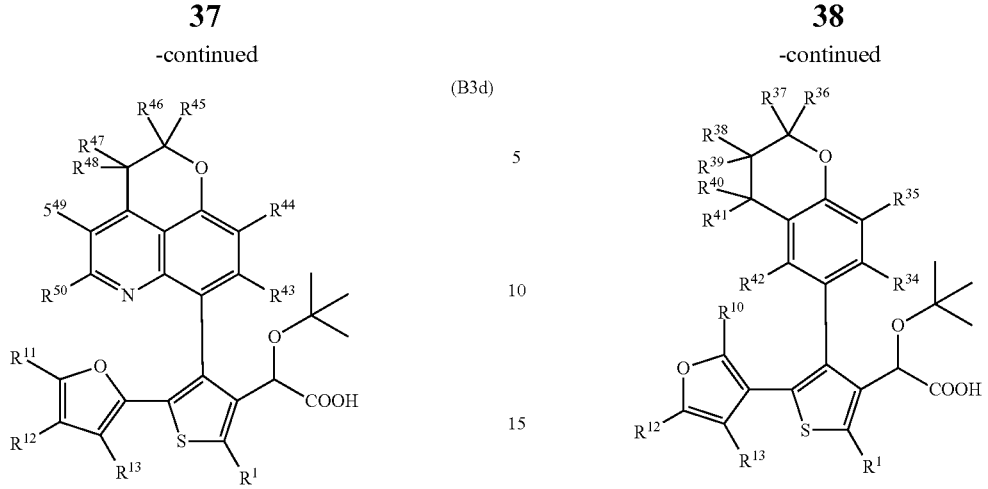
(B4c)
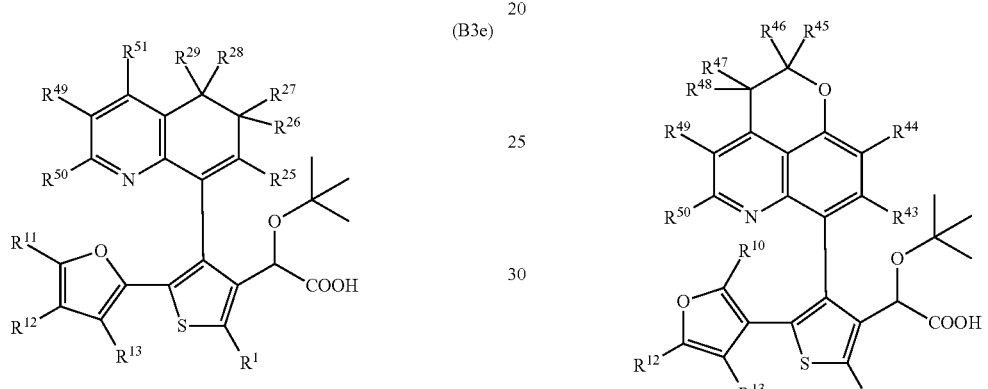
(B4d)
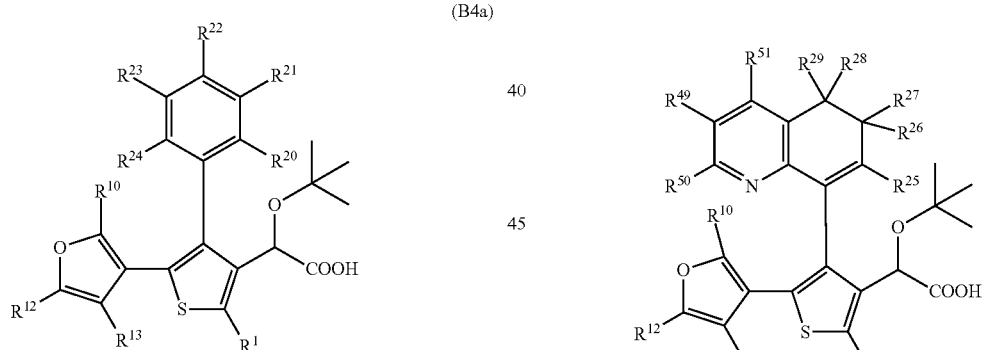
(B4e)
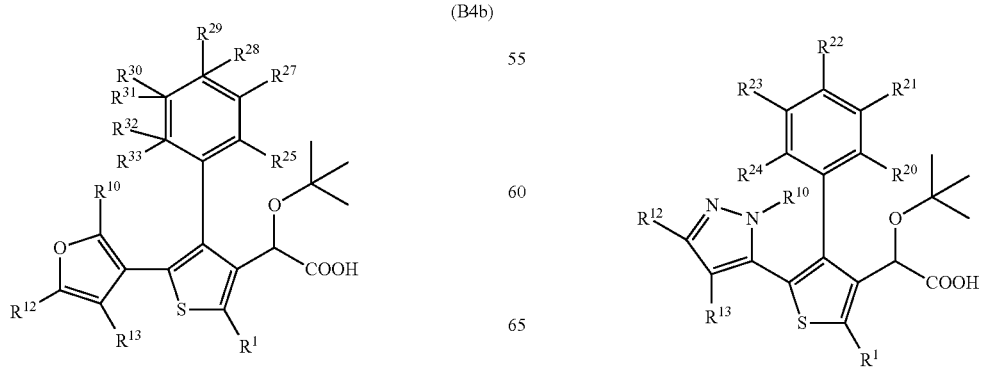
(B5a)

(B5b) 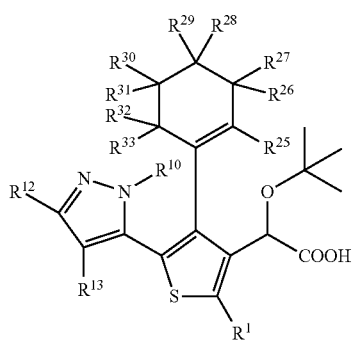
(B5c) 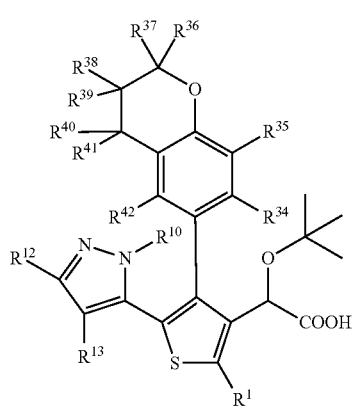
(B5d) 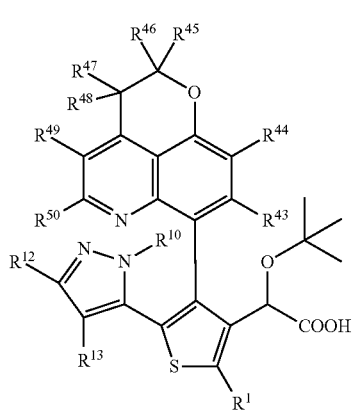
(B5e) 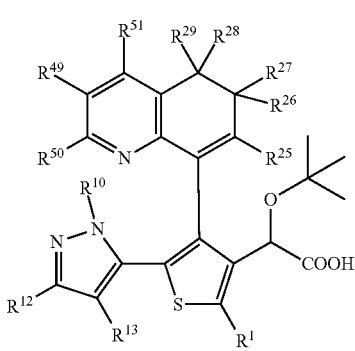
(B6a) 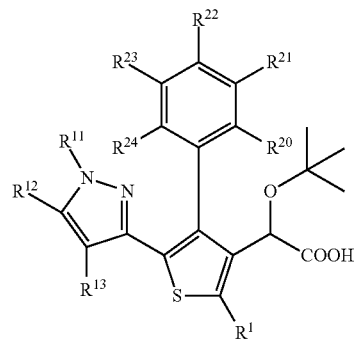
(B6b) 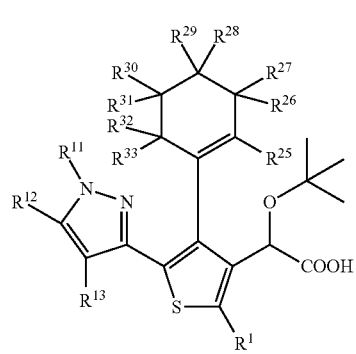
(B6c) 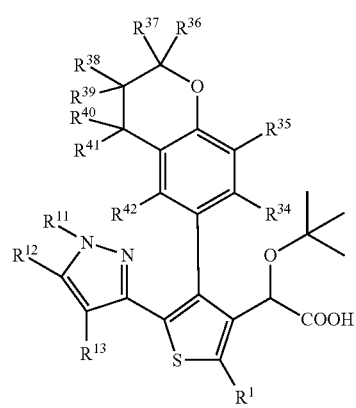
(B6d) 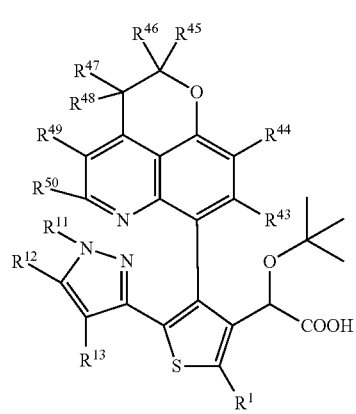

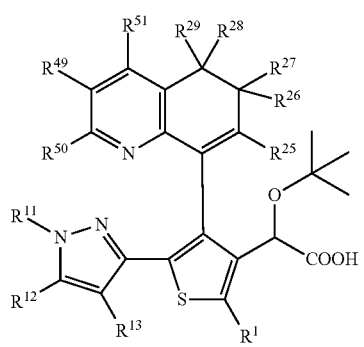
(B6e)
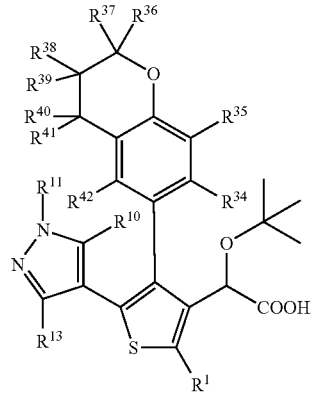
(B7c)
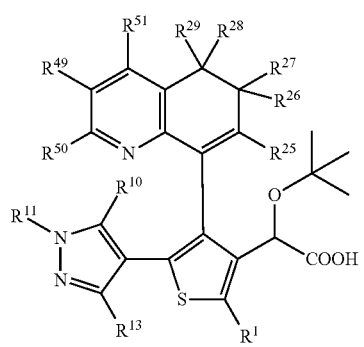
(B7e)
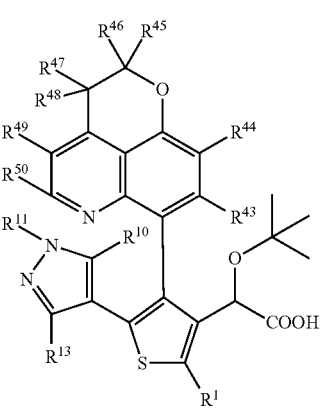
(B7d)
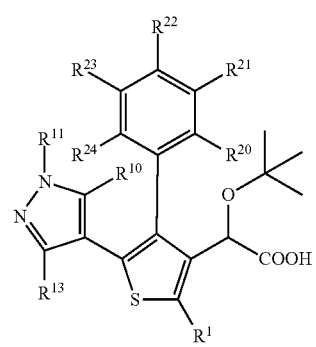
(B7a)
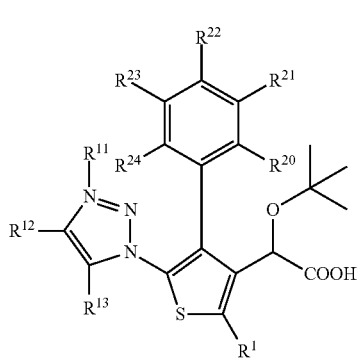
(B8a)
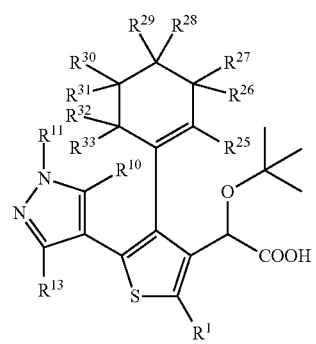
(B7b)
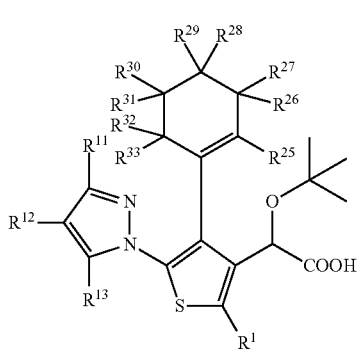
(B8b)

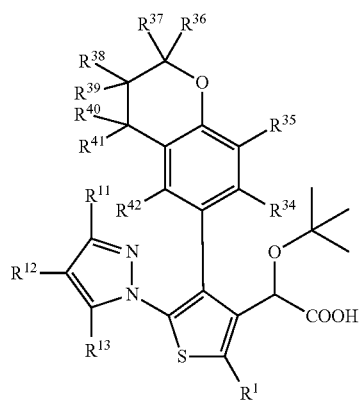
(B8c)
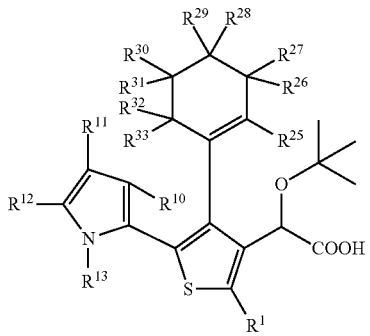
(B9b)
(B8d)
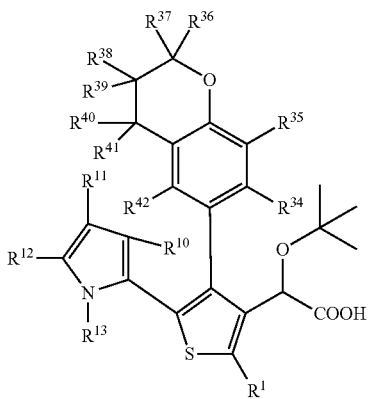
(B9c)
(B8e)
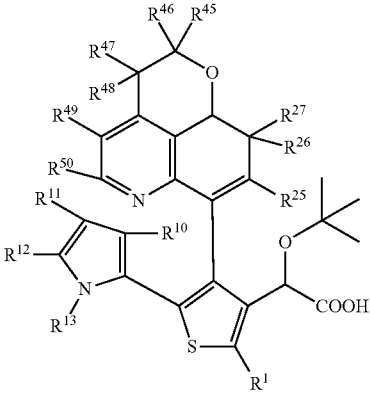
(B9e)
(B9a)
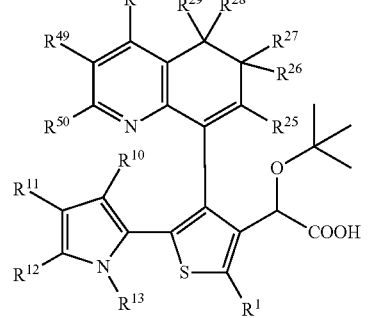
(B9d)

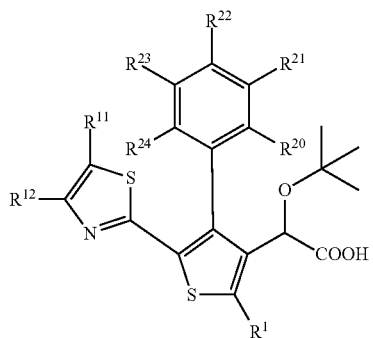
(B10a)
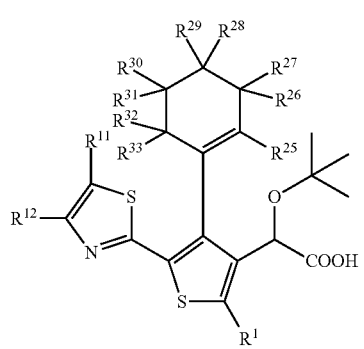
(B10b)
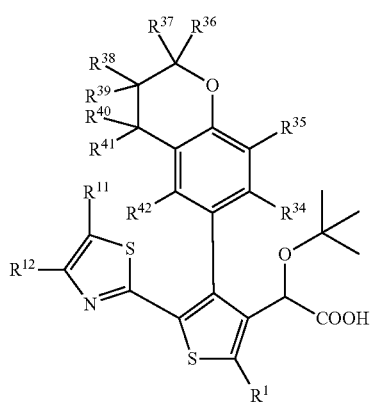
(B10c)
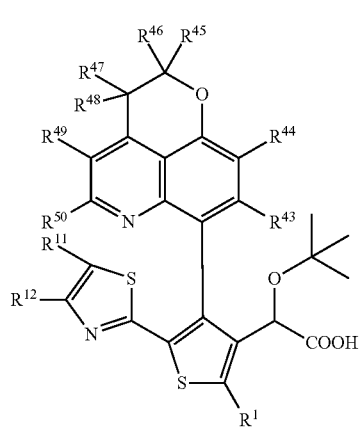
(B10d)
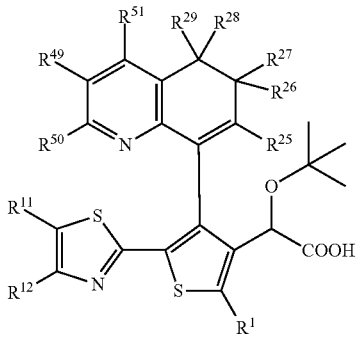
(B10e)
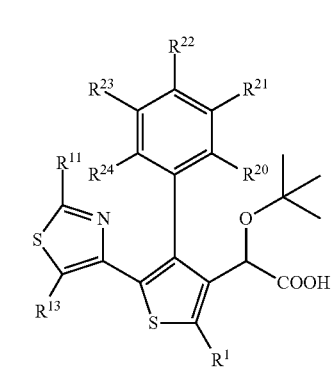
(B11a)
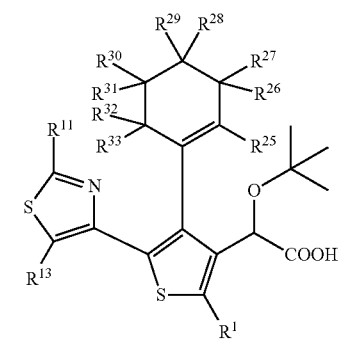
(B11b)
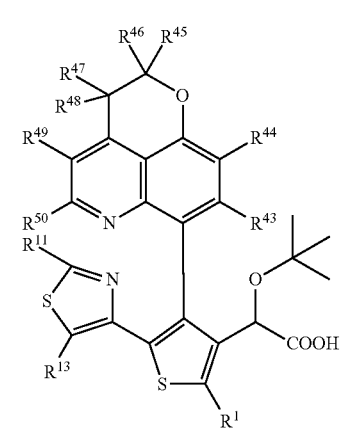
(B11d)

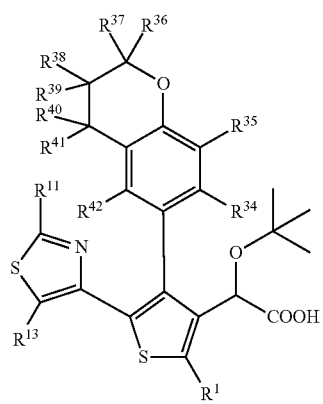
(B11c)
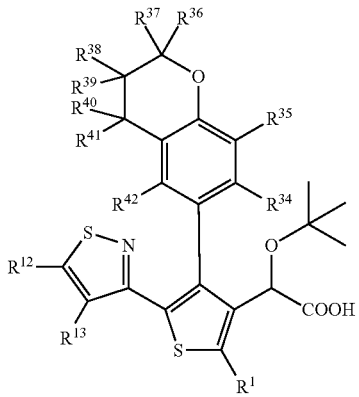
(B12c)
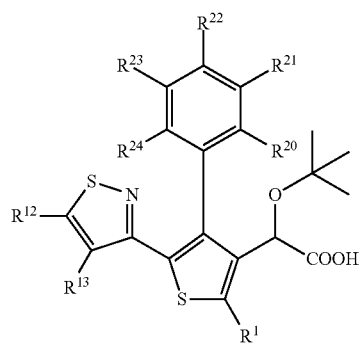
(B11e)
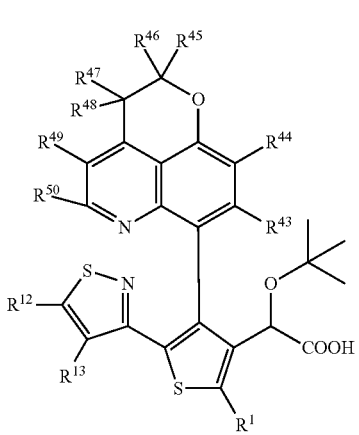
(B12d)
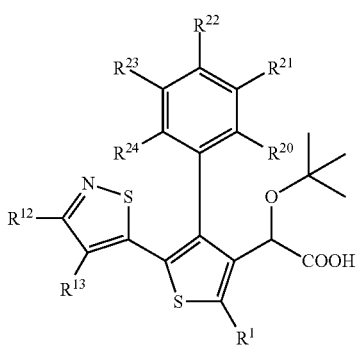
(B12a)
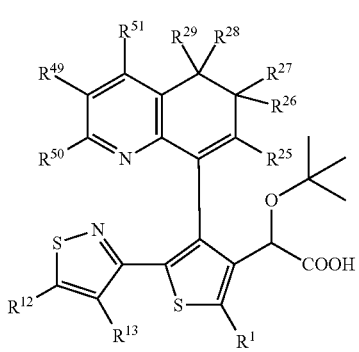
(B12e)
(B12b)
(B13a)

(B13c)
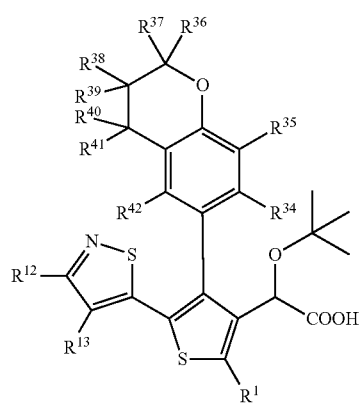
(B14a)
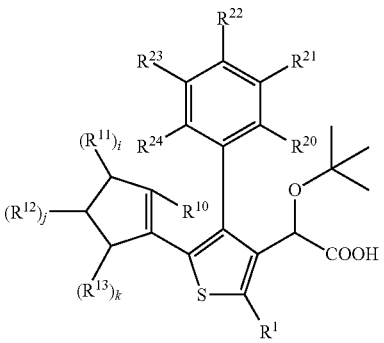
(B13b)
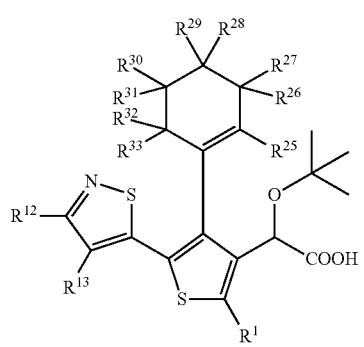
(B14b)
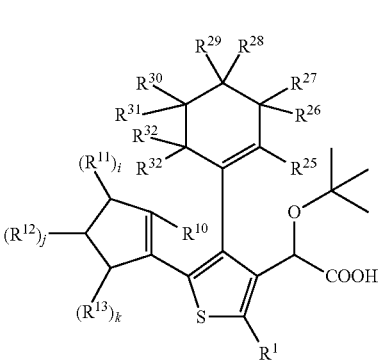
(B13e)
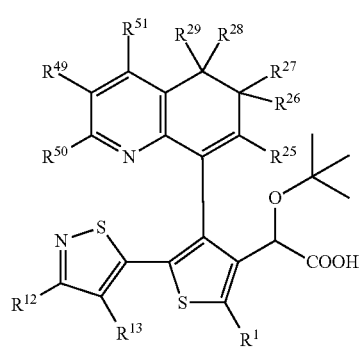
(B14c)
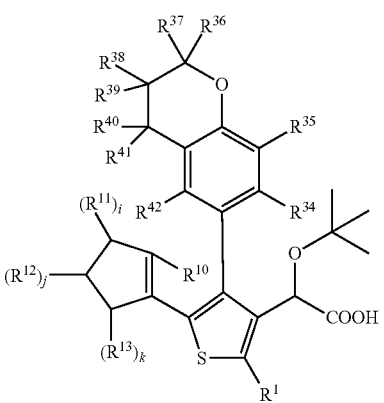
(B13d)
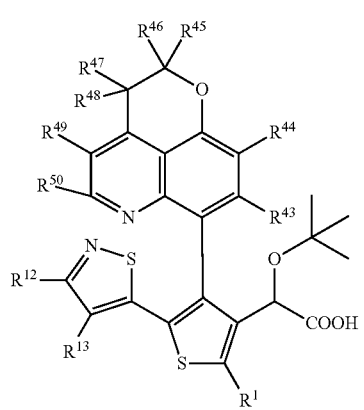
(B14d)
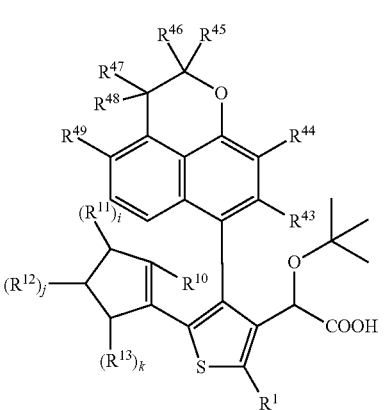

-continued
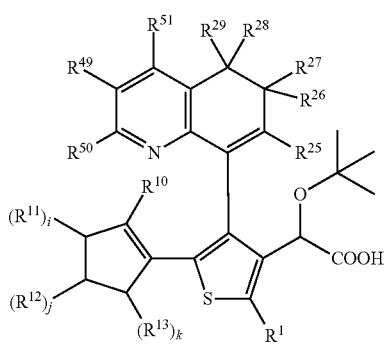
(B14e)
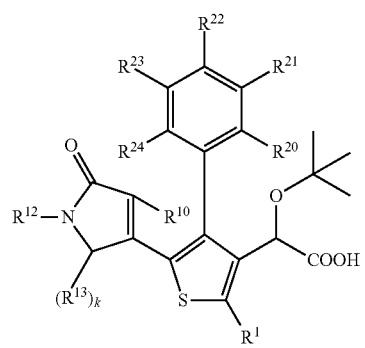
(B15a)
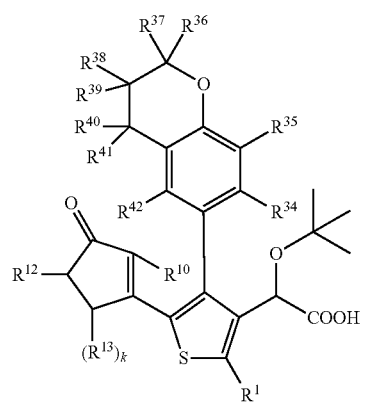
(B15c)
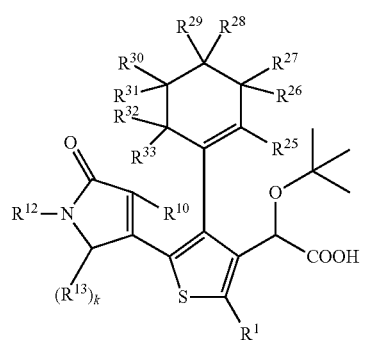
(B15b)
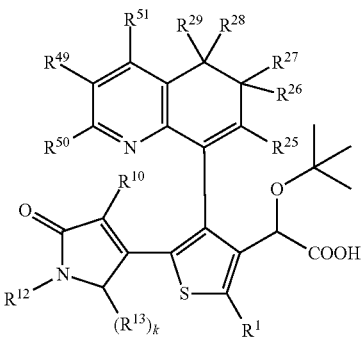
(B15e)
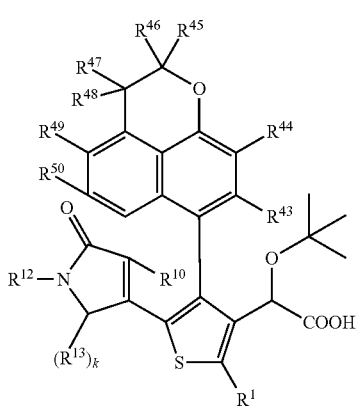
(B15d)
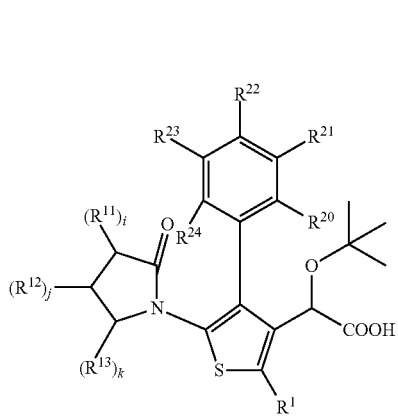
(B16a)
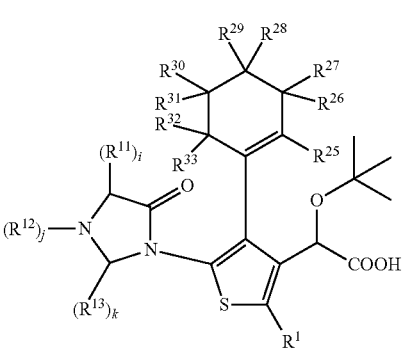
(B16b)

-continued
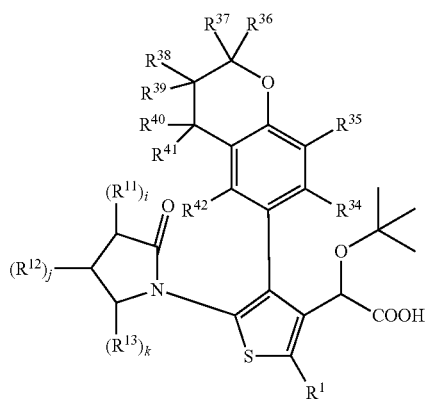
(B16c)
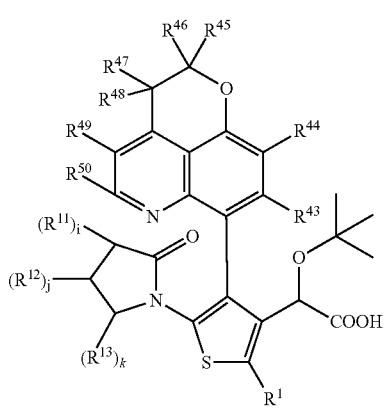
(B16d)
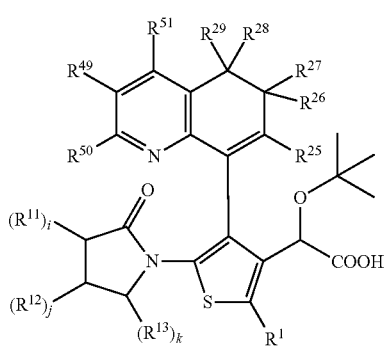
(B16e)
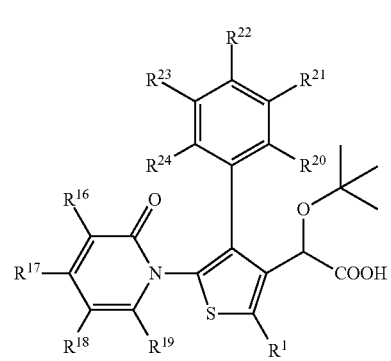
(C1a)
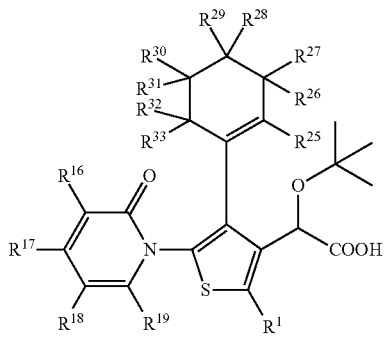
(C1b)
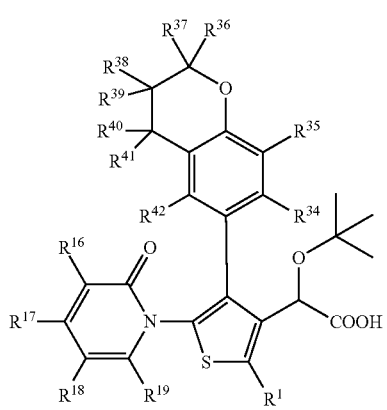
(C1c)
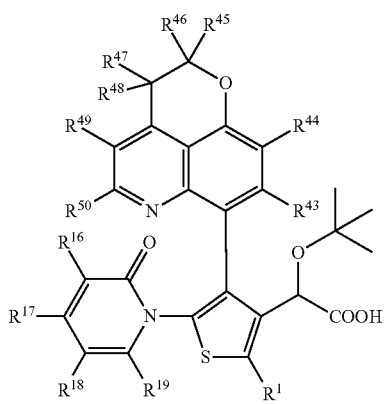
(C1d)
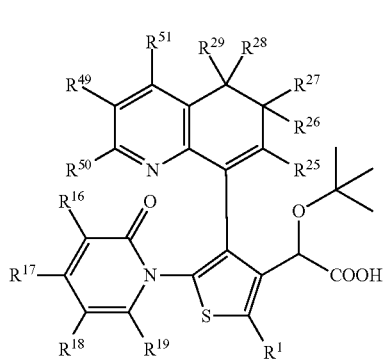
(C1e)

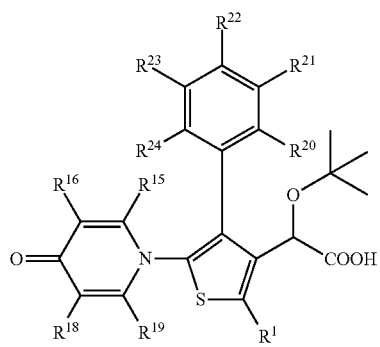
(C2a)
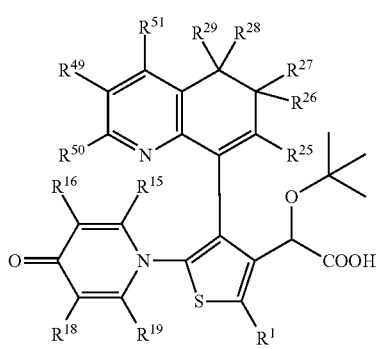
(C2e)
(C2b)
(C3a)
(C2c)
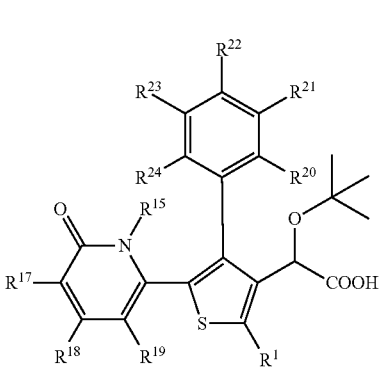
(3Cb)
(C2d)
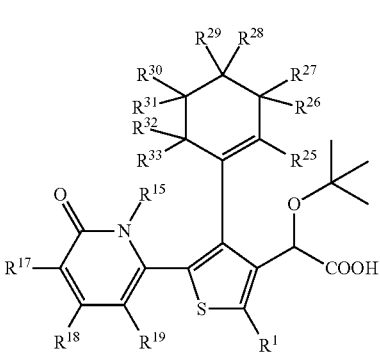
(C3c)
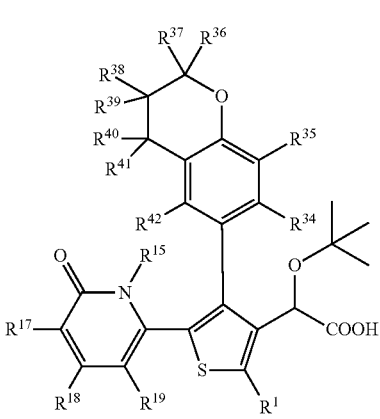

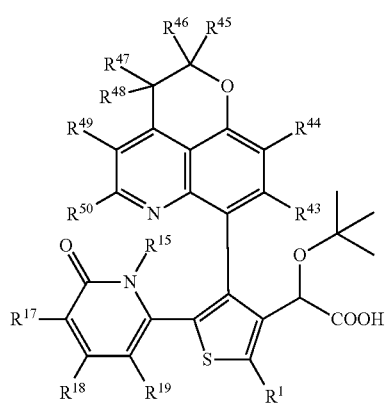
(C3d)
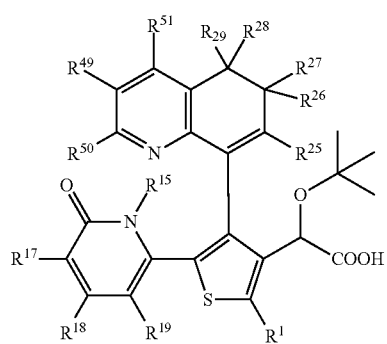
(C3e)
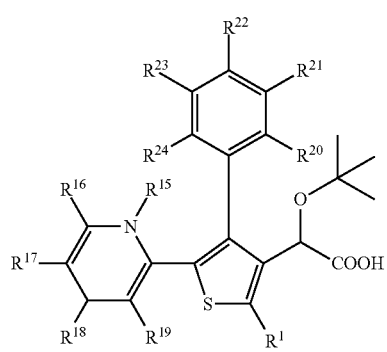
(C4a)
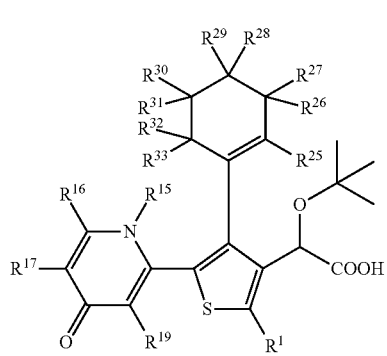
(C4b)
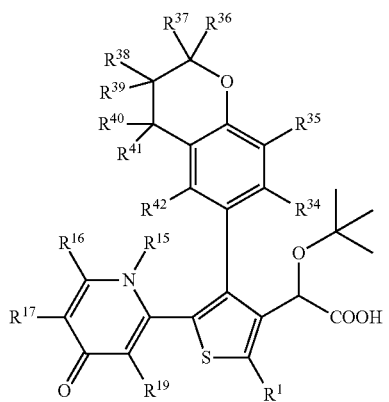
(C4c)
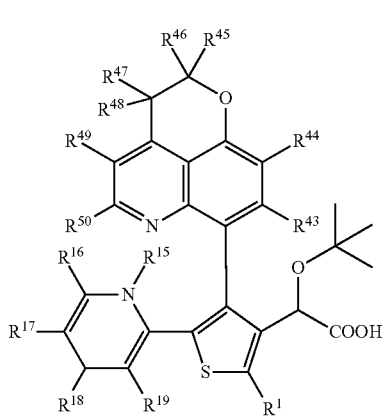
(C4d)
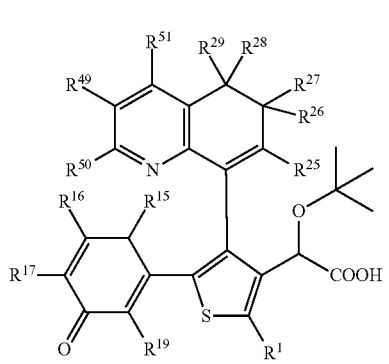
(C4e)
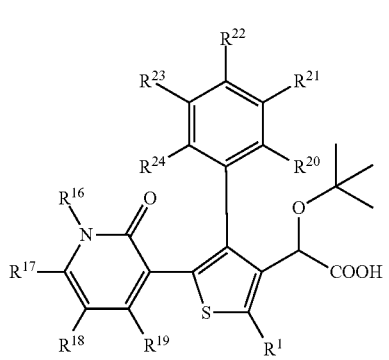
(C5a)

(C5b)
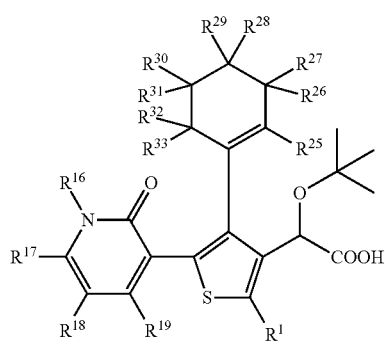
(C5c)
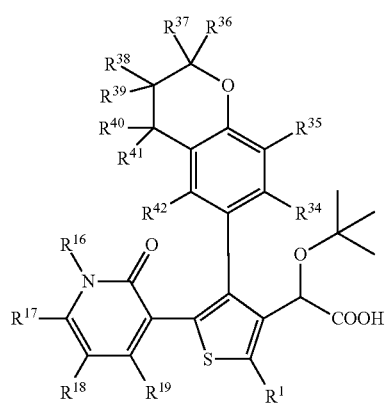
(C5d)
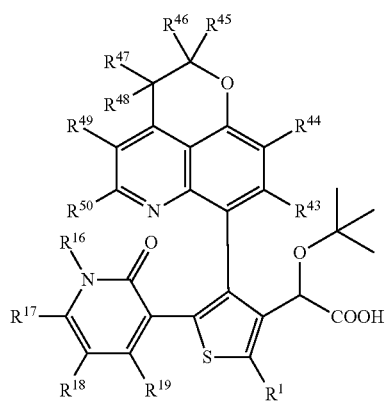
(C5e)
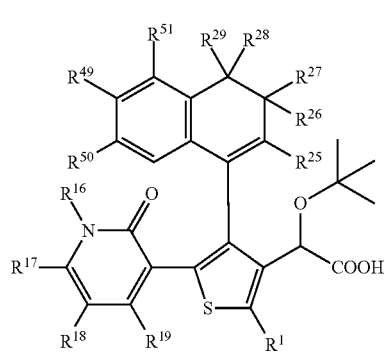
(C6a)
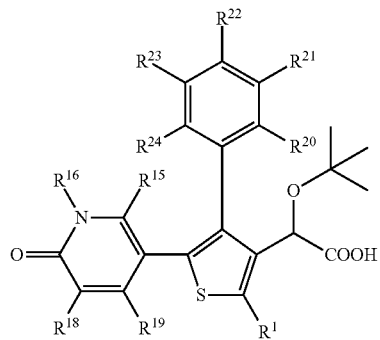
(C6b)
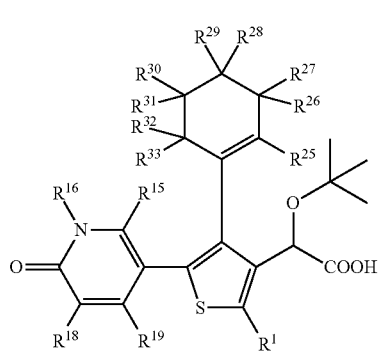
(C6c)
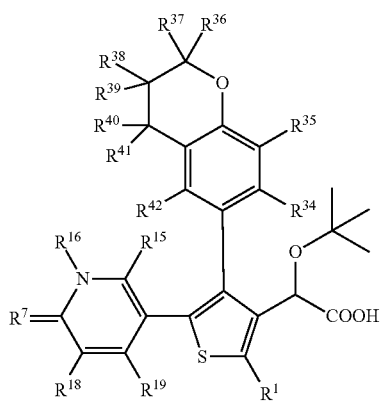
(C6d)
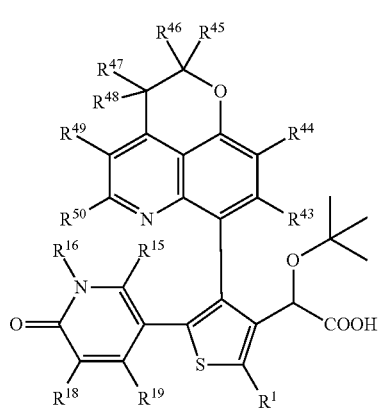

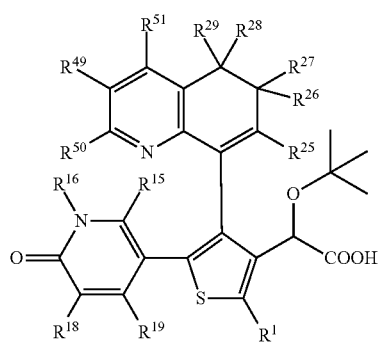
(C7e)
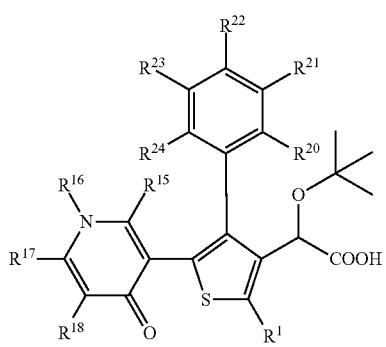
(C7a)
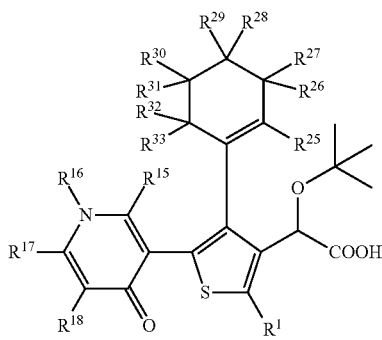
(C7b)
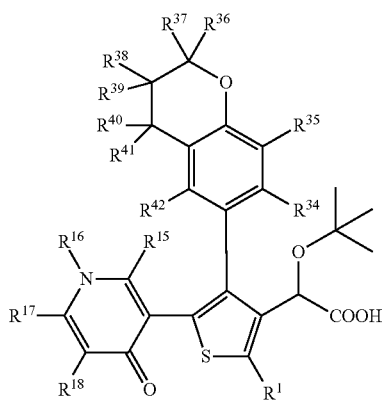
(C7c)
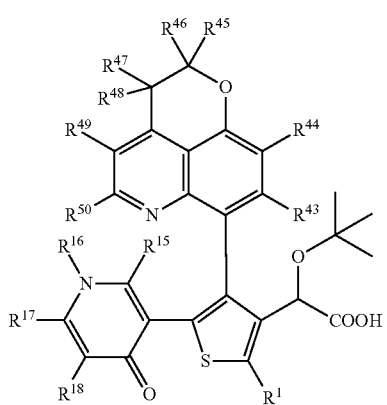
(C7d)
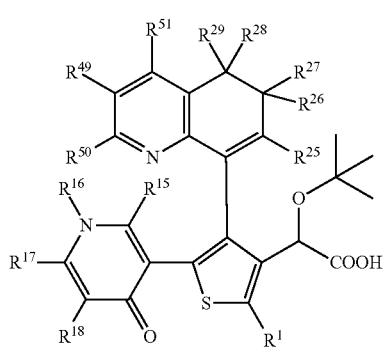
(C7e)
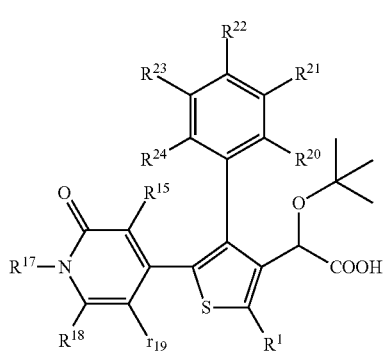
(C8a)
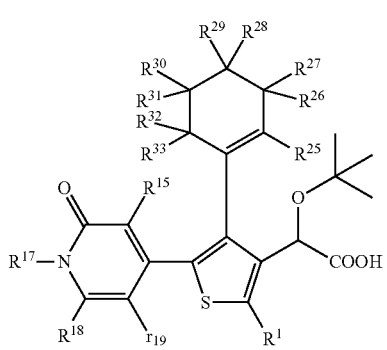
(C8b)

-continued
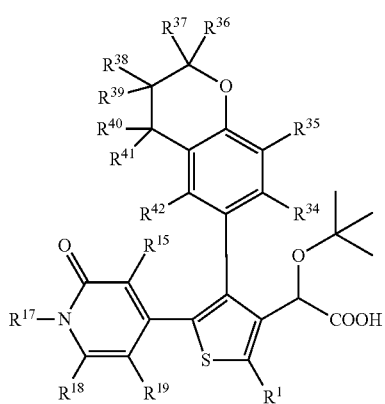
(C8c)
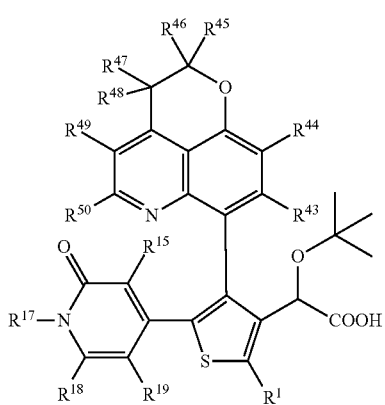
(C8d)
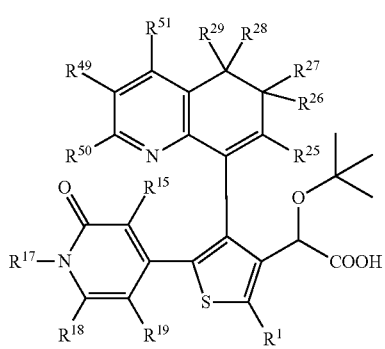
(C8e)
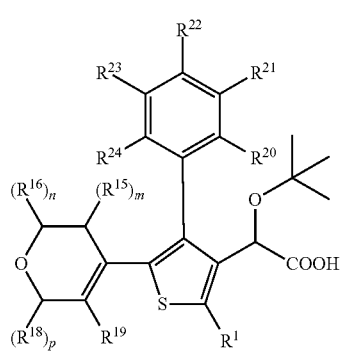
(C9a)
-continued
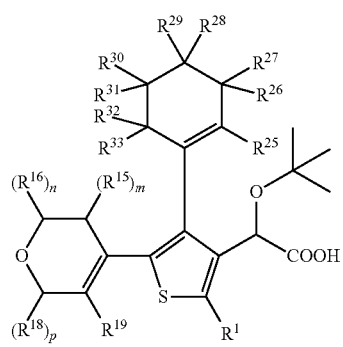
(C9b)
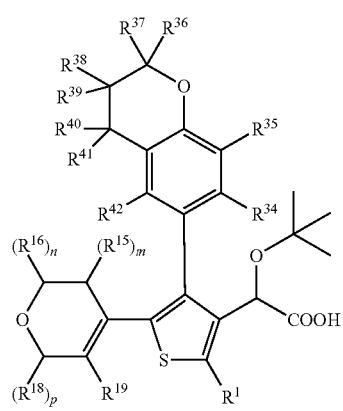
(C9c)
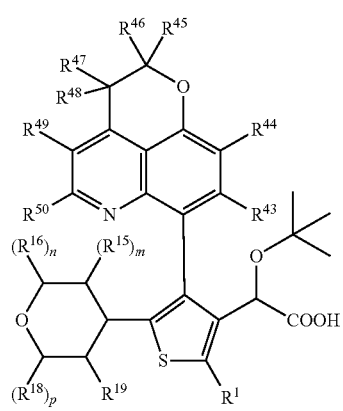
(C9d)
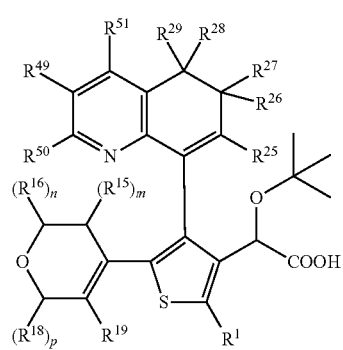
(C9e)

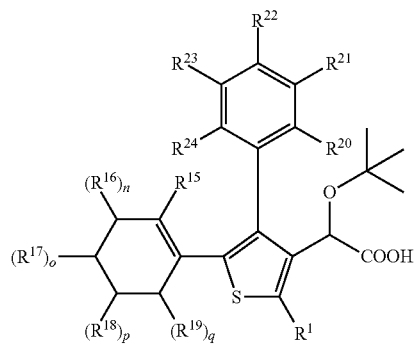
(C10a)
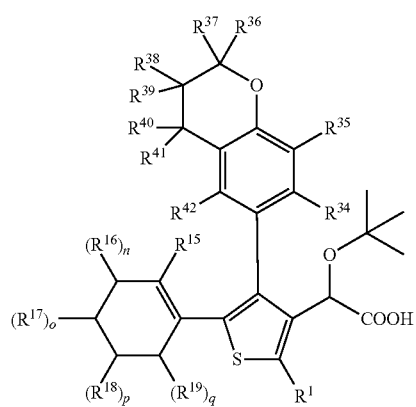
(C10c)
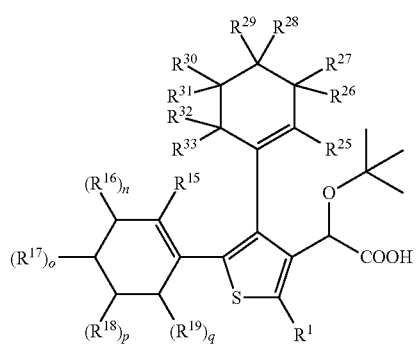
(C10b)
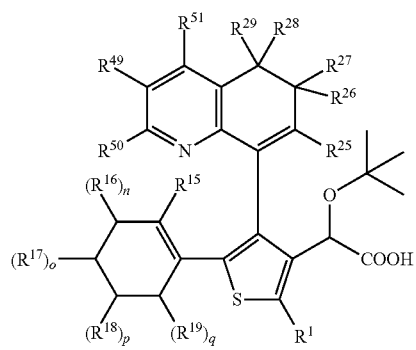
(C10e)
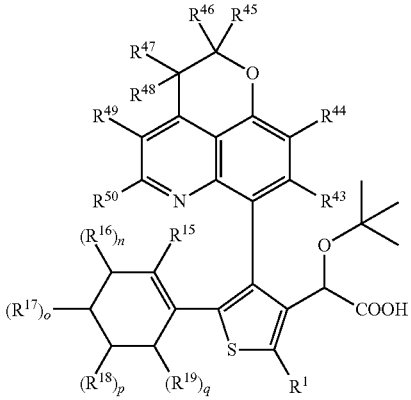
(C10d)
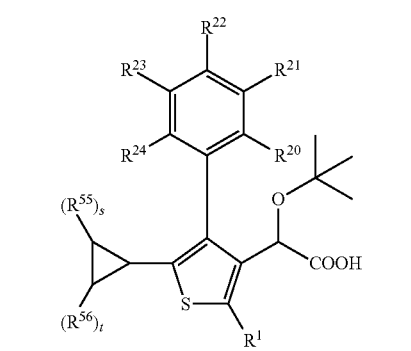
(D1a)
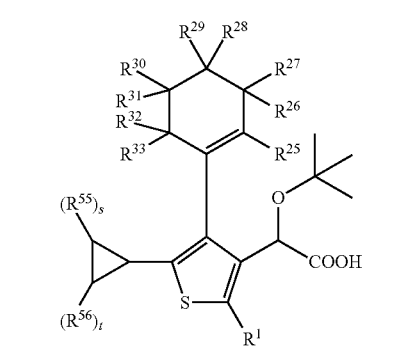
(D1b)
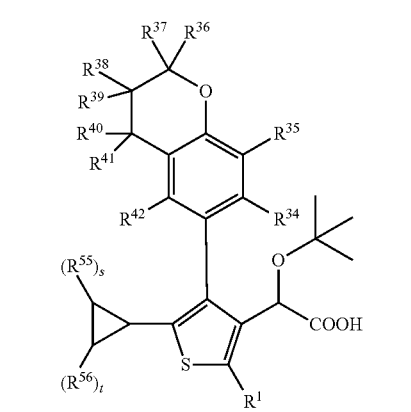
(D1c)

-continued (D1d)

(D1e)

wherein
R⁵, R⁶, R⁷, R⁸, R⁹, R¹⁰, R¹¹, R¹², R¹³, R¹⁴, R¹⁵, R¹⁶, R¹⁷, R¹⁸, R¹⁹, R⁵⁵, R⁵⁶ and R, identical or different, independently represent a hydrogen atom; a halogen atom; —CH₃; —CH₂F; —CHF₂; —CF₃; —OMe; —OCH₂F; —OCHF₂; —OCF₃; —(X)ₐ—C₁-C₆ cycloalkyl; —(X)ₐ—(CT⁵T⁶)ᵦ-(C₁-C₆ cycloalkyl); —(X)ₐ—(CT⁵T⁶)ᵦ-aryl; —(X)ₐ—(CT⁵T⁶)ᵦCN; —(X)ₐ—(CT⁵T⁶)ᵦOT³; —(X)ₐ(CT⁵T⁶)ᵦST³; —(X)ₐ—(CT⁵T⁶)ᵦS(O)T³; —(X)ₐ—(CT⁵T⁶)ᵦS(O)₂T³; —(X)ₐ—(CT⁵T⁶)ᵦNT³T⁴; —(X)ₐ—(CT⁵T⁶)ᵦC(O)T³; —(X)ₐ—(CT⁵T⁶)ᵦC(O)OT³; —(X)ₐ(CT⁵T⁶)ᵦC(O)NT³T⁴; —(X)ₐ(CT⁵T⁶)ᵦNT³C(O)NT³T⁴; —(X)ₐ(CT⁵T⁶)ᵦNT³C(O)T⁴; —(X)ₐ(CT⁵T⁶)ᵦNT³C(O)OT⁴; —(X)ₐ(CT⁵T⁶)ᵦOC(O)NT³T⁴; —(X)ₐ—(CT⁵T⁶)ᵦS(O)₂NT³T⁴ or —(X)ₐ—(CT⁵T⁶)ᵦNT³S(O)₂T⁴;

R²⁰, R²¹, R²², R²³, R²⁴, R²⁵, R²⁶, R²⁷, R²⁸, R²⁹, R³⁰, R³¹, R³², R³³, R³⁴, R³⁵, R³⁶, R³⁷, R³⁸R⁴², R⁴³, R⁴⁴, R⁴⁵, R⁴⁶, R⁴⁷, R⁴⁸, R⁴⁹, R⁵⁰ and R⁵¹, identical or different, independently represent a hydrogen atom; a halogen atom or a linear or branched C₁-C₆ alkyl; optionally R²⁸, R²⁹ and the carbon atom to which they are bounded form a saturated 3-, 4-, 5- or 6-membered carbocycle;

R¹, X, a, b, i, j, k, m, n, o, p, q, s, t and T³ to T⁶ are independently defined as for the compounds of formulae (I), (A), (B), (C), (D), (A1) to (A10), (B1) to (B16) or (C1) to (C10) or (D1).

Advantageously, the invention provides a compound of formulae (A1a) to (A10a), (A1b) to (A10b), (A1c) to (A10c), (A1d) to (A10d), (A1e) to (A10e), (B1a) to (B16a), (B1b) to (B16b), (B1c) to (B16c), (B1d) to (B16d), (B1e) to (B10e), (C1a) to (C10a), (C1b) to (C10b), (C1c) to (C10c), (C1d) to (C10d), (C1e) to (C10e), (D1a), (D1b), (D1c), (D1d) or (D1e) wherein:

R⁵, R⁶ and the carbon atoms to which they are bonded form a saturated, partially or totally unsaturated or aromatic 6-membered carbo- or heterocycle;

R⁶, R⁷ and the carbon atoms to which they are bonded form a saturated, partially or totally unsaturated or aromatic 6-membered carbo- or heterocycle;

R⁷, R⁸ and the carbon atoms to which they are bonded form a saturated, partially or totally unsaturated or aromatic 6-membered carbo- or heterocycle; or R⁸, R⁹ and the carbon atoms to which they are bonded form a saturated, partially or totally unsaturated or aromatic 6-membered carbo- or heterocycle.

More advantageously, in compounds of formulae (A1a) to (A10a), (A1b) to (A10b), (A1c) to (A10c), (A1d) to (A10d), (A1e) to (A10e), (B1a) to (B16a), (B1b) to (B16b), (B1c) to (B16c), (B1d) to (B16d), (B1e) to (B16e), (C1a) to (C10a), (C1b) to (C10b), (C1c) to (C10c) or (C1d) to (C10d), (C1e) to (C10e), (D1a), (D1b), (D1c), (D1d) or (D1e), R⁵, R⁶, R⁷, R⁸, R⁹, R¹⁰, R¹¹, R¹², R¹³, R¹⁴, R¹⁵, R¹⁶, R¹⁷, R¹⁸, R¹⁹, R⁵⁵, R⁵⁶ and R, identical or different, independently represent a hydrogen atom; a halogen atom; a linear or branched C₁-C₆ alkyl; a linear or branched —O—C₁-C₆ alkyl; a linear or branched C₁-C₆ fluoroalkyl; a linear or branched —O—C₁-C₁₀ alkylaryl; a linear or branched —C₁-C₁₀ alkylaryl; a cyclopropyl; a linear or branched —C₁-C₁₀ alkylcyclopropyl —C(O)NH₂, —C(O)NHCH₃; C(O)N(CH₃)₂; C(O)N (CH₂)₂CH₃; —CH₂NHC(O)CH₃; —NHC(O)CH₃; or —S(O)₂N(CH₃)₂.

As examples of compounds of formula (A1b), the invention provides compounds selected from the group consisting of:

2-(tert-butoxy)-2-[4-(4,4-dimethylcyclohex-1-en-1-yl)-2-methyl-5-(benzenesulfonamide-4-yl)thiophen-3-yl]acetic acid 2-(tert-butoxy)-2-[5-(4-carbamoylphenyl)-4-(4,4-dimethyl-cyclohex-1-en-1-yl)-2-methylthiophen-3-yl]acetic acid;

2-(tert-butoxy)-2-[4-(4,4-dimethylcyclohex-1-en-1-yl)-2-methyl-5-(N-methyl-4-aminocarbonylphenyl)thiophen-3-yl]acetic acid;

2-(tert-butoxy)-2-[4-(4,4-dimethylcyclohex-1-en-1-yl)-2-methyl-5-(aminocarbonylphen-3-yl)thiophen-3-yl]acetic acid 2-(tert-butoxy)-2-[4-(4,4-dimethylcyclohex-1-en-1-yl)-2-methyl-5-(aminocarbonylphen-3-yl)thiophen-3-yl]acetic acid;

2-(tert-butoxy)-2-[4-(4,4-dimethylcyclohex-1-en-1-yl)-2-methyl-5-(methylaminocarbonylphen-3-yl)thiophen-3-yl]acetic acid;

2-(tert-butoxy)-2-[4-(4,4-dimethylcyclohex-1-en-1-yl)-2-methyl-5-[3-(propylcarbamoyl)phenyl]thiophen-3-yl] acetic acid;

2-(tert-butoxy)-2-[4-(4,4-dimethylcyclohex-1-en-1-yl)-2-methyl-5-phenylthiophen-3-yl]acetic acid;

2-(tert-butoxy)-2-[4-(4,4-dimethylcyclohex-1-en-1-yl)-2-methyl-5-[4-(propylcarbamoyl)phenyl]thiophen-3-yl] acetic acid; 2-(tert-butoxy)-2-{2-methyl-4-[4,4-dimethyl-cyclohex-1-en-1-yl]-5-(carboxamidephen-2-yl)thiophen-3-yl}acetic acid;

2-(tert-butoxy)-2-[4-(4,4-dimethylcyclohex-1-en-1-yl)-2-methyl-5-(dimethylcarboamidophen-4-yl)thiophen-3-yl]] acetic acid;

2-(tert-butoxy)-2-[4-(4,4-dimethylcyclohex-1-en-1-yl)-5-[4-(dimethylsulfamoyl)phenyl]-2-methylthiophen-3-yl] acetic acid;

2-(tert-butoxy)-2-[4-(4,4-dimethylcyclohex-1-en-1-yl)-2-methyl-5-(acetamidophen-4-yl)thiophen-3-yl]acetic acid.

As examples of compounds of formula (A1c), the invention provides compounds selected from the group consisting of:

2-(tert-butoxy)-2-[4-(3,4-dihydro-2H-1-benzopyran-6-yl)-2-methyl-5-phenylthiophen-3-yl]acetic acid;
2-(tert-butoxy)-2-[4-(3,4-dihydro-2H-1-benzopyran-6-yl)-5-(4-fluorophenyl)-2-methylthiophen-3-yl]acetic acid;
2-(tert-butoxy)-2-[4-(3,4-dihydro-2H-1-benzopyran-6-yl)-5-(4-methoxyphenyl)-2-methylthiophen-3-yl]acetic acid;
2-(tert-butoxy)-2-[4-(3,4-dihydro-2H-1-benzopyran-6-yl)-5-[4-(acetamidomethyl)phenyl]-2-methylthiophen-3-yl]acetic acid;
2-(tert-butoxy)-2-[5-(4-carbamoylphenyl)-4-(3,4-dihydro-2H-1-benzopyran-6-yl)-2-methylthiophen-3-yl]acetic acid,
2-[4,5-bis(8-fluoro-3,4-dihydro-2H-1-benzopyran-6-yl)-2-methylthiophen-3-yl]-2-(tert-butoxy)acetic acid,
2-(tert-butoxy)-2-[4-(3,4-dihydro-2H-1-benzopyran-6-yl)-5-phenyl-2-(trifluoromethyl)thiophen-3-yl]acetic acid.

As examples of compounds of formula (A1d), the invention provides compound being:

2-(tert-butoxy)-2-[2-methyl-4-(2,3-dihydropyrano[4,3,2-de]quinolin-7-yl)-5-phenyl-thiophen-3-yl]acetic acid.

As an example of compounds of formula (A1e), the invention provides 2-(tert-butoxy)-2-[4-(5,5-dimethyl-5,6-dihydroquinolin-8-yl)-2-methyl-5-phenylthiophen-3-yl]acetic acid.

As examples of compounds of formula (A2b), the invention provides compounds selected from the group consisting of:

2-(tert-butoxy)-2-[4-(4,4-dimethylcyclohex-1-en-1-yl)-2-methyl-5-(pyridin-2-yl)thiophen-3-yl]acetic acid;
2-(tert-butoxy)-2-[4-(4,4-dimethylcyclohex-1-en-1-yl)-2-methyl-5-(5-methylpyridin-2-yl)thiophen-3-yl]acetic acid;
2-(tert-butoxy)-2-[4-(4,4-dimethylcyclohex-1-en-1-yl)-2-methyl-5-(3-methylpyridin-2-yl)thiophen-3-yl]acetic acid;
2-(tert-butoxy)-2-{2-methyl-4-[4,4-dimethylcyclohex-1-en-1-yl]-5-(4-methylpyridin-2-yl)thiophen-3-yl}acetic acid;
2-(tert-butoxy)-2-{2-methyl-4-[4,4-dimethylcyclohex-1-en-1-yl]-5-(6-methylpyridin-2-yl)thiophen-3-yl}acetic acid;
2-(tert-butoxy)-2-{2-methyl-4-[4,4-dimethylcyclohex-1-en-1-yl]-5-(6-(n-propyl)pyridin-2-yl)thiophen-3-yl}acetic acid;
2-(tert-butoxy)-2-{2-methyl-4-[4,4-dimethylcyclohex-1-en-1-yl]-5-(5-(n-propyl)pyridin-2-yl)thiophen-3-yl}acetic acid;
2-(tert-butoxy)-2-{2-methyl-4-[4,4-dimethylcyclohex-1-en-1-yl]-5-(4-(n-propyl)pyridin-2-yl)thiophen-3-yl}acetic acid.

As examples of compounds of formula (A3b), the invention provides a compound selected from the group consisting of:

2-(tert-butoxy)-2-[4-(3,4-dihydro-2H-1-benzopyran-6-yl)-2-methyl-5-{2H,3H,4H-pyrano[2,3-b]pyridin-6-yl}thiophen-3-yl]acetic acid;
2-(tert-butoxy)-2-[4-(4-methoxy-4-methylcyclohex-1-en-1-yl)-2-methyl-5-{2H,3H,4H-pyrano[2,3-b]pyridin-6-yl}thiophen-3-yl]acetic acid.

As examples of compounds of formula (A3c), the invention provides compounds selected from the groups consisting of:

2-(tert-butoxy)[4-(3,4-dihydro-2H-1-benzopyran-6-yl)-2-methyl-5-{2H,3H,4H-pyrano[2,3-b]pyridin-6-yl}thiophen-3-yl]acetic acid;
2-(tert-butoxy)-2-[4-(3,4-dihydro-2H-1-benzopyran-6-yl)-2-methyl-5-(pyridin-3-yl)thiophen-3-yl]acetic acid;
2-(tert-butoxy)-2-[4-(3,4-dihydro-2H-1-benzopyran-6-yl)-5-(6-methoxypyridin-3-yl)-2-methylthiophen-3-yl]acetic acid.

As examples of compounds of formula (A4 b), the invention provides compounds selected from the group consisting of:

2-(tert-butoxy)-2-[4-(4,4-dimethylcyclohex-1-en-1-yl)-2-methyl-5-(pyridin-4-yl)thiophen-3-yl]acetic acid;
2-(tert-butoxy)-2-{2-methyl-4-[4-(propan-2-yl)cyclohex-1-en-1-yl]-5-(pyridin-4-yl)thiophen-3-yl}acetic acid;
2-(tert-butoxy)-2-[2-methyl-4-(4-methylcyclohex-1-en-1-yl)-5-(pyridin-4-yl)thiophen-3-yl]acetic acid;
(2S)-2-(tert-butoxy)-2-[4-(4,4-dimethylcyclohex-1-en-1-yl)-2-methyl-5-(pyridin-4-yl)thiophen-3-yl]acetic acid;
2-(tert-butoxy)-2-[2-methyl-5-(pyridin-4-yl)-4-{spiro[2,5]oct-5-en-6-yl}thiophen-3-yl]acetic acid;
2-(tert-butoxy)-2-[2-methyl-4-(4,4-difluorocyclohex-1-en-1-yl)-5-(pyridin-4-yl)thiophen-3-yl]acetic acid;
[4-(4,4-bis-fluoromethyl-cyclohex-1-enyl)-2-methyl-5-pyridin-4-yl-thiophen-3-yl]-tert-butoxy-acetic acid;
[4-(4-fluoromethyl-4-methylcyclohex-1-enyl)-2-methyl-5-pyridin-4-yl-thiophen-3-yl]-tert-butoxy-acetic acid.

As examples of compounds of formula (A4c), the invention provides compounds selected from the group consisting of:

2-(tert-butoxy)-2-[4-(3,4-dihydro-2H-1-benzopyran-6-yl)-2-methyl-5-(pyridin-4-yl)thiophen-3-yl]acetic acid;
2-(tert-butoxy)-2-[4-(3,4-dihydro-2H-1-benzopyran-6-yl)-5-(2-fluoropyridin-4-yl)-2-methylthiophen-3-yl) acetic acid;
2-(tert-butoxy)-2-[4-(3,4-dihydro-2H-1-benzopyran-6-yl)-2-methyl-5-(2-methylpyridin-4-yl)thiophen-3-yl]acetic acid;
2-(tert-butoxy)-2-[4-(3,4-dihydro-2H-1-benzopyran-6-yl)-2-methyl-5-(quinolin-4-yl)thiophen-3-yl]acetic acid;
2-{5-[2-(benzyloxy)pyridin-4-yl]-4-(3,4-dihydro-2H-1-benzopyran-6-yl)-2-methylthiophen-3-yl}-2-(tert-butoxy) acetic acid;
2-(tert-butoxy)-2-[4-(3,4-dihydro-2H-1-benzopyran-6-yl)-5-(2-methoxypyridin-4-yl)-2-methylthiophen-3-yl]acetic acid;
2-(tert-butoxy)-2-[4-(3,4-dihydro-2H-1-benzopyran-6-yl)-2-(hydroxymethyl)-5-(pyridin-4-yl)thiophen-3-yl]acetic acid;
2-(tert-butoxy)-2-[4-(8-fluoro-5-methyl-3,4-dihydro-2H-1-benzopyran-6-yl)-2-methyl-5-(pyridin-4-yl)thiophen-3-yl]acetic acid;
2-(tert-butoxy)-2-[4-(8-fluoro-3,4-dihydro-2H-1-benzopyran-6-yl)-2-methyl-5-(pyridin-4-yl)thiophen-3-yl]acetic acid.

As an example of compounds of formula (A4d), the invention provides 2-(tert-butoxy)-2-(2-methyl-4-(2,3-dihydropyrano[4,3,2-de]quinolin-7-yl)-5-(pyridin-4-yl)thiophen-3-yl)acetic acid.

As an example of compounds of formula (A8b), the invention provides 2-(tert-butoxy)-2-{2-methyl-4-[4,4-dimethylcyclohex-1-en-1-yl]-5-(pyrimidin-2-yl)thiophen-3-yl}acetic acid.

As an example of compounds of formula (A10b), the invention provides 2-(tert-butoxy)-2-[4-(4,4-dimethylcyclohex-1-en-1-yl)-2-methyl-5-(pyrimidin-5-yl)thiophen-3-yl]acetic acid.

As an example of compounds of formula (A10c), the invention provides 2-(tert-butoxy)-2-[4-(3,4-dihydro-2H-1-benzopyran-6-yl)-2-methyl-5-(pyrimidin-5-yl)thiophen-3-yl]acetic acid.

As an example of compounds of formula (B1c), the invention provides 2-(tert-butoxy)-2-[4-(3,4-dihydro-2H-1-benzopyran-6-yl)-2-methyl-5-(thiophen-2-yl)thiophen-3-yl] acetic acid.

As an example of compounds of formula (B2c), the invention provides 2-(tert-butoxy)-2-[4-(3,4-dihydro-2H-1-benzopyran-6-yl)-2-methyl-5-(thiophen-3-yl)thiophen-3-yl] acetic acid.

As an example of compounds of formula (B4c), the invention provides 2-(tert-butoxy)-2-[4-(3,4-dihydro-2H-1-benzopyran-6-yl)-5-(furan-3-yl)-2-methylthiophen-3-yl] acetic acid.

As an example of compounds of formula (B5c), the invention provides 2-(tert-butoxy)-2-[4-(3,4-dihydro-2H-1-benzopyran-6-yl)-2-methyl-5-[1-methyl-3-(trifluoromethyl)-1H-pyrazol-5-yl]thiophen-3-yl]acetic acid As examples of compounds of formula (B7b), the invention provides compounds selected from the group consisting of:
2-(tert-butoxy)-2-[4-(4,4-dimethylcyclohex-1-en-1-yl)-2-methyl-5-(N-methylpyrazol-4-yl)thiophen-3-yl]acetic acid;
2-(tert-butoxy)-2-{2-methyl-4-[4-(propan-2-yl)cyclohex-1-en-1-yl]-5-(N-methylpyrazol-4-yl)thiophen-3-yl}acetic acid.

As examples of compounds of formula (B7c), the invention provides compounds selected from the group consisting of:
2-(tert-butoxy)-2-[4-(3,4-dihydro-2H-1-benzopyran-6-yl)-2-methyl-5-(1-methyl-1H-pyrazol-4-yl)thiophen-3-yl] acetic acid;
2-[5-(1-benzyl-1H-pyrazol-4-yl)-4-(3,4-dihydro-2H-1-benzopyran-6-yl)-2-methylthiophen-3-yl]-2-(tert-butoxy) acetic acid.

As an example of compounds of formula (B8b), the invention provides 2-(tert-butoxy)-2-[4-(4,4-dimethylcyclohex-1-en-1-yl)-2-methyl-5-(1H-pyrazol-1-yl)thiophen-3-yl] acetic acid.

As an example of compounds of formula (B8c), the invention provides 2-(tert-butoxy)-2-[4-(3,4-dihydro-2H-1-benzopyran-6-yl)-2-methyl-5-(1H-pyrazol-1-yl)thiophen-3-yl]acetic acid.

As an example of compounds of formula (B9c), the invention provides 2-(tert-butoxy)-2-[4-(3,4-dihydro-2H-1-benzopyran-6-yl)-2-methyl-5-(1-methyl-1H-pyrrol-2-yl) thiophen-3-yl]acetic acid.

As an example of compounds of formula (B10b), the invention provides 2-(tert-butoxy)-2-[4-(4,4-dimethylcyclohex-1-en-1-yl)-2-methyl-5-(1,3-thiazol-2-yl)thiophen-3-yl] acetic acid.

As an example of compounds of formula (B11 b), the invention provides 2-(tert-butoxy)-2-{2-methyl-4-[4,4-dimethylcyclohex-1-en-1-yl]-5-(thiazol-4-yl)thiophen-3-yl}acetic acid.

As examples of compounds of formula (B12b), the invention provides compounds selected from the group consisting of:
2-(tert-butoxy)-2-{2-methyl-4-[4,4-dimethylcyclohex-1-en-1-yl]-5-(isothiazol-3-yl)thiophen-3-yl}acetic acid;
2-(tert-butoxy)-2-{2-methyl-4-[4,4-dimethylcyclohex-1-en-1-yl]-5-(5-chloro-4-methyl-isothiazol-3-yl)thiophen-3-yl}acetic acid;
2-(tert-butoxy)-2-{2-methyl-4-[4,4-dimethylcyclohex-1-en-1-yl]-5-(4-methylisothiazol-3-yl)thiophen-3-yl}acetic acid.

As an example of compounds of formula (B12c), the invention provides 2-(tert-butoxy)-2-[4-(3,4-dihydro-2H-1-benzopyran-6-yl)-2-methyl-5-(1,2-thiazol-3-yl)thiophen-3-yl]acetic acid.

As an example of compounds of formula (B13b), the invention provides 2-(tert-butoxy)-2-{2-methyl-4-[4,4-dimethylcyclohex-1-en-1-yl]-5-(isothiazol-5-yl)thiophen-3-yl}acetic acid.

As an example of compounds of formula (B14b), the invention provides 2-(tert-butoxy)-2-[4-(4,4-dimethylcyclohex-1-en-1-yl)-5-(cyclopenten-1-yl)-2-methylthiophen-3-yl]acetic acid.

As an example of compounds of formula (B15b), the invention provides 2-(tert-butoxy)-2-[4-(4,4-dimethylcyclohex-1-en-1-yl)-2-methyl-5-(1-methyl-5-oxo-2,5-dihydro-1H-pyrrol-3-yl)thiophen-3-yl]acetic acid.

As an example of compounds of formula (B16b), the invention provides 2-(tert-butoxy)-2-{2-methyl-4-[4,4-dimethylcyclohex-1-en-1-yl]-5-(N-pyrrolidinone)thiophen-3-yl}acetic acid.

As an example of compounds of formula (D1b), the invention provides 2-(tert-butoxy)-2-{2-methyl-4-[4,4-dimethylcyclohex-1-en-1-yl]-5-(cyclopropyl)thiophen-3-yl}acetic acid.

As examples of compounds of formula (C6b), the invention provides compounds selected from the group consisting of:
2-(tert-butoxy)-2-[4-(4,4-dimethylcyclohex-1-en-1-yl)-2-methyl-5-(N-Methyl-1H-pyridin-2-one-4-yl)thiophen-3-yl]acetic acid;
2-(tert-butoxy)-2-[4-(4,4-dimethylcyclohex-1-en-1-yl)-2-methyl-5-(N-propyl-1H-pyridin-2-one-4-yl)thiophen-3-yl]acetic acid;
2-(tert-butoxy)-2-[4-(4,4-dimethylcyclohex-1-en-1-yl)-2-methyl-5-(N-benzyl-1H-pyridin-2-one-4-yl)thiophen-3-yl]acetic acid;
2-(tert-butoxy)-2-[4-(4,4-dimethylcyclohex-1-en-1-yl)-2-methyl-5-(N-(methylenecyclopropyl)-1H-pyridin-2-one-4-yl)thiophen-3-yl]acetic acid.

As an example of compounds of formula (C6c), the invention provides 2-(tert-butoxy)-2-[4-(3,4-dihydro-2H-1-benzopyran-6-yl)-2-methyl-5-(1-methyl-6-oxo-1,6-dihydropyridin-3-yl)thiophen-3-yl]acetic acid.

As an example of compounds of formula (C9c), the invention provides 2-(tert-butoxy)-2-[4-(3,4-dihydro-2H-1-benzopyran-6-yl)-5-(3,6-dihydro-2H-pyran-4-yl)-2-methylthiophen-3-yl]acetic acid.

As an example of compounds of formula (C10b), the invention provides 2-(tert-butoxy)-2-[4-(4,4-dimethylcyclohex-1-en-1-yl)-5-(cyclohexen-1-yl)-2-methylthiophen-3-yl] acetic acid.

As examples of compounds of formula (I), the invention provides compounds selected from the group consisting of:
2-[5-(3-amino-3-methylbut-1-yn-1-yl)-4-(3,4-dihydro-2H-1-benzopyran-6-yl)-2-methylthiophen-3-yl]-2-(tert-butoxy)acetic acid;
2-(tert-butoxy)-2-{2-methyl-4-[4,4-dimethylcyclohex-1-en-1-yl]-5-(phenylethyl)thiophen-3-yl}acetic acid;
2-(tert-butoxy)-2-[4-(3,4-dihydro-2H-1-benzopyran-6-yl)-5-propyl)-2-methylthiophen-3-yl]acetic acid
2-(tert-butoxy)-2-{2-methyl-4-[4,4-dimethylcyclohex-1-en-1-yl]-5-(2-propenyl)thiophen-3-yl}acetic acid.

EXAMPLES

The following Examples are provided for the purpose of illustrating the present invention and by no means should be interpreted to limit the scope of the present invention. The first part represents the preparation of the compounds (intermediates and final compounds) whereas the second part describes the evaluation of antiviral activity of compounds according to the invention.

Preparation of the Compounds

Abbreviations or symbols used herein include:

DMSO: dimethylsulfoxide
MS: Mass Spectrometry
NMR: Nuclear Magnetic Resonance Spectroscopy
s: singlet
bs: broad singlet
d: doublet
t: triplet
q: quadruplet
dd: doubled doublet
ddd: doubled doubled doublet
dt: doubled triplet
m: massif
TLC: Thin Layer Chromatography Example 1

Synthesis of 2-(tert-butoxy)-2-[4-(3,4-dihydro-2H-1-benzopyran-6-yl)-2-methyl-5-phenylthiophen-3-yl]acetic acid

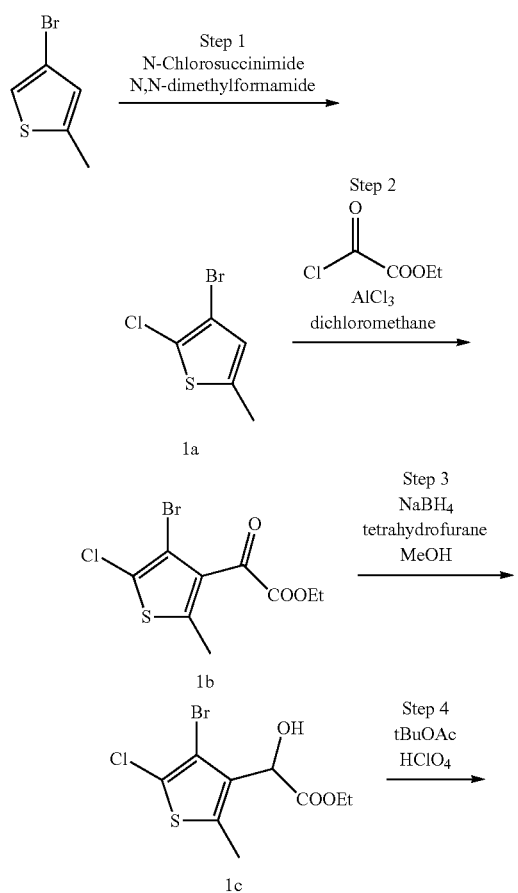

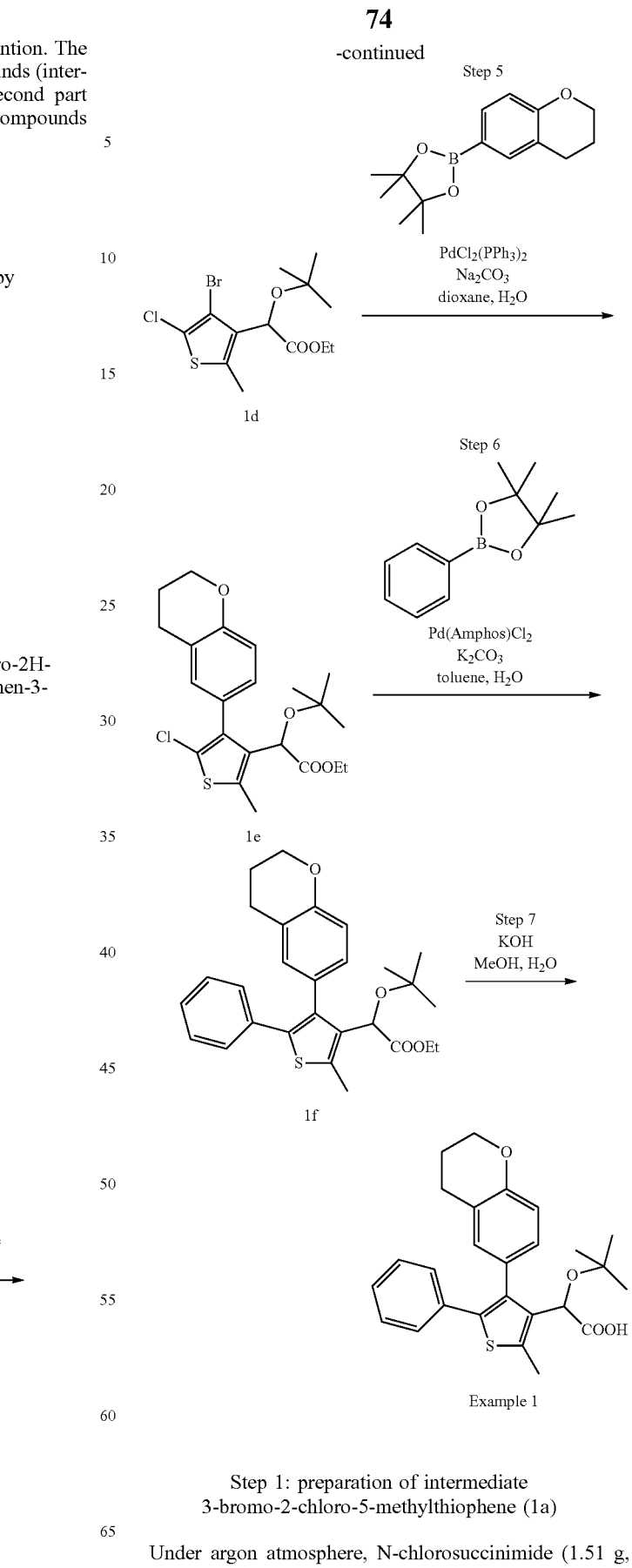

Step 1: preparation of intermediate 3-bromo-2-chloro-5-methylthiophene (1a)

Under argon atmosphere, N-chlorosuccinimide (1.51 g, 11.3 mmol) was added at −5° C. per portion to a solution of 4-bromo-2-methylthiophene (2 g, 11.3 mmol) in N,N-dimethylformamide (6 mL) in an amber round bottom flask. After 1 hour at 0° C., the reaction mixture was warmed to room temperature and stirred for 3 hours more. Water was then added at 0° C. and the mixture was extracted with dichloromethane twice. The organic layer was washed with brine, dried over sodium sulfate, filtered, and evaporated under reduced pressure. The residue was purified by flash chromatography on silica gel (cyclohexane as the eluent) to afford the 3-bromo-2-chloro-5-methylthiophene (1a) as yellow oil (1.71 g, 8.1 mmol, 71%).

$^1$H NMR (400 MHz, CDCl$_3$) δ 2.40 (d, J=1.1 Hz, 3H), 6.58 (d, J=1.1 Hz, 1H).

Step 2: preparation of intermediate ethyl 2-(4-bromo-5-chloro-2-methylthiophen-3-yl)-2-oxoacetate (1b)

Under a nitrogen atmosphere, ethyl chlorooxoacetate (898 µL, 8.04 mmol) and aluminum chloride (III) (2.14 g, 16.07 mmol) were added successively at −10° C. to a solution of 3-bromo-2-chloro-5-methylthiophene (1a) (1.7 g, 8.04 mmol) in dichloromethane (84 mL). After 1 hour at 0° C., the reaction mixture was stirred at room temperature for 8 hours and then slowly hydrolyzed at 0° C. with water. The organic layer was separated, washed with an 1N hydrochloric acid aqueous solution, brine, dried over sodium sulfate, filtered and evaporated under reduced pressure. The residue was purified by flash chromatography on silica gel (cyclohexane/ethyl acetate 90/10) to give ethyl 2-(4-bromo-5-chloro-2-methylthiophen-3-yl)-2-oxoacetate (1b) as an orange solid (1.44 g, 4.6 mmol, 56%).

$^1$H NMR (400 MHz, CDCl$_3$) δ 1.41 (t, J=7.2 Hz, 3H), 2.61 (s, 3H), 4.41 (q, J=7.2 Hz, 2H).

Step 3: preparation of intermediate ethyl 2-(4-bromo-5-chloro-2-methylthiophen-3-yl)-2-hydroxyacetate (1c)

To a solution of ethyl 2-(4-bromo-5-chloro-2-methylthiophen-3-yl)-2-oxoacetate (1b) (340 mg, 1.09 mmol) in a mixture of tetrahydrofuran (7 mL) and ethanol (1.7 mL) was added sodium tetraborohydride (37.2 mg, 0.98 mmol) at 0° C. The mixture was stirred at 0° C. for 2 hours. The mixture was quenched with a 1N hydrochloric acid aqueous solution and extracted with ethyl acetate twice. The organic extract was washed with brine twice, dried over sodium sulfate, filtered and concentrated to afford the crude ethyl 2-(4-bromo-5-chloro-2-methylthiophen-3-yl)-2-hydroxyacetate (1c) as a colorless oil (335 mg, 1.07 mmol, 98%).

$^1$H NMR (400 MHz, CDCl$_3$) δ 1.27 (t, J=7.1 Hz, 3H), 2.42 (s, 3H), 4.23-4.32 (m, 2H), 5.27 (s, 1H).

Step 4: preparation of intermediate ethyl 2-(4-bromo-5-chloro-2-methylthiophen-3-yl)-2-(tert-butoxy)acetate (1d)

To a suspension of ethyl 2-(4-bromo-5-chloro-2-methyl-thiophen-3-yl)-2-hydroxyacetate (1c) (334 mg, 1.065 mmol) in tert-butylacetate (10.9 mL) at −5° C. was added perchloric acid (70%, 0.4 mL). The reaction mixture was stirred at −5° C. for 1 hour then at 0° C. for 30 minutes more and at room temperature for 1 hour more. The reaction mixture was basified with a saturated aqueous solution of sodium bicarbonate until pH 8. The aqueous layer was extracted with ethyl acetate. The organic layer was washed with brine, dried over sodium sulfate, filtered and concentrated in vacuo. The residue was purified by flash chromatography on silica gel (cyclohexane/ethyl acetate 95/5) to afford ethyl 2-(4-bromo-5-chloro-2-methylthiophen-3-yl)-2-(tert-butoxy)acetate (1d) as a colorless oil (324 mg, 0.88 mmol, 82%).

$^1$H NMR (400 MHz, CDCl$_3$) δ 1.20-1.23 (m, 12H), 2.51 (s, 3H), 4.08-4.21 (m, 2H), 5.22 (s, 1H).

Step 5: preparation of intermediate ethyl 2-(tert-butoxy)-2-[5-chloro-4-(3,4-dihydro-2H-1-benzopyran-6-yl)-2-methylthiophen-3-yl]acetate (1e)

Under argon atmosphere, ethyl 2-(4-bromo-5-chloro-2-methylthiophen-3-yl)-2-(tert-butoxy)acetate (1d) (500 mg, 1.35 mmol), 6-(4,4,5,5-tetramethyl-1,3,2-dioxaborolan-2-yl)chroman (351.8 mg, 1.5 mmol), sodium carbonate (429 mg, 4.05 mmol) were dissolved in dioxane (28 mL) and water (4 mL). The solution was degassed under argon for 10 minutes and bis(triphenylphosphine)palladium (II) dichloride (142 mg, 0.20 mmol) was added. The reaction was heated and shaken at 85° C., for 8 hours. After cooling at room temperature, the mixture was filtered through Celite®, rinsed with methanol. The filtrate was concentrated in vacuo and partitioned between ethyl acetate and water. The organic layer was washed with brine, dried over sodium sulfate, filtered and concentrated under reduced pressure. The crude material was purified by flash chromatography on silica gel (cyclohexane/ethyl acetate 97/3) to give ethyl 2-(tert-butoxy)-2-[5-chloro-4-(3,4-dihydro-2H-1-benzopyran-6-yl)-2-methylthiophen-3-yl]acetate (1e) (308 mg, 0.73 mmol, 54%).

$^1$H NMR (400 MHz, CDCl$_3$) δ 1.00 (s, 9H), 1.24 (t, J=7.1 Hz, 3H), 2.03-2.08 (m, 2H), 2.50 (s, 3H), 2.79-2.84 (m, 2H), 4.09-4.18 (m, 2H), 4.24 (t, J=5.2 Hz, 2H), 4.80 (s, 1H), 6.84 (d, J=8.3 Hz, 1H), 7.04-7.06 (m, 2H).

Step 6: preparation of intermediate ethyl 2-(tert-butoxy)-2-[4-(3,4-dihydro-2H-1-benzopyran-6-yl)-2-methyl-5-phenylthiophen-3-yl]acetate (1f)

Under argon atmosphere, ethyl 2-(tert-butoxy)-2-[5-chloro-4-(3,4-dihydro-2H-1-benzopyran-6-yl)-2-methylthiophen-3-yl]acetate (1e) (140 mg, 0.331 mmol), phenylboronic acid pinacol ester (81 mg, 0.40 mmol), potassium carbonate (91.5 mg, 0.66 mmol) were dissolved in toluene (1.65 mL) and water (0.16 mL). The solution was degassed under argon for 10 minutes and bis(di-tert-butyl(4-dimethylaminophenyl)phosphine)dichloropalladium(11) (35.2 mg, 0.05 mmol) was added. The reaction was heated and shaken at 90° C. for 18 hours. After cooling at room temperature, water was added and the mixture was extracted twice with ethyl acetate. The organic layer was washed with brine, dried over sodium sulfate, filtered, and concentrated under reduced pressure. The crude material was purified by preparative TLC (petroleum ether/ethyl acetate 90/10) to give ethyl 2-(tert-butoxy)-2-[4-(3,4-dihydro-2H-1-benzopyran-6-yl)-2-methyl-5-phenylthiophen-3-yl]acetate (19 (115 mg, 0.25 mmol, 75%).

$^1$H NMR (400 MHz, CDCl$_3$) δ 1.01 (s, 9H), 1.24-1.28 (m, 3H), 2.00-2.04 (m, 2H), 2.59 (s, 3H), 2.72-2.81 (m, 2H), 4.10-4.23 (m, 4H), 4.86 (s, 1H), 6.73-6.75 (m, 1H), 6.80-7.18 (m, 7H).

Step 7: preparation of 2-(tert-butoxy)-2-[4-(3,4-dihydro-2H-1-benzopyran-6-yl)-2-methyl-5-phenyl-thiophen-3-yl]acetic acid (example 1)

Potassium hydroxide (28.5 mg, 0.51 mmol) was added to a solution of ethyl 2-(tert-butoxy)-2-[4-(3,4-dihydro-2H-1- benzopyran-6-yl)-2-methyl-5-phenylthiophen-3-yl]acetate (19 (115 mg, 0.25 mmol) in a mixture of methanol (3.3 mL) and water (4 mL). The mixture was sonicated for 20 minutes and heated at 90° C. for 16 hours. The mixture was concentrated in vacuo to evaporate methanol. The aqueous layer was acidified with a 1N hydrochloric acid aqueous solution and extracted with ethyl acetate twice. The organic layer was washed with brine, dried over sodium sulfate, filtered and concentrated in vacuo. The residue was purified by preparative TLC, using dichloromethane/methanol (95/5) to give 2-(tert-butoxy)-2-[4-(3,4-dihydro-2H-1-benzopyran-6-yl)-2-methyl-5-phenylthiophen-3-yl]acetic acid (example 1) (54 mg, 0.12 mmol, 46%).

$^1$H NMR (400 MHz, CDCl$_3$) δ 1.03 (s, 9H), 1.97-2.04 (m, 2H), 2.50 (s, 3H), 2.69-2.77 (m, 2H), 4.19-4.22 (m, 2H), 5.01 (s, 1H), 6.68-6.77 (m, 2H), 7.12-7.20 (m, 6H).

MS m/z ([M−H]$^-$) 435.

Example 2

Synthesis of 2-(tert-butoxy)-2-[4-(3,4-dihydro-2H-1-benzopyran-6-yl)-5-(4-fluorophenyl)-2-methylthiophen-3-yl]acetic acid

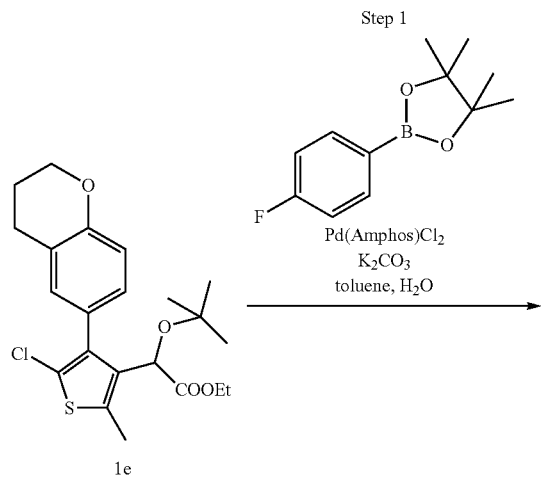

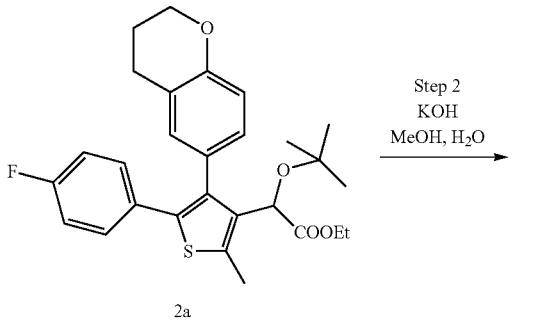

Step 1: preparation of intermediate ethyl 2-(tert-butoxy)-2-[4-(3,4-dihydro-2H-1-benzopyran-6-yl)-5-(4-fluorophenyl)-2-methylthiophen-3-yl]acetate (2a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (70 mg, 0.165 mmol), is converted by reaction with (4-fluorophenyl)boronic acid (27.7 mg, 0.20 mmol) into ethyl 2-(tert-butoxy)-2-[4-(3,4-dihydro-2H-1-benzopyran-6-yl)-5-(4-fluorophenyl)-2-methylthiophen-3-yl]acetate (2a) (72 mg, 0.15 mmol, 90%) after purification by preparative TLC (petroleum ether/ethyl acetate 90/10).

$^1$H NMR (400 MHz, CDCl$_3$) δ 1.01 (s, 9H), 1.24-1.28 (m, 3H), 2.0-2.04 (m, 2H), 2.59 (s, 3H), 2.68-2.76 (m, 2H), 4.08-4.23 (m, 4H), 4.85 (s, 1H), 6.73-6.75 (m, 1H), 6.73-7.12 (m, 6H).

MS m/z ([M+H]$^+$) 483.

Step 2: preparation of 2-(tert-butoxy)-2-[4-(3,4-dihydro-2H-1-benzopyran-6-yl)-5-(4-fluorophenyl)-2-methylthiophen-3-yl]acetic acid (example 2)

Potassium hydroxide (17 mg, 0.30 mmol) was added to a solution of ethyl 2-(tert-butoxy)-2-[4-(3,4-dihydro-2H-1-benzopyran-6-yl)-5-(4-fluorophenyl)-2-methylthiophen-3-yl]acetate (2a) (72 mg, 0.15 mmol) in a mixture of methanol (2 mL) and water (2.4 mL). The mixture was heated at 110° C. for 17 hours. After 15 hours, the reaction was not finished and an excess of potassium hydroxide was then added. The mixture was heated at 110° C. for 17 hours more. The mixture was concentrated to evaporate methanol in vacuo. The aqueous layer was acidified with a 1N hydrochloric acid aqueous solution and extracted with ethyl acetate twice. The organic layer was washed with brine, dried over sodium sulfate, filtered and concentrated in vacuo. The residue was purified by preparative TLC (dichloromethane/methanol 95/5) to give the desired acid 2-(tert-butoxy)-2-[4-(3,4-dihydro-2H-1-benzopyran-6-yl)-5-(4-fluoro phenyl)-2-methyl thiophen-3-yl]acetic acid (example 2) (40 mg, 0.09 mmol, 59%).

$^1$H NMR (400 MHz, CDCl$_3$) δ 1.03 (s, 9H), 1.99-2.04 (m, 2H), 2.49 (s, 3H), 2.69-2.77 (m, 2H), 4.20-4.22 (m, 2H), 5.00 (s, 1H), 6.63-6.81 (m, 2H), 6.83-6.91 (m, 3H), 7.10 (dd, J=5.5 Hz, J=8.4 Hz, 2H).

MS m/z ([M−H]$^-$) 453.

Example 3

Synthesis of 2-(tert-butoxy)-2-[4-(3,4-dihydro-2H-1-benzopyran-6-yl)-2-methyl-5-(pyridin-4-yl)thiophen-3-yl]acetic acid

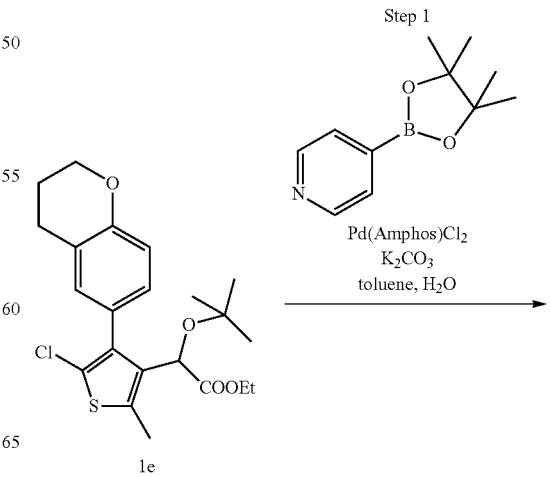

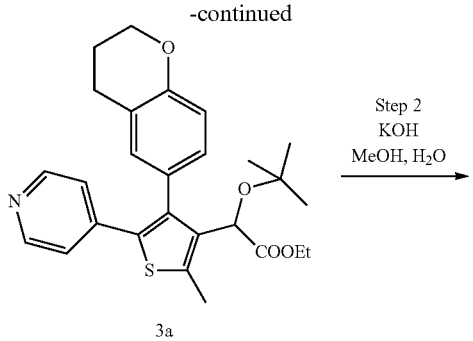

$^{1}$H NMR (400 MHz, DMSO-d$_{6}$) δ 0.90 (s, 9H), 1.90-1.95 (m, 2H), 2.54 (s, 3H), 2.65-2.70 (m, 2H), 4.16-4.19 (m, 2H), 4.67-4.70 (m, 1H), 6.70-6.98 (m, 3H), 6.99 (d, J=6.1 Hz, 2H), 8.36 (d, J=6.1 Hz, 2H).

MS m/z ([M−H]$^{−}$) 436.

Example 4

Synthesis of (tert-butoxy)[4-(3,4-dihydro-2H-1-benzopyran-6-yl)-2-methyl-5-{2H,3H,4H-pyrano[2,3-b]pyridin-6-yl}thiophen-3-yl]acetic acid

Step 1: preparation of intermediate ethyl 2-(tert-butoxy)-2-[4-(3,4-dihydro-2H-1-benzopyran-6-yl)-2-methyl-5-(pyridin-4-yl)thiophen-3-yl]acetate (3a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (150 mg, 0.35 mmol) is converted by reaction with 4-pyridine boronic acid pinacol ester (87.3 mg, 0.43 mmol) into ethyl 2-(tert-butoxy)-2-[4-(3,4-dihydro-2H-1-benzopyran-6-yl)-2-methyl-5-(pyridin-4-yl)thiophen-3-yl]acetate (3a) (129 mg, 0.28 mmol, 79%) after purification by preparative TLC (cyclohexane/ethyl acetate 70/30).

$^{1}$H NMR (400 MHz, CDCl$_{3}$) δ 1.02 (s, 9H), 1.24-1.27 (m, 3H), 2.05-2.10 (m, 2H), 2.65-2.85 (m, 5H), 4.12-4.31 (m, 4H), 4.83 (s, 1H), 6.72-7.22 (m, 3H), 7.30-7.31 (m, 2H), 8.31-8.33 (m, 2H).

MS m/z ([M+H]$^{+}$) 466.

Step 2: preparation of 2-(tert-butoxy)-2-[4-(3,4-dihydro-2H-1-benzopyran-6-yl)-2-methyl-5-(pyridin-4-yl)thiophen-3-yl]acetic acid (example 3)

Potassium hydroxide (15.5 mg, 0.28 mmol) was added to a solution of ethyl 2-(tert-butoxy)-2-[4-(3,4-dihydro-2H-1-benzopyran-6-yl)-2-methyl-5-(pyridin-4-yl)thiophen-3-yl]acetate (3a) (129 mg, 0.28 mmol) in a mixture of methanol (3.7 mL) and water (4.4 mL). The mixture was sonicated for 10 minutes and heated at 90° C. for 7 hours. The mixture was concentrated to evaporate methanol in vacuo. The aqueous layer was acidified to pH 4-5 with a 1N hydrochloric acid aqueous solution and extracted three times with ethyl acetate. The organic layer was washed with brine, dried over sodium sulfate, filtered and concentrated in vacuo. The residue was purified by preparative TLC (dichloromethane/methanol 90/10) to give 2-(tert-butoxy)-2-[4-(3,4-dihydro-2H-1-benzopyran-6-yl)-2-methyl-5-(pyridin-4-yl)thiophen-3-yl]acetic acid (example 3) (39 mg, 0.09 mmol, 32%).

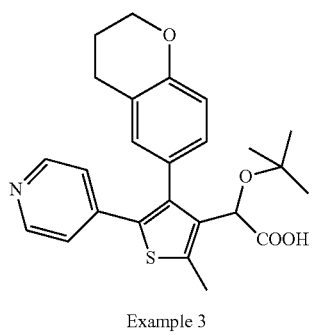

Step 1: preparation of intermediate ethyl (tert-butoxy)[4-(3,4-dihydro-2H-1-benzopyran-6-yl)-2-methyl-5-{2H,3H,4H-pyrano[2,3-b]pyridin-6-yl}thiophen-3-yl]acetate (4a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (100 mg, 0.24 mmol) is converted by reaction with 6-(tetramethyl-1,3,2-dioxaborolan-2-yl)-2H,3H,4H-pyrano[2,3-b]pyridine (65 mg, 0.25 mmol) into ethyl (tert-butoxy)[4-(3,4-dihydro-2H-1-benzopyran-6-yl)-2-methyl-5-{2H,3H,4H-pyrano[2,3-b]pyridin-6-yl}thiophen-3-yl]acetate (4a) (35 mg, 0.067 mmol, 28%) after purification by preparative TLC (dichloromethane/ethyl acetate 90/10).

$^1$H NMR (400 MHz, CDCl$_3$) δ 1.02 (s, 9H), 1.23-1.28 (t, J=7.1 Hz, 3H), 1.94-2.04 (m, 4H), 2.59 (s, 3H), 2.64-2.69 (m, 2H), 2.71-2.77 (m, 2H), 4.09-4.19 (m, 2H), 4.21 (t, J=5.4 Hz, 2H), 4.32 (t, J=5.4 Hz, 2H), 4.83 (s, 1H), 6.73 (d, J=7.1 Hz, 1H), 6.80-7.06 (m, 2H), 7.18 (d, J=2.3 Hz, 1H), 7.83 (d, J=2.3 Hz, 1H).

MS m/z ([M+H]$^+$) 522.

Step 2: preparation of (tert-butoxy)[4-(3,4-dihydro-2H-1-benzopyran-6-yl)-2-methyl-5-{2H,3H,4H-pyrano[2,3-b]pyridin-6-yl}thiophen-3-yl]acetic acid (example 4)

Using the procedure described in example 3, step 2, ethyl (tert-butoxy)[4-(3,4-dihydro-2H-1-benzopyran-6-yl)-2-methyl-5-{2H,3H,4H-pyrano[2,3-b]pyridin-6-yl}thiophen-3-yl]acetate (4a) (35 mg, 0.067 mmol) is converted into (tert-butoxy)[4-(3,4-dihydro-2H-1-benzopyran-6-yl)-2-methyl-5-{2H,3H,4H-pyrano[2,3-b]pyridin-6-yl}thiophen-3-yl]acetic acid (example 4) (20 mg, 0.04 mmol, 60%) after purification by preparative TLC (dichloromethane/methanol 95/5).

$^1$H NMR (400 MHz, CDCl$_3$) δ 1.03 (s, 9H), 1.91-2.01 (m, 4H), 2.50 (s, 3H), 2.58-2.83 (m, 4H), 4.19 (t, J=5.1 Hz, 2H), 4.29 (t, J=5.1 Hz, 2H), 4.97 (s, 1H), 6.61-7.07 (m, 3H), 7.10 (d, J=2.2 Hz, 1H), 7.85 (d, J=2.2 Hz, 1H).

MS m/z ([M−H]$^−$) 492.

Example 5

Synthesis of 2-(tert-butoxy)-2-[4-(4,4-dimethylcyclohex-1-en-1-yl)-2-methyl-5-(pyridin-4-yl)thiophen-3-yl]acetic acid

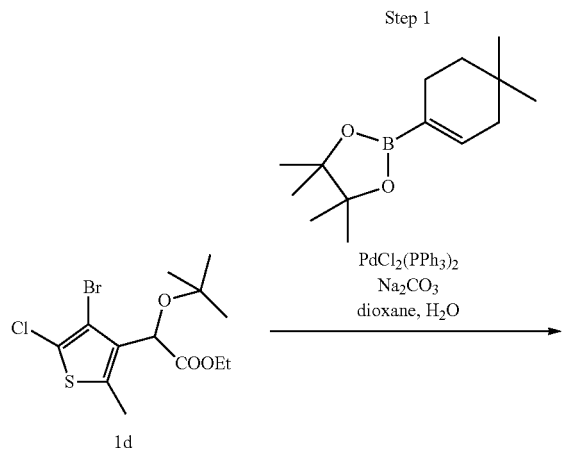

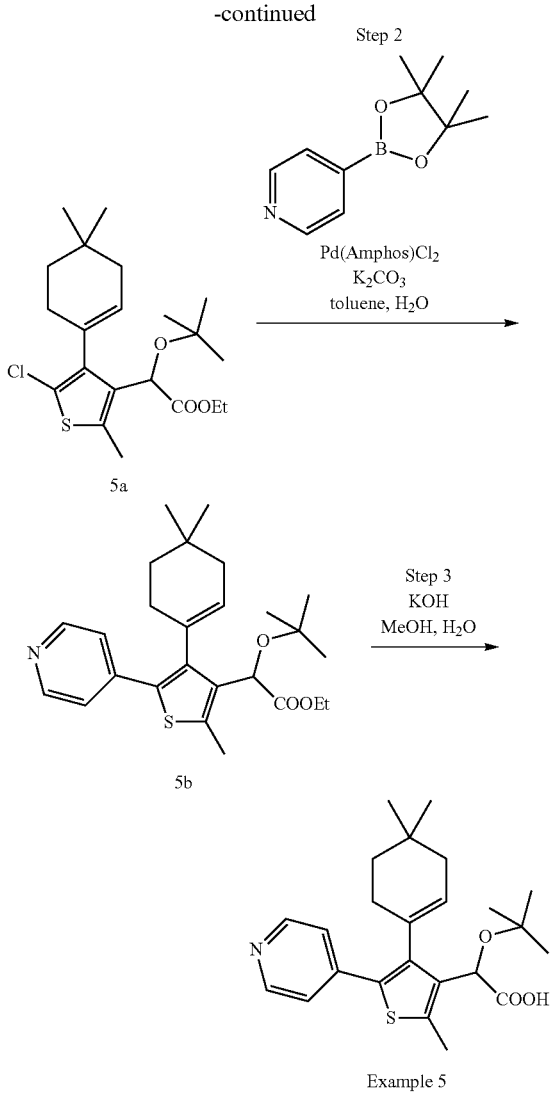

Step 1: preparation of intermediate ethyl 2-(tert-butoxy)-2-[5-chloro-4-(4,4-dimethylcyclohex-1-en-1-yl)-2-methylthiophen-3-yl]acetate (5a)

Using the procedure described in example 1, step 5, ethyl 2-(4-bromo-5-chloro-2-methylthiophen-3-yl)-2-(tert-butoxy)acetate (1d) (500 mg, 1.35 mmol) is converted by reaction with 4,4-(dimethylcyclohexene-1-yl)boronic acid pinacol ester (319.5 mg, 1.35 mmol) into ethyl 2-(tert-butoxy)-2-[5-chloro-4-(4,4-dimethylcyclohex-1-en-1-yl)-2-methylthiophen-3-yl]acetate (5a) (268 mg, 0.67 mmol, 37%) after purification by flash chromatography on silica gel (cyclohexane/ethyl acetate 97/3).

$^1$H NMR (400 MHz, CDCl$_3$) δ 1.02 (s, 3H), 1.03 (s, 3H), 1.17 (s, 9H), 1.21 (t, J=7.1 Hz, 3H), 1.47-1.51 (m, 2H), 1.91-2.03 (m, 2H), 2.07-2.15 (m, 1H), 2.31-2.39 (m, 1H), 2.48 (s, 3H), 4.06-4.18 (m, 2H), 4.97 (s, 1H), 5.53-5.60 (bs, 1H).

Step 2: preparation of intermediate ethyl 2-(tert-butoxy)-2-[4-(4,4-dimethylcyclohex-1-en-1-yl)-2-methyl-5-(pyridin-4-yl)thiophen-3-yl]acetate (5b)

Using the procedure described in example 1, step 6, ethyl 2-(tert-butoxy)-2-[5-chloro-4-(4,4-dimethylcyclohex-1-en- 1-yl)-2-methylthiophen-3-yl]acetate (5a) (100 mg, 0.251 mmol) is converted by reaction with 4-pyridine boronic acid pinacol ester (128.5 mg, 0.63 mmol) into ethyl 2-(tert-butoxy)-2-[4-(4,4-dimethylcyclohex-1-en-1-yl)-2-methyl-5-(pyridin-4-yl)thiophen-3-yl]acetate (5b) (75 mg, 0.17 mmol, 91%) after purification by preparative TLC (cyclohexane/ethyl acetate 70/30).

$^1$H NMR (400 MHz, CDCl$_3$) δ 1.02 (s, 3H), 1.04 (s, 3H), 1.20 (s, 9H), 1.22 (t, J=7.1 Hz, 3H), 1.37-1.44 (m, 2H), 1.88-2.10 (m, 4H), 2.62 (s, 3H), 4.13-4.20 (m, 2H), 5.11 (s, 1H), 5.70-5.74 (m, 1H), 7.46 (dd, J=1.6 Hz, J=4.7 Hz, 2H), 8.50 (dd, J=1.5 Hz, J=4.7 Hz, 2H).

MS m/z ([M+H]$^+$) 442.

Step 3: preparation of intermediate 2-(tert-butoxy)-2-[4-(4,4-dimethylcyclohex-1-en-1-yl)-2-methyl-5-(pyridin-4-yl)thiophen-3-yl]acetic acid (example 5)

Using the procedure described in Example 3, step 2, ethyl 2-(tert-butoxy)-2-[4-(4,4-dimethylcyclohex-1-en-1-yl)-2-methyl-5-(pyridin-4-yl)thiophen-3-yl]acetate (5b) (75 mg, 0.17 mmol) is converted into 2-(tert-butoxy)-2-[4-(4,4-dimethylcyclohex-1-en-1-yl)-2-methyl-5-(pyridin-4-yl)thiophen-3-yl]acetic acid (example 5) (39 mg, 0.09 mmol, 55%) after purification by preparative TLC (dichloromethane/methanol 90/10).

$^1$H NMR (400 MHz, CDCl$_3$) δ 0.98 (s, 3H), 1.00 (s, 3H), 1.24 (s, 9H), 1.35-1.43 (m, 2H), 1.86-2.05 (m, 4H), 2.53 (s, 3H), 5.16-5.20 (bs, 1H), 5.64-5.73 (bs, 1H), 7.40-7.48 (bs, 2H), 8.50-8.58 (bs, 2H).

MS m/z ([M−H]$^-$) 412.

Example 6

Synthesis of 2-(tert-butoxy)-2-{2-methyl-4-[4-(propan-2-yl)cyclohex-1-en-1-yl]-5-(pyridin-4-yl)thiophen-3-yl}acetic acid

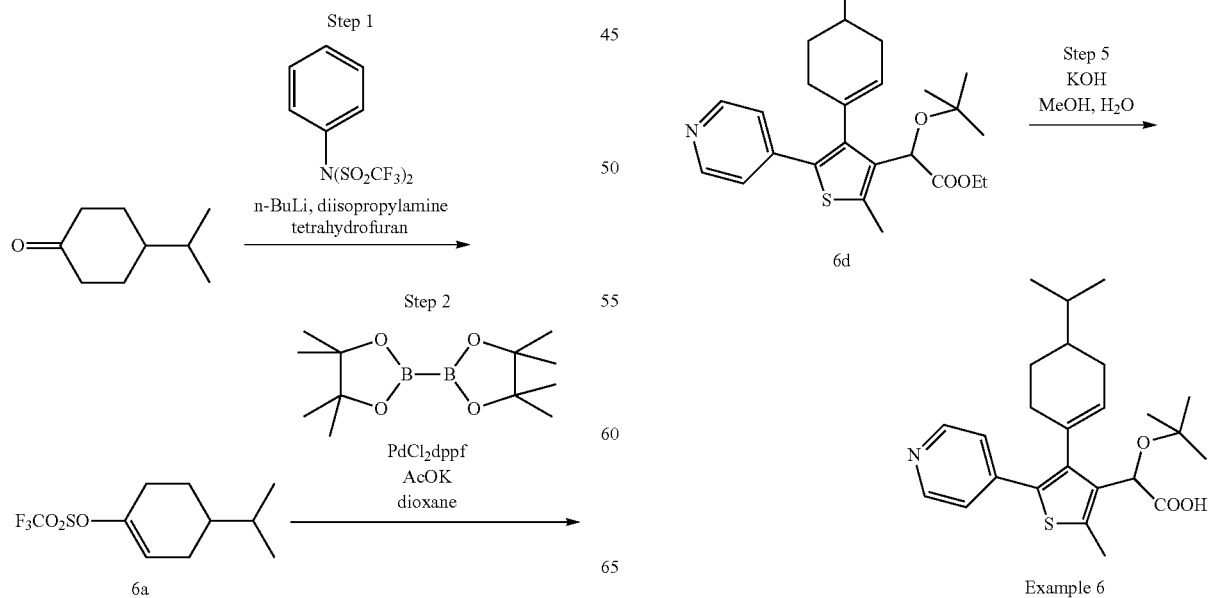

Step 1: preparation of intermediate 4-(propan-2-yl)cyclohex-1-en-1-yl trifluoromethanesulfonate (6a)

n-Butyllithium (1.6 M in hexane, 4.9 mL, 7.84 mmol) was added to a solution of diisopropylamine (1.1 mL, 7.84 mmol) in tetrahydrofuran (16.5 mL) at −78° C. The solution was stirred at −78° C. for 20 minutes and then at 0° C. for 15 minutes. Then the mixture was cooled at −78° C. and a solution of 4-(propan-2-yl)cyclohexan-1-one (1 g, 7.13 mmol) in tetrahydrofuran (10.5 mL) was added. After stirring at −78° C. for 1 hour, a solution of N-phenyltrifluoromethanesulfonimide (2.72 g, 7.63 mmol) in tetrahydrofuran (10.5 mL) was added. The reaction mixture was stirred at −78° C. for 2 hours, then warmed at room temperature for 12 hours more and concentrated under reduced pressure. Then it was partitioned between diethyl ether and an aqueous saturated solution of sodium bicarbonate. The organic layer was washed with water then brine, dried over sodium sulfate, filtered and concentrated under reduced pressure. The crude material was purified by flash chromatography on silica gel (cyclohexane) to provide (6a) (1.346 g, 4.94 mmol, 70%).

$^1$H NMR (400 MHz, CDCl$_3$) δ 0.90-0.92 (m, 6H), 1.33-1.58 (m, 3H), 1.87-1.96 (m, 2H), 2.17-2.43 (m, 3H), 5.73-5.74 (m, 1H).

Step 2: preparation of intermediate 4,4,5,5-tetramethyl-2-[4-(propan-2-yl)cyclohex-1-en-1-yl]-1,3,2-dioxaborolane (6b)

Under argon atmosphere, 4-(propan-2-yl)cyclohex-1-en-1-yl trifluoromethane sulfonate (6a) (1.2 g, 4.41 mmol), bis(pinacolto)diboron (1.7 g, 6.61 mmol) and potassium acetate (1.3 g, 13.23 mmol) were dissolved in dioxane (30 mL). The solution was degassed under argon for 10 minutes and [1,1'-bis(diphenylphosphino)ferrocene]dichloro palladium(II) (360 mg, 0.44 mmol) was added. The reaction mixture was heated and shaken at 85° C. for 18 hours then cooled to room temperature, diluted with ethyl acetate, filtered through Celite®, and rinsed with ethyl acetate. The filtrate was concentrated in vacuo and partitioned between ethyl acetate. Then the combined organic layers were washed with saturated sodium bicarbonate solution and saturated brine, dried over sodium sulfate and concentrated in vacuo. The residue was purified was purified by flash chromatography on silica gel (cyclohexane) to afford 4,4,5,5-tetramethyl-2-[4-(propan-2-yl)cyclohex-1-en-1-yl]-1,3,2-dioxaborolane (6b) (619 mg, 2.47 mmol, 56%).

$^1$H NMR (400 MHz, CDCl$_3$) δ 0.86-0.89 (m, 6H), 1.22-1.26 (m, 12H), 1.42-1.48 (m, 2H), 1.73-2.27 (m, 6H), 6.57 (bs, 1H).

Step 3: preparation of intermediate ethyl 2-(tert-butoxy)-2-{5-chloro-2-methyl-4-[4-(propan-2-yl)cyclohex-1-en-1-yl]thiophen-3-yl}acetate (6c)

Using the procedure described in example 1, step 5, ethyl 2-(4-bromo-5-chloro-2-methylthiophen-3-yl)-2-(tert-butoxy)acetate (1d) (150 mg, 0.41 mmol) is converted by reaction with 4,4,5,5-tetramethyl-2-[4-(propan-2-yl)cyclohex-1-en-1-yl]-1,3,2-dioxaborolane (6b) (101.5 mg, 0.41 mmol) into ethyl 2-(tert-butoxy)-2-{5-chloro-2-methyl-4-[4-(propan-2-yl)cyclohex-1-en-1-yl]thiophen-3-yl}acetate (6c) (51 mg, 0.12 mmol, 30%, atropisomers mixture) after purification by 2 preparative TLC (cyclohexane/ethyl acetate 9/1).

$^1$H NMR (400 MHz, CDCl$_3$) δ 0.94-0.96 (m, 6H), 1.17-1.25 (m, 14H), 1.86-2.39 (m, 6H), 2.46 (s, 3H), 4.08-4.16 (m, 2H), 4.97 and 4.98 (s, 1H), 5.65-5.67 (m, 1H).

Step 4: preparation of intermediate ethyl 2-(tert-butoxy)-2-{2-methyl-4-[4-(propan-2-yl)cyclohex-1-en-1-yl]-5-(pyridin-4-yl)thiophen-3-yl}acetate (6d)

Using the procedure described in example 1, step 6, ethyl 2-(tert-butoxy)-2-{5-chloro-2-methyl-4-[4-(propan-2-yl)cyclohex-1-en-1-yl]thiophen-3-yl}acetate (6c) (77 mg, 0.186 mmol) is converted by reaction with 4-pyridine boronic acid pinacol ester (76.5 mg, 0.37 mmol) into ethyl 2-(tert-butoxy)-2-{2-methyl-4-[4-(propan-2-yl)cyclohex-1-en-1-yl]-5-(pyridin-4-yl)thiophen-3-yl}acetate (6d) (67 mg, 0.15 mmol, 79%, atropisomers mixture) after purification by 2 preparative TLC (cyclohexane/ethyl acetate 70/30).

$^1$H NMR (400 MHz, CDCl$_3$) δ 0.94-0.96 (m, 6H), 1.20-1.26 (m, 14H), 1.53-1.61 (m, 1H), 1.80-2.31 (m, 5H), 2.60 (s, 3H), 4.09-4.20 (m, 2H), 5.11 (s, 1H), 5.77-5.86 (bs, 1H), 7.46-7.48 (m, 2H), 8.50-8.52 (m, 2H).

MS m/z ([M+H]$^+$) 456

Step 5: preparation of 2-(tert-butoxy)-2-{2-methyl-4-[4-(propan-2-yl)cyclohex-1-en-1-yl]-5-(pyridin-4-yl)thiophen-3-yl}acetic acid (example 6)

Using the procedure described in example 3, step 2, ethyl 2-(tert-butoxy)-2-{2-methyl-4-[4-(propan-2-yl)cyclohex-1-en-1-yl]-5-(pyridin-4-yl)thiophen-3-yl}acetate (6d) (65 mg, 0.14 mmol) is converted into 2-(tert-butoxy)-2-{2-methyl-4-[4-(propan-2-yl)cyclohex-1-en-1-yl]-5-(pyridin-4-yl)thiophen-3-yl}acetic acid (example 6) (41 mg, 0.10 mmol, 67% yield, atropisomers mixture) after purification by preparative TLC (dichloromethane/methanol 95/5).

$^1$H NMR (400 MHz, CDCl$_3$) δ 0.92-0.94 (m, 6H), 1.24-1.31 (m, 9H), 1.49-2.29 (m, 8H), 2.52 (s, 3H), 5.19-5.34 (m, 1H), 5.82 (bs, 1H), 7.40-7.46 (m, 2H), 8.48-8.56 (m, 2H).

MS m/z ([M−H]$^−$) 426

Example 7

Synthesis of 2-(tert-butoxy)-2-[4-(3,4-dihydro-2H-1-benzopyran-6-yl)-2-methyl-5-{2H,3H,4H-pyrano[2,3-b]pyridin-6-yl}thiophen-3-yl]acetic acid

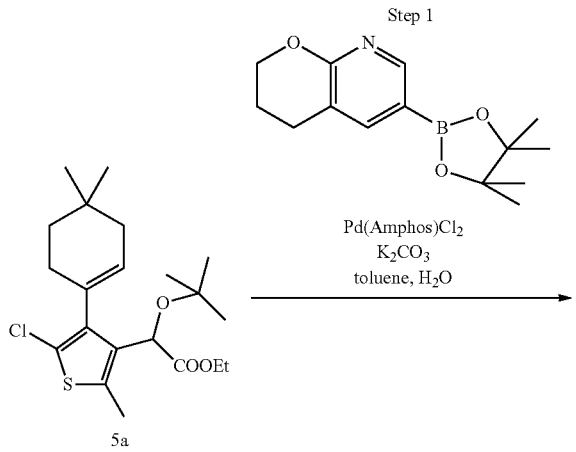

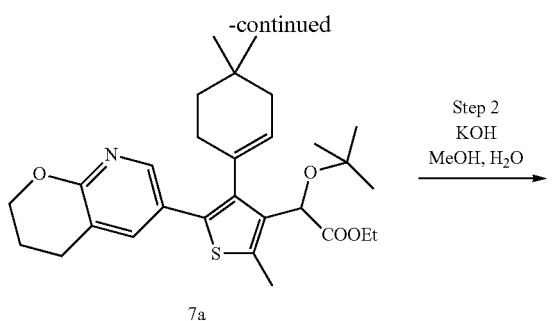

1H), 5.64-5.87 (bs, 1H), 7.48 (d, J=2.3 Hz, 1H), 8.17 (d, J=2.3 Hz, 1H), 9.72 (bs, 1H).
MS m/z ([M−H]⁻) 468.

Example 8

Synthesis of 2-(tert-butoxy)-2-[4-(3,4-dihydro-2H-1-benzopyran-6-yl)-2-methyl-5-(pyridin-3-yl)thiophen-3-yl]acetic acid

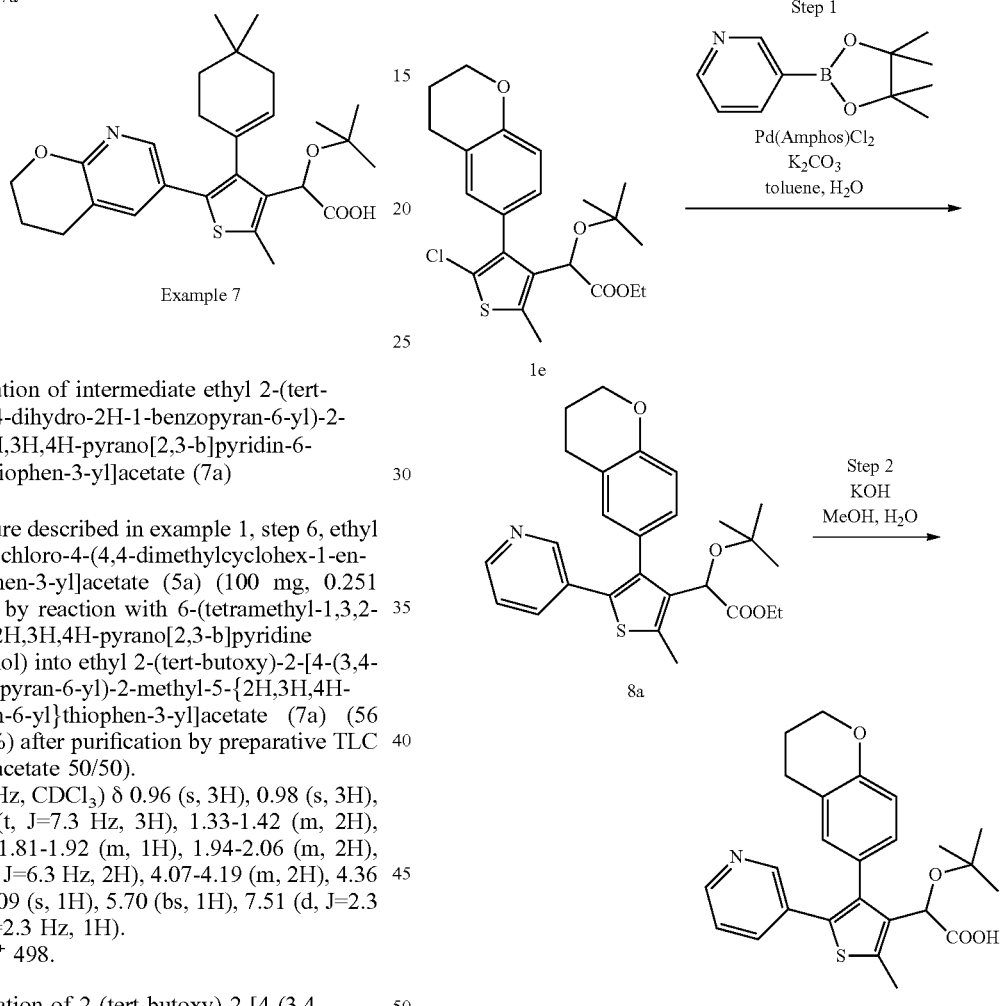

Step 1: preparation of intermediate ethyl 2-(tert-butoxy)-2-[4-(3,4-dihydro-2H-1-benzopyran-6-yl)-2-methyl-5-{2H,3H,4H-pyrano[2,3-b]pyridin-6-yl}thiophen-3-yl]acetate (7a)

Using the procedure described in example 1, step 6, ethyl 2-(tert-butoxy)-2-[5-chloro-4-(4,4-dimethylcyclohex-1-en-1-yl)-2-methylthiophen-3-yl]acetate (5a) (100 mg, 0.251 mmol) is converted by reaction with 6-(tetramethyl-1,3,2-dioxaborolan-2-yl)-2H,3H,4H-pyrano[2,3-b]pyridine (163.6 mg, 0.63 mmol) into ethyl 2-(tert-butoxy)-2-[4-(3,4-dihydro-2H-1-benzopyran-6-yl)-2-methyl-5-{2H,3H,4H-pyrano[2,3-b]pyridin-6-yl}thiophen-3-yl]acetate (7a) (56 mg, 0.11 mmol, 61%) after purification by preparative TLC (cyclohexane/ethyl acetate 50/50).

¹H NMR (400 MHz, CDCl₃) δ 0.96 (s, 3H), 0.98 (s, 3H), 1.10 (s, 9H), 1.22 (t, J=7.3 Hz, 3H), 1.33-1.42 (m, 2H), 1.48-1.62 (m, 3H), 1.81-1.92 (m, 1H), 1.94-2.06 (m, 2H), 2.58 (s, 3H), 2.78 (t, J=6.3 Hz, 2H), 4.07-4.19 (m, 2H), 4.36 (t, J=5.2 Hz, 2H), 5.09 (s, 1H), 5.70 (bs, 1H), 7.51 (d, J=2.3 Hz, 1H), 8.20 (d, J=2.3 Hz, 1H).
MS m/z ([M+H])⁺ 498.

Step 2: preparation of 2-(tert-butoxy)-2-[4-(3,4-dihydro-2H-1-benzopyran-6-yl)-2-methyl-5-{2H,3H,4H-pyrano[2,3-b]pyridin-6-yl}thiophen-3-yl]acetic acid (example 7)

Using the procedure described in example 3, step 2, ethyl 2-(tert-butoxy)-2-[4-(3,4-dihydro-2H-1-benzopyran-6-yl)-2-methyl-5-{2H,3H,4H-pyrano[2,3-b]pyridin-6-yl}thiophen-3-yl]acetate (7a) (55 mg, 0.11 mmol) is converted into 2-(tert-butoxy)-2-[4-(3,4-dihydro-2H-1-benzopyran-6-yl)-2-methyl-5-{2H,3H,4H-pyrano[2,3-b]pyridin-6-yl}thiophen-3-yl]acetic acid (example 7) (19 mg, 0.04 mmol, 36.5% yield) after purification by preparative TLC (dichloromethane/methanol 90/10).

¹H NMR (400 MHz, CDCl₃) δ 0.92 (s, 3H), 0.94 (s, 3H), 1.23 (s, 9H), 1.29-1.39 (m, 1H), 1.40-1.77 (m, 2H), 1.79-1.91 (m, 1H), 1.92-1.98 (m, 2H), 1.99-2.05 (m, 2H), 2.48 (s, 3H), 2.77 (t, J=6.4 Hz, 2H), 4.36 (t, J=5.2 Hz, 2H), 5.16 (bs, 3H), 5.64-5.87 (bs, 1H), 7.48 (d, J=2.3 Hz, 1H), 8.17 (d, J=2.3 Hz, 1H), 9.72 (bs, 1H).

Step 1: preparation of intermediate ethyl 2-(tert-butoxy)-2-[4-(3,4-dihydro-2H-1-benzopyran-6-yl)-2-methyl-5-(pyridin-3-yl)thiophen-3-yl]acetate (8a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (123 mg, 0.29 mmol) is converted by reaction with 3-(4,4,5,5-tetramethyl-1,3,2-dioxaborolan-2-yl)-pyridine (71 mg, 0.35 mmol) into ethyl 2-(tert-butoxy)-2-[4-(3,4-dihydro-2H-1-benzopyran-6-yl)-2-methyl-5-pyridin-3-yl-thiophen-3-yl]acetate (8a) (85 mg, 0.18 mmol, 63%) after purification by preparative TLC (cyclohexane/ethyl acetate 90/10).
MS m/z ([M+H])⁺ 466.

Step 2: preparation of 2-(tert-butoxy)-2-[4-(3,4-dihydro-2H-1-benzopyran-6-yl)-2-methyl-5-(pyridin-3-yl)thiophen-3-yl]acetic acid (example 8)

A solution of potassium hydroxide (0.1N, 3.6 mL, 0.36 mmol) was added to a solution of ethyl 2-(tert-butoxy)-2-[4-(3,4-dihydro-2H-1-benzopyran-6-yl)-2-methyl-5-(pyridin-3-yl)thiophen-3-yl]acetate (8a) (85 mg, 0.18 mmol) in methanol (3.5 mL). The mixture was heated at 90° C. for 40 hours and was then concentrated to evaporate methanol in vacuo. The solution was diluted with water and acidified to pH 4-5 with monosodium phosphate. After extraction with ethyl acetate, the organic layer was washed with brine, dried over sodium sulfate, filtered and concentrated in vacuo to give 2-(tert-butoxy)-2-[4-(3,4-dihydro-2H-1-benzopyran-6-yl)-2-methyl-5-(pyridin-3-yl)thiophen-3-yl]acetic acid (example 8) (71 mg, 0.16 mmol, 88%).

$^1$H NMR (400 MHz, DMSO-$d_6$) δ 0.93 (s, 9H), 1.85-1.96 (m, 2H), 2.52 (s, 3H), 2.63-2.73 (m, 2H), 4.13-4.20 (m, 2H), 4.75 (s, 1H), 6.68-6.78 (m, 1H), 6.79-7.11 (m, 2H), 7.28 (dd, J=4.8 Hz, J=7.9 Hz, 1H), 7.48 (ddd, J=1.7 Hz, J=2.1 Hz, J=7.9 Hz, 1H), 8.27 (d, J=2.1 Hz, 1H), 8.36 (dd, J=1.7 Hz, J=4.8 Hz, 1H), 12.62 (bs, 1H).

MS m/z ([M–H]$^-$) 436.

Example 9

Synthesis of 2-(tert-butoxy)-2-[4-(3,4-dihydro-2H-1-benzopyran-6-yl)-5-(4-methoxyphenyl)-2-methyl-thiophen-3-yl]acetic acid

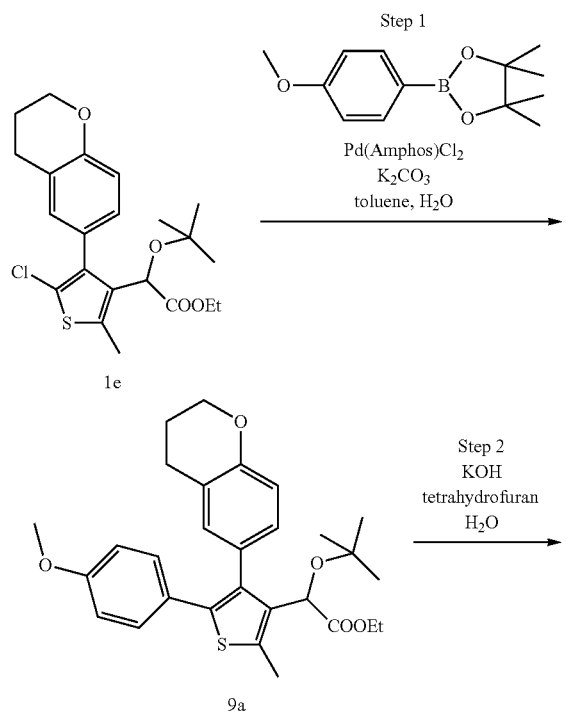

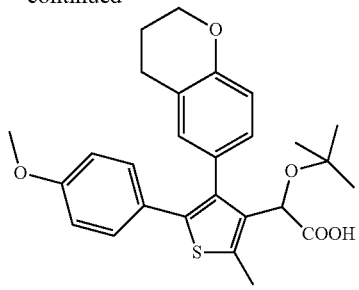

Example 9

Step 1: preparation of intermediate ethyl 2-(tert-butoxy)-2-[4-(3,4-dihydro-2H-1-benzopyran-6-yl)-2-methyl-5-(4-methoxy-phenyl)3-yl-thiophen-3-yl]acetate (9a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (109 mg, 0.26 mmol) is converted by reaction with 2-(4-methoxy-phenyl)-4,4,5,5-tetramethyl-1,3,2-dioxaborolane (88 mg, 0.31 mmol) into ethyl 2-(tert-butoxy)-2-[4-(3,4-dihydro-2H-1-benzopyran-6-yl)-5-(4-methoxyphenyl)-2-methylthiophen-3-yl]acetate (9a) (75 mg, 0.15 mmol, 59%) after purification by flash chromatography on silica gel (cyclohexane/ethyl acetate 90/10).

MS m/z ([M+Na]$^+$) 517.

Step 2: preparation of 2-(tert-butoxy)-2-[4-(3,4-dihydro-2H-1-benzopyran-6-yl)-5-(4-methoxyphenyl)-2-methylthiophen-3-yl]acetic acid (example 9)

A solution of potassium hydroxide (0.1N, 2.8 mL, 0.28 mmol) was added to a solution of ethyl 2-(tert-butoxy)-2-[4-(3,4-dihydro-2H-1-benzopyran-6-yl)-5-(4-methoxyphenyl)-2-methylthiophen-3-yl]acetate (9a) (70 mg, 0.14 mmol) in tetrahydrofuran (5 mL). The mixture was heated at 90° C. for 72 hours and was then concentrated to evaporate tetrahydrofuran in vacuo. The solution was diluted with water and acidified to pH 4-5 with monosodium phosphate. After extraction with ethyl acetate, the organic layer was washed with brine, dried over sodium sulfate, filtered and concentrated in vacuo. The residue was purified by flash chromatography on silica gel (cyclohexane/ethyl acetate 65/35) to give 2-(tert-butoxy)-2-[4-(3,4-dihydro-2H-1-benzopyran-6-yl)-5-(4-methoxyphenyl)-2-methylthiophen-3-yl]acetic acid (example 9) (25 mg, 0.053 mmol, 38%).

$^1$H NMR (400 MHz, DMSO-$d_6$) δ 0.91 (s, 9H), 1.86-1.95 (m, 2H), 2.47 (s, 3H), 2.62-2.70 (m, 2H), 3.70 (s, 3H), 4.15 (t, J=5.0 Hz, 2H), 4.71 (s, 1H), 6.70 (d, J=8.0 Hz, 1H), 6.80 (d, J=8.8 Hz, 2H), 6.83-7.00 (m, 2H), 7.03 (d, J=8.8 Hz, 2H), 12.54 (bs, 1H).

MS m/z ([M–H]$^-$) 465.

Example 10

Synthesis of 2-(tert-butoxy)-2-[2-methyl-4-(4-methylcyclohex-1-en-1-yl)-5-(pyridin-4-yl)thiophen-3-yl]acetic acid

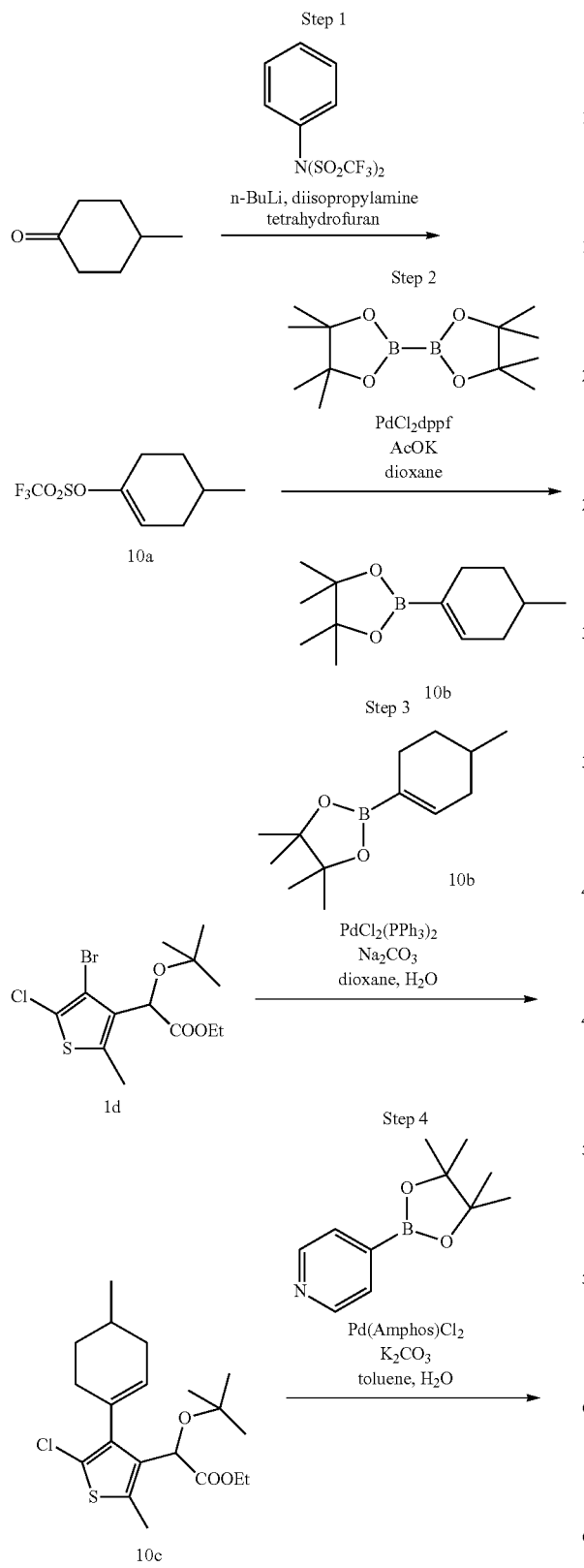

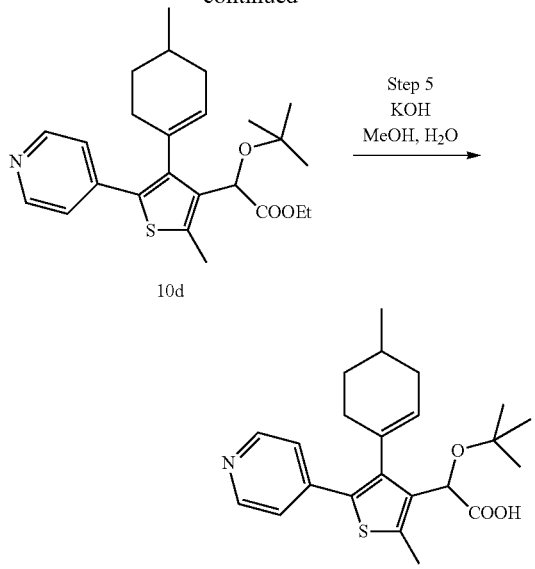

Step 1: preparation of intermediate 4-methylcyclohex-1-en-1-yl trifluoromethane-sulfonate (10a)

Using the procedure described in example 6, step 1,4-methylcyclohexan-1-one (1 g, 8.91 mmol) is converted by reaction with N-phenyltrifluoromethanesulfonimide (3.50 g, 9.81 mmol) into 4-methylcyclohex-1-en-1-yl trifluoromethanesulfonate (10a) (793 mg, 3.25 mmol, 36%) after purification by flash chromatography on silica gel (cyclohexane).

$^1$H NMR (400 MHz, CDCl$_3$) δ 0.98-1.0 (m, 3H), 1.39-1.49 (m, 1H), 1.70-1.86 (m, 3H), 2.21-2.44 (m, 3H), 5.70-5.72 (m, 1H).

Step 2: preparation of intermediate 4,4,5,5-tetramethyl-2-(4-methylcyclohex-1-en-1-yl)-1,3,2-dioxaborolane (10b)

Using the procedure described in example 6, step 2,4-methylcyclohex-1-en-1-yl trifluoromethanesulfonate (10a) (793 mg, 3.25 mmol) is converted by reaction with bis(pinacolto)diboron (1.23 g, 4.87 mmol) into 4,4,5,5-tetramethyl-2-(4-methylcyclohex-1-en-1-yl)-1,3,2-dioxaborolane (10b) (355 mg, 1.60 mmol, 49%) after purification by flash chromatography on silica gel (cyclohexane/ethyl acetate 95/5).

$^1$H NMR (400 MHz, CDCl$_3$) δ 0.93-0.96 (m, 3H), 1.14-1.26 (m, 13H), 1.61-1.71 (m, 3H), 2.07-2.24 (m, 3H), 6.53-6.54 (m, 1H).

Step 3: preparation of intermediate ethyl 2-(tert-butoxy)-2-[5-chloro-2-methyl-4-(4-methylcyclohex-1-en-1-yl)thiophen-3-yl]acetate (10c)

Using the procedure described in example 1, step 5, ethyl 2-(4-bromo-5-chloro-2-methylthiophen-3-yl)-2-(tert-butoxy)acetate (1d) (200 mg, 0.54 mmol) is converted by reaction with 4,4,5,5-tetramethyl-2-(4-methylcyclohex-1-en-1-yl)-1,3,2-dioxaborolane (10b) (156 mg, 0.70 mmol) into ethyl 2-(tert-butoxy)-2-[5-chloro-2-methyl-4-(4-methylcyclohex-1-en-1-yl)thiophen-3-yl]acetate (10c) (105 mg, 0.27 mmol, 50.5%) as a mixture of diastereoisomers, after purification by 3 preparative TLC (cyclohexane/ethyl acetate 95/5).

$^1$H NMR (400 MHz, CDCl$_3$) δ 1.03-1.05 (m, 3H), 1.17-1.23 (m, 12H), 1.33-1.42 (m, 1H), 1.79-1.85 (m, 3H), 2.05-2.37 (m, 3H), 2.46-2.47 (m, 3H), 4.06-4.17 (m, 2H), 4.97 and 4.98 (s, 1H), 5.62-5.63 (m, 1H).

Step 4: preparation of intermediate ethyl 2-(tert-butoxy)-2-[2-methyl-4-(4-methyl cyclohex-1-en-1-yl)-5-(pyridin-4-yl)thiophen-3-yl]acetate (10d)

Using the procedure described in example 1, step 6, ethyl 2-(tert-butoxy)-2-[5-chloro-2-methyl-4-(4-methylcyclohex-1-en-1-yl)thiophen-3-yl]acetate (10c) (103 mg, 0.270 mmol) is converted by reaction with 4-pyridine boronic acid pinacol ester (66 mg, 0.32 mmol) into ethyl 2-(tert-butoxy)-2-[2-methyl-4-(4-methylcyclohex-1-en-1-yl)-5-(pyridin-4-yl)thiophen-3-yl]acetate (10d) (69 mg, 0.16 mmol, 60%) as a mixture of diastereoisomers, after purification by 2 preparative TLC (cyclohexane/ethyl acetate 70/30).

$^1$H NMR (400 MHz, CDCl$_3$) δ 1.04-1.07 (m, 3H), 1.20-1.35 (m, 13H), 1.73-2.39 (m, 6H), 2.61 (s, 3H), 4.10-4.21 (m, 2H), 5.11 (s, 1H), 5.71-5.89 (bs, 1H), 7.50-7.54 (m, 2H), 8.49-8.51 (m, 2H).

MS m/z ([M+H]$^+$) 428.

Step 5: preparation of 2-(tert-butoxy)-2-[2-methyl-4-(4-methylcyclohex-1-en-1-yl)-5-(pyridin-4-yl)thiophen-3-yl]acetic acid (example 10)

Using the procedure described in example 3, step 2, ethyl 2-(tert-butoxy)-2-[2-methyl-4-(4-methylcyclohex-1-en-1-yl)-5-(pyridin-4-yl)thiophen-3-yl]acetate (10d) (66 mg, 0.15 mmol) is converted into 2-(tert-butoxy)-2-[2-methyl-4-(4-methylcyclohex-1-en-1-yl)-5-(pyridin-4-yl)thiophen-3-yl]acetic acid (example 10) (20 mg, 0.05 mmol, 32.5%, diastereoisomers mixture) after purification by preparative TLC (dichloromethane/methanol 90/10).

$^1$H NMR (400 MHz, CDCl$_3$) δ 1.02-1.04 (m, 3H), 1.24-1.32 (m, 10H), 1.61-2.36 (m, 6H), 2.53 (s, 3H), 5.18-5.20 (bs, 1H), 5.64-6.15 (bs, 1H), 7.51-7.54 (m, 2H), 8.52-8.53 (m, 2H).

MS m/z ([M−H]$^-$) 398.

Example 11

Preparation of (2S)-2-(tert-butoxy)-2-[4-(4,4-dimethylcyclohex-1-en-1-yl)-2-methyl-5-(pyridin-4-yl)thiophen-3-yl]acetic acid A sample of the compound example 5, 2-(tert-butoxy)-2-[4-(4,4-dimethylcyclohex-1-en-1-yl)-2-methyl-5-(pyridin-4-yl)thiophen-3-yl]acetic acid, has been loaded onto a Chiralcel OD column (20 μm, 250×21.7 mm) and eluted with a mixture of heptane/isopropanol/acetic acid (95/5/0.1%) at ambient temperature and a flow rate of 21 mL/min. Chiral purity has been assessed by chiral HPLC with a Chiralcel OD column (10 μm, 250×4.6 mm) eluted with a mixture of heptane/isopropanol/acetic acid (95/5/0.1%) and a flow rate of 2 mL/min. Fractions containing a single enantiomer with a retention time of 7.3 min (analytic HPLC) were combined and evaporated under reduced pressure to give the pure enantiomer, the (2S)-2-(tert-butoxy)-2-[4-(4,4-dimethylcyclohex-1-en-1-yl)-2-methyl-5-(pyridin-4-yl)thiophen-3-yl]acetic acid (example 11) with an enantiomeric excess of 98.04%.

Example 12

Synthesis of 2-(tert-butoxy)-2-[2-methyl-5-(pyridin-4-yl)-4-{spiro[2,5]oct-5-en-6-yl}thiophen-3-yl]acetic acid

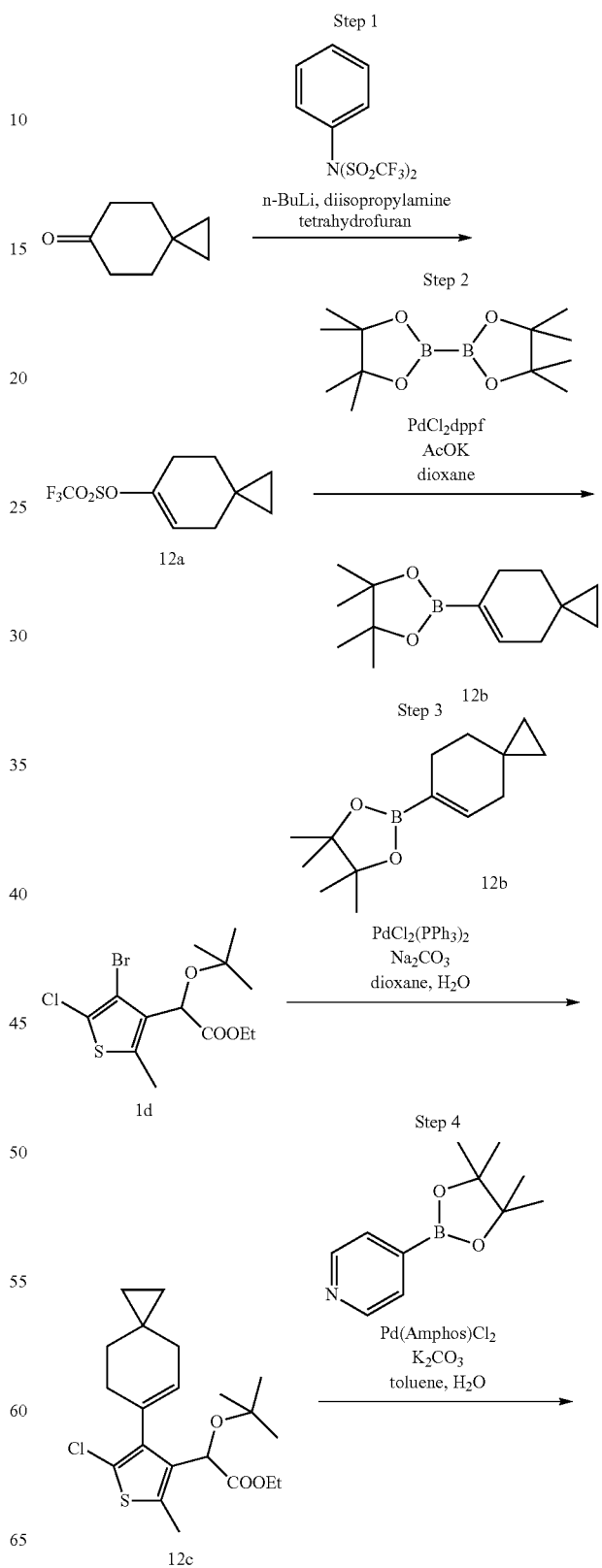

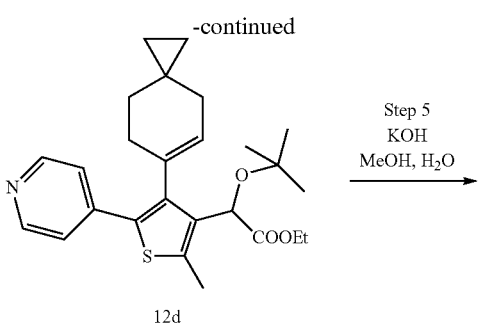

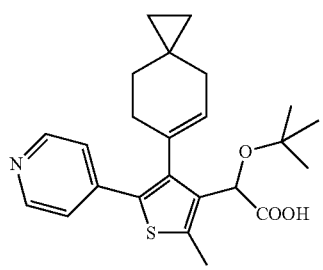

Example 12

Step 1: preparation of intermediate spiro[2,5]oct-5-en-6-yl trifluoromethanesulfonate (12a)

Using the procedure described in example 6, step 1, spiro[2,5]octan-6-one (665 mg, 5.33 mmol) is converted by reaction with N-phenyltrifluoromethanesulfonimide (2 g, 5.85 mmol) into spiro[2,5]oct-5-en-6-yl trifluoromethanesulfonate (12a) (514 mg, 2.0 mmol, 36%) after purification by flash chromatography on silica gel (cyclohexane).

$^1$H NMR (400 MHz, CDCl$_3$) δ 0.39 (s, 4H), 1.54-1.57 (m, 2H), 2.03-2.05 (m, 2H), 2.39-2.42 (m, 2H), 5.77-5.79 (m, 1H).

Step 2: preparation of intermediate 4,4,5,5-tetramethyl-2-{spiro[2,5]oct-5-en-6-yl}-1,3,2-dioxaborolane (12b)

Using the procedure described in example 6, step 2, spiro[2,5]oct-5-en-6-yl trifluoromethanesulfonate (12a) (500 mg, 1.95 mmol) is converted by reaction with bis(pinacolto)diboron (743.3 mg, 2.93 mmol) into 4,4,5,5-tetramethyl-2-{spiro[2,5]oct-5-en-6-yl}-1,3,2-dioxaborolane (12b) (193 mg, 0.82 mmol, 42%) after purification by flash chromatography on silica gel (cyclohexane/ethyl acetate 95/5).

$^1$H NMR (400 MHz, CDCl$_3$) δ 0.26-0.28 (m, 4H), 1.24-1.27 (m, 12H), 1.34-1.37 (m, 2H), 1.97-1.99 (m, 2H), 2.20-2.23 (m, 2H), 6.57-6.59 (m, 1H).

Step 3: preparation of intermediate ethyl 2-(tert-butoxy)-2-(5-chloro-2-methyl-4-{spiro[2,5]oct-5-en-6-yl}thiophen-3-yl)acetate (12c)

Using the procedure described in example 1, step 5, ethyl 2-(4-bromo-5-chloro-2-methylthiophen-3-yl)-2-(tert-butoxy)acetate (1d) (200 mg, 0.54 mmol) is converted by reaction with 4,4,5,5-tetramethyl-2-{spiro[2,5]oct-5-en-6-yl}-1,3,2-dioxaborolane (12b) (178 mg, 0.76 mmol) into ethyl 2-(tert-butoxy)-2-(5-chloro-2-methyl-4-{spiro[2,5]oct-5-en-6-yl}thiophen-3-yl)acetate (12c) (125 mg, 0.31 mmol, 58%) after purification by 2 preparative TLC (cyclohexane/ethyl acetate 95/5).

$^1$H NMR (400 MHz, CDCl$_3$) δ 0.37 (s, 4H), 1.18-1.23 (m, 12H), 1.47-1.59 (m, 2H), 2.08-2.20 (m, 3H), 2.41-2.47 (m, 4H), 4.07-4.17 (m, 2H), 5.03 (s, 1H), 5.68-5.70 (bs, 1H).

Step 4: preparation of intermediate ethyl 2-(tert-butoxy)-2-[2-methyl-5-(pyridin-4-yl)-4-{spiro[2,5]oct-5-en-6-yl}thiophen-3-yl]acetate (12d)

Using the procedure described in example 1, step 6, ethyl 2-(tert-butoxy)-2-(5-chloro-2-methyl-4-{spiro[2,5]oct-5-en-6-yl}thiophen-3-yl)acetate (12c) (125 mg, 0.31 mmol) is converted by reaction with 4-pyridine boronic acid pinacol ester (76 mg, 0.37 mmol) into ethyl 2-(tert-butoxy)-2-(5-chloro-2-methyl-4-{spiro[2,5]oct-5-en-6-yl}thiophen-3-yl)acetate (12d) (125 mg, 0.31 mmol, 58%) after purification by 2 preparative TLC (cyclohexane/ethyl acetate 70/30).

$^1$H NMR (400 MHz, CDCl$_3$) δ 0.41 (s, 4H), 1.21-1.26 (m, 12H), 1.53-2.20 (m, 6H), 2.61 (s, 3H), 4.09-4.22 (m, 2H), 5.16 (s, 1H), 5.71-6.03 (bs, 1H), 7.54 (d, J=6.2 Hz, 2H), 8.50 (d, J=6.2 Hz, 2H).

MS m/z ([M+H]$^+$) 440.

Step 5: preparation of 2-(tert-butoxy)-2-[2-methyl-5-(pyridin-4-yl)-4-{spiro[2,5]oct-5-en-6-yl}thiophen-3-yl]acetic acid (example 12)

Potassium hydroxide (25.5 mg, 0.45 mmol) was added to a solution of ethyl 2-(tert-butoxy)-2-[2-methyl-5-(pyridin-4-yl)-4-{spiro[2,5]oct-5-en-6-yl}thiophen-3-yl]acetate (12d) (66 mg, 0.15 mmol) in a mixture of methanol (2 mL) and water (2.3 mL). The reaction mixture was sonicated for 5 minutes, then heated at 100° C. for 3 hours and then concentrated in vacuo. The aqueous layer was slowly acidified with a 1N hydrochloric acid aqueous solution (pH 5-6) and extracted with ethyl acetate twice. The organic layer was washed with brine, dried over sodium sulfate, filtered and concentrated in vacuo. The residue was purified by preparative TLC (dichloromethane/methanol 90/10) to give 2-(tert-butoxy)-2-[2-methyl-5-(pyridin-4-yl)-4-{spiro[2,5]oct-5-en-6-yl}thiophen-3-yl]acetic acid (example 12) (50 mg, 0.12 mmol, 86% yield).

$^1$H NMR (400 MHz, CDCl$_3$) δ 0.38 (s, 4H), 1.25 (s, 9H), 1.34-1.55 (m, 3H), 2.01-2.22 (m, 3H), 2.53 (s, 3H), 5.15-5.30 (bs, 1H), 5.68-5.75 (bs, 1H), 7.50-7.54 (m, 2H), 8.51-8.54 (m, 2H).

MS m/z ([M−H]$^−$) 410.

Example 13

Synthesis of 2-(tert-butoxy)-2-[4-(3,4-dihydro-2H-1-benzopyran-6-yl)-5-(2-fluoropyridin-4-yl)-2-methylthiophen-3-yl) acetic acid

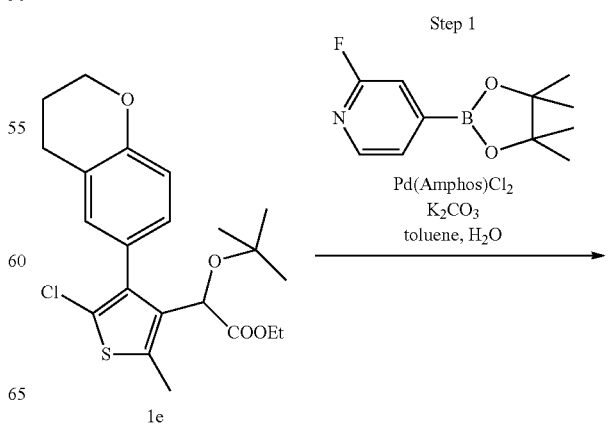

-continued

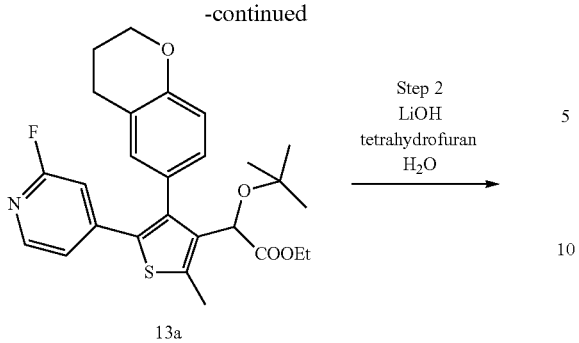

13a

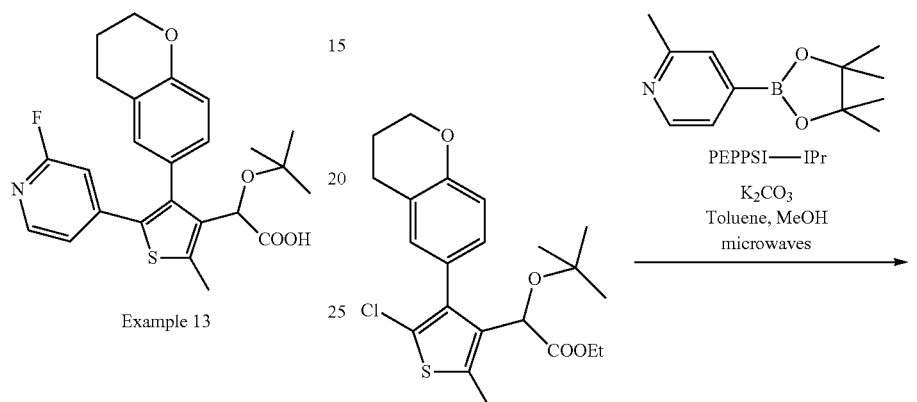

Example 13

Step 1: preparation of intermediate ethyl 2-(tert-butoxy)-2-[4-(3,4-dihydro-2H-1-benzopyran-6-yl)-5-(2-fluoropyridin-4-yl)-2-methylthiophen-3-yl]acetate (13a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (168 mg, 0.40 mmol) is converted by reaction with 2-fluoro-4-(4,4,5,5-tetramethyl-1,3,2-dioxaborolan-2-yl)-pyridine (106 mg, 0.48 mmol) into ethyl 2-(tert-butoxy)-2-[4-(3,4-dihydro-2H-1-benzopyran-6-yl)-5-(2-fluoropyridin-4-yl)-2-methylthiophen-3-yl]acetate (13a) (58 mg, 0.11 mmol, 28%) after purification by flash chromatography on silica gel (cyclohexane/ethyl acetate 90/10).

MS m/z ([M+H]$^+$) 484.

Step 2: preparation of 2-(tert-butoxy)-2-[4-(3,4-dihydro-2H-1-benzopyran-6-yl)-5-(2-fluoropyridin-4-yl)-2-methylthiophen-3-yl) acetic acid (example 13)

A solution of lithium hydroxide (1N, 0.24 mL, 0.24 mmol) was added to a solution of ethyl 2-(tert-butoxy)-2-[4-(3,4-dihydro-2H-1-benzopyran-6-yl)-5-(2-fluoropyridin-4-yl)-2-methylthiophen-3-yl]acetate (13a) (58 mg, 0.12 mmol) in tetrahydrofuran (3 mL). The reaction mixture was stirred at room temperature for 72 hours. The mixture was concentrated in vacuo, diluted with water and acidified to pH 4-5 with monosodium phosphate. After extraction with ethyl acetate, the organic layer was washed with brine, dried over sodium sulfate, filtered and concentrated in vacuo. The residue was purified by flash chromatography on silica gel (dichloromethane/methanol 95/5) and triturated in diethyl ether to give 2-(tert-butoxy)-2-[4-(3,4-dihydro-2H-1-benzopyran-6-yl)-5-(2-fluoropyridin-4-yl)-2-methylthiophen-3-yl) acetic acid (example 13) (21 mg, 0.045 mmol, 38%).

$^1$H NMR (400 MHz, DMSO-d$_6$) δ 0.93 (s, 9H), 1.88-1.98 (m, 2H), 2.54 (s, 3H), 2.65-2.76 (m, 2H), 4.16-4.22 (m, 2H), 4.73 (s, 1H), 6.70 (s, 1H), 6.73-6.90 (m, 3H), 6.97 (dt, J=5.3 Hz, J=1.5 Hz, 1H), 8.06 (d, J=5.3 Hz, 1H), 12.75 (bs, 1H).

MS m/z ([M−H]$^−$) 454.

Example 14

Synthesis of 2-(tert-butoxy)-2-[4-(3,4-dihydro-2H-1-benzopyran-6-yl)-2-methyl-5-(2-methylpyridin-4-yl)thiophen-3-yl]acetic acid

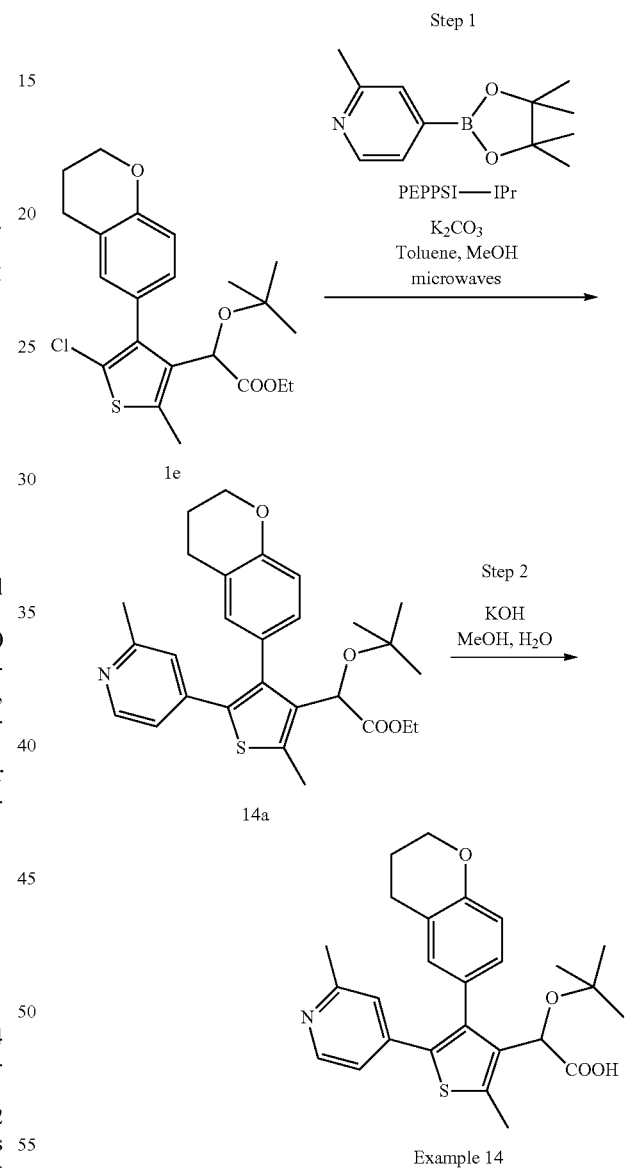

Example 14

Step 1: preparation of intermediate ethyl 2-(tert-butoxy)-2-[4-(3,4-dihydro-2H-1-benzopyran-6-yl)-2-methyl-5-(2-methylpyridin-4-yl)thiophen-3-yl]acetate (14a)

In a specific micro-wave vial, a solution of ethyl 2-(tert-butoxy)-2-[5-chloro-4-(3,4-dihydro-2H-1-benzopyran-6-yl)-2-methylthiophen-3-yl]acetate (1e) (114 mg, 0.27 mmol), 2-methyl-4-(4,4,5,5-tetramethyl-1,3,2-dioxaborolan-2-yl)-pyridine (74 mg, 0.54 mmol), potassium carbonate 1H), 7.00 (d, J=1.9 Hz, 1H), 7.35 (d, J=4.3 Hz, 1H), 7.37 (d, J=4.0 Hz, 1H), 7.45-7.55 (m, 2H), 7.70 (t, J=8.1 Hz, 1H), 7.77 (d, J=8.4 Hz, 1H), 12.70 (bs, 1H).

MS m/z ([M−H]⁻) 486. (82 mg, 0.59 mmol) were dissolved in a mixture of toluene (1 mL) and methanol (1 mL). The solution was degassed under argon for 5 minutes and [1,3-bis(2,6-diisopropylphenyl)imidazol-2-ylidene](3-chloropyridyl) palladium(11) dichloride (PEPPSI-IPr, 18 mg, 0.027 mmol) was added. The reaction was then heated under micro-waves at 120° C. for 15 minutes. The reaction mixture was concentrated in vacuo and the crude material was purified by flash chromatography on silica gel (cyclohexane/ethyl acetate 80/20) to give ethyl 2-(tert-butoxy)-2-[4-(3,4-dihydro-2H-1-benzopyran-6-yl)-2-methyl-5-(2-methylpyridin-4-yl)thiophen-3-yl]acetate (14a) (118 mg, 0.25 mmol, 92%).

MS m/z ([M+H])⁺) 480.

Step 2: preparation of 2-(tert-butoxy)-2-[4-(3,4-dihydro-2H-1-benzopyran-6-yl)-2-methyl-5-(2-methylpyridin-4-yl)thiophen-3-yl]acetic acid (example 14)

Using the procedure described in example 3, step 2, ethyl 2-(tert-butoxy)-2-[4-(3,4-dihydro-2H-1-benzopyran-6-yl)-2-methyl-5-(2-methylpyridin-4-yl)thiophen-3-yl]acetate (14a) (118 mg, 0.25 mmol) is converted into 2-(tert-butoxy)-2-[4-(3,4-dihydro-2H-1-benzopyran-6-yl)-2-methyl-5-(2-methylpyridin-4-yl)thiophen-3-yl]acetic acid (example 14) (85 mg, 0.19 mmol, 76%) without further purification.

¹H NMR (400 MHz, DMSO-d₆) δ 0.92 (s, 9H), 1.88-1.95 (m, 2H), 2.34 (s, 3H), 2.52 (s, 3H), 2.60-2.75 (m, 2H), 4.17 (t, J=5.1 Hz, 2H), 4.75 (s, 1H), 6.71 (dd, J=1.2 Hz, J=5.3 Hz, 1H), 6.74-6.90 (m, 3H), 6.97 (d, J=1.2 Hz, 1H), 8.20 (d, J=5.3 Hz, 1H), 12.63 (bs, 1H).

MS m/z ([M−H]⁻) 450.

Example 15

Synthesis of 2-(tert-butoxy)-2-[4-(3,4-dihydro-2H-1-benzopyran-6-yl)-2-methyl-5-(quinolin-4-yl)thiophen-3-yl]acetic acid

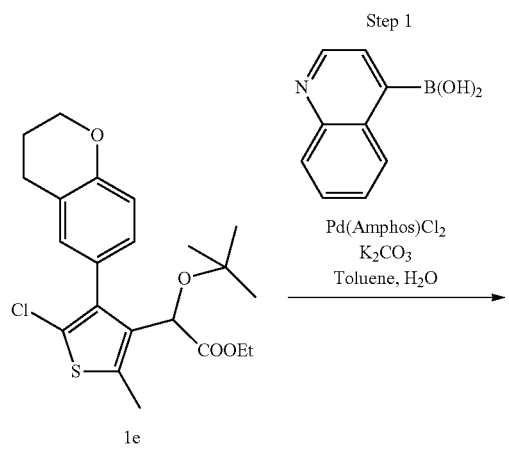

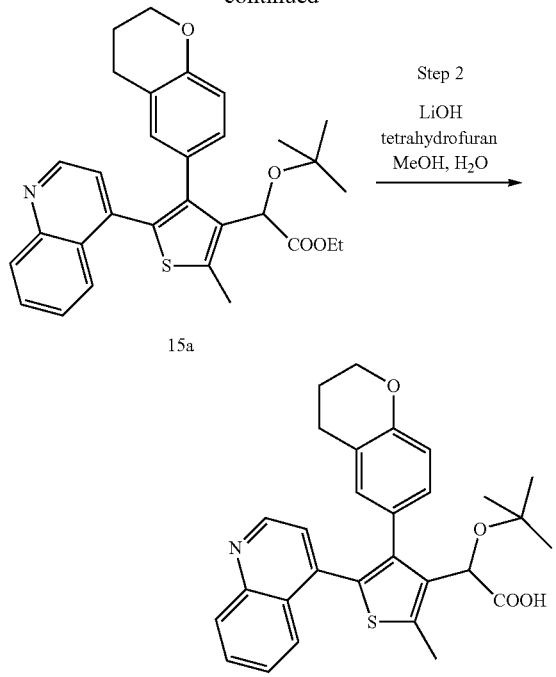

Example 15

Step 1: preparation of intermediate ethyl 2-(tert-butoxy)-2-[4-(3,4-dihydro-2H-1-benzopyran-6-yl)-2-methyl-5-(quinolin-4-yl)thiophen-3-yl]acetate (15a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (113 mg, 0.27 mmol) is converted by reaction with 4-quinolinylboronic acid (55 mg, 0.32 mmol) into ethyl 2-(tert-butoxy)-2-[4-(3,4-dihydro-2H-1-benzopyran-6-yl)-2-methyl-5-(quinolin-4-yl)thiophen-3-yl]acetate (15a) (58 mg, 0.11 mmol, 42%) after purification by flash chromatography on silica gel (cyclohexane/ethyl acetate 80/20).

MS m/z ([M+Na]⁺) 516.

Step 2: preparation of 2-(tert-butoxy)-2-[4-(3,4-dihydro-2H-1-benzopyran-6-yl)-2-methyl-5-(quinolin-4-yl)thiophen-3-yl]acetic acid (example 15)

A solution of lithium hydroxide (1N, 1.1 mL, 1.1 mmol) was added to a solution of ethyl 2-(tert-butoxy)-2-[4-(3,4-dihydro-2H-1-benzopyran-6-yl)-2-methyl-5-(quinolin-4-yl)thiophen-3-yl]acetate (15a) (58 mg, 0.11 mmol) in a mixture of tetrahydrofuran (8 mL) and methanol (2 mL). The mixture was agitated at room temperature for 72 hours. The mixture was cooled to 0° C. and acidified to pH 4-5 with a solution of monosodium phosphate. After extraction with ethyl acetate, the organic layer was washed with brine, dried over sodium sulfate, filtered and concentrated in vacuo to give 2-(tert-butoxy)-2-[4-(3,4-dihydro-2H-1-benzopyran-6-yl)-2-methyl-5-(quinolin-4-yl)thiophen-3-yl]acetic acid (example 15) (50 mg, 0.1 mmol, 91%) without further purification.

¹H NMR (400 MHz, DMSO-d₆) δ 0.93 (s, 9H), 1.74-1.94 (m, 2H), 2.51-2.58 (m, 5H), 4.02 (t, J=4.8 Hz, 2H), 4.13 (s, 1H), 6.44 (d, J=8.4 Hz, 1H), 6.70 (dd, J=2.2 Hz, J=8.4 Hz, 1H), 7.00 (d, J=1.9 Hz, 1H), 7.35 (d, J=4.3 Hz, 1H), 7.37 (d, J=4.0 Hz, 1H), 7.45-7.55 (m, 2H), 7.70 (t, J=8.1 Hz, 1H), 7.77 (d, J=8.4 Hz, 1H), 12.70 (bs, 1H).

MS m/z ([M−H]⁻) 486.

Example 16

Synthesis of 2-(tert-butoxy)-2-[4-(3,4-dihydro-2H-1-benzopyran-6-yl)-5-(furan-3-yl)-2-methylthiophen-3-yl]acetic acid

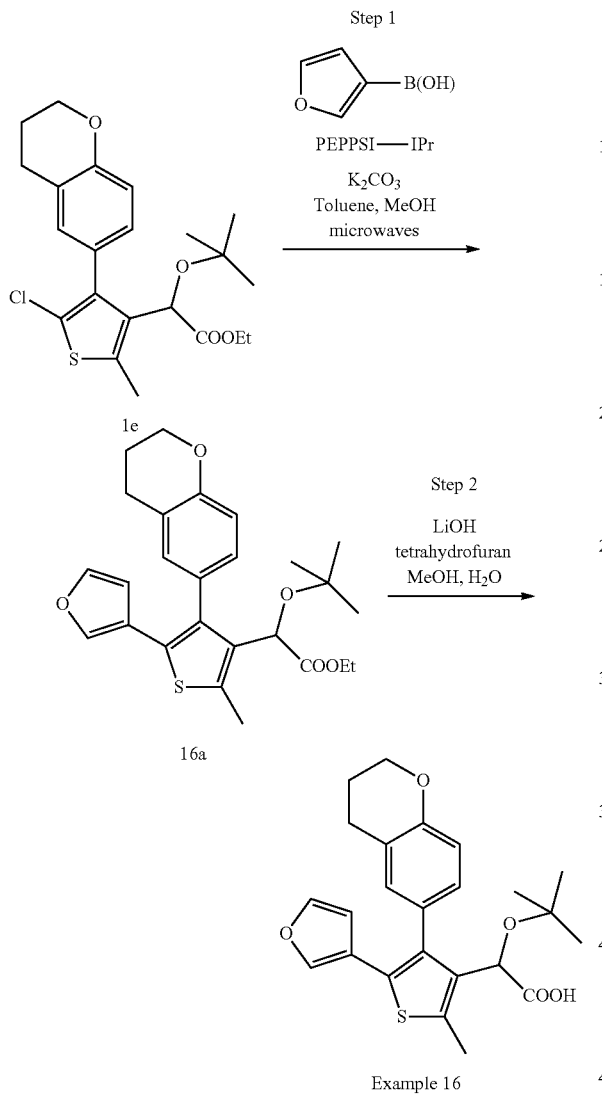

Example 16

Step 1: preparation of intermediate ethyl 2-(tert-butoxy)-2-[4-(3,4-dihydro-2H-1-benzopyran-6-yl)-5-(furan-3-yl)-2-methylthiophen-3-yl]acetate (16a)

Using the procedure described in example 14, step 1, ethyl 2-(tert-butoxy)-2-[5-chloro-4-(3,4-dihydro-2H-1-benzopyran-6-yl)-2-methylthiophen-3-yl]acetate (1e) (100 mg, 0.24 mmol) is converted by reaction with 3-furylboronic acid (53 mg, 0.48 mmol) into ethyl 2-(tert-butoxy)-2-[4-(3,4-dihydro-2H-1-benzopyran-6-yl)-5-(furan-3-yl)-2-methylthiophen-3-yl]acetate (16a) (43 mg, 0.093 mmol, 39%) after purification by flash chromatography on silica gel (cyclohexane/ethyl acetate 97/3).

MS m/z ([M+Na]$^+$) 477.

Step 2: preparation of 2-(tert-butoxy)-2-[4-(3,4-dihydro-2H-1-benzopyran-6-yl)-5-(furan-3-yl)-2-methylthiophen-3-yl]acetic acid (example 16)

Using the procedure described in example 15, step 2, ethyl 2-(tert-butoxy)-2-[4-(3,4-dihydro-2H-1-benzopyran-6-yl)-5-(furan-3-yl)-2-methylthiophen-3-yl]acetate (16a) (58 mg, 0.11 mmol) is converted into 2-(tert-butoxy)-2-[4-(3,4-dihydro-2H-1-benzopyran-6-yl)-5-(furan-3-yl)-2-methylthiophen-3-yl]acetic acid (example 16) (50 mg, 0.1 mmol, 92%) without further purification.

$^1$H NMR (400 MHz, DMSO-d$_6$) δ 0.94 (s, 9H), 1.83-2.00 (m, 2H), 2.46 (s, 3H), 2.64-2.80 (m, 2H), 4.18 (t, J=5.2 Hz, 2H), 4.66 (s, 1H), 6.05 (dd, J=0.7 Hz, J=1.8 Hz, 1H), 6.78 (d, J=8.1 Hz, 1H), 6.87-7.02 (m, 2H), 7.31 (m, 1H), 7.54 (t, J=1.7 Hz, 1H), 12.53 (bs, 1H).

MS m/z ([M−H]$^-$) 425.

Example 17

Synthesis of 2-{5-[2-(benzyloxy)pyridin-4-yl]-4-(3,4-dihydro-2H-1-benzopyran-6-yl)-2-methylthiophen-3-yl}-2-(tert-butoxy)acetic acid Step 1

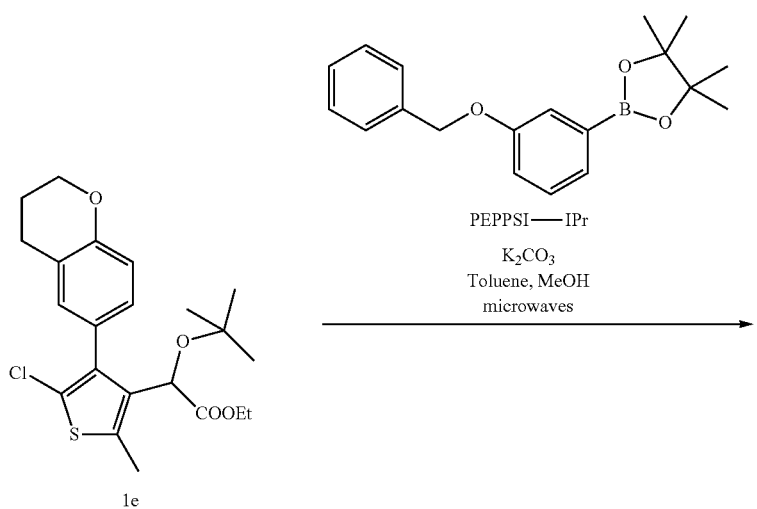

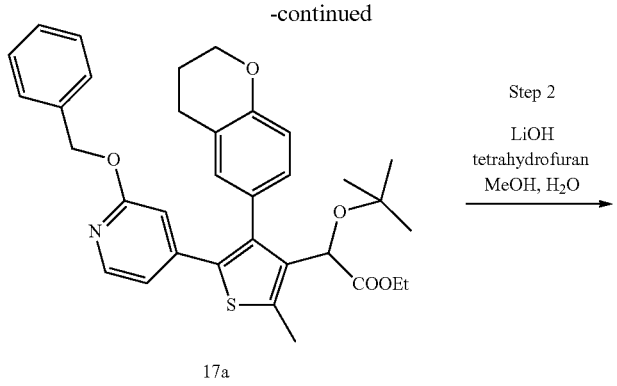

17a

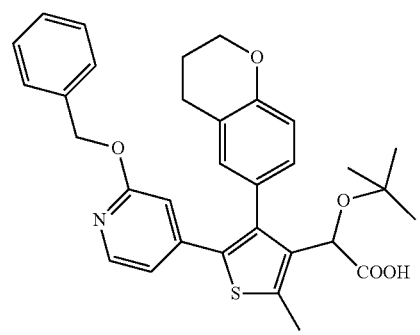

Example 17

Step 1: preparation of intermediate ethyl 2-{5-[2-(benzyloxy)pyridin-4-yl]-4-(3,4-dihydro-2H-1-benzopyran-6-yl)-2-methylthiophen-3-yl}-2-(tert-butoxy)acetate (17a)

Using the procedure described in example 14, step 1, ethyl 2-(tert-butoxy)-2-[5-chloro-4-(3,4-dihydro-2H-1-benzopyran-6-yl)-2-methylthiophen-3-yl]acetate (1e) (114 mg, 0.27 mmol) is converted by reaction with 2-benzyloxy-4-(4,4,5,5-tetramethyl-1,3,2-dioxaborolan-2-yl)-pyridine (124 mg, 0.4 mmol) into ethyl 2-{5-[2-(benzyloxy)pyridin-4-yl]-4-(3,4-dihydro-2H-1-benzopyran-6-yl)-2-methylthiophen-3-yl}-2-(tert-butoxy)acetate (17a) (25 mg, 0.043 mmol, 16%) after purification by flash chromatography on silica gel (cyclohexane/ethyl acetate 95/5).

MS m/z ([M+H]$^+$) 572.

Step 2: preparation of 2-{5-[2-(benzyloxy)pyridin-4-yl]-4-(3,4-dihydro-2H-1-benzopyran-6-yl)-2-methylthiophen-3-yl}-2-(tert-butoxy)acetic acid (example 17)

Using the procedure described in example 15, step 2, ethyl 2-{5-[2-(benzyloxy)pyridin-4-yl]-4-(3,4-dihydro-2H-1-benzopyran-6-yl)-2-methylthiophen-3-yl}-2-(tert-butoxy)acetate (17a) (68 mg, 0.12 mmol) is converted into -{5-[2-(benzyloxy)pyridin-4-yl]-4-(3,4-dihydro-2H-1-benzopyran-6-yl)-2-methylthiophen-3-yl}-2-(tert-butoxy)acetic acid (example 17) (56 mg, 0.1 mmol, 86%) without further purification.

$^1$H NMR (400 MHz, DMSO-d$_6$) δ 0.91 (s, 9H), 1.87-1.96 (m, 2H), 2.51 (s, 3H), 2.63-2.73 (m, 2H), 4.13-4.20 (m, 2H), 4.72 (s, 1H), 5.26 (s, 2H), 6.50 (s, 1H), 6.61 (dd, J=1.0 Hz, J=5.3 Hz, 1H), 6.73-6.82 (m, 2H), 7.27-7.41 (m, 6H), 7.96 (d, J=5.4 Hz, 1H), 12.68 (bs, 1H).

MS m/z ([M−H]$^−$) 542.

Example 18

Synthesis of 2-(tert-butoxy)-2-[4-(3,4-dihydro-2H-1-benzopyran-6-yl)-2-methyl-5-(pyrimidin-5-yl)thiophen-3-yl]acetic acid

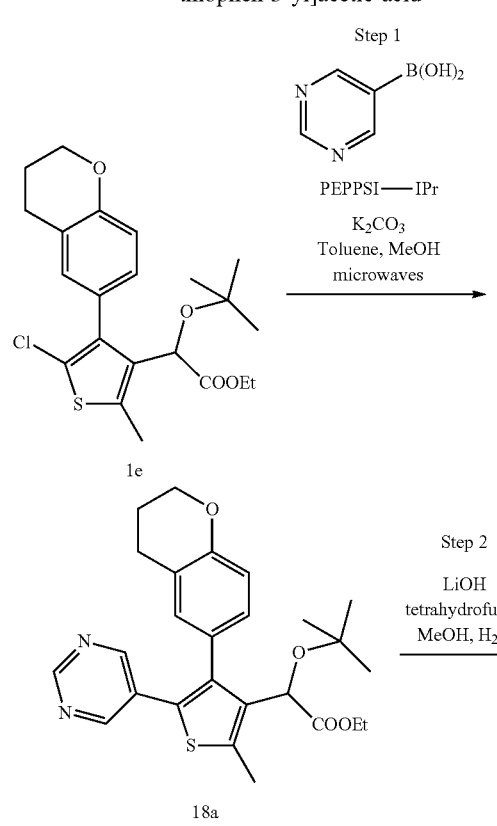

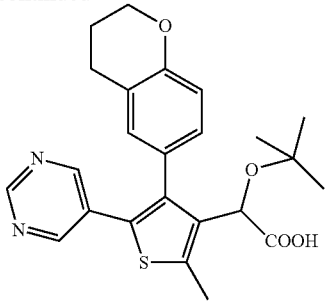

Example 18

Step 1: preparation of intermediate ethyl 2-(tert-butoxy)-2-[4-(3,4-dihydro-2H-1-benzopyran-6-yl)-2-methyl-5-(pyrimidin-5-yl)thiophen-3-yl]acetate (18a)

Using the procedure described in example 14, step 1, ethyl 2-(tert-butoxy)-2-[5-chloro-4-(3,4-dihydro-2H-1-benzopyran-6-yl)-2-methylthiophen-3-yl]acetate (1e) (90 mg, 0.21 mmol) is converted by reaction with 5-pyrimidylboronic acid (53 mg, 0.42 mmol) into ethyl 2-(tert-butoxy)-2-[4-(3,4-dihydro-2H-1-benzopyran-6-yl)-2-methyl-5-(pyrimidin-5-yl)thiophen-3-yl]acetate (18a) (60 mg, 0.13 mmol, 61%) after purification by flash chromatography on silica gel (cyclohexane/ethyl acetate 80/20).

MS m/z ([M+H]$^+$) 467.

Step 2: preparation of 2-(tert-butoxy)-2-[4-(3,4-dihydro-2H-1-benzopyran-6-yl)-2-methyl-5-(pyrimidin-5-yl)thiophen-3-yl]acetic acid (example 18)

Using the procedure described in example 15, step 2, ethyl 2-(tert-butoxy)-2-[4-(3,4-dihydro-2H-1-benzopyran-6-yl)-2-methyl-5-(pyrimidin-5-yl)thiophen-3-yl]acetate (18a) (130 mg, 0.28 mmol) is converted into 2-(tert-butoxy)-2-[4-(3,4-dihydro-2H-1-benzopyran-6-yl)-2-methyl-5-(pyrimidin-5-yl)thiophen-3-yl]acetic acid (example 18) (110 mg, 0.25 mmol, 90%) without further purification.

$^1$H NMR (400 MHz, DMSO-d$_6$) δ 0.94 (s, 9H), 1.83-1.99 (m, 2H), 2.54 (s, 3H), 2.61-2.77 (m, 2H), 4.17 (t, J=5.0 Hz, 2H), 4.77 (s, 1H), 6.69-6.81 (m, 1H), 6.82-7.15 (m, 2H), 8.47 (s, 2H), 8.98 (s, 1H), 12.67 (bs, 1H).

MS m/z ([M−H]$^−$) 437.

Example 19

Synthesis of 2-(tert-butoxy)-2-[4-(3,4-dihydro-2H-1-benzopyran-6-yl)-2-methyl-5-(1-methyl-6-oxo-1,6-dihydropyridin-3-yl)thiophen-3-yl]acetic acid Step 1

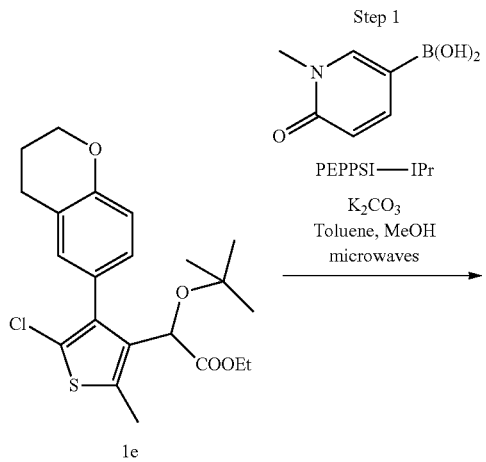

PEPPSI—IPr
K$_2$CO$_3$
Toluene, MeOH
microwaves

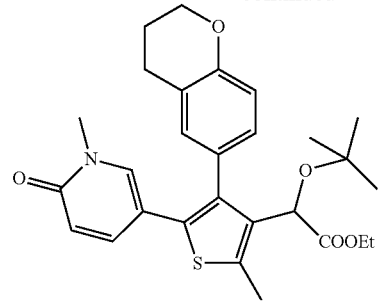

19a

Step 2
LiOH
tetrahydrofuran
MeOH, H$_2$O

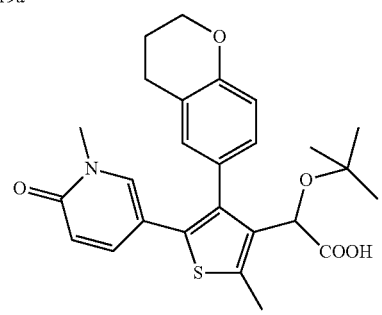

Example 19

Step 1: preparation of intermediate ethyl 2-(tert-butoxy)-2-[4-(3,4-dihydro-2H-1-benzopyran-6-yl)-2-methyl-5-(1-methyl-6-oxo-1,6-dihydropyridin-3-yl)thiophen-3-yl]acetate (19a)

Using the procedure described in example 14, step 1, ethyl 2-(tert-butoxy)-2-[5-chloro-4-(3,4-dihydro-2H-1-benzopyran-6-yl)-2-methylthiophen-3-yl]acetate (1e) (148 mg, 0.35 mmol) is converted by reaction with (1,6-dihydro-1-methyl-6-oxo-3-pyridinyl)boronic acid (164 mg, 0.7 mmol) into ethyl 2-(tert-butoxy)-2-[4-(3,4-dihydro-2H-1-benzopyran-6-yl)-2-methyl-5-(1-methyl-6-oxo-1,6-dihydropyridin-3-yl)thiophen-3-yl]acetate (19a) (90 mg, 0.16 mmol, 45%) after purification by flash chromatography on silica gel (cyclohexane/ethyl acetate 30/70).

MS m/z ([M+H]$^+$) 496.

Step 2: preparation of 2-(tert-butoxy)-2-[4-(3,4-dihydro-2H-1-benzopyran-6-yl)-2-methyl-5-(1-methyl-6-oxo-1,6-dihydropyridin-3-yl)thiophen-3-yl]]acetic acid (example 19)

Using the procedure described in example 15, step 2, ethyl 2-(tert-butoxy)-2-[4-(3,4-dihydro-2H-1-benzopyran-6-yl)-2-methyl-5-(1-methyl-6-oxo-1,6-dihydropyridin-3-yl)-thiophen-3-yl]acetate (19a) (90 mg, 0.18 mmol) is converted into 2-(tert-butoxy)-2-[4-(3,4-dihydro-2H-1-benzopyran-6-yl)-2-methyl-5-(1-methyl-6-oxo-1,6-dihydropyridin-3-yl)thiophen-3-yl]]acetic acid (example 19) (80 mg, 0.25 mmol, 94%) without further purification.

$^1$H NMR (400 MHz, DMSO-d$_6$) δ 0.91 (s, 9H), 1.87-1.95 (m, 2H), 2.47 (s, 3H), 2.63-2.73 (m, 2H), 3.36 (s, 3H), 4.15 (t, J=5.1 Hz, 2H), 4.74 (s, 1H), 6.20 (d, J=9.4 Hz, 1H), 6.74 (d, J=8.3 Hz, 1H), 6.93 (dd, J=2.6 Hz, J=9.4 Hz, 1H), 6.95-7.07 (m, 2H), 7.65 (d, J=2.6 Hz, 1H), 12.59 (bs, 1H).

MS m/z ([M−H]$^−$) 466.

Example 20

Synthesis of 2-(tert-butoxy)-2-[4-(3,4-dihydro-2H-1-benzopyran-6-yl)-2-methyl-5-(thiophen-3-yl)thiophen-3-yl]acetic acid

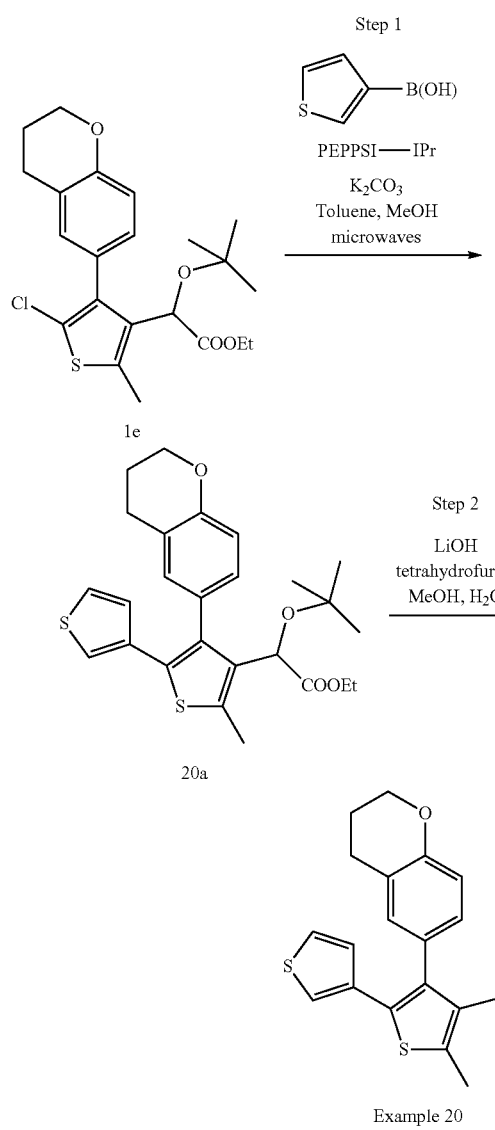

Step 1: preparation of intermediate ethyl 2-(tert-butoxy)-2-[4-(3,4-dihydro-2H-1-benzopyran-6-yl)-2-methyl-5-(thiophen-3-yl)thiophen-3-yl]acetate (20a)

Using the procedure described in example 14, step 1, ethyl 2-(tert-butoxy)-2-[5-chloro-4-(3,4-dihydro-2H-1-benzopyran-6-yl)-2-methylthiophen-3-yl]acetate (1e) (115 mg, 0.27 mmol) is converted by reaction with 3-thienylboronic acid (70 mg, 0.54 mmol) into ethyl 2-(tert-butoxy)-2-[4-(3,4-dihydro-2H-1-benzopyran-6-yl)-2-methyl-5-(thiophen-3-yl)thiophen-3-yl]acetate (20a) (35 mg, 0.073 mmol, 27%) after purification by flash chromatography on silica gel (cyclohexane/ethyl acetate 97/3).

MS m/z ([M+Na]$^+$) 493.

Step 2: preparation of 2-(tert-butoxy)-2-[4-(3,4-dihydro-2H-1-benzopyran-6-yl)-2-methyl-5-(thiophen-3-yl)thiophen-3-yl]acetic acid (example 20)

Using the procedure described in example 15, step 2, ethyl 2-(tert-butoxy)-2-[4-(3,4-dihydro-2H-1-benzopyran-6-yl)-2-methyl-5-(thiophen-3-yl)thiophen-3-yl]acetate (20a) (35 mg, 0.073 mmol) is converted into 2-(tert-butoxy)-2-[4-(3,4-dihydro-2H-1-benzopyran-6-yl)-2-methyl-5-(thiophen-3-yl)thiophen-3-yl]acetic acid (example 20) (28 mg, 0.066 mmol, 90%) without further purification.

$^1$H NMR (400 MHz, DMSO-d$_6$) δ 0.94 (s, 9H), 1.88-1.98 (m, 2H), 2.46 (s, 3H), 2.66-2.73 (m, 2H), 4.17 (t, J=5.1 Hz, 2H), 4.67 (s, 1H), 6.67 (dd, J=1.1 Hz, J=5.0 Hz, 1H), 6.76 (d, J=8.2 Hz, 1H), 6.84-7.02 (m, 2H), 7.09 (dd, J=1.1 Hz, J=2.8 Hz, 1H), 7.42 (dd, J=2.8 Hz, J=5.0 Hz, 1H), 12.52 (bs, 1H).

MS m/z ([M−H]$^−$) 441.

Example 21

Synthesis of 2-(tert-butoxy)-2-[4-(3,4-dihydro-2H-1-benzopyran-6-yl)-5-[4-(acetamidomethyl)phenyl]-2-methylthiophen-3-yl]acetic acid

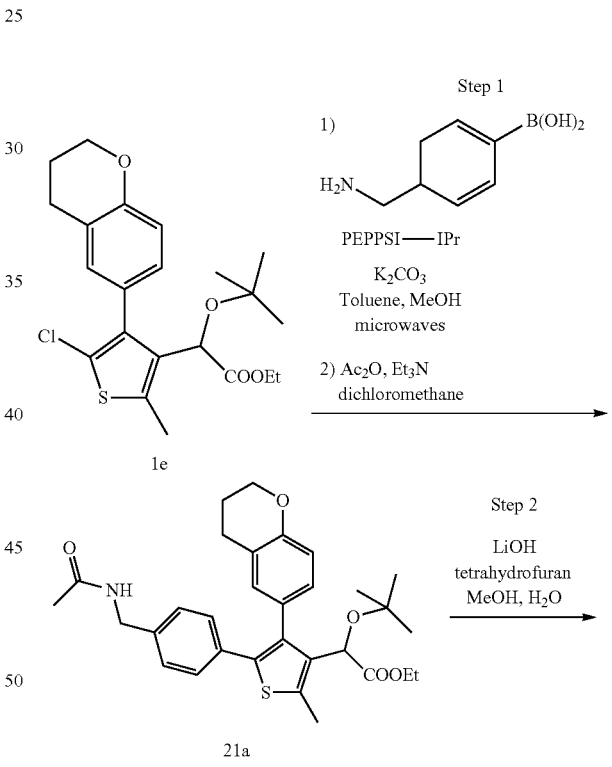

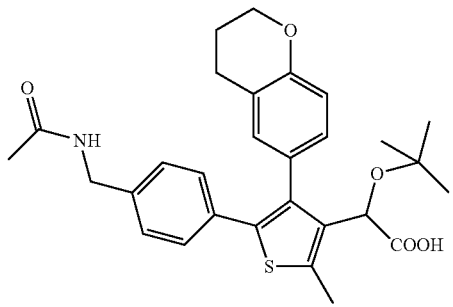

Example 21

Step 1: preparation of intermediate ethyl 2-(tert-butoxy)-2-[4-(3,4-dihydro-2H-1-benzopyran-6-yl)-5-[4-(acetamidomethyl)phenyl]-2-methylthiophen-3-yl]acetate (21a)

In a specific micro-wave vial, a solution of ethyl 2-(tert-butoxy)-2-[5-chloro-4-(3,4-dihydro-2H-1-benzopyran-6-yl)-2-methylthiophen-3-yl]acetate (1e) (100 mg, 0.24 mmol), 4-(aminomethyl)phenylboronic acid (133 mg, 0.48 mmol), potassium carbonate (196 mg, 1.42 mmol) were dissolved in a mixture of toluene (1.5 mL) and methanol (1.5 mL). The solution was degassed under argon for 5 minutes and [1,3-bis(2,6-diisopropylphenyl)imidazol-2-ylidene](3-chloropyridyl)palladium(II) dichloride (PEPPSI-IPr, 16 mg, 0.024 mmol) was added. The reaction was then heated under micro-wave at 120° C. for 15 minutes. The reaction mixture was filtered through Celite® and the filtrate was concentrated under reduced pressure. The residue was diluted with dichloromethane (10 mL). Triethylamine (0.5 mL) and acetic anhydride (0.5 mL) were added and the middle was stirred at room temperature for 20 hours. The mixture was concentrated and the crude material was purified by flash chromatography on silica gel (cyclohexane/ethyl acetate 50/50) to give ethyl 2-(tert-butoxy)-2-[4-(3,4-dihydro-2H-1-benzopyran-6-yl)-5-[4-(acetamidomethyl)phenyl]-2-methylthiophen-3-yl]acetate (21a) (94 mg, 0.17 mmol, 74%).

MS m/z ([M+H]$^+$) 536.

Step 2: preparation of 2-(tert-butoxy)-2-[4-(3,4-dihydro-2H-1-benzopyran-6-yl)-5-[4-(acetamidomethyl)phenyl]-2-methylthiophen-3-yl]acetic acid (example 21)

Using the procedure described in example 15, step 2, ethyl 2-(tert-butoxy)-2-[4-(3,4-dihydro-2H-1-benzopyran-6-yl)-5-[4-(acetamidomethyl)phenyl]-2-methylthiophen-3-yl]acetate (21a) (94 mg, 0.17 mmol) is converted into 2-(tert-butoxy)-2-[4-(3,4-dihydro-2H-1-benzopyran-6-yl)-5-[4-(acetamidomethyl)phenyl]-2-methylthiophen-3-yl]acetic acid (example 21) (31 mg, 0.06 mmol, 35%) after a purification by flash chromatography on silica gel (dichloromethane/methanol 95/5).

$^1$H NMR (400 MHz, DMSO-d$_6$) δ 0.90 (s, 9H), 1.84 (s, 3H), 1.87-1.95 (m, 2H), 2.49 (s, 3H), 2.62-2.72 (m, 2H), 4.11-4.21 (m, 4H), 4.68 (s, 1H), 6.64-6.73 (m, 1H), 6.75-7.01 (m, 2H), 7.05 (d, J=8.4 Hz, 2H), 7.08 (d, J=8.4 Hz, 2H), 8.29 (t, J=8.4 Hz, 1H), 12.55 (bs, 1H).

MS m/z ([M−H]$^-$) 506.

Example 22

Synthesis of 2-(tert-butoxy)-2-[5-(4-carbamoylphenyl)-4-(3,4-dihydro-2H-1-benzopyran-6-yl)-2-methylthiophen-3-yl]acetic acid

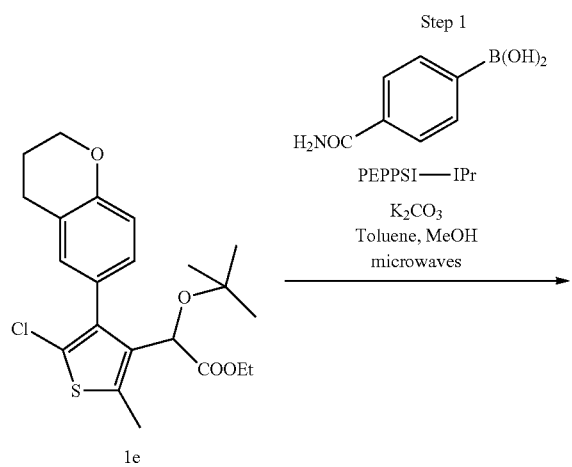
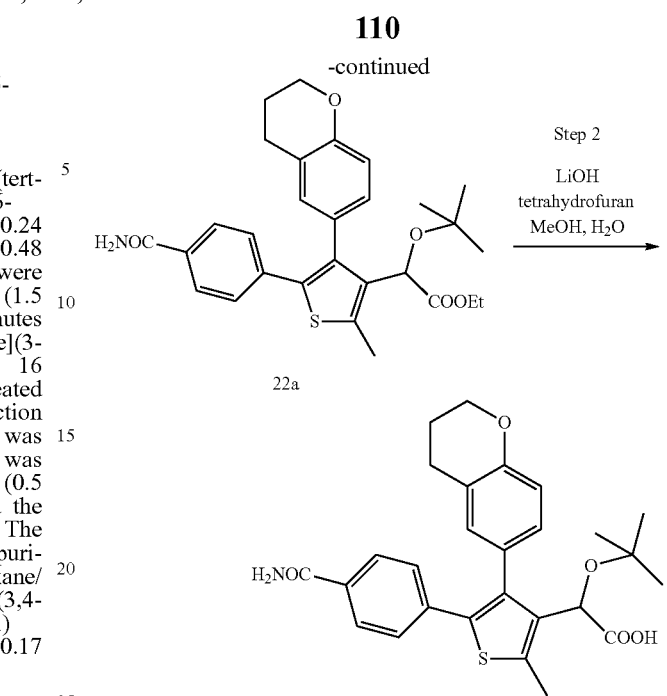

Example 22

Step 1: preparation of intermediate ethyl 2-(tert-butoxy)-2-[5-(4-carbamoylphenyl)-4-(3,4-dihydro-2H-1-benzopyran-6-yl)-2-methylthiophen-3-yl]acetate (22a)

Using the procedure described in example 14, step 1, ethyl 2-(tert-butoxy)-2-[5-chloro-4-(3,4-dihydro-2H-1-benzopyran-6-yl)-2-methylthiophen-3-yl]acetate (1e) (150 mg, 0.35 mmol) is converted by reaction with 4-carbamoylphenylboronic acid (116 mg, 0.70 mmol) into ethyl 2-(tert-butoxy)-2-[5-(4-carbamoylphenyl)-4-(3,4-dihydro-2H-1-benzopyran-6-yl)-2-methylthiophen-3-yl]acetate (22a) (126 mg, 0.25 mmol, 71%) after purification by flash chromatography on silica gel (cyclohexane/ethyl acetate 97/3).

MS m/z ([M+H]$^+$) 508.

Step 2: preparation of 2-(tert-butoxy)-2-[5-(4-carbamoylphenyl)-4-(3,4-dihydro-2H-1-benzopyran-6-yl)-2-methylthiophen-3-yl]acetic acid (example 22)

Using the procedure described in example 15, step 2, ethyl 2-(tert-butoxy)-2-[5-(4-carbamoylphenyl)-4-(3,4-dihydro-2H-1-benzopyran-6-yl)-2-methylthiophen-3-yl]acetate (22a) (147 mg, 0.29 mmol) is converted into 2-(tert-butoxy)-2-[5-(4-carbamoylphenyl)-4-(3,4-dihydro-2H-1-benzopyran-6-yl)-2-methylthiophen-3-yl]acetic acid (example 22) (70 mg, 0.15 mmol, 50%) after purification by flash chromatography on silica gel (cyclohexane/ethyl acetate 98/2).

$^1$H NMR (400 MHz, DMSO-d$_6$) δ 0.91 (s, 9H), 1.87-1.95 (m, 2H), 2.49 (s, 3H), 2.61-2.74 (m, 2H), 4.16 (t, J=4.8 Hz, 2H), 4.72 (s, 1H), 6.67-6.76 (m, 1H), 6.78-7.11 (m, 2H), 7.15 (d, J=8.4 Hz, 2H), 7.32 (s, 1H), 7.69 (d, J=8.4 Hz, 2H), 7.88 (s, 1H), 12.63 (bs, 1H).

MS m/z ([M−H]$^-$) 478.

Example 23

Synthesis of 2-(tert-butoxy)-2-[4-(3,4-dihydro-2H-1-benzopyran-6-yl)-2-methyl-5-(thiophen-2-yl)thiophen-3-yl]acetic acid

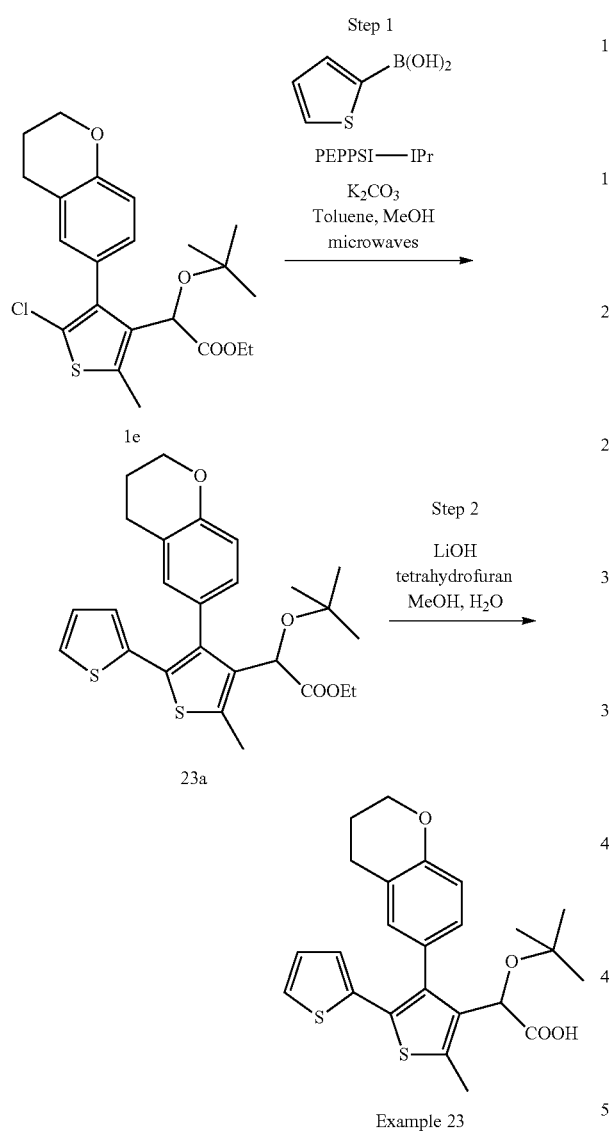

Step 1: preparation of intermediate ethyl 2-(tert-butoxy)-2-[4-(3,4-dihydro-2H-1-benzopyran-6-yl)-2-methyl-5-(thiophen-2-yl)thiophen-3-yl]acetate (20a)

Using the procedure described in example 14, step 1, ethyl 2-(tert-butoxy)-2-[5-chloro-4-(3,4-dihydro-2H-1-benzopyran-6-yl)-2-methylthiophen-3-yl]acetate (1e) (120 mg, 0.28 mmol) is converted by reaction with 2-thienylboronic acid (73 mg, 0.57 mmol) into ethyl 2-(tert-butoxy)-2-[4-(3,4-dihydro-2H-1-benzopyran-6-yl)-2-methyl-5-(thiophen-3-yl)thiophen-2-yl]acetate (23a) (43 mg, 0.092 mmol, 33%) after purification by flash chromatography on silica gel (cyclohexane/ethyl acetate 97/3).

MS m/z ([M+Na]⁺) 493.

Step 2: preparation of 2-(tert-butoxy)-2-[4-(3,4-dihydro-2H-1-benzopyran-6-yl)-2-methyl-5-(thiophen-3-yl)thiophen-2-yl]acetic acid (example 23)

Using the procedure described in example 15, step 2, ethyl 2-(tert-butoxy)-2-[4-(3,4-dihydro-2H-1-benzopyran-6-yl)-2-methyl-5-(thiophen-2-yl)thiophen-3-yl]acetate (23a) (43 mg, 0.092 mmol) is converted into 2-(tert-butoxy)-2-[4-(3,4-dihydro-2H-1-benzopyran-6-yl)-2-methyl-5-(thiophen-3-yl)thiophen-2-yl]acetic acid (example 23) (30 mg, 0.068 mmol, 73%) after purification by flash chromatography (dichloromethane/methanol 99/1).

$^1$H NMR (400 MHz, DMSO-$d_6$) δ 0.95 (s, 9H), 1.89-1.97 (m, 2H), 2.46 (s, 3H), 2.66-2.74 (m, 2H), 4.18 (t, J=5.2 Hz, 2H), 4.62 (s, 1H), 6.79 (d, J=8.2 Hz, 1H), 6.89 (dd, J=1.2 Hz, J=3.6 Hz, 1H), 6.91 (dd, J=3.6 Hz, J=5.0 Hz, 1H), 6.92-7.00 (m, 2H), 7.32 (dd, J=1.2 and 5.0 Hz, 1H), 12.54 (bs, 1H).
MS m/z ([M−H]⁻) 441.

Example 24

Synthesis of 2-(tert-butoxy)-2-[4-(4,4-dimethylcyclohex-1-en-1-yl)-2-methyl-5-(N-methylpyrazol-4-yl)thiophen-3-yl]acetic acid

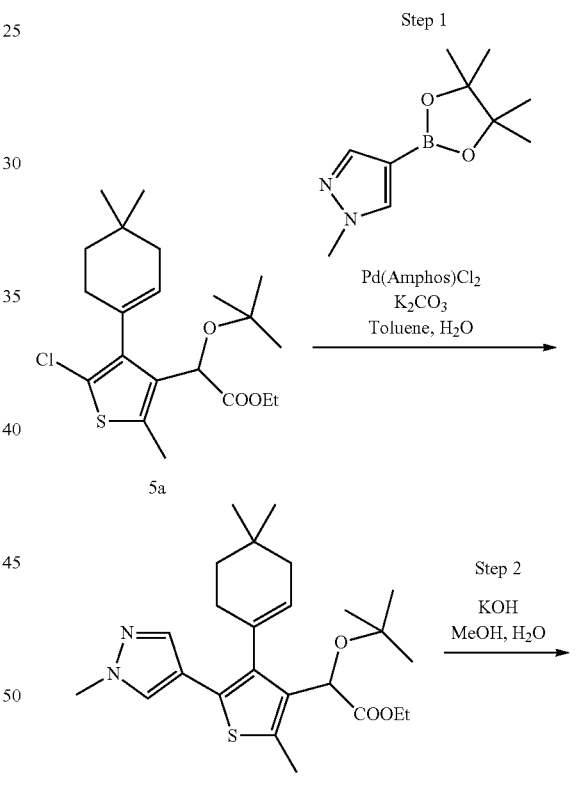

Step 1: preparation of intermediate ethyl 2-(tert-butoxy)-2-[4-(4,4-dimethylcyclohex-1-en-1-yl)-2-methyl-5-(N-methylpyrazol-4-yl)thiophen-3-yl]acetate (24a)

Using the procedure described in example 1, step 6, ethyl 2-(tert-butoxy)-2-[5-chloro-4-(4,4-dimethylcyclohex-1-en-1-yl)-2-methylthiophen-3-yl]acetate (5a) (200 mg, 0.501 mmol) is converted by reaction with N-methyl-4-pyrazole boronic acid pinacol ester (261 mg, 1.253 mmol) into ethyl 2-(tert-butoxy)-2-[4-(4,4-dimethylcyclohex-1-en-1-yl)-2-methyl-5-(N-methylpyrazol-4-yl)thiophen-3-yl]acetate (24a) (31 mg, 0.070 mmol, 14%) after purification by preparative TLC (cyclohexane/ethyl acetate 70/30).

$^1$H NMR (400 MHz, CDCl$_3$) δ 1.01 (s, 3H), 1.04 (s, 3H), 1.18 (s, 9H), 1.20 (t, J=7.2 Hz, 3H), 1.40-1.50 (m, 4H), 1.93-2.01 (m, 2H), 2.54 (s, 3H), 3.87 (s, 3H), 4.02-4.19 (m, 2H), 5.04 (s, 1H), 5.59-5.68 (m, 1H), 7.40 (s, 1H), 7.56 (s, 1H).

MS m/z ([M+H]$^+$) 445.

Step 2: preparation of 2-(tert-butoxy)-2-[4-(4,4-dimethylcyclohex-1-en-1-yl)-2-methyl-5-(N-methylpyrazol-4-yl)thiophen-3-yl]acetic acid (example 24)

Using the procedure described in example 3, step 2, ethyl 2-(tert-butoxy)-2-[4-(4,4-dimethylcyclohex-1-en-1-yl)-2-methyl-5-(N-methylpyrazol-4-yl)thiophen-3-yl]acetate (24a) (31 mg, 0.070 mmol) is converted into 2-(tert-butoxy)-2-[4-(4,4-dimethylcyclohex-1-en-1-yl)-2-methyl-5-(N-methylpyrazol-4-yl)thiophen-3-yl]acetic acid (example 24) (24 mg, 0.058 mmol, 83%) after purification by preparative TLC (dichloromethane/methanol 90/10).

$^1$H NMR (400 MHz, CDCl$_3$) δ 0.97 (s, 3H), 0.99 (s, 3H), 1.22 (s, 9H), 1.24-1.25 (m, 2H), 1.35-1.46 (m, 2H), 1.88-2.02 (m, 2H), 2.46 (s, 3H), 3.87 (s, 3H), 5.09 (s, 1H), 5.51-5.81 (m, 1H), 7.40 (s, 1H), 7.55 (s, 1H).

MS m/z ([M−H]$^−$) 415.

Example 25

Synthesis of 2-(tert-butoxy)-2-[4-(4,4-dimethylcyclohex-1-en-1-yl)-2-methyl-5-(pyrimidin-5-yl)thiophen-3-yl]acetic acid

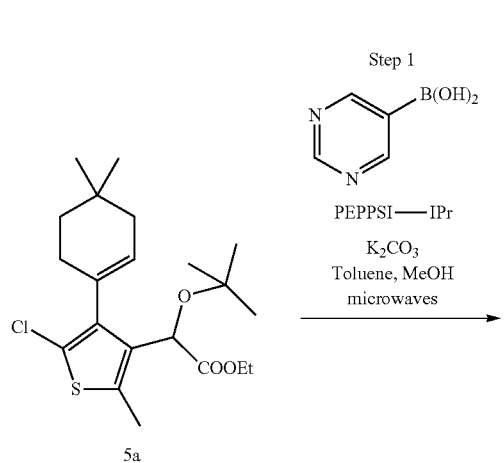

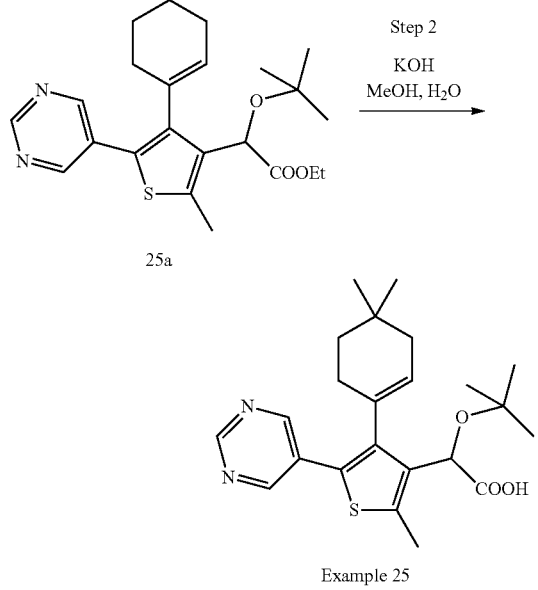

Step 1: preparation of intermediate ethyl 2-(tert-butoxy)-2-[4-(4,4-dimethylcyclohex-1-en-1-yl)-2-methyl-5-(pyrimidin-5-yl)thiophen-3-yl]acetate (25a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (196 mg, 0.491 mmol) is converted by reaction with 5-pyrimidylboronic acid (122 mg, 0.982 mmol) into ethyl 2-(tert-butoxy)-2-[4-(4,4-dimethylcyclohex-1-en-1-yl)-2-methyl-5-(pyrimidin-5-yl)thiophen-3-yl]acetate (25a) (74 mg, 0.167 mmol, 34%) after purification by preparative TLC (cyclohexane/ethyl acetate 70/30).

$^1$H NMR (400 MHz, CDCl$_3$) δ 0.96 (s, 3H), 0.99 (s, 3H), 1.19 (s, 9H), 1.22 (t, J=7.2 Hz, 3H), 1.38-1.45 (m, 2H), 1.77-2.06 (m, 4H), 2.62 (s, 3H), 4.05-4.22 (m, 2H), 5.08 (s, 1H), 5.64-5.80 (m, 1H), 8.83 (d, J=6.0 Hz, 2H), 9.05 (d, J=5.6 Hz, 1H).

MS m/z ([M+H]$^+$) 443.

Step 2: preparation of 2-(tert-butoxy)-2-[4-(4,4-dimethylcyclohex-1-en-1-yl)-2-methyl-5-(pyrimidin-5-yl)thiophen-3-yl]acetic acid (example 25)

Using the procedure described in example 3, step 2, ethyl 2-(tert-butoxy)-2-[4-(4,4-dimethylcyclohex-1-en-1-yl)-2-methyl-5-(pyrimidin-5-yl)thiophen-3-yl]acetate (25a) (69 mg, 0.156 mmol) is converted into 2-(tert-butoxy)-2-[4-(4,4-dimethylcyclohex-1-en-1-yl)-2-methyl-5-(pyrimidin-5-yl)thiophen-3-yl]acetic acid (example 25) (49 mg, 0.118 mmol, 76%) after purification by preparative TLC (dichloromethane/methanol 90/10).

$^1$H NMR (400 MHz, CDCl$_3$) δ 0.91 (s, 3H), 0.94 (s, 3H), 1.21 (s, 9H), 1.31-1.44 (m, 2H), 1.77-2.03 (m, 4H), 2.54 (s, 3H), 5.13 (s, 1H), 5.74-5.80 (m, 1H), 8.83 (bs, 2H), 9.06 (bs, 1H).

MS m/z ([M−H]$^−$) 413.

Example 26

Synthesis of 2-(tert-butoxy)-2-{2-methyl-4-[4-(propan-2-yl)cyclohex-1-en-1-yl]-5-(N-methylpyrazol-4-yl)thiophen-3-yl}acetic acid

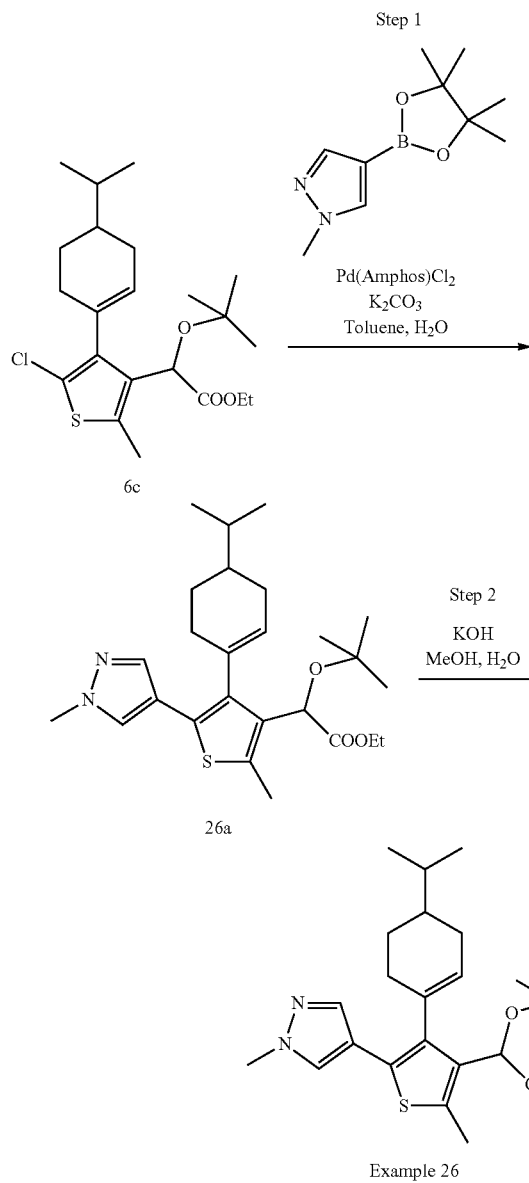

Example 26

Step 1: preparation of intermediate ethyl 2-(tert-butoxy)-2-{2-methyl-4-[4-(propan-2-yl)cyclohex-1-en-1-yl]-5-(N-methylpyrazol-4-yl)thiophen-3-yl}acetate (26a)

Using the procedure described in example 1, step 6, ethyl 2-(tert-butoxy)-2-{5-chloro-2-methyl-4-[4-(propan-2-yl)cyclohex-1-en-1-yl]thiophen-3-yl}acetate (6c) (277 mg, 0.671 mmol) is converted by reaction with N-methyl-4-pyrazole boronic acid pinacol ester (349 mg, 1.677 mmol) into ethyl 2-(tert-butoxy)-2-{2-methyl-4-[4-(propan-2-yl)cyclohex-1-en-1-yl]-5-(N-methylpyrazol-4-yl)thiophen-3-yl}acetate (26a) (18 mg, 0.039 mmol, 6%) after purification by preparative TLC (cyclohexane/ethyl acetate 60/40).

$^1$H NMR (400 MHz, CDCl$_3$) δ 0.93 (s, 3H), 0.94 (s, 3H), 1.18 (s, 9H), 1.19-1.24 (m, 5H), 1.51-1.58 (m, 2H), 1.82-2.04 (m, 4H), 2.51 (s, 3H), 3.87 (s, 3H), 4.05-4.17 (m, 2H), 5.03 (s, 1H), 5.66-5.79 (m, 1H), 7.41 (d, J=4.4 Hz, 1H), 7.58 (d, J=6.0 Hz, 1H).
MS m/z ([M+H]$^+$) 459.

Step 2: preparation of 2-(tert-butoxy)-2-{2-methyl-4-[4-(propan-2-yl)cyclohex-1-en-1-yl]-5-(N-methylpyrazol-4-yl)thiophen-3-yl}acetic acid (example 26)

Using the procedure described in example 3, step 2, ethyl 2-(tert-butoxy)-2-{2-methyl-4-[4-(propan-2-yl)cyclohex-1-en-1-yl]-5-(N-methylpyrazol-4-yl)thiophen-3-yl}acetate (26a) (18 mg, 0.039 mmol) is converted into 2-(tert-butoxy)-2-{2-methyl-4-[4-(propan-2-yl)cyclohex-1-en-1-yl]-5-(N-methylpyrazol-4-yl)thiophen-3-yl}acetic acid (example 26) (14 mg, 0.033 mmol, 83% yield) after purification by preparative TLC (dichloromethane/methanol 90/10).

$^1$H NMR (400 MHz, CDCl$_3$) δ 0.92 (s, 3H), 0.93 (s, 3H), 1.24 (s, 9H), 1.25-1.26 (m, 2H), 1.48-1.56 (m, 2H), 1.82-1.94 (m, 2H), 2.21-2.28 (m, 2H), 2.44 (d, J=1.6 Hz, 3H), 3.89 (s, 3H), 5.10 (s, 1H), 5.58-5.96 (m, 1H), 7.42 (d, J=4.8 Hz, 1H), 7.59 (d, J=6.8 Hz, 1H).
MS m/z ([M-H]$^-$) 429.

Example 27

Synthesis of 2-(tert-butoxy)-2-[5-(4-carbamoylphenyl)-4-(4,4-dimethylcyclohex-1-en-1-yl)-2-methylthiophen-3-yl]acetic acid

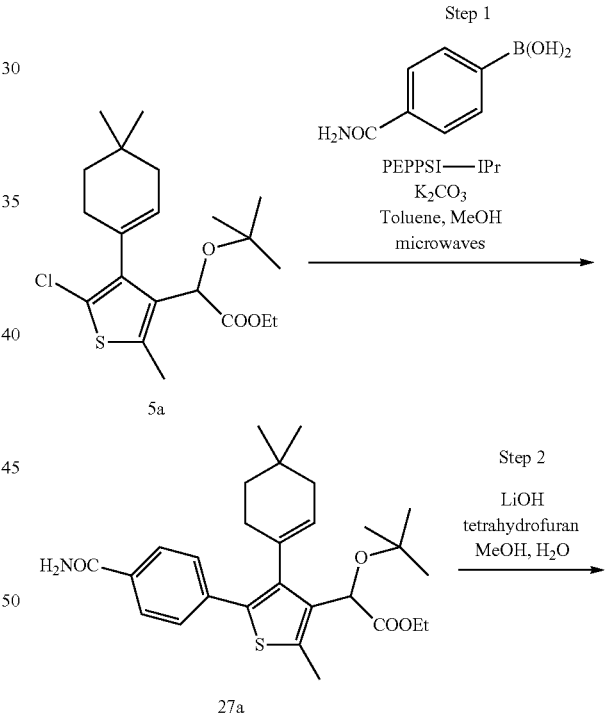

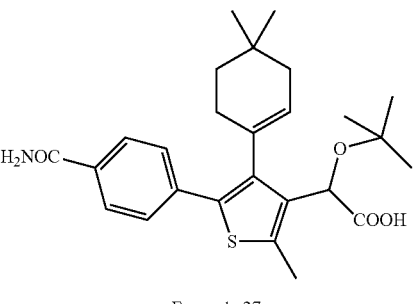

Example 27

Step 1: preparation of intermediate ethyl 2-(tert-butoxy)-2-[5-(4-carbamoylphenyl)-4-(4,4-dimethyl-cyclohex-1-en-1-yl)-2-methylthiophen-3-yl]acetate (27a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (102 mg, 0.256 mmol) is converted by reaction with 4-carbamoylphenylboronic acid (85 mg, 0.501 mmol) into ethyl 2-(tert-butoxy)-2-[5-(4-carbamoylphenyl)-4-(4,4-dimethylcyclohex-1-en-1-yl)-2-methylthiophen-3-yl]acetate (27a) (51 mg, 0.105 mmol, 41%) after purification by preparative TLC (cyclohexane/ethyl acetate 50/50).

$^1$H NMR (400 MHz, CDCl$_3$) δ 0.98 (s, 3H), 1.01 (s, 3H), 1.20 (s, 9H), 1.22 (t, J=7.2 Hz, 3H), 1.35-1.39 (m, 2H), 1.85-2.00 (m, 4H), 2.60 (s, 3H), 4.05-4.21 (m, 2H), 5.12 (s, 1H), 5.68-5.78 (m, 1H), 7.60 (dd, J=2.0 Hz, J=8.4 Hz, 2H), 7.75 (dd, J=2.0 Hz, J=8.8 Hz, 2H).

MS m/z ([M+H]$^+$) 484.

Step 2: preparation of 2-(tert-butoxy)-2-[5-(4-carbamoylphenyl)-4-(4,4-dimethylcyclohex-1-en-1-yl)-2-methylthiophen-3-yl]acetic acid (Example 27)

Using the procedure described in example 15, step 2, ethyl 2-(tert-butoxy)-2-[5-(4-carbamoylphenyl)-4-(4,4-dimethylcyclohex-1-en-1-yl)-2-methylthiophen-3-yl]acetate (27a) (51 mg, 0.105 mmol) is converted into 2-(tert-butoxy)-2-[5-(4-carbamoylphenyl)-4-(4,4-dimethyl cyclohex-1-en-1-yl)-2-methylthiophen-3-yl]acetic acid (example 27) (38 mg, 0.083 mmol, 79%) after purification by preparative TLC (dichloromethane/methanol 90/10).

$^1$H NMR (400 MHz, DMSO-d$_6$) δ 0.95 (s, 3H), 0.97 (s, 3H), 1.14 (s, 9H), 1.29-1.41 (m, 2H), 1.77-2.01 (m, 4H), 3.31 (s, 3H), 5.00 (s, 1H), 5.68 (bs, 1H), 7.34 (bs, 1H), 7.53 (dd, J=2.0 Hz, J=6.8 Hz, 2H), 7.85 (dd, J=2.0 Hz, J=6.8 Hz, 2H), 7.95 (bs, 1H), 12.50 (bs, 1H).

MS m/z ([M−H]$^−$) 454.

Example 28

Synthesis of 2-(tert-butoxy)-2-[2-methyl-4-(4,4-difluorocyclohex-1-en-1-yl)-5-(pyridin-4-yl)thiophen-3-yl]acetic acid Step 1

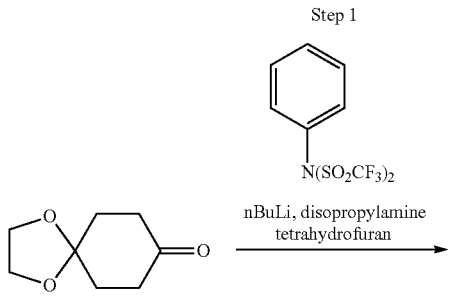

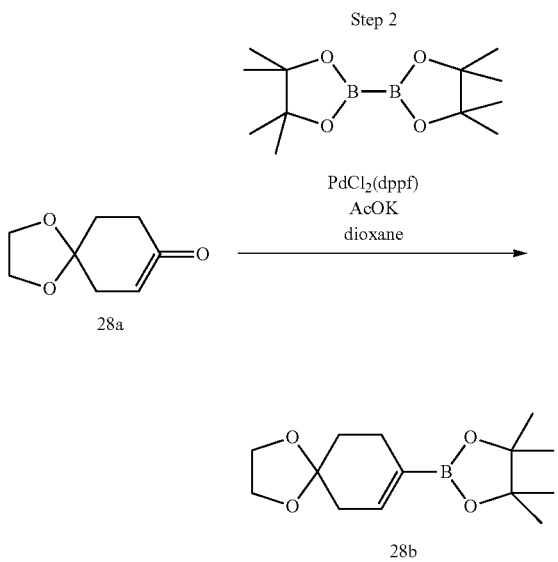

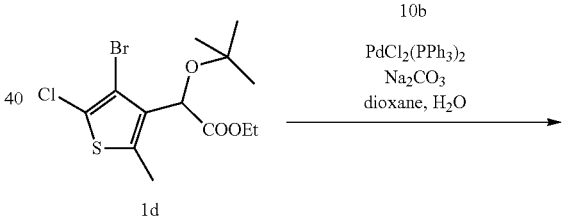

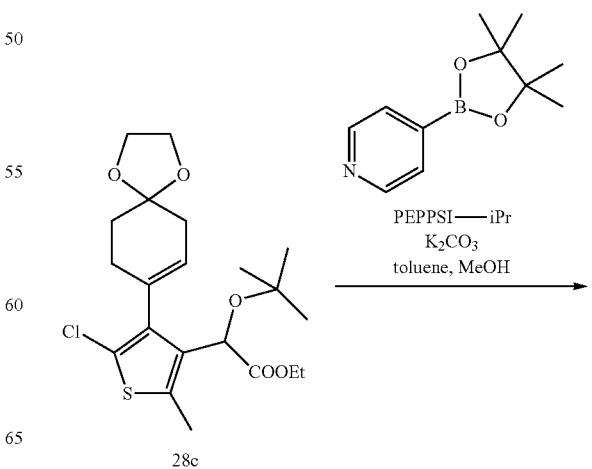

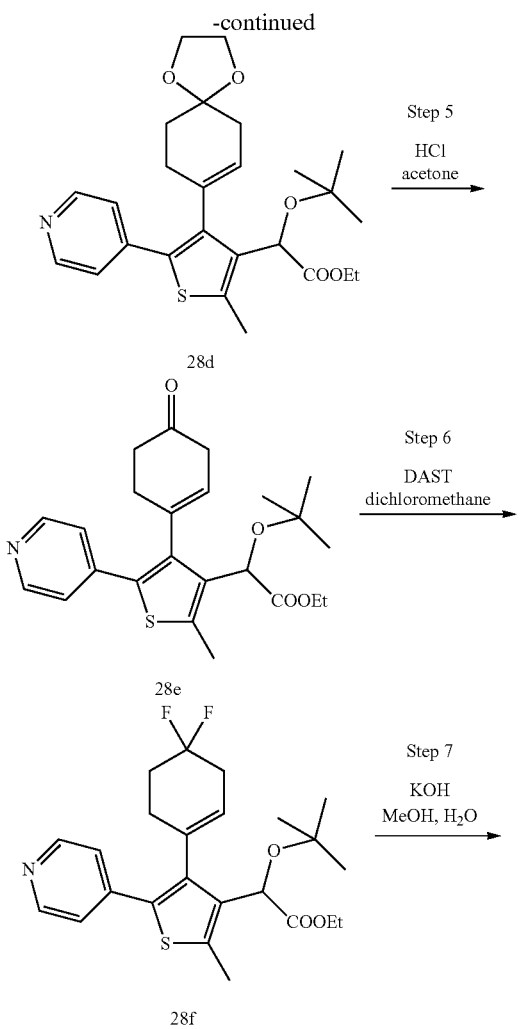

Example 28

Step 1: preparation of intermediate 1,4-dioxaspiro[4.5]dec-7-en-8-yl trifluoromethanesulfonate (28a)

Using the procedure described in example 6, step 1, 1,4-cyclohexanedione monoethylene acetal (1.21 g, 7.45 mmol) is converted by reaction with N-phenyltrifluoromethanesulfonimide (3.50 g, 9.69 mmol) into 1,4-dioxaspiro[4.5]dec-7-en-8-yl trifluoromethanesulfonate (28a) (2.25 g, 7.45 mmol, 100%) after purification by flash chromatography on silica gel (cyclohexane/ethyl acetate 80/20).

$^1$H NMR (300 MHz, CDCl$_3$) δ 1.90 (dd, J=6.6 Hz, J=6.6 Hz, 2H), 2.39-2.42 (m, 2H), 2.51-2.57 (m, 2H), 3.98-4.00 (m, 4H), 5.64-5.68 (m, 1H).

Step 2: preparation of intermediate 8-(4,4,5,5-tetramethyl-1,3,2-dioxoborolan-2-yl)-1,4-dioxaspiro[4.5]dec-7-ene (28b)

Using the procedure described in example 6, step 2, 1,4-dioxaspiro[4.5]dec-7-en-8-yl trifluoromethanesulfonate (28a) (2.25 g, 7.45 mmol) is converted by reaction with bis(pinacolto)diboron (2.87 g, 11.18 mmol) into 8-(4,4,5,5-tetramethyl-1,3,2-dioxoborolan-2-yl)-1,4-dioxaspiro[4.5]dec-7-ene (28b) (2.05 g, 7.34 mmol, 99%) after purification by flash chromatography on silica gel (cyclohexane/ethyl acetate 80/20).

$^1$H NMR (400 MHz, CDCl$_3$) δ 1.24 (s, 6H), 1.25 (s, 6H), 1.73 (dd, J=6.4 Hz, J=6.4 Hz, 2H), 2.35-2.39 (m, 4H), 3.99 (s, 4H), 6.45-6.47 (m, 1H).

Step 3: preparation of intermediate ethyl 2-(tert-butoxy)-2-[5-chloro-2-methyl-4-(1,4-dioxaspiro[4.5]dec-7-en-1-yl)thiophen-3-yl]acetate (28c)

Using the procedure described in example 1, step 5, ethyl 2-(4-bromo-5-chloro-2-methylthiophen-3-yl)-2-(tert-butoxy)acetate (1d) (500 mg, 1.35 mmol) is converted by reaction with 8-(4,4,5,5-tetramethyl-1,3,2-dioxoborolan-2-yl)-1,4-dioxaspiro[4.5]dec-7-ene (28b) (432 mg, 1.62 mmol) into ethyl 2-(tert-butoxy)-2-[5-chloro-2-methyl-4-(1,4-dioxaspiro[4.5]dec-7-en-1-yl)thiophen-3-yl]acetate (28c) (342 mg, 0.80 mmol, 58%) after purification by flash chromatography on silica gel (cyclohexane/ethyl acetate 80/20).

$^1$H NMR (400 MHz, CDCl$_3$) δ 1.17 (s, 9H), 1.21 (t, J=7.2 Hz, 3H), 1.71-1.75 (m, 1H), 1.85-1.94 (m, 2H), 2.35-2.44 (m, 3H), 2.46 (s, 3H), 4.00-4.03 (m, 4H), 4.07-4.17 (m, 2H), 5.00 (s, 1H), 5.55-5.61 (bs, 1H).

MS m/z ([M+H-O$^t$Bu]$^+$) 455.

Step 4: preparation of intermediate ethyl 2-(tert-butoxy)-2-[2-methyl-4-(1,4-dioxaspiro[4.5]dec-7-en-1-yl)-5-(pyridin-4-yl)thiophen-3-yl]acetate (28d)

Using the procedure described in example 1, step 6, ethyl 2-(tert-butoxy)-2-[5-chloro-2-methyl-4-(1,4-dioxaspiro[4.5]dec-7-en-1-yl)thiophen-3-yl]acetate (28c) (381 mg, 0.89 mmol) is converted by reaction with 4-pyridine boronic acid pinacol ester (376 mg, 1.78 mmol) into ethyl 2-(tert-butoxy)-2-[2-methyl-4-(1,4-dioxaspiro[4.5]dec-7-en-1-yl)-5-(pyridin-4-yl)thiophen-3-yl]acetate (28d) (71 mg, 0.15 mmol, 17%) after purification by flash chromatography on silica gel (cyclohexane/ethyl acetate 70/30 to 0/100).

$^1$H NMR (400 MHz, CDCl$_3$) δ 1.18-1.26 (m, 12H), 1.85-1.94 (m, 2H), 2.35-2.44 (m, 4H), 2.55 (s, 3H), 3.94-4.03 (m, 4H), 4.05-4.21 (m, 2H), 5.08 (s, 1H), 5.47-5.87 (bs, 1H), 7.46 (dd, J=1.6 Hz, J=4.8 Hz, 2H), 8.44 (d, J=4.8 Hz, 2H).

MS m/z ([M+H]$^+$) 472.

Step 5: preparation of ethyl 2-(tert-butoxy)-2-[4-(oxo-cyclohexen-1-yl)-2-methyl-5-(pyridin-4-yl)thiophen-3-yl]acetate (28e)

Aqueous hydrogen chloride solution (1.0M) (4.71 mL, 4.71 mmol) was added to a solution of ethyl 2-(tert-butoxy)-

2-[2-methyl-4-(1,4-dioxaspiro[4.5]dec-7-en-1-yl)-5-(pyridin-4-yl)thiophen-3-yl]acetate (28d) (222 mg, 0.47 mmol) in acetone (5.0 mL). The reaction mixture was stirred at room temperature for 5 hours before the reaction was neutralized with sodium hydrogenocarbonate until pH 7. The mixture was extracted with ethyl acetate twice. The organic layer was washed with brine, dried over sodium sulfate, filtered and concentrated in vacuo. The residue was purified by preparative TLC (ethyl acetate) to give ethyl 2-(tert-butoxy)-2-[4-(oxo-cyclohexen-1-yl)-2-methyl-5-(pyridin-4-yl)thiophen-3-yl]acetate (28e) (127 mg, 0.30 mmol, 63%).

$^1$H NMR (400 MHz, CDCl$_3$) δ 1.19 (s, 9H), 1.22 (t, J=7.2 Hz, 3H), 1.22-1.23 (m, 2H), 2.38-2.53 (m, 2H), 2.59 (s, 3H), 3.02-3.07 (m, 2H), 4.06-4.20 (m, 2H), 5.07 (s, 1H), 5.75-5.91 (bs, 1H), 7.38 (dd, J=1.6 Hz, J=4.4 Hz, 2H), 8.52 (dd, J=1.6 Hz, J=4.4 Hz, 2H).

MS m/z ([M+H]$^+$) 428.

Step 6: preparation of ethyl 2-(tert-butoxy)-2-[4-(4,4-difluorocyclohex-1-en-1-yl)-2-methyl-5-(pyridin-4-yl)thiophen-3-yl]acetate (28f)

At −78° C., (diethylamino)sulfur trifluoride (DAST) (250 μL, 1.65 mmol) was added to a solution of ethyl 2-(tert-butoxy)-2-[4-(oxo-cyclohexen-1-yl)-2-methyl-5-(pyridin-4-yl)thiophen-3-yl]acetate (28e) (141 mg, 0.33 mmol) in dichloromethane (3.5 mL). The reaction mixture was stirred at room temperature for 4 hours before the reaction was diluted with dichloromethane and washed with aqueous sodium hydrogenocarbonate (4%), water and then brine, dried over sodium sulfate, filtered and concentrated in vacuo. The residue was purified by preparative TLC (cyclohexane/ethyl acetate 50/50) to give ethyl 2-(tert-butoxy)-2-[4-(4,4-difluorocyclohex-1-en-1-yl)-2-methyl-5-(pyridin-4-yl)thiophen-3-yl]acetate (28f) (42 mg, 0.09 mmol, 28%).

$^1$H NMR (300 MHz, CDCl$_3$) δ 1.19 (s, 9H), 1.22 (t, J=7.2 Hz, 3H), 2.02-2.15 (m, 2H), 2.22-2.34 (m, 2H), 2.59 (s, 3H), 2.67-2.76 (m, 2H), 4.05-4.23 (m, 2H), 5.05 (s, 1H), 5.47-5.86 (bs, 1H), 7.39 (dd, J=1.5 Hz, J=4.5 Hz, 2H), 8.52 (d, J=4.5 Hz, 2H).

MS m/z ([M+H]$^+$) 450.

Step 7: preparation of 2-(tert-butoxy)-2-[2-methyl-4-(4,4-difluorocyclohex-1-en-1-yl)-5-(pyridin-4-yl)thiophen-3-yl]acetic acid (example 28)

Using the procedure described in example 3, step 2, ethyl 2-(tert-butoxy)-2-[4-(4,4-difluorocyclohex-1-en-1-yl)-2-methyl-5-(pyridin-4-yl)thiophen-3-yl]acetate (28f) (42 mg, 0.093 mmol) is converted into 2-(tert-butoxy)-2-[2-methyl-4-(4,4-difluorocyclohex-1-en-1-yl)-5-(pyridin-4-yl)thiophen-3-yl]acetic acid (example 28) (37 mg, 0.088 mmol, 93%) as a white solid after purification by preparative TLC (dichloromethane/methanol 95/5).

$^1$H NMR (400 MHz, CDCl$_3$) δ 1.13 (s, 9H), 2.11-2.24 (m, 2H), 2.50 (s, 3H), 2.42-2.59 (m, 2H), 2.65-2.84 (m, 2H), 4.99 (s, 1H), 5.24-5.80 (bs, 1H), 7.45 (dd, J=1.5 Hz, J=4.5 Hz, 2H), 8.53 (dd, J=1.5 Hz, J=4.5 Hz, 2H), 12.61 (bs, 1H).

$^{19}$F NMR (282 MHz, DMSO-d$_6$): δ −94.7 (s, 2F).

MS m/z ([M+H]$^+$) 422.

MS m/z ([M−H]$^-$) 420.

Example 29

Synthesis of 2-(tert-butoxy)-2-[4-(4,4-dimethylcyclohex-1-en-1-yl)-2-methyl-5-(N-methyl-4-aminocarbonylphenyl)thiophen-3-yl]acetic acid

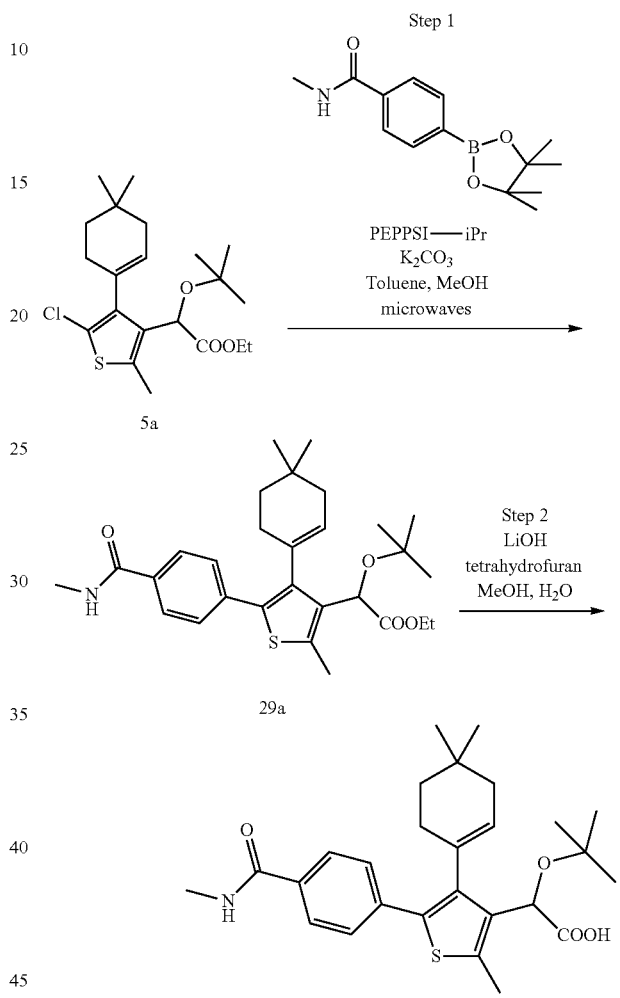

Example 29

Step 1: preparation of intermediate ethyl 2-(tert-butoxy)-2-[4-(4,4-dimethylcyclohex-1-en-1-yl)-2-methyl-5-(N-methyl-4-aminocarbonylphenyl)thiophen-3-yl]acetate (29a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (172 mg, 0.431 mmol) is converted by reaction with N-Methyl-(aminocarbonylphenyl)boronic acid pinacol ester (230 mg, 0.862 mmol) into ethyl 2-(tert-butoxy)-2-[4-(4,4-dimethylcyclohex-1-en-1-yl)-2-methyl-5-(N-methyl-4-aminocarbonylphenyl)thiophen-3-yl]acetate (29a) (21 mg, 0.042 mmol, 10%) after purification by preparative TLC (cyclohexane/ethyl acetate 50/50).

$^1$H NMR (400 MHz, CDCl$_3$) δ 0.97 (s, 3H), 1.00 (s, 3H), 1.19 (s, 9H), 1.22 (t, J=7.2 Hz, 3H), 1.31-1.42 (m, 2H), 1.80-2.02 (m, 4H), 2.59 (s, 3H), 3.01 (d, J=4.8 Hz, 3H), 4.04-4.21 (m, 2H), 5.12 (s, 1H), 5.62-5.80 (m, 1H), 6.15 (d, J=4.4 Hz, 1H), 7.57 (d, J=8.0 Hz, 2H), 7.70 (d, J=8.0 Hz, 2H).

MS m/z ([M+H]⁺) 498.

Step 2: preparation of 2-(tert-butoxy)-2-[4-(4,4-dimethylcyclohex-1-en-1-yl)-2-methyl-5-(N-methyl-4-aminocarbonylphenyl)thiophen-3-yl]acetic acid (example 29)

Using the procedure described in example 15, step 2, ethyl 2-(tert-butoxy)-2-[4-(4,4-dimethylcyclohex-1-en-1-yl)-2-methyl-5-(N-methyl-4-aminocarbonylphenyl)thiophen-3-yl]acetate (29a) (21 mg, 0.042 mmol) is converted into 2-(tert-butoxy)-2-[4-(4,4-dimethylcyclohex-1-en-1-yl)-2-methyl-5-(N-methyl-4-aminocarbonylphenyl)thiophen-3-yl]acetic acid (example 29) (17 mg, 0.036 mmol, 86%) after purification by preparative TLC (ethyl acetate 100%).

¹H NMR (400 MHz, CDCl₃) δ 0.93 (s, 3H), 0.95 (s, 3H), 1.22 (s, 9H), 1.30-1.36 (m, 2H), 1.82-1.97 (m, 4H), 2.49 (s, 3H), 3.01 (d, J=4.8 Hz, 3H), 5.18 (s, 1H), 5.57-5.93 (bs, 1H), 6.20 (d, J=3.6 Hz, 1H), 7.54 (d, J=8.4 Hz, 2H), 7.70 (d, J=8.4 Hz, 2H).

MS m/z ([M+H]⁺) 470.
MS m/z ([M−H]⁻) 468.

Example 30

Synthesis of 2-(tert-butoxy)-2-[4-(4,4-dimethylcyclohex-1-en-1-yl)-2-methyl-5-(N-Methyl-1H-pyridin-2-one-4-yl)thiophen-3-yl]acetic acid

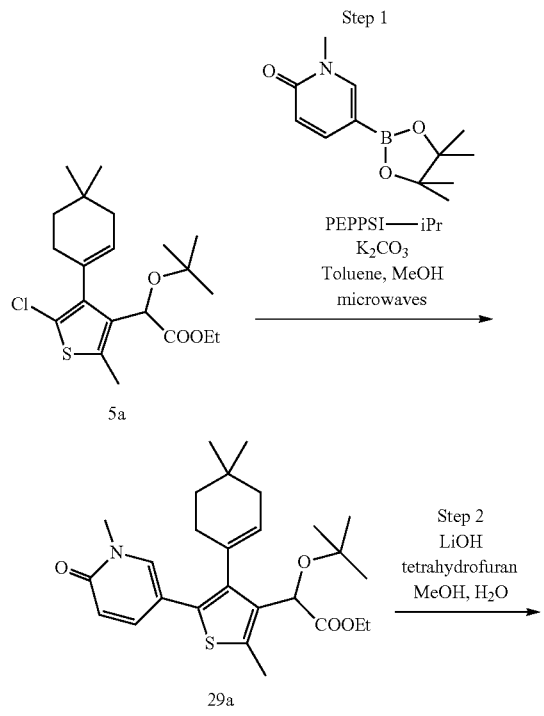

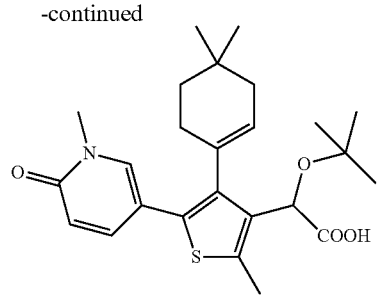

Example 30

Step 1: preparation of intermediate ethyl 2-(tert-butoxy)-2-[4-(4,4-dimethylcyclohex-1-en-1-yl)-2-methyl-5-(N-Methyl-1H-pyridin-2-one-4-yl)thiophen-3-yl]acetate (30a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (150 mg, 0.336 mmol) is converted by reaction with N-Methyl-1H-pyridin-2-one-5-boronic acid pinacol ester (166 mg, 0.672 mmol) into ethyl 2-(tert-butoxy)-2-[4-(4,4-dimethylcyclohex-1-en-1-yl)-2-methyl-5-(N-Methyl-1H-pyridin-2-one-4-yl)thiophen-3-yl]acetate (30a) (45 mg, 0.095 mmol, 28%) after purification by preparative TLC (ethyl acetate 100%).

¹H NMR (400 MHz, CDCl₃) δ 0.96 (s, 3H), 0.98 (s, 3H), 1.18 (s, 9H), 1.22 (t, J=6.8 Hz, 3H), 1.31-1.43 (m, 2H), 1.67-2.29 (m, 4H), 2.55 (s, 3H), 3.53 (s, 3H), 4.04-4.20 (m, 2H), 5.05 (s, 1H), 5.60-5.73 (bs, 1H), 6.53 (d, J=9.6 Hz, 1H), 7.41 (d, J=2.4 Hz, 1H), 7.48 (dd, J=2.4 Hz, J=9.6 Hz, 1H).

MS m/z ([M+H]⁺) 472.

Step 2: preparation of 2-(tert-butoxy)-2-[4-(4,4-dimethylcyclohex-1-en-1-yl)-2-methyl-5-(N-Methyl-1H-pyridin-2-one-4-yl)thiophen-3-yl]acetic acid (example 30)

Using the procedure described in example 15, step 2, ethyl 2-(tert-butoxy)-2-[4-(4,4-dimethylcyclohex-1-en-1-yl)-2-methyl-5-(N-Methyl-1H-pyridin-2-one-4-yl)thiophen-3-yl]acetate (30a) (45 mg, 0.095 mmol) is converted into 2-(tert-butoxy)-2-[4-(4,4-dimethylcyclohex-1-en-1-yl)-2-methyl-5-(N-Methyl-1H-pyridin-2-one-4-yl)thiophen-3-yl]acetic acid (example 30) (17 mg, 0.038 mmol, 40%) after purification by preparative TLC (dichloromethane/methanol 95/5).

¹H NMR (400 MHz, CDCl₃) δ 0.93 (s, 3H), 0.95 (s, 3H), 1.22 (s, 9H), 1.30-1.42 (m, 2H), 1.82-2.00 (m, 4H), 2.47 (s, 3H), 3.53 (s, 3H), 5.12 (s, 1H), 5.57-5.98 (bs, 1H), 6.56 (d, J=9.6 Hz, 1H), 7.41 (d, J=2.4 Hz, 1H), 7.46 (dd, J=2.4 Hz, J=9.6 Hz, 1H), 9.47-10.56 (bs, 1H).

MS m/z ([M+H]⁺) 444.
MS m/z ([M−H]⁻) 442.

Example 31

Synthesis of 2-(tert-butoxy)-2-[4-(4,4-dimethylcyclohex-1-en-1-yl)-2-methyl-5-(aminocarbonylphen-3-yl)thiophen-3-yl]acetic acid

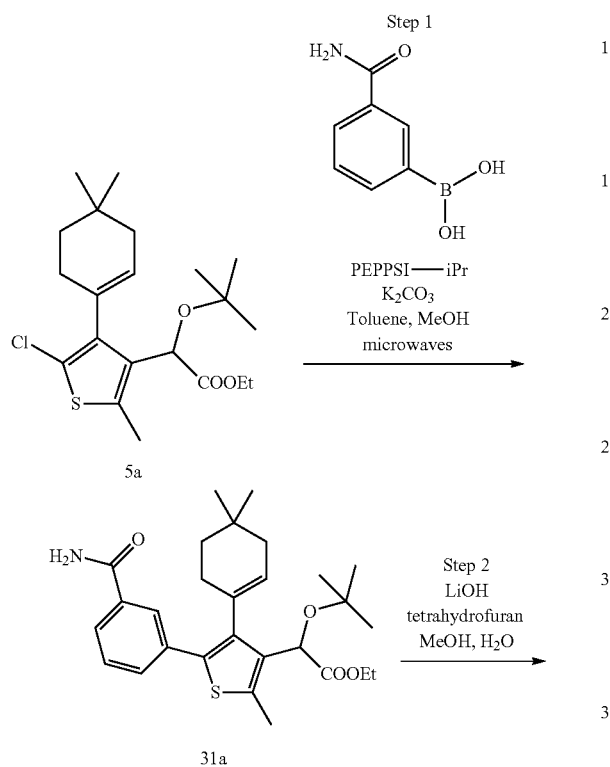

Example 31

Step 1: preparation of intermediate ethyl 2-(tert-butoxy)-2-[4-(4,4-dimethylcyclohex-1-en-1-yl)-2-methyl-5-(aminocarbonylphen-3-yl)thiophen-3-yl]acetate (31a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (158 mg, 0.360 mmol) is converted by reaction with 3-aminocarbonylphenyl boronic acid (119 mg, 0.720 mmol) into ethyl 2-(tert-butoxy)-2-[4-(4,4-dimethylcyclohex-1-en-1-yl)-2-methyl-5-(aminocarbonylphen-3-yl)thiophen-3-yl]acetate (31a) (99 mg, 0.205 mmol, 57%) after purification by preparative TLC (cyclohexane/ethyl acetate 50/50).

$^1$H NMR (400 MHz, CDCl$_3$) δ 0.95 (s, 3H), 0.98 (s, 3H), 1.20 (s, 9H), 1.22 (t, J=7.2 Hz, 3H), 1.34-1.38 (m, 2H), 1.79-2.16 (m, 4H), 2.59 (s, 3H), 4.07-4.21 (m, 2H), 5.12 (s, 1H), 5.62-5.83 (bs, 2H), 5.91-6.02 (bs, 1H), 7.39 (dd, J=7.6 Hz, J=8.0 Hz, 1H), 7.65-7.69 (m, 2H), 7.94 (dd, J=1.6 Hz, J=1.6 Hz, 1H).

MS m/z ([M+H]$^+$) 484.

Step 2: preparation of 2-(tert-butoxy)-2-[4-(4,4-dimethylcyclohex-1-en-1-yl)-2-methyl-5-(aminocarbonylphen-3-yl)thiophen-3-yl]acetic acid (example 31)

Using the procedure described in example 15, step 2, ethyl 2-(tert-butoxy)-2-[4-(4,4-dimethylcyclohex-1-en-1-yl)-2-methyl-5-(aminocarbonylphen-3-yl)thiophen-3-yl]acetate (31a) (99 mg, 0.205 mmol) is converted into 2-(tert-butoxy)-2-[4-(4,4-dimethylcyclohex-1-en-1-yl)-2-methyl-5-(aminocarbonylphen-3-yl)thiophen-3-yl]acetic acid (example 31) (76 mg, 0.167 mmol, 81%) after purification by preparative TLC (dichloromethane/methanol 95/5).

$^1$H NMR (400 MHz, DMSO-d$_6$) δ 0.90 (s, 3H), 0.93 (s, 3H), 1.14 (s, 9H), 1.29-1.36 (m, 2H), 1.73-1.96 (m, 4H), 2.50 (s, 3H), 5.00 (s, 1H), 5.58-5.75 (m, 1H), 7.35 (bs, 1H), 7.43 (dd, J=7.6 Hz, J=8.0 Hz, 1H), 7.55-7.61 (m, 1H), 7.73-7.79 (m, 1H), 7.92-7.98 (m, 2H), 12.46 (bs, 1H).

MS m/z ([M+H]$^+$) 456.
MS m/z ([M−H]$^−$) 454.

Example 32

Synthesis of 2-(tert-butoxy)-2-[4-(4,4-dimethylcyclohex-1-en-1-yl)-2-methyl-5-(benzenesulfonamide-4-yl)thiophen-3-yl]acetic acid

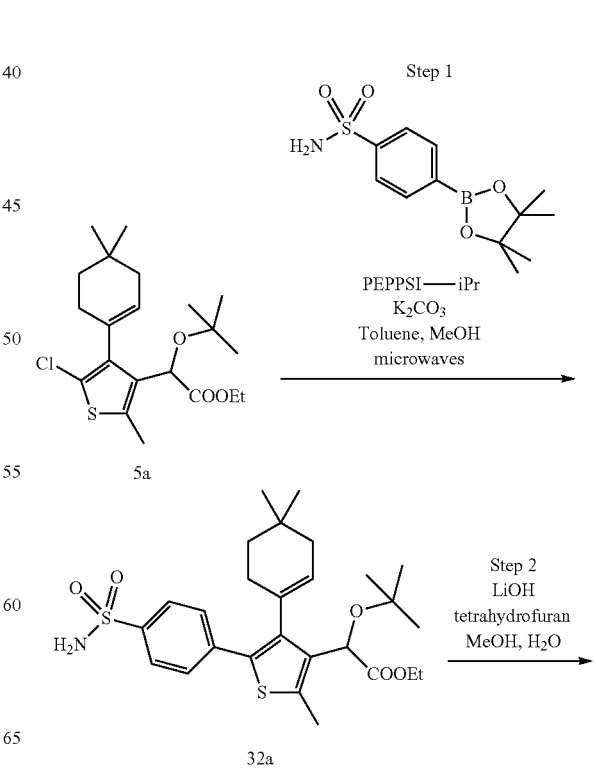

127

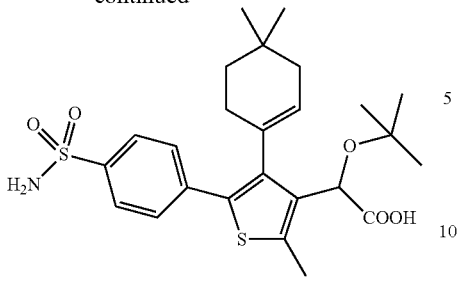

Example 32

Step 1: preparation of intermediate ethyl 2-(tert-butoxy)-2-[4-(4,4-dimethylcyclohex-1-en-1-yl)-2-methyl-5-(benzenesulfonamide-4-yl)thiophen-3-yl]acetate (32a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (157 mg, 0.358 mmol) is converted by reaction with benzenesulfonamide-4-boronic acid pinacol ester (207 mg, 0.716 mmol) into ethyl 2-(tert-butoxy)-2-[4-(4,4-dimethylcyclohex-1-en-1-yl)-2-methyl-5-(benzenesulfonamide-4-yl)thiophen-3-yl]acetate (32a) (8 mg, 0.015 mmol, 4%) after purification by preparative TLC (cyclohexane/ethyl acetate 50/50).

$^1$H NMR (400 MHz, CDCl$_3$) δ 0.99 (s, 3H), 1.01 (s, 3H), 1.20 (s, 9H), 1.23 (t, J=7.2 Hz, 3H), 1.36-1.40 (m, 2H), 1.85-2.01 (m, 4H), 2.61 (s, 3H), 4.07-4.22 (m, 2H), 4.81 (s, 2H), 5.11 (s, 1H), 5.67-5.80 (bs, 1H), 7.66 (d, J=8.8 Hz, 2H), 7.85 (d, J=8.8 Hz, 2H),

MS m/z ([M−H]$^−$) 518.

Step 2: preparation of 2-(tert-butoxy)-2-[4-(4,4-dimethylcyclohex-1-en-1-yl)-2-methyl-5-(benzenesulfonamide-4-yl)thiophen-3-yl]acetic acid (example 32)

Using the procedure described in example 15, step 2, ethyl 2-(tert-butoxy)-2-[4-(4,4-dimethylcyclohex-1-en-1-yl)-2-methyl-5-(benzenesulfonamide-4-yl)thiophen-3-yl]acetate (32a) (6.5 mg, 0.013 mmol) is converted into 2-(tert-butoxy)-2-[4-(4,4-dimethylcyclohex-1-en-1-yl)-2-methyl-5-(benzenesulfonamide-4-yl)thiophen-3-yl]acetic acid (example 32) (4 mg, 0.008 mmol, 63%) after purification by preparative TLC (dichloromethane/methanol 90/10).

$^1$H NMR (400 MHz, CDCl$_3$) δ 0.95 (s, 3H), 0.97 (s, 3H), 1.24 (s, 9H), 1.32-1.40 (m, 2H), 1.79-2.06 (m, 4H), 2.51 (s, 3H), 4.82 (s, 2H), 5.18 (s, 1H), 5.50-6.22 (bs, 1H), 7.64 (d, J=8.8 Hz, 2H), 7.86 (d, J=8.8 Hz, 2H), 9.35-10.11 (bs, 1H).

MS m/z ([M−H]$^−$) 490.

128

Example 33

Synthesis of 2-(tert-butoxy)-2-[4-(4,4-dimethylcyclohex-1-en-1-yl)-2-methyl-5-(acetamidophen-4-yl)thiophen-3-yl]acetic acid

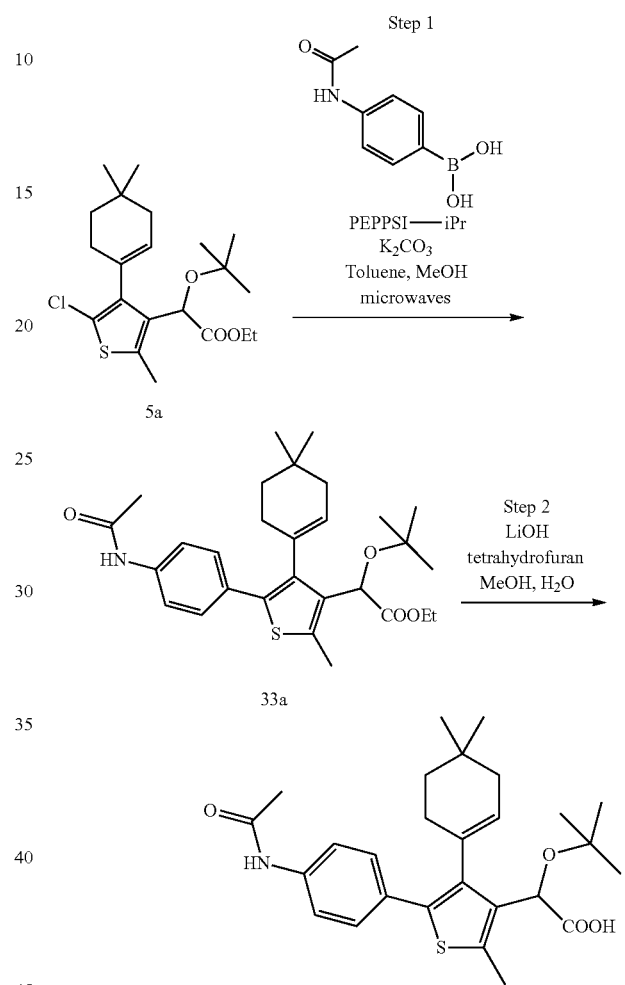

Example 33

Step 1: preparation of intermediate ethyl 2-(tert-butoxy)-2-[4-(4,4-dimethylcyclohex-1-en-1-yl)-2-methyl-5-(acetamidophen-4-yl)thiophen-3-yl]acetate (33a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (157 mg, 0.358 mmol) is converted by reaction with 4-acetamidophenylboronic acid (128 mg, 0.716 mmol) into ethyl 2-(tert-butoxy)-2-[4-(4,4-dimethylcyclohex-1-en-1-yl)-2-methyl-5-(acetamidophen-4-yl)thiophen-3-yl]acetate (33a) (103 mg, 0.207 mmol, 56%) after purification by preparative TLC (cyclohexane/ethyl acetate 50/50).

$^1$H NMR (400 MHz, CDCl$_3$) δ 0.96 (s, 3H), 0.98 (s, 3H), 1.19 (s, 9H), 1.21 (t, J=7.2 Hz, 3H), 1.32-1.37 (m, 2H), 1.76-1.98 (m, 4H), 2.16 (s, 3H), 2.57 (s, 3H), 4.04-4.21 (m, 2H), 5.12 (s, 1H), 5.97 (bs, 1H), 7.40-7.50 (m, 4H), 7.55 (s, 1H).

MS m/z ([M+H]$^+$) 498.

Step 2: preparation of 2-(tert-butoxy)-2-[4-(4,4-dimethylcyclohex-1-en-1-yl)-2-methyl-5-(acetamidophen-4-yl)thiophen-3-yl]acetic acid (example 33)

Using the procedure described in example 15, step 2, ethyl 2-(tert-butoxy)-2-[4-(4,4-dimethylcyclohex-1-en-1-yl)-2-methyl-5-(acetamidophen-4-yl)thiophen-3-yl]acetate (33a) (103 mg, 0.207 mmol) is converted into 2-(tert-butoxy)-2-[4-(4,4-dimethylcyclohex-1-en-1-yl)-2-methyl-5-(acetamidophen-4-yl)thiophen-3-yl]acetic acid (example 33) (85 mg, 0.181 mmol, 87%) after purification by preparative TLC (dichloromethane/methanol 95/5).

$^1$H NMR (400 MHz, CDCl$_3$) δ 0.91 (s, 3H), 0.94 (s, 3H), 1.22 (s, 9H), 1.28-1.35 (m, 2H), 1.77-1.99 (m, 4H), 2.16 (s, 3H), 2.47 (s, 3H), 5.17 (s, 1H), 5.43-6.09 (m, 1H), 7.40 (d, J=8.8 Hz, 2H), 7.44 (d, J=8.8 Hz, 2H), 7.53 (bs, 1H).

MS m/z ([M+H]$^+$) 470.
MS m/z ([M−H]$^−$) 468.

Example 34

Synthesis of 2-(tert-butoxy)-2-[4-(4,4-dimethylcyclohex-1-en-1-yl)-2-methyl-5-(N-benzyl-1H-pyridin-2-one-4-yl)thiophen-3-yl]acetic acid Step 1: preparation of intermediate ethyl 2-(tert-butoxy)-2-[4-(4,4-dimethylcyclohex-1-en-1-yl)-2-methyl-5-(N-benzyl-1H-pyridin-2-one-4-yl)thiophen-3-yl]acetate (34a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (150 mg, 0.336 mmol) is converted by reaction with N-benzyl-1H-pyridin-2-one-5-boronic acid pinacol ester (210 mg, 0.672 mmol) into ethyl 2-(tert-butoxy)-2-[4-(4,4-dimethylcyclohex-1-en-1-yl)-2-methyl-5-(N-benzyl-1H-pyridin-2-one-4-yl)thiophen-3-yl]acetate (34a) (91 mg, 0.166 mmol, 49%) after purification by preparative TLC (cyclohexane/ethyl acetate 50/50).

$^1$H NMR (400 MHz, CDCl$_3$) δ 0.92 (s, 3H), 0.96 (s, 3H), 1.17 (s, 9H), 1.20 (t, J=6.8 Hz, 3H), 1.27-1.36 (m, 2H), 1.73-2.23 (m, 4H), 2.54 (s, 3H), 4.02-4.19 (m, 2H), 5.02 (s, 1H), 5.09 (d, J=14.4 Hz, 1H), 5.16 (d, J=14.8 Hz, 1H), 5.53-5.64 (bs, 1H), 6.58 (d, J=9.6 Hz, 1H), 7.27-7.46 (m, 7H).

MS m/z ([M+H]$^+$) 548.

Step 2: preparation of 2-(tert-butoxy)-2-[4-(4,4-dimethylcyclohex-1-en-1-yl)-2-methyl-5-(N-benzyl-1H-pyridin-2-one-4-yl)thiophen-3-yl]acetic acid (example 34)

Using the procedure described in example 15, step 2, ethyl 2-(tert-butoxy)-2-[4-(4,4-dimethylcyclohex-1-en-1-yl)-2-methyl-5-(N-benzyl-1H-pyridin-2-one-4-yl)thiophen-3-yl]acetate (34a) (91 mg, 0.166 mmol) is converted into 2-(tert-butoxy)-2-[4-(4,4-dimethylcyclohex-1-en-1-yl)-2-methyl-5-(N-benzyl-1H-pyridin-2-one-4-yl)thiophen-3-yl] acetic acid (example 34) (84 mg, 0.162 mmol, 97%) after trituration in n-pentane at room temperature.

$^1$H NMR (400 MHz, CDCl$_3$) δ 0.88 (s, 3H), 0.92 (s, 3H), 1.21 (s, 9H), 1.49-1.60 (m, 3H), 1.76-1.93 (m, 3H), 2.44 (s, 3H), 5.10 (s, 1H), 5.13 (bs, 2H), 5.49-5.85 (bs, 1H), 6.60 (d, J=9.2 Hz, 1H), 7.27-7.46 (m, 7H).

MS m/z ([M+H]$^+$) 520.
MS m/z ([M−H]$^−$) 518.

Example 35

Synthesis of 2-(tert-butoxy)-2-[4-(4,4-dimethylcyclohex-1-en-1-yl)-2-methyl-5-(N-propyl-1H-pyridin-2-one-4-yl)thiophen-3-yl]acetic acid

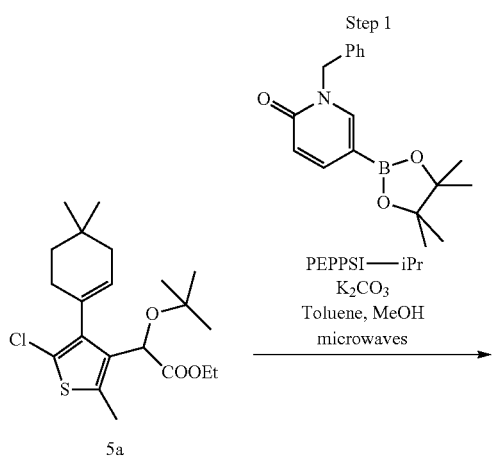

5a

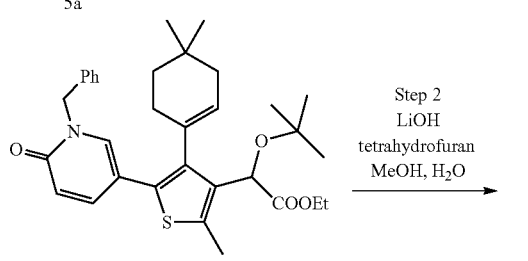

34a

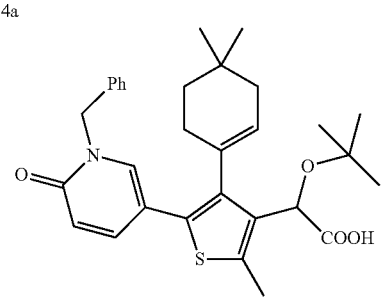

Example 34

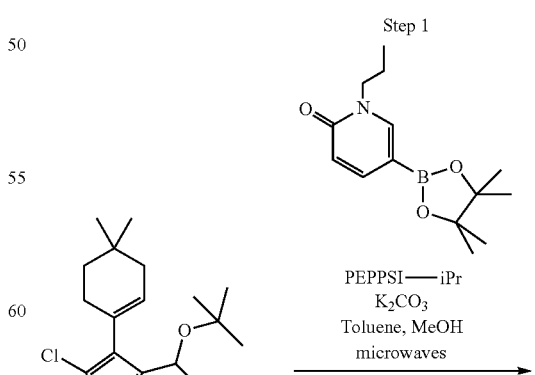

5a

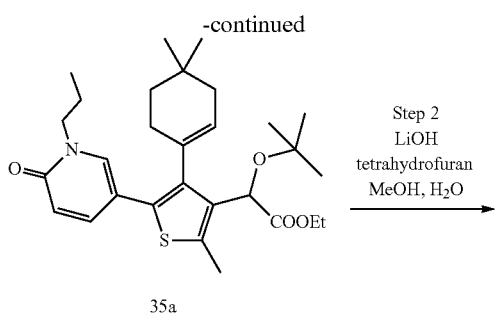

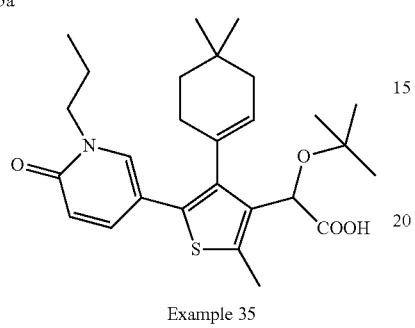

Example 35

Step 1: preparation of intermediate ethyl 2-(tert-butoxy)-2-[4-(4,4-dimethylcyclohex-1-en-1-yl)-2-methyl-5-(N-propyl-1H-pyridin-2-one-4-yl)thiophen-3-yl]acetate (35a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (150 mg, 0.336 mmol) is converted by reaction with N-benzyl-1H-pyridin-2-one-5-boronic acid pinacol ester (177 mg, 0.672 mmol) into ethyl 2-(tert-butoxy)-2-[4-(4,4-dimethylcyclohex-1-en-1-yl)-2-methyl-5-(N-propyl-1H-pyridin-2-one-4-yl)thiophen-3-yl]acetate (35a) (82 mg, 0.164 mmol, 49%) after purification by preparative TLC (cyclohexane/ethyl acetate 50/50).

$^1$H NMR (400 MHz, CDCl$_3$) δ 0.94 (s, 3H), 0.96 (s, 3H), 0.98 (m, 3H), 1.18 (s, 9H), 1.22 (t, J=6.8 Hz, 3H), 1.31-1.44 (m, 2H), 1.74-1.81 (m, 2H), 1.83-2.31 (m, 4H), 2.55 (s, 3H), 3.81-3.93 (m, 2H), 4.04-4.20 (m, 2H), 5.05 (s, 1H), 5.60-5.73 (bs, 1H), 6.51 (d, J=9.6 Hz, 1H), 7.38-7.42 (m, 1H), 7.46-7.52 (m, 1H).

MS m/z ([M+H]$^+$) 500.

Step 2: preparation of 2-(tert-butoxy)-2-[4-(4,4-dimethylcyclohex-1-en-1-yl)-2-methyl-5-(N-propyl-1H-pyridin-2-one-4-yl)thiophen-3-yl]acetic acid (example 35)

Using the procedure described in example 15, step 2, ethyl 2-(tert-butoxy)-2-[4-(4,4-dimethylcyclohex-1-en-1-yl)-2-methyl-5-(N-propyl-1H-pyridin-2-one-4-yl)thiophen-3-yl]acetate (35a) (82 mg, 0.164 mmol) is converted into 2-(tert-butoxy)-2-[4-(4,4-dimethylcyclohex-1-en-1-yl)-2-methyl-5-(N-propyl-1H-pyridin-2-one-4-yl)thiophen-3-yl]acetic acid (example 35) (40 mg, 0.085 mmol, 52%) after purification by preparative TLC (dichloromethane/methanol 95/5).

$^1$H NMR (400 MHz, CDCl$_3$) δ 0.92-0.97 (m, 9H), 1.22 (s, 9H), 1.33-1.38 (m, 2H), 1.75-1.81 (m, 2H), 1.83-2.00 (m, 4H), 2.48 (s, 3H), 3.81-3.93 (m, 2H), 5.12 (s, 1H), 5.61-5.91 (bs, 1H), 6.56 (d, J=9.6 Hz, 1H), 7.36 (d, J=1.8 Hz, 1H), 7.44 (dd, J=1.8 Hz, J=9.6 Hz, 1H).

MS m/z ([M+H]$^+$) 472.
MS m/z ([M−H]$^-$) 470.

Example 36

Synthesis of 2-(tert-butoxy)-2-[4-(4,4-dimethylcyclohex-1-en-1-yl)-2-methyl-5-[4-(propylcarbamoyl)phenyl]thiophen-3-yl]acetic acid

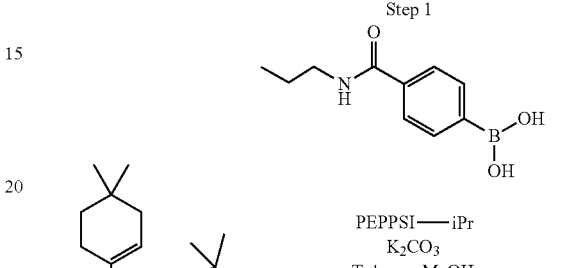

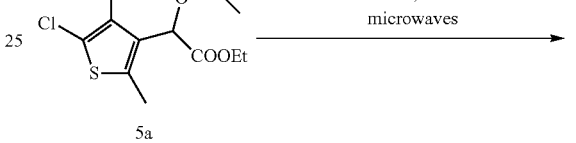

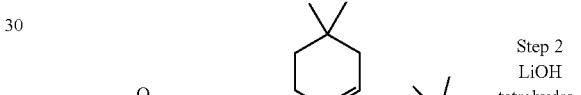

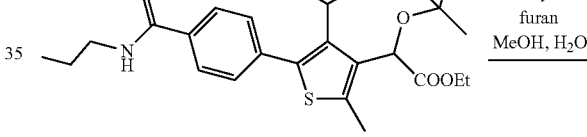

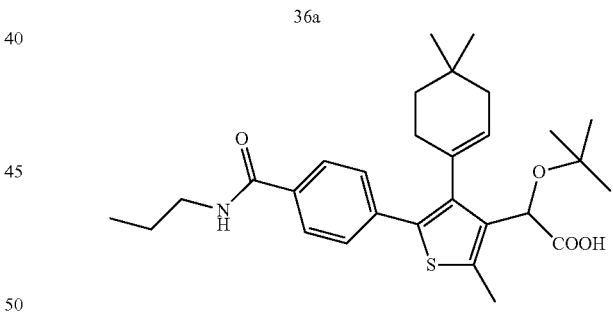

Example 36

Step 1: preparation of intermediate ethyl 2-(tert-butoxy)-2-[4-(4,4-dimethylcyclohex-1-en-1-yl)-2-methyl-5-[4-(propylcarbamoyl)phenyl]thiophen-3-yl]acetate (36a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (158 mg, 0.350 mmol) is converted by reaction with [4-(propylcarbamoyl)phenyl]boronic acid (145 mg, 0.70 mmol) into ethyl 2-(tert-butoxy)-2-[4-(4,4-dimethylcyclohex-1-en-1-yl)-2-methyl-5-[4-(propylcarbamoyl)phenyl]thiophen-3-yl]acetate (36a) (110 mg, 0.210 mmol, 60%) after purification by two preparative TLC (cyclohexane/ethyl acetate 60/40).

$^1$H NMR (400 MHz, CDCl$_3$) δ 0.98-1.02 (m, 9H), 1.20-1.28 (m, 12H), 1.35-1.38 (m, 2H), 1.60-1.70 (m, 2H), 1.83-2.00 (m, 4H), 2.60 (s, 3H), 3.41-3.46 (m, 2H), 4.11-4.20 (m, 2H), 5.12 (s, 1H), 6.07-6.10 (m, 1H), 7.58 (d, J=8.3 Hz, 2H), 7.70 (d, J=8.3 Hz, 2H).

MS m/z ([M+H])$^+$ 527.

Step 2: preparation of 2-(tert-butoxy)-2-[4-(4,4-dimethylcyclohex-1-en-1-yl)-2-methyl-5-[4-(propylcarbamoyl)phenyl]thiophen-3-yl]acetic acid (example 36)

Using the procedure described in example 15, step 2, ethyl 2-(tert-butoxy)-2-[4-(4,4-dimethylcyclohex-1-en-1-yl)-2-methyl-5-[4-(propyl carbamoyl)phenyl]thiophen-3-yl]acetate (36a) (105 mg, 0.20 mmol) is converted into 2-(tert-butoxy)-2-[4-(4,4-dimethylcyclohex-1-en-1-yl)-2-methyl-5-[4-(propylcarbamoyl)phenyl]thiophen-3-yl]acetic acid (example 36) (53 mg, 0.11 mmol, 53%) after purification by preparative TLC (dichloromethane/methanol 95/5).

$^1$H NMR (400 MHz, CDCl$_3$) δ 0.94-1.02 (m, 9H), 1.23 (s, 9H), 1.32-1.34 (m, 2H), 1.61-1.98 (m, 6H), 2.49 (s, 3H), 3.41-3.46 (m, 2H), 5.16-5.21 (m, 1H), 6.07-6.14 (m, 1H), 7.56 (d, J=8.3 Hz, 2H), 7.71 (d, J=8.3 Hz, 2H).

MS m/z ([M−H])$^-$ 496.

Example 37

Synthesis of 2-(tert-butoxy)-2-[4-(4,4-dimethylcyclohex-1-en-1-yl)-2-methyl-5-(N-(methylenecyclopropyl)-1H-pyridin-2-one-4-yl)thiophen-3-yl]acetic acid

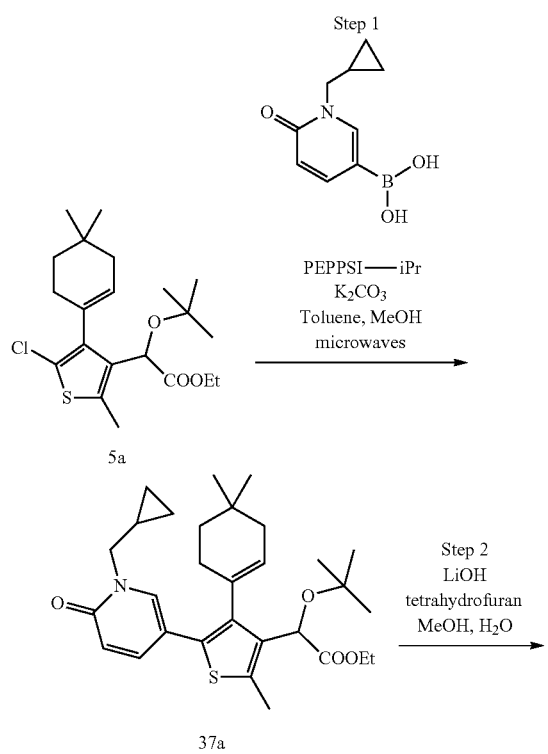

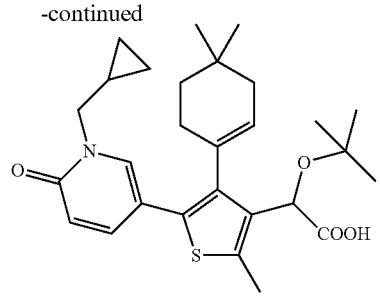

Example 37

Step 1: preparation of intermediate ethyl 2-(tert-butoxy)-2-[4-(4,4-dimethylcyclohex-1-en-1-yl)-2-methyl-5-(N-(methylenecyclopropyl)-1H-pyridin-2-one-4-yl)thiophen-3-yl]acetate (37a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (150 mg, 0.336 mmol) is converted by reaction with 4-dimethylcarboamidophenyl boronic acid (185 mg, 0.672 mmol) into ethyl 2-(tert-butoxy)-2-[4-(4,4-dimethylcyclohex-1-en-1-yl)-2-methyl-5-(N-(methylenecyclopropyl)-1H-pyridin-2-one-4-yl)thiophen-3-yl]acetate (37a) (43 mg, 0.084 mmol, 25%) after purification by preparative TLC (cyclohexane/ethyl acetate 50/50).

$^1$H NMR (400 MHz, CDCl$_3$) δ 0.37-0.41 (m, 2H), 0.59-0.64 (m, 2H), 0.95 (s, 3H), 0.99 (m, 3H), 1.19 (s, 10H), 1.23 (t, J=7.2 Hz, 3H), 1.31-1.44 (m, 2H), 1.87-2.21 (m, 4H), 2.57 (s, 3H), 3.74-3.84 (m, 2H), 4.05-4.21 (m, 2H), 5.06 (s, 1H), 5.67 (bs, 1H), 6.53 (d, J=9.6 Hz, 1H), 7.47 (dd, J=2.8 Hz, J=9.6 Hz, 1H), 7.50 (d, J=2.8 Hz, 1H).

MS m/z ([M+H]$^+$) 512.

Step 2: preparation of 2-(tert-butoxy)-2-[4-(4,4-dimethylcyclohex-1-en-1-yl)-2-methyl-5-(N-(methylenecyclopropyl)-1H-pyridin-2-one-4-yl)thiophen-3-yl]acetic acid (example 37)

Using the procedure described in example 15, step 2, ethyl 2-(tert-butoxy)-2-[4-(4,4-dimethylcyclohex-1-en-1-yl)-2-methyl-5-(N-(methylenecyclopropyl)-1H-pyridin-2-one-4-yl)thiophen-3-yl]acetate (37a) (43 mg, 0.084 mmol) is converted into 2-(tert-butoxy)-2-[4-(4,4-dimethylcyclohex-1-en-1-yl)-2-methyl-5-(N-(methylenecyclopropyl)-1H-pyridin-2-one-4-yl)thiophen-3-yl]acetic acid (example 37) (21 mg, 0.043 mmol, 52%) after purification by preparative TLC (dichloromethane/methanol 90/10).

$^1$H NMR (400 MHz, CDCl$_3$) δ 0.35-0.41 (m, 2H), 0.58-0.65 (m, 2H), 0.91 (s, 3H), 0.95 (m, 3H), 1.23 (s, 10H), 1.32-1.38 (m, 2H), 1.82-1.99 (m, 4H), 2.48 (s, 3H), 3.73-3.85 (m, 2H), 5.12 (s, 1H), 5.76 (bs, 1H), 6.57 (d, J=9.3 Hz, 1H), 7.45 (dd, J=2.7 Hz, J=9.3 Hz, 1H), 7.50 (d, J=2.1 Hz, 1H).

MS m/z ([M+H]$^+$) 484.
MS m/z ([M−H]$^-$) 482.

Example 38

Synthesis of 2-(tert-butoxy)-2-[4-(3,4-dihydro-2H-1-benzopyran-6-yl)-2-(hydroxymethyl)-5-(pyridin-4-yl)thiophen-3-yl]acetic acid

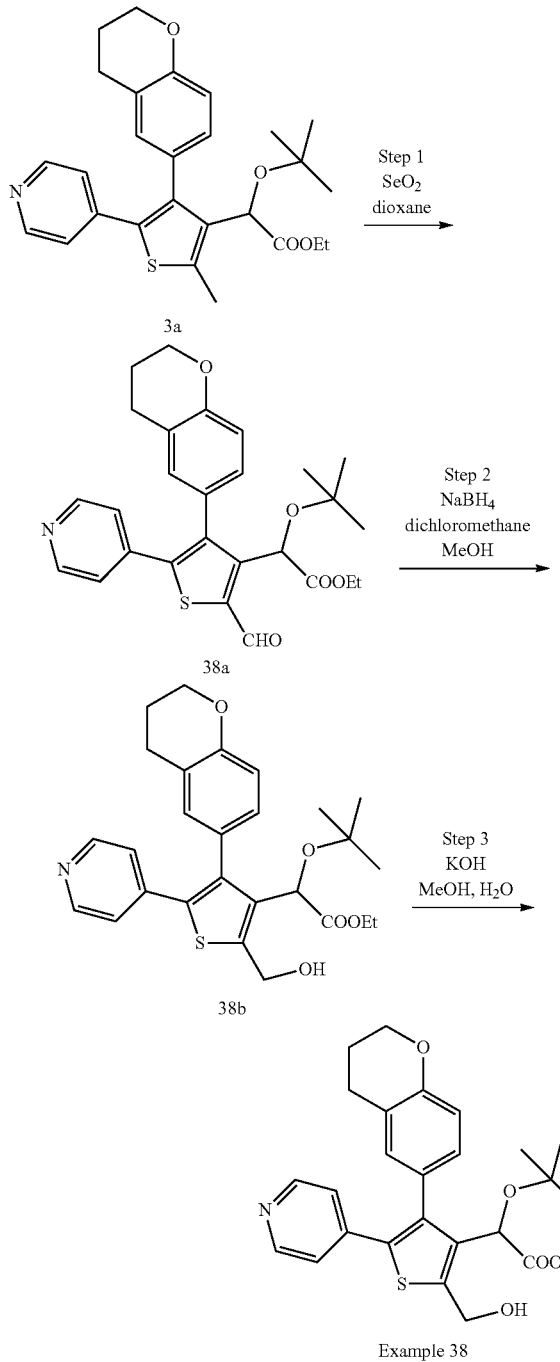

Example 38

Step 1: preparation of intermediate ethyl 2-(tert-butoxy)-2-[4-(3,4-dihydro-2H-1-benzopyran-6-yl)-2-formyl-5-(pyridin-4-yl)thiophen-3-yl]acetate (38a)

A solution of ethyl 2-(tert-butoxy)-2-[4-(3,4-dihydro-2H-1-benzopyran-6-yl)-2-methyl-5-(pyridin-4-yl)thiophen-3-yl]acetate (3a) (50 mg, 0.11 mmol) in dioxane (1 mL) was heated at 65° C. for 4 hours with selenium dioxide (13 mg, 0.12 mmol). Then, selenium dioxide (13 mg, 0.12 mmol) was added again and the reaction mixture was heated at 85° C. for the night. The reaction is uncompleted so selenium dioxide (130 mg, 1.2 mmol) was added again and the reaction mixture was heated at 110° C. for 4 additional days. The reaction mixture was diluted with ethyl acetate and filtered through a pad of Celite® and concentrated in vacuo to provide the crude ethyl 2-(tert-butoxy)-2-[4-(3,4-dihydro-2H-1-benzopyran-6-yl)-2-formyl-5-(pyridin-4-yl)thiophen-3-yl]acetate (38a) (100 mg, >100%) which was used without further purification.

$^1$H NMR (400 MHz, CDCl$_3$) δ 1.07 (s, 9H), 1.23-1.28 (m, 3H), 2.05-2.20 (m, 2H), 2.65-2.85 (m, 2H), 4.12-4.34 (m, 4H), 5.00 (s, 1H), 6.72-6.92 (m, 3H), 7.15 (d, J=6.4 Hz, 2H), 8.50 (d, J=6.4 Hz, 2H), 10.55 (s, 1H).

MS m/z ([M+H]$^+$) 480.

Step 2: preparation of intermediate ethyl 2-(tert-butoxy)-2-[4-(3,4-dihydro-2H-1-benzopyran-6-yl)-2-(hydroxymethyl)-5-(pyridin-4-yl)thiophen-3-yl]acetate (38b)

At 0° C., sodium tetraborohydride (3.2 mg, 0.085 mmol) was added to a solution of the crude 2-(tert-butoxy)-2-[4-(3,4-dihydro-2H-1-benzopyran-6-yl)-2-formyl-5-(pyridin-4-yl)thiophen-3-yl]acetic (38a) (40 mg, 0.083 mmol) in a mixture of dichloromethane (1.5 mL) and ethanol (1.5 mL). The reaction mixture was stirred at 0° C. for 3 hours. The reaction mixture was concentrated in vacuo and the residue was diluted with ethyl acetate. The organic layer was washed with brine, dried over sodium sulfate, filtered and concentrated in vacuo. The residue was purified by preparative TLC (dichloromethane/methanol 95/5) to give ethyl 2-(tert-butoxy)-2-[4-(3,4-dihydro-2H-1-benzopyran-6-yl)-2-(hydroxymethyl)-5-(pyridin-4-yl)thiophen-3-yl]acetate (38b) (12 mg, 0.025 mmol, 30%).

MS m/z ([M+H]$^+$) 482.

Step 3: preparation of 2-(tert-butoxy)-2-[4-(3,4-dihydro-2H-1-benzopyran-6-yl)-2-(hydroxymethyl)-5-(pyridin-4-yl)thiophen-3-yl]acetic acid (example 38)

Using the procedure described in example 3, step 2, ethyl 2-(tert-butoxy)-2-[4-(3,4-dihydro-2H-1-benzopyran-6-yl)-2-(hydroxymethyl)-5-(pyridin-4-yl)thiophen-3-yl]acetate (38b) (12 mg, 0.025 mmol) is converted into 2-(tert-butoxy)-2-[4-(3,4-dihydro-2H-1-benzopyran-6-yl)-2-(hydroxymethyl)-5-(pyridin-4-yl)thiophen-3-yl]acetic acid (example 38) (1.8 mg, 0.004 mmol, 16%).

MS m/z ([M+H]$^+$) 454.
MS m/z ([M−H]$^-$) 452.

Example 39

Synthesis of 2-(tert-butoxy)-2-[4-(8-fluoro-5-methyl-3,4-dihydro-2H-1-benzopyran-6-yl)-2-methyl-5-(pyridin-4-yl)thiophen-3-yl]acetic acid Step 1

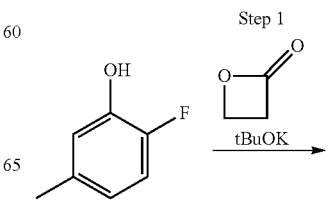

Step 1: preparation of intermediate
3-(2-fluoro-5-methylphenoxy)propanoic acid (39a)

To a suspension of 2-fluoro-5-methylphenol (1.0 g, 7.9 mmol) in tetrahydrofuran (10 mL) at 0-5° C. was dropwise added potassium tert-butoxide 1N in tetrahydrofuran (8.3 mL, 8.3 mmol), followed by 3-propiolactone (0.55 mL, 8.7 mmol) in one portion. The mixture was warmed to room temperature for 1 hour, then heated at 50° C. for 2 hours. After cooling to room temperature, the mixture was quenched with a saturated solution of sodium hydrogenocarbonate (1 mL) and diluted with water (9 mL). The aqueous layer was washed with ethyl acetate (10 mL), acidified with 1M hydrochloric acid until pH 2 and extracted with ethyl acetate (2×10 mL). The organic layer was dried over sodium sulfate and concentrated in vacuo to provide 3-(2-fluoro-5-methylphenoxy)propanoic acid (39a) (0.96 g, 4.8 mol, 60%) which was used without further purification.

MS m/z ([M–H]⁻) 197.

Step 2: preparation of intermediate 8-fluoro-5-methyl-3,4-dihydro-2H-1-benzopyran-4-one (39b)

A mixture of 3-(2-fluoro-5-methylphenoxy)propanoic acid (39a) (860 mg, 4.64 mmol) in polyphosphoric acid (12.8 g, 130.3 mmol) was stirred at 100° C. for 2 hours. After cooling to room temperature, the mixture was diluted with water (90 mL), and extracted with ethyl acetate (2×60 mL). The organic layers were combined, washed with brine, dried over sodium sulfate, and concentrated in vacuo to provide 8-fluoro-5-methyl-3,4-dihydro-2H-1-benzopyran-4-one (39b) (573 mg, 3.18 mol, 73%) which was used without further purification.

MS m/z ([M+H]⁺) 181.

Step 3: preparation of intermediate 8-fluoro-5-methyl-3,4-dihydro-2H-1-benzopyran (39c)

A solution of 8-fluoro-5-methyl-3,4-dihydro-2H-1-benzopyran-4-one (39b) (570 mg, 3.16 mmol) in acetic acid (4 mL) was added to a suspension of zinc dust (2.69 g, 41.1 mmol) in acetic acid (4 mL). The reaction mixture was heated at 100° C. for 5 hours. After cooling to room temperature, the mixture was filtered through a pad of Celite® and successively rinsed with ethyl acetate (10 mL) and toluene (10 mL). The filtrate was concentrated in vacuo to provide 8-fluoro-5-methyl-3,4-dihydro-2H-1-benzopyran (39c) (233 mg, 1.40 mol, 44%) which was used without further purification.

¹H NMR (300 MHz, CDCl₃) δ 2.00-2.12 (m, 2H), 2.16 (s, 3H), 2.64 (t, J=6.6 Hz, 2H), 4.17-4.26 (m, 2H), 6.60 (dd, J=5.3 Hz, J=8.2 Hz, 1H), 6.81 (dd, J=10.8 Hz, J=8.2 Hz, 1H).

Step 4: preparation of intermediate 6-bromo-8-fluoro-5-methyl-3,4-dihydro-2H-1-benzopyran (39d)

To a solution of the 8-fluoro-5-methyl-3,4-dihydro-2H-1-benzopyran (39c) (228 mg, 1.37 mmol) in acetic acid (2.4 mL) was added a solution of bromine (0.084 mL, 1.37 mmol) in acetic acid (1.4 mL). The mixture was stirred at room temperature for 20 minutes, then diluted with toluene (20 mL). The mixture was concentrated in vacuo. The residue was dissolved in ethyl acetate (20 mL) and successively washed with a 15% sodium thiosulfate solution (20 mL) and a saturated solution of sodium hydrogenocarbonate (20 mL). The organic layer was dried over sodium sulfate and concentrated in vacuo to provide 6-bromo-8-fluoro-5-methyl-3,4-dihydro-2H-1-benzopyran (39d) (336 mg, 1.37 mmol, 100%) which was used without further purification.

¹H NMR (300 MHz, CDCl₃) δ 2.00-2.11 (m, 2H), 2.25 (s, 3H), 2.70 (t, J=6.6 Hz, 2H), 4.15-4.22 (m, 2H), 7.15 (d, J=10.3 Hz, 1H).

Step 5: preparation of intermediate 2-(8-fluoro-5-methyl-3,4-dihydro-2H-1-benzopyran-6-yl)-4,4,5,5-tetramethyl-1,3,2-dioxaborolane (39e)

Using the procedure described in example 6, step 2,6-bromo-8-fluoro-5-methyl-3,4-dihydro-2H-1-benzopyran (39d) (336 mg, 1.37 mmol) is converted into 2-(8-fluoro-5-methyl-3,4-dihydro-2H-1-benzopyran-6-yl)-4,4,5,5-tetramethyl-1,3,2-dioxaborolane (39e) (190 mg, 0.65 mmol, 47%) after purification by preparative TLC (cyclohexane/ethyl acetate 92/8).

¹H NMR (400 MHz, CDCl₃) δ 1.32 (s, 12H), 2.02-2.09 (m, 2H), 2.38 (s, 3H), 2.65 (t, J=6.6 Hz, 2H), 4.18-4.24 (m, 2H), 7.34 (d, J=11.7 Hz, 1H).

MS m/z ([M+H]⁺) 293.

Step 6: preparation of intermediate ethyl 2-(tert-butoxy)-2-[5-chloro-4-(8-fluoro-5-methyl-3,4-dihydro-2H-1-benzopyran-6-yl)-2-methylthiophen-3-yl]acetate (39f)

Under argon atmosphere, ethyl 2-(4-bromo-5-chloro-2-methylthiophen-3-yl)-2-(tert-butoxy)acetate (1d) (200 mg, 0.541 mmol), 2-(8-fluoro-5-methyl-3,4-dihydro-2H-1-benzopyran-6-yl)-4,4,5,5-tetramethyl-1,3,2-dioxaborolane (39e) (221 mg, 0.757 mmol), potassium carbonate (227 mg, 1.623 mmol) were dissolved in tetrahydrofuran (4.5 mL) and water (0.9 mL). The solution was degassed under argon for 10 minutes and tetrakis(triphenylphosphine)palladium (0) (63 mg, 0.054 mmol) was added. The reaction was heated and shaken at 90° C. for 16 hours. After cooling at room temperature, the mixture was partitioned between ethyl acetate and water. The organic layer was washed with brine, dried over sodium sulfate, filtered and concentrated under reduced pressure. The crude material was purified by preparative TLC (cyclohexane/ethyl acetate 90/10) to give ethyl 2-(tert-butoxy)-2-[5-chloro-4-(8-fluoro-5-methyl-3,4-dihydro-2H-1-benzopyran-6-yl)-2-methylthiophen-3-yl]acetate (39f) (215 mg, 0.473 mmol, 87%).

¹H NMR (300 MHz, CDCl₃) δ 1.11 (s, 9H), 1.16 (t, J=7.2 Hz, 3H), 1.90 (s, 3H), 2.09-2.16 (m, 2H), 2.54 (s, 3H), 2.67-2.74 (m, 2H), 4.01-4.10 (m, 2H), 4.20-4.29 (m, 2H), 4.61 (s, 1H), 6.68 (d, J=11.1 Hz, 1H).

MS m/z ([M+H]⁺-O^tBu) 381.

Step 7: preparation of intermediate ethyl 2-(tert-butoxy)-2-[4-(8-fluoro-5-methyl-3,4-dihydro-2H-1-benzopyran-6-yl)-2-methyl-5-(pyridin-4-yl)thiophen-3-yl]acetate (39g)

Using the procedure described in example 1, step 6, ethyl 2-(tert-butoxy)-2-[5-chloro-4-(8-fluoro-5-methyl-3,4-dihydro-2H-1-benzopyran-6-yl)-2-methylthiophen-3-yl]acetate (39f) (215 mg, 0.473 mmol) is converted by reaction with 4-pyridine boronic acid pinacol ester (150 mg, 0.709 mmol) into ethyl 2-(tert-butoxy)-2-[4-(8-fluoro-5-methyl-3,4-dihydro-2H-1-benzopyran-6-yl)-2-methyl-5-(pyridin-4-yl)thiophen-3-yl]acetate (39g) (48 mg, 0.096 mmol, 20%) after purification by preparative TLC (cyclohexane/ethyl acetate 30/70).

¹H NMR (400 MHz, CDCl₃) δ 1.15 (t, J=7.2 Hz, 3H), 1.23 (s, 9H), 1.70 (s, 3H), 2.07-2.13 (m, 2H), 2.60-2.63 (m, 2H), 2.65 (s, 3H), 3.98-4.16 (m, 2H), 4.26-4.28 (m, 2H), 4.66 (s, 1H), 6.78 (d, J=11.2 Hz, 1H), 6.92 (dd, J=1.6 Hz, J=4.8 Hz, 2H), 8.33 (dd, J=1.6 Hz, J=4.8 Hz, 2H).

MS m/z ([M+H]⁺) 498.

Step 8: preparation of 2-(tert-butoxy)-2-[4-(8-fluoro-5-methyl-3,4-dihydro-2H-1-benzopyran-6-yl)-2-methyl-5-(pyridin-4-yl)thiophen-3-yl]acetic acid (example 39)

Using the procedure described in example 3, step 2, ethyl 2-(tert-butoxy)-2-[4-(8-fluoro-5-methyl-3,4-dihydro-2H-1-benzopyran-6-yl)-2-methyl-5-(pyridin-4-yl)thiophen-3-yl]acetate (39g) (48 mg, 0.096 mmol) is converted into 2-(tert-butoxy)-2-[4-(8-fluoro-5-methyl-3,4-dihydro-2H-1-benzopyran-6-yl)-2-methyl-5-(pyridin-4-yl)thiophen-3-yl]acetic acid (example 39) (15 mg, 0.032 mmol, 33%) after purification by preparative TLC (dichloromethane/methanol 90/10).

¹H NMR (400 MHz, CDCl₃) δ 1.15 (s, 9H), 1.79 (s, 3H), 2.07-2.13 (m, 2H), 2.61 (s, 3H), 2.58-2.66 (m, 2H), 4.25-4.28 (m, 2H), 4.76 (s, 1H), 6.76 (d, J=11.2 Hz, 1H), 6.96 (dd, J=1.6 Hz, J=4.8 Hz, 2H), 8.34 (dd, J=1.2 Hz, J=4.8 Hz, 2H).

MS m/z ([M+H]⁺) 470.
MS m/z ([M−H]⁻) 468.

Example 40

Synthesis of 2-(tert-butoxy)-2-[4-(8-fluoro-3,4-dihydro-2H-1-benzopyran-6-yl)-2-methyl-5-(pyridin-4-yl)thiophen-3-yl]acetic acid

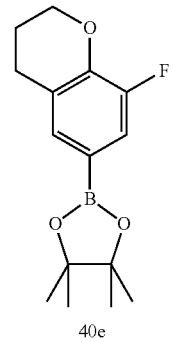

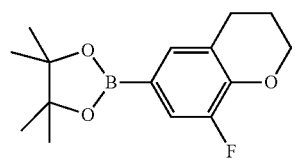

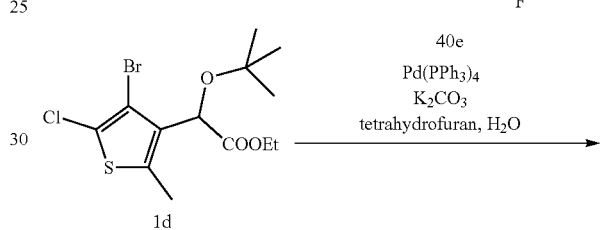

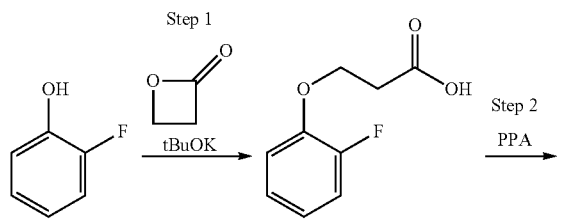

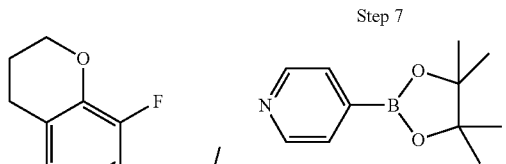

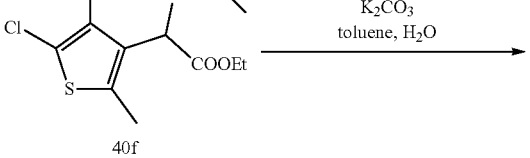

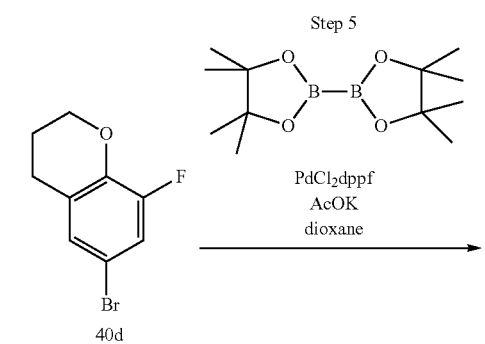

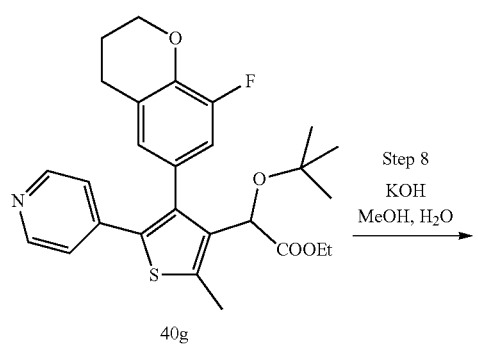

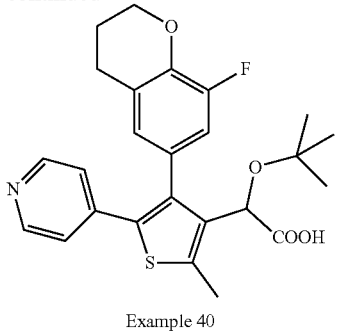

Example 40

Step 1: preparation of intermediate 3-(2-fluorophenoxy)propanoic acid (40a)

Using the procedure described in example 39, step 1, 2-fluorophenol (3.0 g, 26.8 mmol) is converted to 3-(2-fluorophenoxy)propanoic acid (40a) (3.73 g, 20.3 mmol, 76%) which was used without further purification.

MS m/z ([M−H]⁻) 183.

Step 2: preparation of intermediate 8-fluoro-3,4-dihydro-2H-1-benzopyran-4-one (40b)

Using the procedure described in example 39, step 2, 3-(2-fluorophenoxy)propanoic acid (40a) (3.7 g, 20.3 mmol) is converted to 8-fluoro-3,4-dihydro-2H-1-benzopyran-4-one (40b) (1.80 g, 10.8 mmol, 53%) which was used without further purification.

$^1$H NMR (300 MHz, CDCl$_3$) δ 2.81-2.91 (m, 2H), 4.59-4.68 (m, 2H), 6.95 (td, J=8.0 Hz, J=4.4 Hz, 1H), 7.30 (ddd, J=1.4 Hz, J=8.0 Hz, J=10.6 Hz, 1H), 7.67 (td, J=1.4 Hz, J=8.0 Hz, 1H).

MS m/z ([M+H]⁺) 167.

Step 3: preparation of intermediate 8-fluoro-3,4-dihydro-2H-1-benzopyran (40c)

Using the procedure described in example 39, step 3, 8-fluoro-3,4-dihydro-2H-1-benzopyran-4-one (40b) (1.80 g, 10.83 mmol) is converted, after purification by flash chromatography on silica gel (cyclohexane/ethyl acetate from 100/0 to 95/05) into 8-fluoro-3,4-dihydro-2H-1-benzopyran (40c) (827 mg, 5.43 mmol, 50%).

$^1$H NMR (300 MHz, CDCl$_3$) δ 1.98-2.09 (m, 2H), 2.81 (t, J=6.5 Hz, 2H), 4.21-4.30 (m, 2H), 6.68-6.95 (m, 3H).

Step 4: preparation of intermediate 6-bromo-8-fluoro-3,4-dihydro-2H-1-benzopyran (40d)

Using the procedure described in example 39, step 4, 8-fluoro-3,4-dihydro-2H-1-benzopyran (40c) (820 mg, 5.39 mmol) is converted to 6-bromo-8-fluoro-3,4-dihydro-2H-1-benzopyran (40d) (1.21 g, 5.24 mmol, 92%) which was used without further purification.

$^1$H NMR (300 MHz, CDCl$_3$) δ 1.95-2.08 (m, 2H), 2.78 (t, J=6.5 Hz, 2H), 4.19-4.29 (m, 2H), 6.94-6.98 (m, 1H), 7.15 (dd, J=2.3 Hz, J=10.2 Hz, 1H).

Step 5: preparation of intermediate 2-(8-fluoro-3,4-dihydro-2H-1-benzopyran-6-yl)-4,4,5,5-tetramethyl-1,3,2-dioxaborolane (40e)

Using the procedure described in example 6, step 2,6-bromo-8-fluoro-3,4-dihydro-2H-1-benzopyran (40d) (900 mg, 3.89 mmol) is converted, after purification by flash chromatography on silica gel (cyclohexane/ethyl acetate from 100/0 to 95/05) into 2-(8-fluoro-3,4-dihydro-2H-1-benzopyran-6-yl)-4,4,5,5-tetramethyl-1,3,2-dioxaborolane (40e) (515 mg, 1.85 mmol, 47%).

$^1$H NMR (400 MHz, CDCl$_3$) δ 1.32 (s, 12H), 1.97-2.07 (m, 2H), 2.80 (t, J=6.4 Hz, 2H), 4.27 (t, J=5.1 Hz, 2H), 7.26-7.35 (m, 2H).

MS m/z ([M+H]⁺) 279.

Step 6: preparation of intermediate ethyl 2-(tert-butoxy)-2-[5-chloro-4-(8-fluoro-3,4-dihydro-2H-1-benzopyran-6-yl)-2-methylthiophen-3-yl]acetate (40f)

Using the procedure described in example 39, step 6, ethyl 2-(4-bromo-5-chloro-2-methylthiophen-3-yl)-2-(tert-butoxy)acetate (1d) (200 mg, 0.54 mmol) is converted by reaction with 2-(8-fluoro-3,4-dihydro-2H-1-benzopyran-6-yl)-4,4,5,5-tetramethyl-1,3,2-dioxaborolane (40e) (196 mg, 0.70 mmol) into ethyl 2-(tert-butoxy)-2-[5-chloro-4-(8-fluoro-3,4-dihydro-2H-1-benzopyran-6-yl)-2-methylthiophen-3-yl]acetate (40f) (163 mg, 0.37 mmol, 69%) after purification by preparative TLC (cyclohexane/ethyl acetate 90/10).

$^1$H NMR (400 MHz, CDCl$_3$) δ 1.02 (s, 9H), 1.23-1.26 (m, 3H), 2.07-2.10 (m, 2H), 2.50 (s, 3H), 2.81-2.86 (m, 2H), 4.09-4.19 (m, 2H), 4.31-4.33 (m, 2H), 4.78 (s, 1H), 6.83 (s, 1H), 6.92-6.95 (m, 1H).

Step 7: preparation of intermediate ethyl 2-(tert-butoxy)-2-[4-(8-fluoro-3,4-dihydro-2H-1-benzopyran-6-yl)-2-methyl-5-(pyridin-4-yl)thiophen-3-yl]acetate (40g)

Using the procedure described in example 1, step 6, ethyl 2-(tert-butoxy)-2-[5-chloro-4-(8-fluoro-3,4-dihydro-2H-1-benzopyran-6-yl)-2-methylthiophen-3-yl]acetate (40f) (160 mg, 0.36 mmol) is converted by reaction with 4-(tetramethyl-1,3,2-dioxaborolan-2-yl)pyridine (97 mg, 0.47 mmol) into ethyl 2-(tert-butoxy)-2-[4-(8-fluoro-3,4-dihydro-2H-1-benzopyran-6-yl)-2-methyl-5-(pyridin-4-yl)thiophen-3-yl]acetate (40g) (139 mg, 0.29 mmol, 79%) after purification by preparative TLC (cyclohexane/ethyl acetate 70/30).

$^1$H NMR (400 MHz, CDCl$_3$) δ 1.03 (s, 9H), 1.24-1.28 (m, 3H), 2.04-2.09 (m, 2H), 2.62 (s, 3H), 2.69-2.80 (m, 2H), 4.10-4.20 (m, 2H), 4.32-4.34 (m, 2H), 4.81 (s, 1H), 6.68-7.00 (m, 4H), 8.38-8.39 (m, 2H).

MS m/z ([M+H]⁺) 484.

Step 8: preparation of 2-(tert-butoxy)-2-[4-(8-fluoro-3,4-dihydro-2H-1-benzopyran-6-yl)-2-methyl-5-(pyridin-4-yl)thiophen-3-yl]acetic acid (example 40)

Using the procedure described in example 3, step 2, ethyl 2-(tert-butoxy)-2-[4-(8-fluoro-3,4-dihydro-2H-1-benzopyran-6-yl)-2-methyl-5-(pyridin-4-yl)thiophen-3-yl]acetate (40g) (135 mg, 0.28 mmol) is converted into 2-(tert-butoxy)-2-[4-(8-fluoro-3,4-dihydro-2H-1-benzopyran-6-yl)-2- methyl-5-(pyridin-4-yl)thiophen-3-yl]acetic acid (example 39) without purification (100 mg, 0.22 mmol, 78%).

$^1$H NMR (400 MHz, CDCl$_3$) δ 1.07 (s, 9H), 2.0-2.13 (m, 2H), 2.54 (s, 3H), 2.63-2.89 (m, 2H), 4.31-4.33 (m, 2H), 4.97 (s, 1H), 6.48-7.22 (m, 4H), 8.40-8.41 (m, 2H).

MS m/z ([M−H])$^-$ 454.

Example 41

Synthesis of 2-(tert-butoxy)-2-[4-(4,4-dimethylcyclohex-1-en-1-yl)-2-methyl-5-(methylaminocarbonylphen-3-yl)thiophen-3-yl]acetic acid

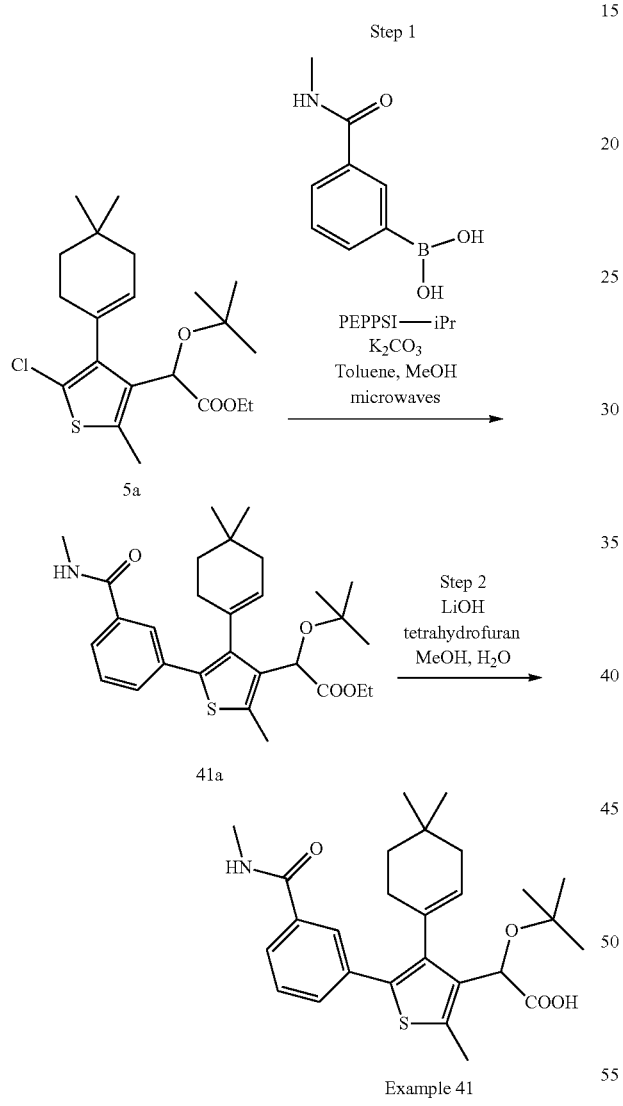

Step 1: preparation of intermediate ethyl 2-(tert-butoxy)-2-[4-(4,4-dimethylcyclohex-1-en-1-yl)-2-methyl-5-(methylaminocarbonylphen-3-yl)thiophen-3-yl]acetate (41a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (111 mg, 0.278 mmol) is converted by reaction with 3-methylaminocarbonylphenyl boronic acid (102 mg, 0.556 mmol) into ethyl 2-(tert-butoxy)-2-[4-(4,4-dimethylcyclohex-1-en-1-yl)-2-methyl-5-(methylaminocarbonylphen-3-yl)thiophen-3-yl]acetate (41a) (41 mg, 0.082 mmol, 30%) after purification by preparative TLC (cyclohexane/ethyl acetate 50/50).

$^1$H NMR (400 MHz, CDCl$_3$) δ 0.95 (s, 3H), 0.98 (s, 3H), 1.20 (s, 9H), 1.22 (t, J=7.2 Hz, 3H), 1.33-1.38 (m, 2H), 1.82-2.04 (m, 4H), 2.59 (s, 3H), 3.01 (d, J=4.8 Hz, 3H), 4.05-4.21 (m, 2H), 5.12 (s, 1H), 5.58-5.79 (bs, 1H), 6.07-6.16 (bs, 1H), 7.36 (dd, J=7.6 Hz, J=7.6 Hz, 1H), 7.63 (dd, J=1.6 Hz, J=8.0 Hz, 2H), 7.84-7.87 (m, 1H).

MS m/z ([M+H]$^+$) 498.

Step 2: preparation of 2-(tert-butoxy)-2-[4-(4,4-dimethylcyclohex-1-en-1-yl)-2-methyl-5-(methylaminocarbonylphen-3-yl)thiophen-3-yl]acetic acid (example 41)

Using the procedure described in example 15, step 2, ethyl 2-(tert-butoxy)-2-[4-(4,4-dimethylcyclohex-1-en-1-yl)-2-methyl-5-(methylaminocarbonylphen-3-yl)thiophen-3-yl]acetate (41a) (41 mg, 0.082 mmol) is converted into 2-(tert-butoxy)-2-[4-(4,4-dimethylcyclohex-1-en-1-yl)-2-methyl-5-(methylaminocarbonylphen-3-yl)thiophen-3-yl] acetic acid (example 41) (16 mg, 0.034 mmol, 41%) after purification by preparative TLC (dichloromethane/methanol 90/10).

$^1$H NMR (400 MHz, CDCl$_3$) δ 0.91 (s, 3H), 0.93 (s, 3H), 1.23 (s, 9H), 1.29-1.35 (m, 2H), 1.73-2.01 (m, 4H), 2.49 (s, 3H), 3.01 (d, J=4.8 Hz, 3H), 5.19 (s, 1H), 5.54-5.99 (bs, 1H), 7.38 (dd, J=7.6 Hz, J=8.0 Hz, 1H), 7.61 (d, J=7.6 Hz, 1H), 7.65 (d, J=8.0 Hz, 1H), 7.84 (s, 1H), 9.44-10.08 (bs, 1H).

MS m/z ([M+H]$^+$) 470.

MS m/z ([M−H]$^-$) 468.

Example 42

Synthesis of 2-(tert-butoxy)-2-[4-(4,4-dimethylcyclohex-1-en-1-yl)-2-methyl-5-[3-(propylcarbamoyl)phenyl]thiophen-3-yl]acetic acid

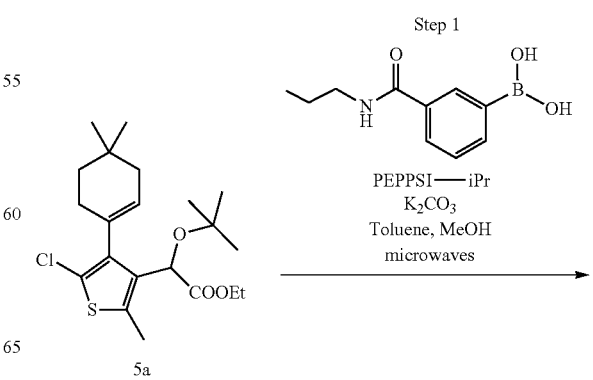

Example 43

Synthesis of 2-(tert-butoxy)-2-[4-(4,4-dimethylcyclohex-1-en-1-yl)-2-methyl-5-(pyridin-2-yl)thiophen-3-yl]acetic acid

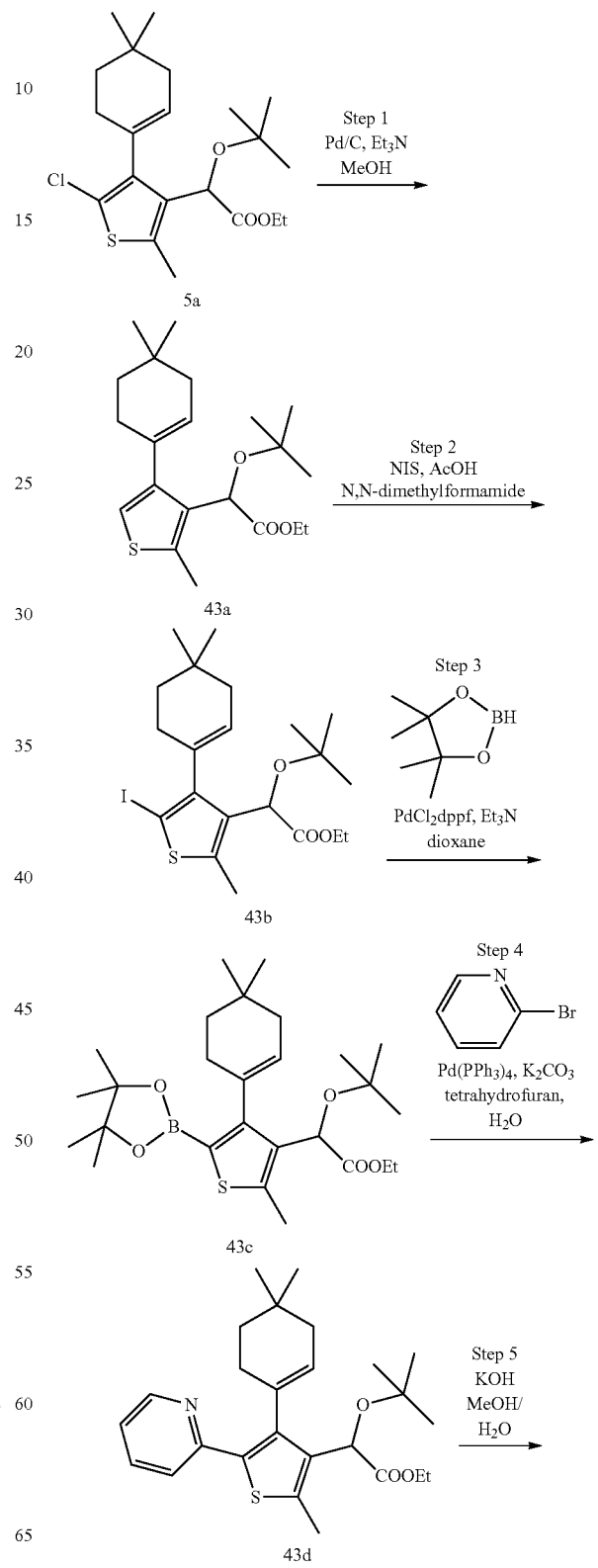

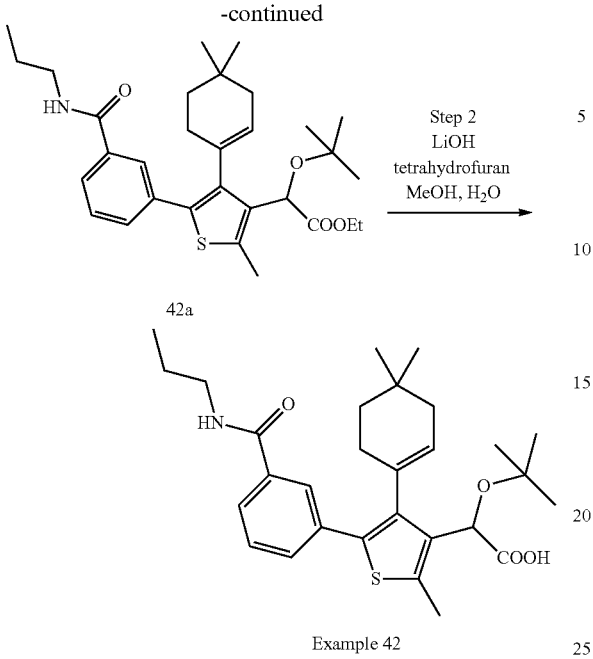

Step 1: preparation of intermediate ethyl 2-(tert-butoxy)-2-[4-(4,4-dimethylcyclohex-1-en-1-yl)-2-methyl-5-[3-(propylcarbamoyl)phenyl]thiophen-3-yl]acetate (42a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (150 mg, 0.38 mmol) is converted by reaction with [3-(propylcarbamoyl)phenyl]boronic acid (164 mg, 0.75 mmol) into ethyl 2-(tert-butoxy)-2-[4-(4,4-dimethylcyclohex-1-en-1-yl)-2-methyl-5-[3-(propylcarbamoyl)phenyl]thiophen-3-yl]acetate (a) (122 mg, 0.23 mmol, 61%) after purification by three preparative TLC (cyclohexane/ethyl acetate 60/40).

$^1$H NMR (400 MHz, CDCl$_3$) δ 0.95-1.01 (m, 9H), 1.20-1.38 (m, 15H), 1.61-1.67 (m, 2H), 1.82-2.00 (m, 3H), 2.60 (s, 3H), 3.40-3.45 (m, 2H), 4.07-4.20 (m, 2H), 5.12 (s, 1H), 6.05-6.07 (m, 1H), 7.35-7.39 (m, 1H), 7.62-7.66 (m, 2H), 7.85 (s, 1H).
MS m/z ([M+H]$^+$ 527.

Step 2: preparation of 2-(tert-butoxy)-2-[4-(4,4-dimethylcyclohex-1-en-1-yl)-2-methyl-5-[3-(propylcarbamoyl)phenyl]thiophen-3-yl]acetic acid (example 42)

Using the procedure described in example 15, step 2, ethyl 2-(tert-butoxy)-2-[4-(4,4-dimethylcyclohex-1-en-1-yl)-2-methyl-5-[3-(propylcarbamoyl)phenyl]thiophen-3-yl]acetate (42a) (119 mg, 0.23 mmol) is converted into 2-(tert-butoxy)-2-[4-(4,4-dimethylcyclohex-1-en-1-yl)-2-methyl-5-[3-(propylcarbamoyl)phenyl]thiophen-3-yl]acetic acid (example 42) (85 mg, 0.17 mmol, 74%) after purification by preparative TLC (dichloromethane/methanol 95/5).

$^1$H NMR (300 MHz, CDCl$_3$) δ 0.90-1.02 (m, 9H), 1.23-1.32 (m, 12H), 1.60-1.70 (m, 2H), 1.78-1.97 (m, 3H), 2.50 (s, 3H), 3.39-3.45 (m, 2H), 5.19 (s, 1H), 6.03-6.08 (m, 1H), 7.38 (t, J=7.7 Hz, 1H), 7.59-7.68 (m, 2H), 7.83 (s, 1H).
MS m/z ([M−H])$^−$ 496.

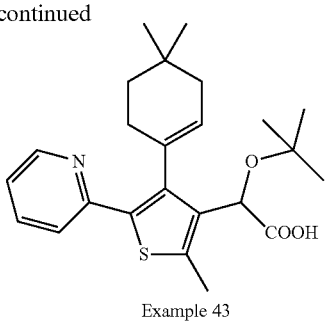

Example 43

Step 1: preparation of intermediate ethyl 2-(tert-butoxy)-2-[4-(4,4-dimethylcyclohex-1-en-1-yl)-2-methylthiophen-3-yl]acetate (43a)

To a solution of ethyl 2-(tert-butoxy)-2-[5-chloro-4-(4,4-dimethylcyclohex-1-en-1-yl)-2-methylthiophen-3-yl]acetate (5a) (1.00 g, 2.50 mmol) in methanol (80 mL) with triethylamine (385 µL, 2.75 mmol) was added palladium 10% dry on carbon powder (27 mg, 0.25 mmol), under argon. Then the reaction mixture was stirred under $H_2$ at room temperature for 20 hours (reaction completion determined by LC-MS). The reaction mixture was filtered through a pad of Celite®, rinsed with MeOH, and concentrated under reduced pressure. The residue was partitioned between ethyl acetate and water and the organic layer was washed with a (1N) hydrochloric acid aqueous solution and brine, dried over sodium sulfate, filtered, and concentrated under reduced pressure. Ethyl 2-(tert-butoxy)-2-[4-(4,4-dimethylcyclohex-1-en-1-yl)-2-methylthiophen-3-yl]acetate (43a) was obtained without purification (955 mg, 2.62 mmol, 100%) as a colorless oil.

$^1$H NMR (400 MHz, CDCl$_3$) δ 1.00-1.01 (m, 6H), 1.15-1.25 (m, 14H), 1.46-1.51 (m, 2H), 1.92-2.00 (m, 2H), 2.54 (s, 3H), 4.08-4.18 (m, 2H), 5.18 (s, 1H), 5.66 (s, 1H), 6.69 (s, 1H).

Step 2: preparation of intermediate ethyl 2-(tert-butoxy)-2-[4-(4,4-dimethylcyclohex-1-en-1-yl)-5-iodo-2-methylthiophen-3-yl]acetate (43b)

Under a nitrogen atmosphere, N-iodosuccinimide (609 mg, 2.65 mmol) was added to a solution of ethyl 2-(tert-butoxy)-2-[4-(4,4-dimethylcyclohex-1-en-1-yl)-2-methylthiophen-3-yl]acetate (43a) (920 mg, 2.52 mmol) in a mixture of acetic acid (22.5 mL) and N,N-dimethylformamide (2.5 mL) in an amber round bottom flask. The reaction mixture was stirred to room temperature for 20 hours. At 0° C., water was added, then at room temperature the mixture was diluted with ethyl acetate and the both layers were separated. The organic layer was washed with a saturated aqueous solution of sodium bicarbonate, solution of sodium thiosulfate and brine, dried over sodium sulfate, filtered, and evaporated under reduced pressure. Ethyl 2-(tert-butoxy)-2-[4-(4,4-dimethylcyclohex-1-en-1-yl)-5-iodo-2-methylthiophen-3-yl]acetate (43b) was obtained without purification as an oil (993 mg, 2.02 mmol, 80%).

$^1$H NMR (400 MHz, CDCl$_3$) δ 1.03-1.07 (m, 6H), 1.17-1.24 (m, 14H), 1.48-1.53 (m, 2H), 1.96-2.04 (m, 2H), 2.53 (s, 3H), 4.05-4.16 (m, 2H), 5.02 (s, 1H), 5.48-5.55 (m, 1H).

Step 3: preparation of intermediate ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c)

Under argon atmosphere, [1,1'-Bis(diphenylphosphino)ferrocene]dichloropalladium (II) (44 mg, 0.05 mmol) was dissolved in dioxane (7.5 mL). Then ethyl 2-(tert-butoxy)-2-[4-(4,4-dimethylcyclohex-1-en-1-yl)-5-iodo-2-methylthiophen-3-yl]acetate (43b) (874 mg, 1.78 mmol), triethylamine (0.74 mL, 5.34 mmol) and pinacolborane (388 µL, 2.67 mmol) were added and the mixture was stirred at 100° C. for 22 h. After cooling at room temperature, water was added and the mixture was extracted twice with ethyl acetate. The organic layer was washed with brine, dried over sodium sulfate, filtered, and concentrated under reduced pressure. The crude material was purified by flash chromatography on silica gel (cyclohexane/ethyl acetate 97/3) to give ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (664 mg, 1.35 mmol, 76%).

$^1$H NMR (400 MHz, CDCl$_3$) δ 1.06 (s, 6H), 1.15-1.21 (m, 14H), 1.27 (s, 12H), 1.45-1.50 (m, 2H), 1.95 (s, 2H), 2.58 (s, 3H), 4.02-4.15 (m, 2H), 5.12 (s, 1H), 5.49 (s, 1H).

Step 4: preparation of intermediate ethyl 2-(tert-butoxy)-2-[4-(4,4-dimethylcyclohex-1-en-1-yl)-2-methyl-5-(pyridin-2-yl)thiophen-3-yl]acetate (43d)

Under argon atmosphere, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (53 mg, 0.11 mmol), 2-bromopyridine (14 µL, 0.14 mmol), potassium carbonate (45 mg, 0.33 mmol) were dissolved in tetrahydrofuran (0.92 mL) and water (0.18 mL). The solution was degassed under argon for 10 minutes and tetrakis(triphenylphosphine)palladium (0) (13 mg, 0.01 mmol) was added. The reaction was heated and shaken at 90° C. for 18 hours. After cooling at room temperature, water was added and the mixture was extracted twice with ethyl acetate. The organic layer was washed with brine, dried over sodium sulfate, filtered, and concentrated under reduced pressure. The crude material was purified by preparative TLC (cyclohexane/ethyl acetate 70/30) to give ethyl 2-(tert-butoxy)-2-[4-(4,4-dimethylcyclohex-1-en-1-yl)-2-methyl-5-(pyridin-2-yl)thiophen-3-yl]acetate (43d) (38 mg, 0.09 mmol, 78%).

$^1$H NMR (400 MHz, CDCl$_3$) δ 1.06-1.08 (m, 6H), 1.20-1.28 (m, 12H), 1.48-1.50 (m, 2H), 1.99-2.42 (m, 4H), 2.60 (s, 3H), 4.07-4.18 (m, 2H), 5.10 (s, 1H), 5.69-5.72 (m, 1H), 7.04-7.08 (m, 1H), 7.56-7.60 (m, 1H), 7.64-7.66 (m, 1H), 8.51-8.53 (m, 1H).

MS m/z ([M+H])$^+$ 442.

Step 5: preparation of 2-(tert-butoxy)-2-[4-(4,4-dimethylcyclohex-1-en-1-yl)-2-methyl-5-(pyridin-2-yl)thiophen-3-yl]acetic acid (example 43)

Using the procedure described in example 3, step 2, ethyl 2-(tert-butoxy)-2-[4-(4,4-dimethylcyclohex-1-en-1-yl)-2-methyl-5-(pyridin-2-yl)thiophen-3-yl]acetate (43d) (36 mg, 0.08 mmol) is converted into 2-(tert-butoxy)-2-[4-(4,4-dimethylcyclohex-1-en-1-yl)-2-methyl-5-(pyridin-2-yl)thiophen-3-yl]acetic acid (example 43) (15 mg, 0.04 mmol, 45%) after purification by preparative TLC (dichloromethane/methanol 95/5).

$^1$H NMR (400 MHz, CDCl$_3$) δ 1.03 (m, 6H), 1.23-1.26 (m, 9H), 1.45-2.11 (m, 6H), 2.50 (s, 3H), 5.12-5.14 (m, 1H), 5.62-5.66 (m, 1H), 7.07-7.11 (m, 1H), 7.58-7.65 (m, 2H), 8.53-8.54 (m, 1H).

MS m/z ([M−H])$^−$ 412.

Example 44

Synthesis of 2-(tert-butoxy)-2-[4-(4,4-dimethylcyclohex-1-en-1-yl)-2-methyl-5-phenylthiophen-3-yl]acetic acid

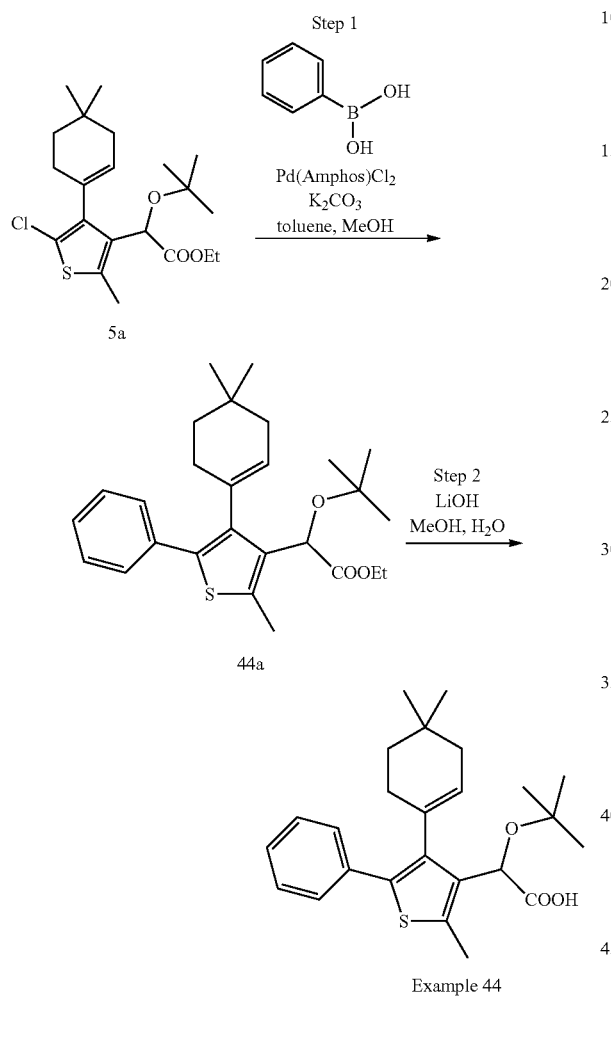

Example 44

Step 1: preparation of intermediate ethyl 2-(tert-butoxy)-2-[4-(4,4-dimethylcyclohex-1-en-1-yl)-2-methyl-5-phenylthiophen-3-yl]acetate (44a)

Using the procedure described in example 1, step 6, ethyl 2-(tert-butoxy)-2-[5-chloro-4-(4,4-dimethylcyclohex-1-en-1-yl)-2-methylthiophen-3-yl]acetate (5a) (140 mg, 0.35 mmol) is converted by reaction with phenylboronic acid (64 mg, 0.53 mmol) into ethyl 2-(tert-butoxy)-2-[4-(4,4-dimethylcyclohex-1-en-1-yl)-2-methyl-5-phenylthiophen-3-yl]acetate (44a) (130 mg, 0.29 mmol, 84%) after purification by preparative TLC (cyclohexane/ethyl acetate 95/5).

$^1$H NMR (400 MHz, CDCl$_3$) δ 0.96-0.99 (m, 6H), 1.20-1.26 (m, 12H), 1.35-1.36 (m, 2H), 1.83-1.99 (m, 4H), 2.59 (s, 3H), 4.07-4.20 (m, 2H), 5.14 (s, 1H), 5.71-5.72 (m, 1H), 7.22-7.24 (m, 1H), 7.28-7.32 (m, 2H), 7.50-7.52 (m, 2H).

Step 2: preparation of 2-(tert-butoxy)-2-[4-(4,4-dimethylcyclohex-1-en-1-yl)-2-methyl-5-phenylthiophen-3-yl]acetic acid (example 44)

Potassium hydroxide (50 mg, 0.88 mmol) was added to a solution of ethyl 2-(tert-butoxy)-2-[4-(4,4-dimethylcyclohex-1-en-1-yl)-2-methyl-5-phenylthiophen-3-yl]acetate (44a) (130 mg, 0.29 mmol) in a mixture of methanol (2.8 mL) and water (3 mL). The mixture was heated at 110° C. for 17 hours. After 15 hours, the reaction was not finished and an excess of potassium hydroxide was then added. The mixture was heated at 110° C. for 23 hours more. The mixture was concentrated to evaporate methanol in vacuo. The aqueous layer was acidified with a 1N hydrochloric acid aqueous solution and extracted with ethyl acetate twice. The organic layer was washed with brine, dried over sodium sulfate, filtered and concentrated in vacuo. The residue was purified by preparative TLC (dichloromethane/methanol 95/5) to give 2-(tert-butoxy)-2-[4-(4,4-dimethylcyclohex-1-en-1-yl)-2-methyl-5-phenylthiophen-3-yl]acetic acid (example 44) (86 mg, 0.21 mmol, 70%).

$^1$H NMR (400 MHz, CDCl$_3$) δ 0.92-0.95 (m, 6H), 1.23 (s, 9H), 1.29-1.32 (m, 2H), 1.84-1.97 (m, 4H), 2.49 (s, 3H), 5.18-5.19 (m, 1H), 5.76-5.80 (m, 1H), 7.22-7.24 (m, 1H), 7.29-7.50 (m, 4H).

MS m/z ([M−H])$^-$ 411.

Example 45

Synthesis of 2-(tert-butoxy)-2-[4-(4,4-dimethylcyclohex-1-en-1-yl)-2-methyl-5-(1,3-thiazol-2-yl)thiophen-3-yl]acetic acid

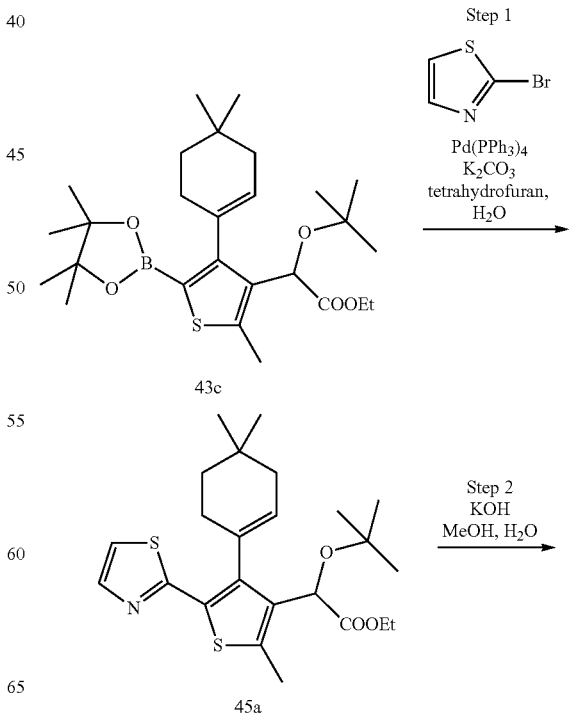

-continued

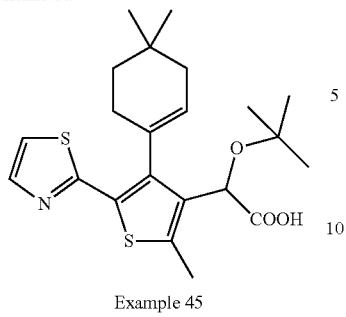

Example 45

Step 1: preparation of intermediate ethyl 2-(tert-butoxy)-2-[4-(4,4-dimethylcyclohex-1-en-1-yl)-2-methyl-5-(1,3-thiazol-2-yl)thiophen-3-yl]acetate (45a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (90 mg, 0.18 mmol) is converted by reaction with 2-bromo-1,3-thiazole (22 μL, 0.24 mmol) into ethyl 2-(tert-butoxy)-2-[4-(4,4-dimethylcyclohex-1-en-1-yl)-2-methyl-5-(1,3-thiazol-2-yl)thiophen-3-yl]acetate (45a) (38 mg, 0.08 mmol, 52%) after purification by preparative TLC (cyclohexane/ethyl acetate 70/30).

$^1$H NMR (400 MHz, CDCl$_3$) δ 1.09-1.11 (m, 6H), 1.19-1.26 (m, 12H), 1.56-1.60 (m, 2H), 2.01-2.13 (m, 4H), 2.60 (s, 3H), 4.08-4.18 (m, 2H), 5.03 (s, 1H), 5.73 (s, 1H), 7.17-7.18 (m, 1H), 7.71-7.72 (m, 1H).

MS m/z ([M+H])$^+$ 448.

Step 2: preparation of 2-(tert-butoxy)-2-[4-(4,4-dimethylcyclohex-1-en-1-yl)-2-methyl-5-(1,3-thiazol-2-yl)thiophen-3-yl]acetic acid (example 45)

Using the procedure described in example 3, step 2, ethyl 2-(tert-butoxy)-2-[4-(4,4-dimethylcyclohex-1-en-1-yl)-2-methyl-5-(1,3-thiazol-2-yl)thiophen-3-yl]acetate (45a) (36 mg, 0.08 mmol) is converted into 2-(tert-butoxy)-2-[4-(4,4-dimethylcyclohex-1-en-1-yl)-2-methyl-5-(1,3-thiazol-2-yl)thiophen-3-yl]acetic acid (example 45) (15 mg, 0.04 mmol, 45%) after purification by preparative TLC (dichloromethane/methanol 95/5).

$^1$H NMR (400 MHz, CDCl$_3$) δ 1.05-1.07 (m, 6H), 1.25-1.27 (m, 9H), 1.52-1.64 (m, 2H), 1.96-2.17 (m, 4H), 2.50 (s, 3H), 5.07 (s, 1H), 5.71 (s, 1H), 7.20-7.21 (m, 1H), 7.72-7.73 (m, 1H).

MS m/z ([M−H])$^−$ 418.

Example 46

Synthesis of 2-(tert-butoxy)-2-[4-(4,4-dimethylcyclohex-1-en-1-yl)-2-methyl-5-(5-methylpyridin-2-yl)thiophen-3-yl]acetic acid

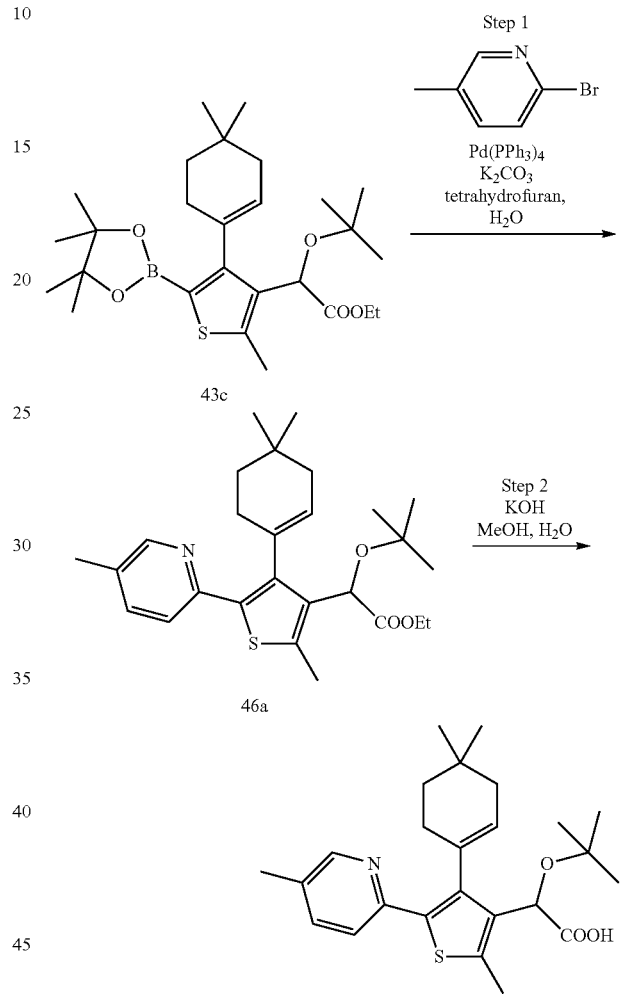

Example 46

Step 1: preparation of intermediate ethyl 2-(tert-butoxy)-2-[4-(4,4-dimethylcyclohex-1-en-1-yl)-2-methyl-5-(5-methylpyridin-2-yl)thiophen-3-yl]acetate (46a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (90 mg, 0.18 mmol) is converted by reaction with 2-bromo-5-methylpyridine (37 mg, 0.22 mmol) into ethyl 2-(tert-butoxy)-2-[4-(4,4-dimethylcyclohex-1-en-1-yl)-2-methyl-5-(5-methylpyridin-2-yl)thiophen-3-yl]acetate (46a) (61 mg, 0.13 mmol, 83%) after purification by preparative TLC (cyclohexane/ethyl acetate 80/20).

¹H NMR (400 MHz, CDCl₃) δ 1.05-1.07 (m, 6H), 1.19-1.26 (m, 12H), 1.46-1.49 (m, 2H), 1.98-2.09 (m, 4H), 2.30 (s, 3H), 2.58 (s, 3H), 4.08-4.17 (m, 2H), 5.10 (s, 1H), 5.68-5.71 (m, 1H), 7.39-7.41 (m, 1H), 7.54-7.56 (m, 1H), 8.35 (s, 1H).

MS m/z ([M+H])⁺ 456.

Step 2: preparation of 2-(tert-butoxy)-2-[4-(4,4-dimethylcyclohex-1-en-1-yl)-2-methyl-5-(5-methyl-pyridin-2-yl)thiophen-3-yl]acetic acid (example 46)

Using the procedure described in example 3, step 2, ethyl 2-(tert-butoxy)-2-[4-(4,4-dimethylcyclohex-1-en-1-yl)-2-methyl-5-(5-methylpyridin-2-yl)thiophen-3-yl]acetate (46a) (60 mg, 0.13 mmol) is converted into 2-(tert-butoxy)-2-[4-(4,4-dimethylcyclohex-1-en-1-yl)-2-methyl-5-(5-methyl-pyridin-2-yl)thiophen-3-yl]acetic acid (example 46) (38 mg, 0.09 mmol, 67%) after purification by preparative TLC (dichloromethane/methanol 95/5).

¹H NMR (400 MHz, CDCl₃) δ 1.02 (s, 6H), 1.23 (s, 9H), 1.58-1.61 (m, 2H), 1.99-2.05 (m, 4H), 2.31 (s, 3H), 2.49 (s, 3H), 5.11-5.16 (m, 1H), 5.61-5.64 (m, 1H), 7.41-7.42 (m, 1H), 7.52-7.54 (m, 1H), 8.36 (s, 1H).

MS m/z ([M−H])⁻ 426.

Example 47

Synthesis of 2-(tert-butoxy)-2-[4-(4,4-dimethylcyclohex-1-en-1-yl)-2-methyl-5-(3-methylpyridin-2-yl)thiophen-3-yl]acetic acid Step 1

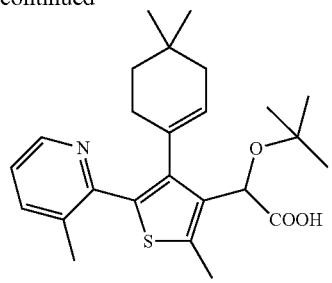

Pd(PPh₃)₄
K₂CO₃
tetrahydrofuran,
H₂O

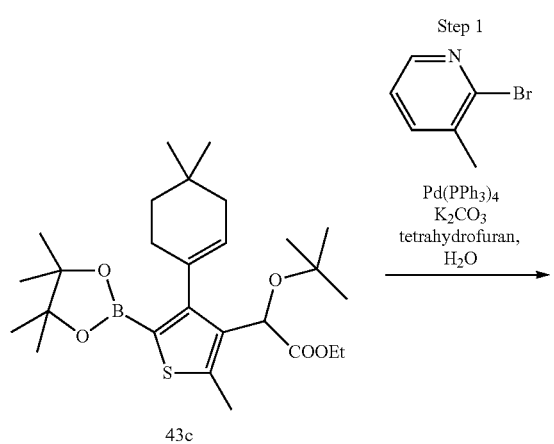

Step 2
KOH
MeOH, H₂O

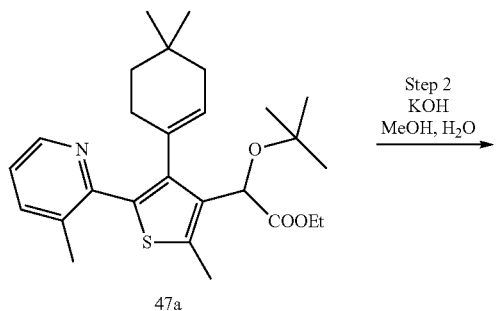

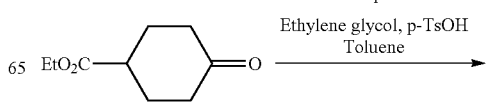

Example 47

Step 1: preparation of intermediate ethyl 2-(tert-butoxy)-2-[4-(4,4-dimethylcyclohex-1-en-1-yl)-2-methyl-5-(3-methylpyridin-2-yl)thiophen-3-yl]acetate (47a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (90 mg, 0.18 mmol) is converted by reaction with 2-bromo-3-methylpyridine (25 μL, 0.22 mmol) into ethyl 2-(tert-butoxy)-2-[4-(4,4-dimethylcyclohex-1-en-1-yl)-2-methyl-5-(3-methylpyridin-2-yl)thiophen-3-yl]acetate (47a) (44 mg, 0.10 mmol, 58%) after purification by preparative TLC (cyclohexane/ethyl acetate 80/20).

¹H NMR (400 MHz, CDCl₃) δ 0.77-0.82 (m, 6H), 1.18-1.26 (m, 14H), 1.77-2.00 (m, 4H), 2.23 (s, 3H), 2.59 (s, 3H), 4.05-4.19 (m, 2H), 5.15 (s, 1H), 5.61 (s, 1H), 7.10-7.15 (m, 1H), 7.48-7.51 (m, 1H), 8.43-8.45 (m, 1H).

MS m/z ([M+H])⁺ 456.

Step 2: preparation of 2-(tert-butoxy)-2-[4-(4,4-dimethylcyclohex-1-en-1-yl)-2-methyl-5-(3-methyl-pyridin-2-yl)thiophen-3-yl]acetic acid (example 47)

Using the procedure described in example 3, step 2, ethyl 2-(tert-butoxy)-2-[4-(4,4-dimethylcyclohex-1-en-1-yl)-2-methyl-5-(3-methylpyridin-2-yl)thiophen-3-yl]acetate (47a) (42 mg, 0.09 mmol) is converted into 2-(tert-butoxy)-2-[4-(4,4-dimethylcyclohex-1-en-1-yl)-2-methyl-5-(3-methyl-pyridin-2-yl)thiophen-3-yl]acetic acid (example 47) (26 mg, 0.06 mmol, 31%) after purification by preparative TLC (dichloromethane/methanol 95/5).

¹H NMR (400 MHz, CDCl₃) δ 0.67-0.77 (m, 6H), 1.16-1.18 (m, 11H), 1.72-1.81 (m, 4H), 2.23 (s, 3H), 2.53 (s, 3H), 5.08 (s, 1H), 5.52-5.56 (m, 1H), 7.20-7.23 (m, 1H), 7.56-7.58 (m, 1H), 8.64-8.67 (m, 1H).

MS m/z ([M−H])⁻ 426.

Example 48

Synthesis of [4-(4,4-bis-fluoromethyl-cyclohex-1-enyl)-2-methyl-5-pyridin-4-yl-thiophen-3-yl]-tert-butoxy-acetic acid Step 1

Ethylene glycol, p-TsOH
Toluene

Step 2
n-BuLi, diisopropylamine
Ethyl chloroformate
THF

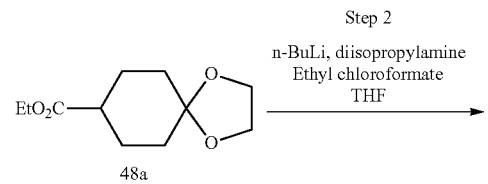
48a

Step 3
LiAlH₄
tetrahydrofuran

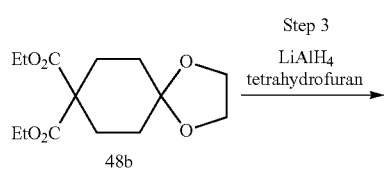
48b

Step 4
Triethylamine, DMAP
Tosyl chloride
dichloromethane

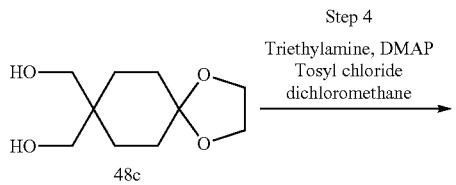
48c

Step 5
TBAF
tetrahydrofuran

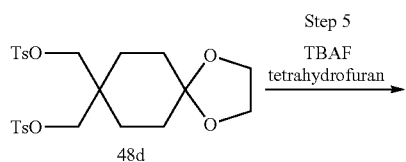
48d

Step 6
AcOH/H₂O

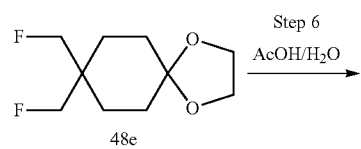
48e

Step 7
KHMDS, PhNOTf₂
tetrahydrofuran

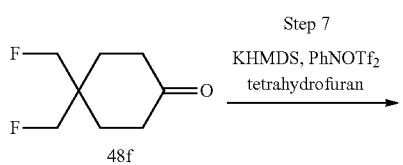
48f

Step 8
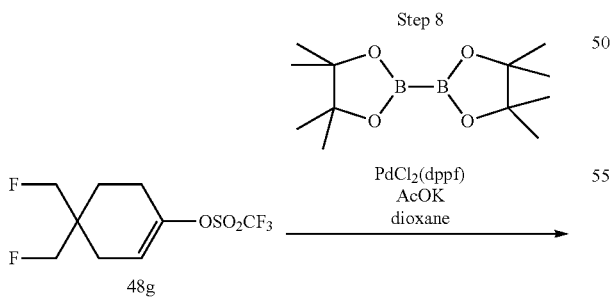
PdCl₂(dppf)
AcOK
dioxane

48g

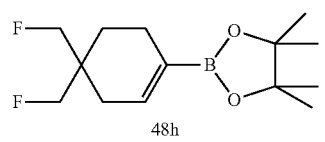
48h

Step 9
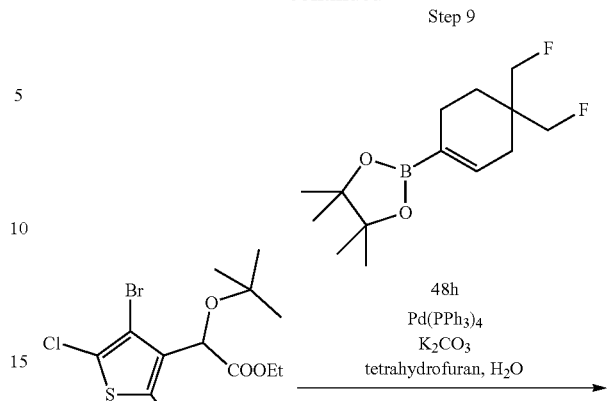
48h
Pd(PPh₃)₄
K₂CO₃
tetrahydrofuran, H₂O

1d

Step 10
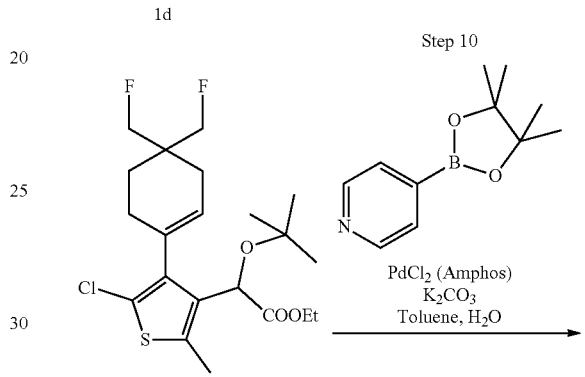
PdCl₂ (Amphos)
K₂CO₃
Toluene, H₂O

48i

Step 11
LiOH
tetrahydrofuran
MeOH, H₂O

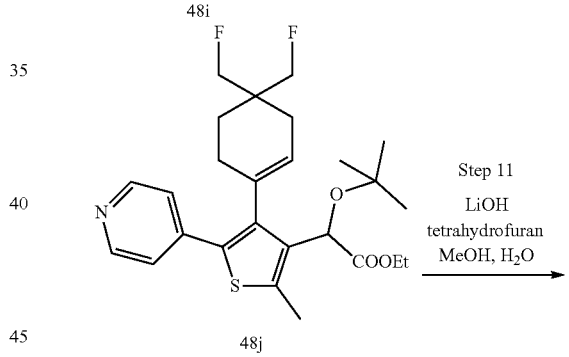
48j

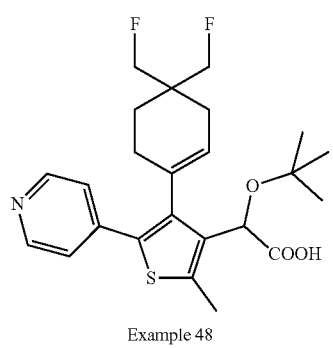
Example 48

Step 1: preparation of intermediate ethyl 1,4-dioxaspiro[4.5]decane-8-carboxylate (48a)

To a solution of ethyl 4-oxocyclohexanecarboxylate (7.66 g, 43.65 mmol) in toluene (40 mL) was added ethylene glycol (12.0 mL, 218.24 mmol) and p-toluenesulfonic acid monohydrate (80 mg, 0.44 mmol). The two phase mixture was stirred vigorously at room temperature for 4 days. The reaction was diluted with water and extracted with Et$_2$O. The organic layer was washed with saturated NaHCO$_3$ solution and brine, dried over sodium sulfate, filtered and concentrated under reduced pressure to give ethyl 1,4-dioxaspiro[4.5]decane-8-carboxylate (48a) (9.97 g, 43.65 mmol, 100%) as a colorless oil without purification.

$^1$H NMR (300 MHz, CDCl$_3$) δ 1.24 (td, J=1.6 Hz, J=7.2 Hz, 3H), 1.52-1.62 (m, 2H), 1.76-1.85 (m, 4H), 1.91-1.95 (m, 2H), 2.30-2.35 (m, 1H), 3.93 (d, J=1.6 Hz, 4H), 4.12 (qd, J=1.6 Hz, J=7.2 Hz, 2H).

MS m/z ([M+H]$^+$) 215.

Step 2: preparation of intermediate ethyl 1,4-dioxaspiro[4.5]decane-8,8-dicarboxylate (48b)

A 500 mL round-bottomed flask was charged with diisopropylamine (8.1 mL, 57.81 mmol) and THF (140 mL) under argon. The solution was cooled to −78° C. and n-BuLi (2.5 M in hexanes, 23.1 mL, 57.81 mmol) was added. The reaction was stirred for 30 minutes at −78° C. and ethyl 1,4-dioxaspiro[4.5]decane-8-carboxylate (48a) (10.322 g, 48.18 mmol) was added as a tetrahydrofuran solution (20 mL). The solution was stirred at −78° C. for 1 hour and ethyl chloroformate (4.8 mL, 48.18 mmol) was added neat. After stirring at −78° C. for 10 minutes, the reaction was warmed to room temperature for 2 hours. The reaction was quenched with saturated ammonium chloride solution and was diluted with diethyl ether. The layers were separated, the aqueous layer was extracted with diethyl ether and the combined organics were dried over sodium sulfate, filtered and concentrated under reduced pressure to give ethyl 1,4-dioxaspiro[4.5]decane-8,8-dicarboxylate (48b) (14.1 g, 46.79 mmol, 97%) as a yellow oil after purification by flash chromatography on silica gel (cyclohexane/ethyl acetate 30/70).

$^1$H NMR (400 MHz, CDCl$_3$) δ 1.24 (t, J=7.2 Hz, 6H), 1.66-1.70 (m, 4H), 2.15-2.20 (m, 4H), 3.93 (s, 4H), 4.18 (q, J=7.2 Hz, 4H).

MS m/z ([M+H]$^+$) 287.

Step 3: preparation of intermediate ethyl 1,4-dioxaspiro[4.5]decane-8,8-diyldimethanol (48c)

To a 500 mL round-bottomed flask was added ethyl 1,4-dioxaspiro[4.5]decane-8,8-dicarboxylate (48b) (13.396 g, 46.79 mmol) and tetrahydrofuran (160 mL) to give a light-yellow solution. The solution was cooled to 0° C. and lithium aluminum hydride (2.0M in tetrahydrofuran, 31 mL, 60.82 mmol) was added via syringe. The reaction was allowed to warm to room temperature and stirred overnight. The mixture was cooled down to 0° C. and quenched slowly with water (2.4 mL), 10% aqueous sodium hydroxide solution (2.4 mL) and water (7 mL). The mixture was allowed to stir until salts were formed and was then filtered (diethyl ether washings). The filtrate was concentrated under reduced pressure to give ethyl 1,4-dioxaspiro[4.5]decane-8,8-diyldimethanol (48c) (8.34 g, 41.28 mmol, 88%) as a white solid after purification by precipitation in cyclohexane and flash chromatography on silica gel (cyclohexane/ethyl acetate 100/0 to 0/100).

$^1$H NMR (400 MHz, CDCl$_3$) δ 1.52-1.65 (m, 8H), 2.32 (dd, J=5.1 Hz, J=5.4 Hz, 2H), 3.65 (d, J=5.1 Hz, 4H), 3.94 (s, 4H).

MS m/z ([M+H]$^+$) 203.

Step 4: preparation of intermediate 1,4-dioxaspiro[4.5]decane-8,8-diylbis(methylene)bis(4-methylbenzenesulfonate) (48d)

To a 250 mL round-bottomed flask was added ethyl 1,4-dioxaspiro[4.5]decane-8,8-diyldimethanol (48c) (3.801 g, 18.79 mmol) and dichloromethane (80 mL) to give a colorless solution. Triethylamine (9.4 mL, 65.78 mmol) and p-toluenesulfonyl chloride (7.609 g, 39.47 mmol) were added followed by 4-dimethylaminopyridine (239 mg, 1.88 mmol) and the reaction was refluxed for 48 hours. Saturated ammonium chloride solution was added followed by dilution with water and additional dichloromethane. The aqueous layer was extracted with dichloromethane twice and the combined organics were dried over sodium sulfate, filtered and concentrated under reduced pressure to give 1,4-dioxaspiro[4.5]decane-8,8-diylbis(methylene)bis(4-methylbenzenesulfonate) (48d) (6.08 g, 11.91 mmol, 61%) as a brown oil after purification by flash chromatography on silica gel (cyclohexane/ethyl acetate 50/50).

$^1$H NMR (400 MHz, CDCl$_3$) δ 1.44-1.54 (m, 8H), 2.46 (s, 6H), 3.84 (s, 4H), 3.88 (s, 4H), 7.35 (d, J=8.0 Hz, 4H), 7.73 (d, J=8.0 Hz, 4H).

MS m/z ([M+H]$^+$) 511.

Step 5: preparation of intermediate 8,8-bis(fluoromethyl)-1,4-dioxaspiro[4.5]decane (48e)

A 250 mL round-bottomed flask was charged with 1,4-dioxaspiro[4.5]decane-8,8-diylbis(methylene)bis(4-methylbenzenesulfonate) (48d) (8.184 g, 16.03 mmol) and tetra-n-butylammonium fluoride (1.0M in THF, 80 mL, 80.14 mmol) and the resulting solution was refluxed for 3 days. The reaction was cooled, diluted with diethyl ether and washed with water (×3) (Caution, gas formation). The organics were dried over sodium sulfate, filtered and concentrated under reduced pressure to give 8,8-bis(fluoromethyl)-1,4-dioxaspiro[4.5]decane (48e) (2.00 g, 9.70 mmol, 60%) as a yellow solid after purification by flash chromatography on silica gel (cyclohexane/ethyl acetate 70/30).

$^1$H NMR (400 MHz, CDCl$_3$) δ 1.57-1.63 (m, 8H), 3.95 (s, 4H), 4.34 (d, J=48.6 Hz, 4H).

$^{19}$F NMR (282 MHz, CDCl$_3$): δ −106.7 (s, 4F).

Step 6: preparation of intermediate 4,4-bis(fluoromethyl)cyclohexanone (48f)

To a 250 mL round-bottomed flask was added 8,8-bis(fluoromethyl)-1,4-dioxaspiro[4.5]decane (48e) (1.908 g, 9.25 mmol) and 80% aqueous acetic acid (100 mL). The reaction was heated at 65° C. for 3 hours, cooled and concentrated under reduced pressure to give 4,4-bis(fluoromethyl)cyclohexanone (48f) (1.57 g, 9.25 mmol, 100%) as a yellow oil after purification by flash chromatography on silica gel (cyclohexane/ethyl acetate 70/30).

$^1$H NMR (300 MHz, CDCl$_3$) δ 1.83 (dd, J=6.6 Hz, J=7.5 Hz, 4H), 2.40 (dd, J=6.9 Hz, J=6.9 Hz, 4H), 4.34 (d, J=48.6 Hz, 4H).

$^{19}$F NMR (282 MHz, CDCl$_3$): δ −107.0 (s, 4F).

Step 7: preparation of intermediate 3,3-bis(fluoromethyl)cyclohex-1-en-2-yl trifluoromethanesulfonate (48g)

To a stirred solution of 4,4-bis(fluoromethyl)cyclohexanone (48f) (1.57 g, 9.25 mmol) and N-phenyltrifluoromethanesulfonimide (4.611 g, 12.55 mmol) in tetrahydrofuran (100 mL) under argon at −78° C. was added potassium bis-trimethylsilylamide (0.5M in toluene, 25.1 mL, 12.55 mmol). The reaction was stirred for 3 hours, then quenched with water and extracted with diethyl ether. The combined ether extract layers were washed with brine, dried over sodium sulfate, filtered and concentrated under reduced pressure to give 3,3-bis(fluoromethyl)cyclohex-1-en-2-yl trifluoromethanesulfonate (48g) (2.72 g, 9.25 mmol, 100%)

as a yellow oil after purification by flash chromatography on silica gel (cyclohexane/ethyl acetate 80/20).

$^1$H NMR (400 MHz, CDCl$_3$) δ 1.79 (dd, J=6.4 Hz, J=6.8 Hz, 2H), 2.14-2.16 (m, 2H), 2.38-2.42 (m, 2H), 4.33 (ddd, J=47.2 Hz, J=17.6 Hz, J=9.2 Hz, 2H), 5.70-5.75 (m, 1H).

Step 8: preparation of intermediate 2-(4,4-bis-fluoromethyl-cyclohex-1-enyl)-4,4,5,5-tetramethyl-[1,3,2]dioxaborolane (48h)

Under argon atmosphere, 3,3-bis(fluoromethyl)cyclohex-1-en-2-yl trifluoromethanesulfonate (48g) (2.72 g, 9.25 mmol), bis(pinacolato)diboron (3.57 g, 13.92 mmol) and potassium acetate (2.77 g, 27.83 mmol) were dissolved in dioxane (62 mL). The solution was degassed with argon for 10 minutes and [1,1'-bis(diphenylphosphino)ferrocene]dichloropalladium(II) (762 mg, 0.93 mmol) was added. The reaction was heated and shaken at 85° C. for 16 hours. The reaction was cooled to room temperature diluted with ethyl acetate and filtered through Celite®. The filtrate was concentrated under reduced pressure and the residue was dissolved with ethyl acetate and water and was extracted with ethyl acetate. Then the combined organic layers were washed with brine, dried over sodium sulfate and concentrated under reduced pressure to give 2-(4,4-bis-fluoromethyl-cyclohex-1-enyl)-4,4,5,5-tetramethyl-[1,3,2]dioxaborolane (48h) (1.81 g, 6.65 mmol, 72%) as a colorless oil after purification by flash chromatography on silica gel (cyclohexane/ethyl acetate 90/10).

$^1$H NMR (400 MHz, CDCl$_3$) δ 1.26 (s, 12H), 1.55 (dd, J=6.3 Hz, J=6.6 Hz, 2H), 1.97-2.03 (m, 2H), 2.14-2.20 (m, 2H), 4.22 (dd, J=1.5 Hz, J=9.0 Hz, 1H), 4.25 (dd, J=1.5 Hz, J=9.0 Hz, 1H), 4.29 (ddd, J=47.5 Hz, J=17.6 Hz, J=9.2 Hz, 2H), 6.44-6.51 (m, 1H).

Step 9: preparation of intermediate ethyl [4-(4,4-bis-fluoromethyl-cyclohex-1-enyl)-5-chloro-2-methyl-thiophen-3-yl]-tert-butoxy-acetic acid ethyl ester (48i)

Using the procedure described in example 39, step 6, ethyl 2-(4-bromo-5-chloro-2-methylthiophen-3-yl)-2-(tert-butoxy)acetate (1d) (200 mg, 0.54 mmol) is converted by reaction with 2-(4,4-bis-fluoromethyl-cyclohex-1-enyl)-4,4,5,5-tetramethyl-[1,3,2]dioxaborolane (48h) (206 mg, 0.76 mmol) into ethyl [4-(4,4-bis-fluoromethyl-cyclohex-1-enyl)-5-chloro-2-methyl-thiophen-3-yl]-tert-butoxy-acetic acid ethyl ester (48i) (195 mg, 0.45 mmol, 80%) as a colorless oil after purification by preparative TLC (cyclohexane/ethyl acetate 90/10).

$^1$H NMR (300 MHz, CDCl$_3$) δ 1.18 (s, 9H), 1.22 (t, J=7.2 Hz, 3H), 1.63-1.80 (m, 3H), 2.06-2.26 (m, 4H), 2.47 (s, 3H), 4.12 (q, J=7.2 Hz, 2H), 4.30-4.64 (m, 4H), 4.93 (s, 1H), 5.48-5.55 (m, 1H).

Step 10: preparation of intermediate [4-(4,4-bis-fluoromethyl-cyclohex-1-enyl)-2-methyl-5-pyridin-4-yl-thiophen-3-yl]-tert-butoxy-acetic acid ethyl ester (48j)

Using the procedure described in example 1, step 6, ethyl [4-(4,4-bis-fluoromethyl-cyclohex-1-enyl)-5-chloro-2-methyl-thiophen-3-yl]-tert-butoxy-acetic acid ethyl ester (48i) (195 mg, 0.45 mmol) is converted by reaction with 4-pyridine boronic acid pinacol ester (142 mg, 0.67 mmol) into [4-(4,4-bis-fluoromethyl-cyclohex-1-enyl)-2-methyl-5-pyridin-4-yl-thiophen-3-yl]-tert-butoxy-acetic acid ethyl ester (48j) (47 mg, 0.01 mmol, 22%) after purification by preparative TLC (cyclohexane/ethyl acetate 50/50).

$^1$H NMR (400 MHz, CDCl$_3$) δ 1.21 (s, 9H), 1.23 (t, J=7.2 Hz, 3H), 1.48-1.78 (m, 2H), 1.86-2.32 (m, 4H), 2.60 (s, 3H), 4.06-4.20 (m, 2H), 4.27-4.69 (m, 4H), 5.05 (s, 1H), 5.55-5.77 (m, 1H), 7.38 (d, J=5.2 Hz, 2H), 8.53 (d, J=5.2 Hz, 2H).

MS m/z ([M+H]$^+$) 478.

Step 11: preparation of [4-(4,4-bis-fluoromethyl-cyclohex-1-enyl)-2-methyl-5-pyridin-4-yl-thiophen-3-yl]-tert-butoxy-acetic acid (example 48)

Using the procedure described in example 15, step 2, [4-(4,4-bis-fluoromethyl-cyclohex-1-enyl)-2-methyl-5-pyridin-4-yl-thiophen-3-yl]-tert-butoxy-acetic acid ethyl ester (48j) (47 mg, 0.01 mmol) is converted into [4-(4,4-bis-fluoromethyl-cyclohex-1-enyl)-2-methyl-5-pyridin-4-yl-thiophen-3-yl]-tert-butoxy-acetic acid (example 48) (27 mg, 0.06 mmol, 61%) after purification by preparative TLC (dichloromethane/methanol 90/10).

$^1$H NMR (300 MHz, CDCl$_3$) δ 1.25 (s, 9H), 1.51-1.71 (m, 2H), 1.87-1.97 (m, 1H), 2.10-2.42 (m, 3H), 2.55 (s, 3H), 4.23-4.54 (m, 4H), 5.13 (s, 1H), 5.57-5.97 (bs, 1H), 7.39 (d, J=6.0 Hz, 2H), 8.56 (d, J=5.6 Hz, 2H).

MS m/z ([M+H]$^+$) 450.
MS m/z ([M−H]$^-$) 448.

Example 49

Synthesis of 2-(tert-butoxy)-2-{2-methyl-4-[4,4-dimethylcyclohex-1-en-1-yl]-5-(Pyrimidin-2-yl)thiophen-3-yl}acetic acid

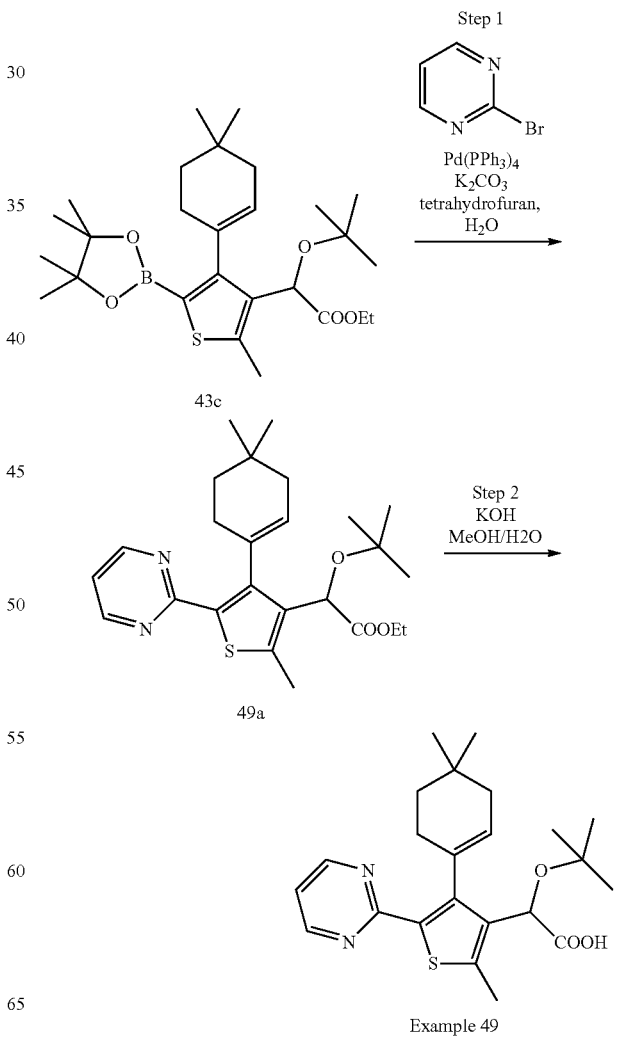

Example 49

Step 1: preparation of intermediate ethyl 2-(tert-butoxy)-2-[4-(4,4-dimethylcyclohex-1-en-1-yl)-2-methyl-5-(pyrimidin-2-yl)thiophen-3-yl]acetate (49a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 2-bromo-pyrimidine (41 mg, 0.25 mmol) into ethyl 2-(tert-butoxy)-2-[4-(4,4-dimethylcyclohex-1-en-1-yl)-2-methyl-5-(pyrimidin-2-yl)thiophen-3-yl]acetate (49a) (71 mg, 0.16 mmol, 83%) after purification by preparative TLC (cyclohexane/ethyl acetate 80/20).

$^1$H NMR (400 MHz, CDCl$_3$) δ 1.08 (s, 3H), 1.12 (s, 3H), 1.19 (t, J=7.0 Hz, 3H), 1.20 (s, 9H), 1.47-1.60 (m, 2H), 1.90-2.01 (m, 2H), 2.25 (m, 1H), 2.46 (m, 1H), 2.61 (s, 3H), 4.08-4.18 (m, 2H), 5.19 (s, 1H), 5.45-5.68 (bs, 1H), 6.96 (t, J=5.2 Hz, 1H), 8.60 (d, J=5.2 Hz, 2H).

MS m/z ([M+H]$^+$) 443.

Step 2: preparation of 2-(tert-butoxy)-2-{2-methyl-4-[4,4-dimethylcyclohex-1-en-1-yl]-5-(pyrimidin-2-yl)thiophen-3-yl}acetic acid (example 49)

Using the procedure described in example 3, step 2, ethyl 2-(tert-butoxy)-2-[4-(4,4-dimethylcyclohex-1-en-1-yl)-2-methyl-5-(pyrimidin-2-yl)thiophen-3-yl]acetate (49a) (71 mg, 0.16 mmol) is converted into 2-(tert-butoxy)-2-{2-methyl-4-[4,4-dimethylcyclohex-1-en-1-yl]-5-(pyrimidin-2-yl)thiophen-3-yl}acetic acid (example 49) (49 mg, 0.12 mmol, 74%) after purification by preparative TLC (dichloromethane/methanol 95/5).

$^1$H NMR (400 MHz, CDCl$_3$) δ 1.03 (s, 3H), 1.13 (s, 3H), 1.24 (s, 9H), 1.34-1.61 (m, 2H), 1.84-1.98 (m, 2H), 2.24-2.40 (m, 1H), 2.48-2.70 (m, 1H), 2.53 (s, 3H), 5.15-5.30 (bs, 1H), 5.41-5.94 (bs, 1H), 6.99 (t, J=4.8 Hz, 1H), 8.61 (d, J=4.8 Hz, 2H).

MS m/z ([M+H]$^+$) 415.
MS m/z ([M–H]$^-$) 413.

Example 50

Synthesis of 2-(tert-butoxy)-2-[4-(4,4-dimethylcyclohex-1-en-1-yl)-2-methyl-5-(1H-pyrazol-1-yl)thiophen-3-yl]acetic acid

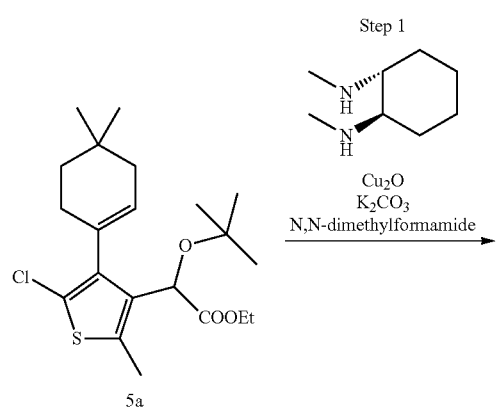

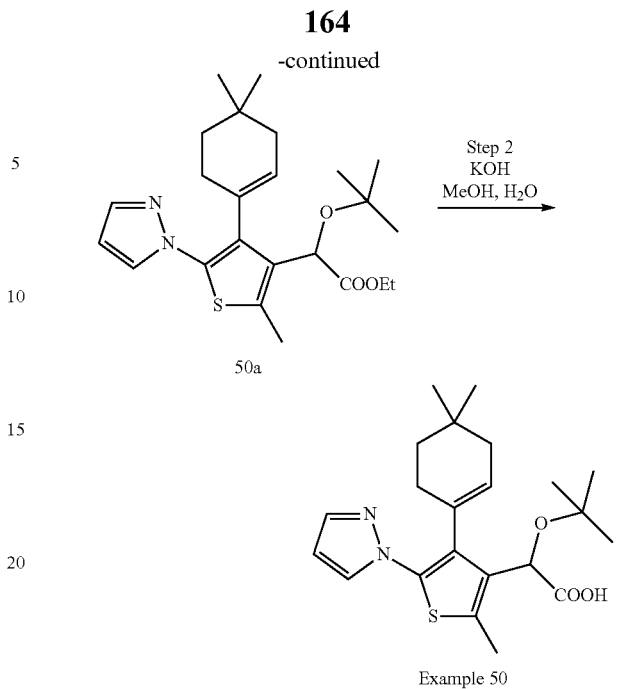

Example 50

Step 1: preparation of intermediate ethyl 2-(tert-butoxy)-2-[4-(4,4-dimethylcyclohex-1-en-1-yl)-2-methyl-5-(1H-pyrazol-1-yl)thiophen-3-yl]acetate (50a)

Under argon atmosphere, ethyl 2-(tert-butoxy)-2-[5-chloro-4-(4,4-dimethylcyclohex-1-en-1-yl)-2-methylthiophen-3-yl]acetate (5a) (50 mg, 0.13 mmol), pyrazole (10 mg, 0.15 mmol), potassium carbonate (35 mg, 0.25 mmol), copper (I) oxide (2 mg, 0.01 mmol) and trans-N,N'-dimethylcyclohexane-1,2-diamine (5 mg, 0.04 mmol) were dissolved in dimethylformamide (0.5 mL). The reaction was heated and shaken at 140° C. for 27 hours. The reaction wasn't complete, pyrazole (10 mg, 0.15 mmol), potassium carbonate (11 mg, 0.08 mmol), copper (I) oxide (2 mg, 0.01 mmol) and trans-N,N'-dimethylcyclohexane-1,2-diamine (5 mg, 0.04 mmol) were added. The mixture was heated at 145° C. for 23 h more. After cooling down to room temperature, the mixture was filtered through Celite® and rinsed with ethyl acetate. The filtrate was concentrated under reduced pressure and partitioned between ethyl acetate and water. The organic layer was washed with brine, dried over sodium sulfate, filtered and concentrated under reduced pressure. The crude material was purified by preparative TLC (cyclohexane/ethyl acetate 80/20) to give ethyl 2-(tert-butoxy)-2-[4-(4,4-dimethylcyclohex-1-en-1-yl)-2-methyl-5-(1H-pyrazol-1-yl)thiophen-3-yl]acetate (50a) (11 mg, 0.03 mmol, 20%).

$^1$H NMR (400 MHz, CDCl$_3$) δ 0.94 (s, 3H), 0.96 (s, 3H), 1.19 (s, 9H), 1.22 (t, J=7.2 Hz, 3H), 1.30-1.42 (m, 2H), 1.79-2.12 (m, 4H), 2.55 (s, 3H), 4.05-4.21 (m, 2H), 5.07 (s, 1H), 5.70-5.75 (m, 1H), 6.32-6.35 (m, 1H), 7.60-7.63 (m, 1H), 7.6-7.70 (m, 1H).

MS m/z [M+H]$^+$ 431

Step 2: preparation of 2-(tert-butoxy)-2-[4-(4,4-dimethylcyclohex-1-en-1-yl)-2-methyl-5-(1H-pyrazol-1-yl)thiophen-3-yl]acetic acid (example 50)

Using the procedure described in example 3, step 2, ethyl 2-(tert-butoxy)-2-[4-(4,4-dimethylcyclohex-1-en-1-yl)-2-methyl-5-(1H-pyrazol-1-yl)thiophen-3-yl]acetate (50a) (22 mg, 0.05 mmol) is converted into 2-(tert-butoxy)-2-[4-(4,4- dimethylcyclohex-1-en-1-yl)-2-methyl-5-(1H-pyrazol-1-yl)thiophen-3-yl]acetic acid (example 50) (17 mg, 0.04 mmol, 85%) without purification further purification.

¹H NMR (400 MHz, CDCl₃) δ 0.91 (s, 3H), 0.93 (s, 3H), 1.23 (s, 9H), 1.29-1.38 (m, 2H), 1.80-2.05 (m, 4H), 2.47 (s, 3H), 5.15 (s, 1H), 5.77-5.88 (m, 1H), 6.35 (dd, J=2.4 Hz, J=2.0 Hz, 1H), 7.63 (dd, J=2.0 Hz, J=0.4 Hz, 1H), 7.67 (d, J=2.4 Hz, J=0.4 Hz, 1H).

MS m/z [M−H]⁻ 401

Example 51

Synthesis of 2-(tert-butoxy)-2-{2-methyl-4-[4,4-dimethylcyclohex-1-en-1-yl]-5-(6-(n-propyl)pyridin-2-yl)thiophen-3-yl}acetic acid

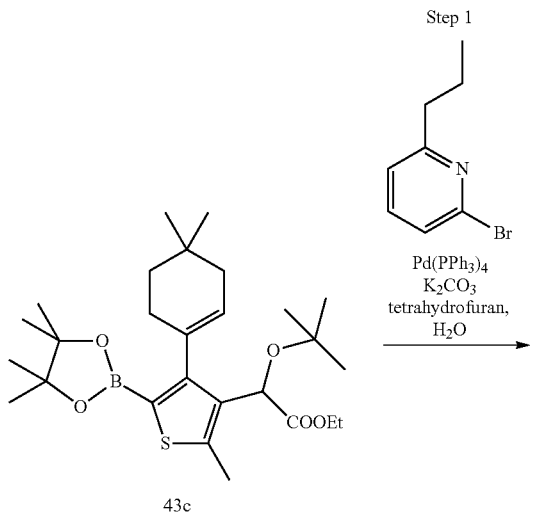

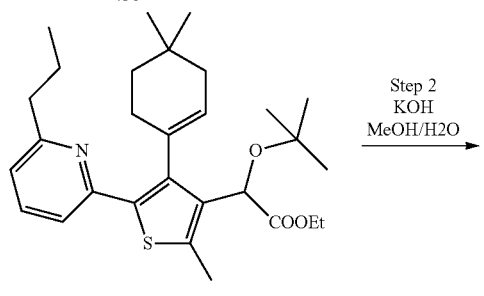

Example 51

Step 1: preparation of intermediate ethyl 2-(tert-butoxy)-2-[4-(4,4-dimethylcyclohex-1-en-1-yl)-2-methyl-5-(6-(n-propyl)pyridin-2-yl)thiophen-3-yl]acetate (51a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 2-bromo-6-(n-propyl)pyridine (49 mg, 0.25 mmol) into ethyl 2-(tert-butoxy)-2-[4-(4,4-dimethylcyclohex-1-en-1-yl)-2-methyl-5-(6-(n-propyl)pyridin-2-yl)thiophen-3-yl]acetate (51a) (99 mg, 0.20 mmol, 100%) after purification by preparative TLC (cyclohexane/ethyl acetate 85/15).

¹H NMR (400 MHz, CDCl₃) δ 0.96 (t, J=7.2 Hz, 3H), 1.04 (s, 3H), 1.06 (s, 3H), 1.19 (s, 9H), 1.24 (t, J=6.8 Hz, 3H), 1.39-1.54 (m, 2H), 1.68-1.83 (m, 2H), 1.92-2.22 (m, 4H), 2.59 (s, 3H), 2.70-2.77 (m, 2H), 4.00-4.18 (m, 2H), 5.12 (s, 1H), 5.60-5.78 (bs, 1H), 6.91 (d, J=8.0 Hz, 1H), 7.42 (d, J=7.6 Hz, 1H), 7.46 (dd, J=7.6 Hz, J=8.0 Hz, 1H).

MS m/z ([M+H]⁺) 484.

Step 2: preparation of 2-(tert-butoxy)-2-{2-methyl-4-[4,4-dimethylcyclohex-1-en-1-yl]-5-(6-(n-propyl)pyridin-2-yl)thiophen-3-yl}acetic acid (example 51)

Using the procedure described in example 3, step 2, ethyl 2-(tert-butoxy)-2-[4-(4,4-dimethylcyclohex-1-en-1-yl)-2-methyl-5-(6-(n-propyl)pyridin-2-yl)thiophen-3-yl]acetate (51a) (99 mg, 0.20 mmol) is converted into 2-(tert-butoxy)-2-{2-methyl-4-[4,4-dimethylcyclohex-1-en-1-yl]-5-(6-(n-propyl)pyridin-2-yl)thiophen-3-yl}acetic acid (example 51) (22 mg, 0.05 mmol, 24%) after purification by preparative TLC (dichloromethane/methanol 95/5).

¹H NMR (400 MHz, CDCl₃) δ 0.99 (t, J=7.2 Hz, 3H), 1.01 (s, 3H), 1.02 (s, 3H), 1.22 (s, 9H), 1.39-1.50 (m, 2H), 1.74-1.83 (m, 2H), 1.91-2.12 (m, 4H), 2.49 (s, 3H), 2.75 (t, J=7.6 Hz, 2H), 5.12 (s, 1H), 5.50-6.28 (bs, 1H), 6.93 (m, 1H), 7.42-7.56 (m, 1H), 7.64-7.69 (m, 1H), 9.67-10.24 (bs, 1H).

MS m/z ([M+H]⁺) 456.

MS m/z ([M−H]⁻) 454.

Example 52

Synthesis of 2-(tert-butoxy)-2-{2-methyl-4-[4,4-dimethylcyclohex-1-en-1-yl]-5-(5-(n-propyl)pyridin-2-yl)thiophen-3-yl}acetic acid

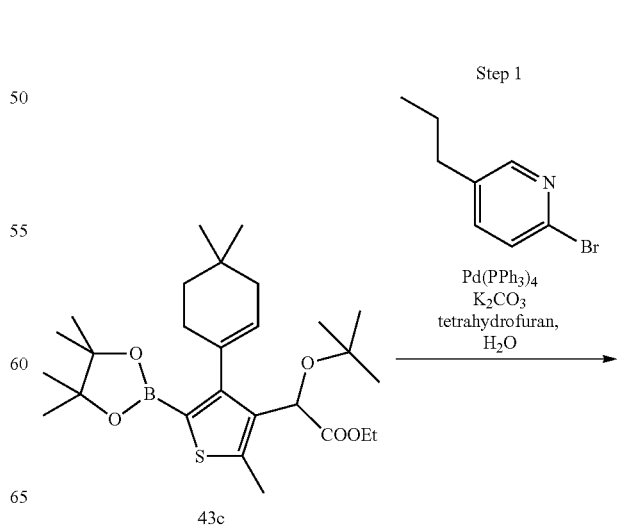

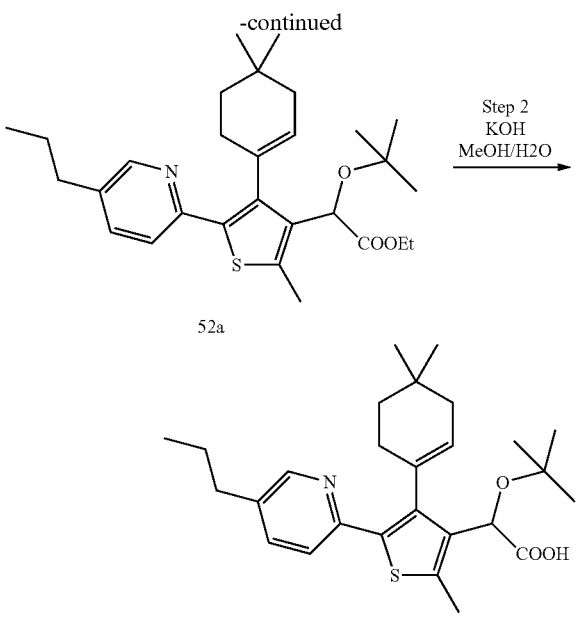

Example 52

Step 1: preparation of intermediate ethyl 2-(tert-butoxy)-2-[4-(4,4-dimethylcyclohex-1-en-1-yl)-2-methyl-5-(5-(n-propyl)pyridin-2-yl)thiophen-3-yl]acetate (52a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 2-bromo-5-(n-propyl)pyridine (52 mg, 0.25 mmol) into ethyl 2-(tert-butoxy)-2-[4-(4,4-dimethylcyclohex-1-en-1-yl)-2-methyl-5-(5-(n-propyl)pyridin-2-yl)thiophen-3-yl]acetate (52a) (89 mg, 0.18 mmol, 90%) after purification by preparative TLC (cyclohexane/ethyl acetate 85/15).

$^1$H NMR (400 MHz, CDCl$_3$) δ 0.93 (t, J=7.2 Hz, 3H), 1.05 (s, 3H), 1.07 (s, 3H), 1.19 (s, 9H), 1.24 (t, J=7.2 Hz, 3H), 1.43-1.53 (m, 2H), 1.53-1.67 (m, 2H), 1.87-2.16 (m, 4H), 2.54 (t, J=7.6 Hz, 2H), 2.58 (s, 3H), 4.02-4.18 (m, 2H), 5.09 (s, 1H), 5.58-5.79 (bs, 1H), 7.40 (dd, J=2.4 Hz, J=8.0 Hz, 1H), 7.56 (d, J=8.0 Hz, 1H), 8.33 (s, 1H).

MS m/z ([M+H]$^+$) 484.

Step 2: preparation of 2-(tert-butoxy)-2-{2-methyl-4-[4,4-dimethylcyclohex-1-en-1-yl]-5-(5-(n-propyl)pyridin-2-yl)thiophen-3-yl}acetic acid (example 52)

Using the procedure described in example 3, step 2, ethyl 2-(tert-butoxy)-2-[4-(4,4-dimethylcyclohex-1-en-1-yl)-2-methyl-5-(5-(n-propyl)pyridin-2-yl)thiophen-3-yl]acetate (52a) (89 mg, 0.18 mmol) is converted into 2-(tert-butoxy)-2-{2-methyl-4-[4,4-dimethylcyclohex-1-en-1-yl]-5-(5-(n-propyl)pyridin-2-yl)thiophen-3-yl}acetic acid (Example 52) (18 mg, 0.04 mmol, 19%) after purification by preparative TLC (dichloromethane/methanol 95/5).

$^1$H NMR (400 MHz, CDCl$_3$) δ 0.95 (t, J=7.2 Hz, 3H), 1.01 (s, 3H), 1.02 (s, 3H), 1.22 (s, 9H), 1.40-1.49 (m, 2H), 1.59-1.69 (m, 2H), 1.94-2.09 (m, 4H), 2.49 (s, 3H), 2.56 (t, J=7.6 Hz, 2H), 5.12 (s, 1H), 5.50-6.23 (bs, 1H), 7.41 (dd, J=2.0 Hz, J=8.0 Hz, 1H), 7.55 (d, J=8.0 Hz, 1H), 8.36 (s, 1H), 9.65-10.38 (bs, 1H).

MS m/z ([M+H]$^+$) 456.
MS m/z ([M−H]$^−$) 454.

Example 53

Synthesis of [4-(4-fluoromethyl-4-methylcyclohex-1-enyl)-2-methyl-5-pyridin-4-yl-thiophen-3-yl]-tert-butoxy-acetic acid

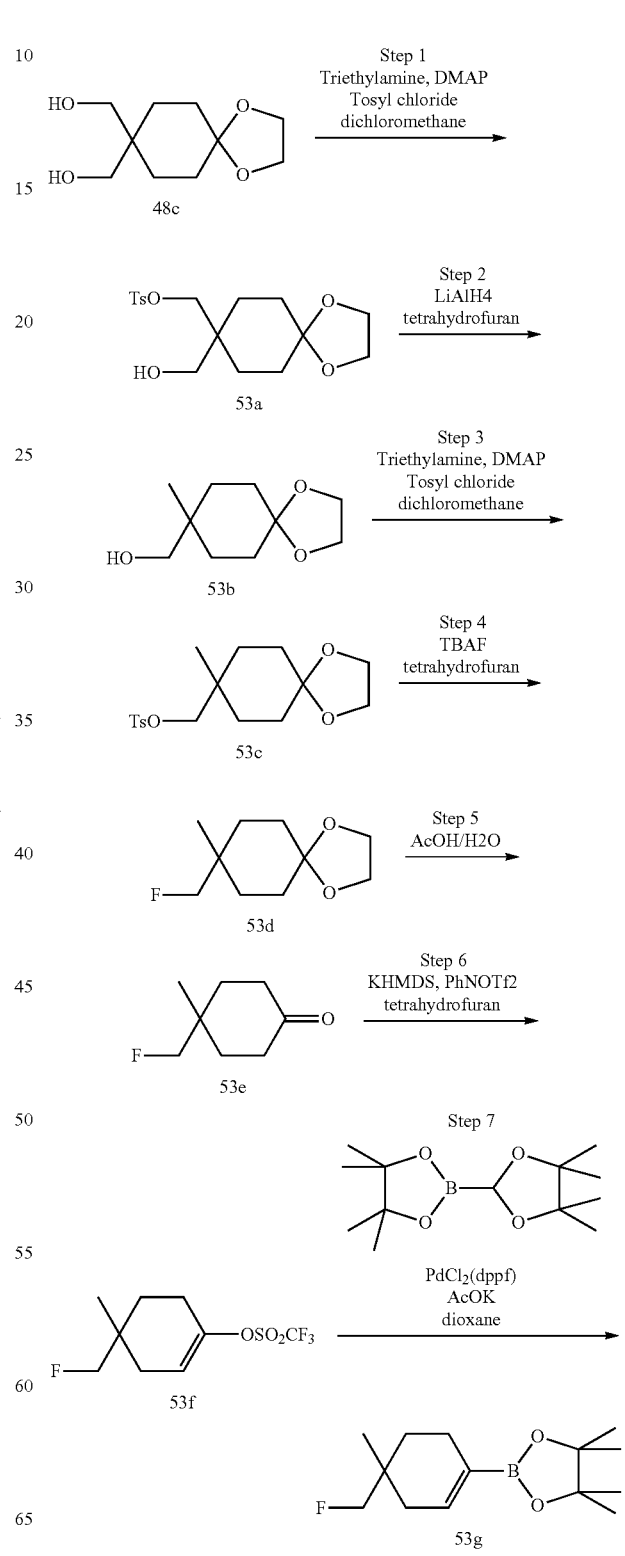

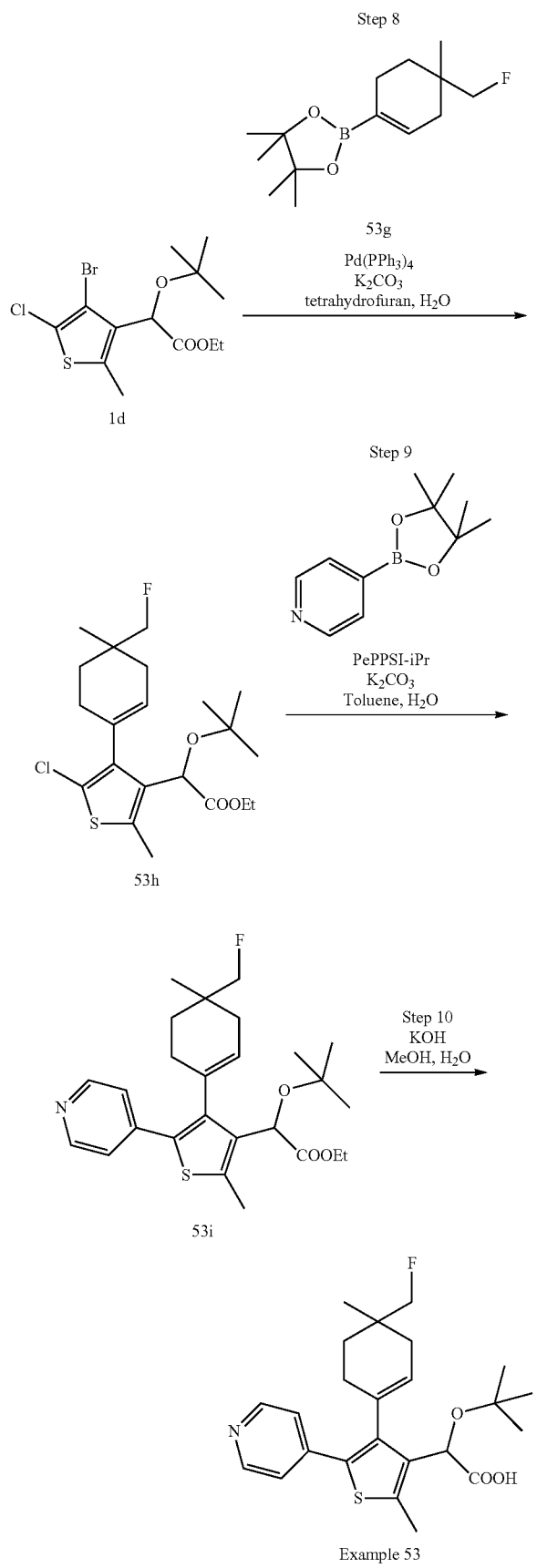

Step 1: preparation of intermediate 1,4-dioxaspiro[4.5]decane-8,8-diylbis(methylene)-hydroxy-(4-methylbenzenesulfonate) (53a)

To a 250 mL round-bottomed flask was added ethyl 1,4-dioxaspiro[4.5]decane-8,8-diyldimethanol (48c) (4.243 g, 20.98 mmol) and dichloromethane (70 mL) to give a colorless solution. Triethylamine (3.0 mL, 20.98 mmol) and p-toluenesulfonyl chloride (4.040 g, 20.98 mmol) were added followed by 4-dimethylaminopyridine (256 mg, 2.10 mmol) and the reaction was refluxed for 24 hours. Saturated ammonium chloride solution was added followed by dilution with water and additional dichloromethane. The aqueous layer was extracted with dichloromethane twice and the combined organics were dried over sodium sulfate, filtered and concentrated under reduced pressure to give 1,4-dioxaspiro[4.5]decane-8,8-diylbis(methylene)-hydroxy-(4-methylbenzenesulfonate) (53a) (4.54 g, 12.75 mmol, 59%) as a colorless oil after purification by flash chromatography on silica gel (cyclohexane/ethyl acetate 50/50).

$^1$H NMR (400 MHz, CDCl$_3$) δ 1.46-1.63 (m, 8H), 1.70 (dd, J=6.0 Hz, J=6.4 Hz, 1H), 2.46 (s, 3H), 3.52 (d, J=6.0 Hz, 2H), 3.91 (s, 4H), 3.94 (s, 2H), 7.35 (d, J=8.4 Hz, 2H), 7.79 (d, J=8.4 Hz, 2H).

MS m/z ([M+H]$^+$) 357.

Step 2: preparation of intermediate 1,4-dioxaspiro[4.5]decane-8-methyl-8-hydroxymethylene (53b)

To a solution of (53a) (6.46 g, 18.12 mmol) in tetrahydrofuran (91 mL) at 0° C. was added lithium aluminum hydride (913 mg, 21.74 mmol) by portions. The resulting mixture was stirred at room temperature for 72 h. The mixture was cooled down to 0° C., quenched slowly with water (0.9 mL), 10% aqueous sodium hydroxide solution (0.9 mL) and water (2.6 mL). The mixture was allowed to stir until salts were formed and was then filtered (diethyl ether washings). The filtrate was concentrated under reduced pressure to give 1,4-dioxaspiro[4.5]decane-8-methyl-8-hydroxymethylene (53b) (3.05 g, 16.35 mmol, 87%) as a colorless oil after purification by flash chromatography on silica gel (ethyl acetate 100%).

$^1$H NMR (400 MHz, CDCl$_3$) δ 0.96 (s, 3H), 1.36-1.43 (m, 2H), 1.51-1.67 (m, 7H), 3.39 (s, 2H), 3.94 (s, 4H).

MS m/z ([M+H]$^+$) 187.

Step 3: preparation of intermediate 1,4-dioxaspiro[4.5]decane-8-methyl-8-(methylene(4-methylbenzenesulfonate)) (53c)

To a 250 mL round-bottomed flask was added 1,4-dioxaspiro[4.5]decane-8-methyl-8-hydroxymethylene (53b) (3.05 g, 16.35 mmol) and dichloromethane (55 mL) to give a colorless solution. Triethylamine (3.5 mL, 24.52 mmol) and p-toluenesulfonyl chloride (3.78 g, 19.62 mmol) were added followed by 4-dimethylaminopyridine (200 mg, 1.64 mmol) and the reaction was refluxed for 48 hours. Saturated ammonium chloride solution was added followed by dilution with water and additional dichloromethane. The aqueous layer was extracted with dichloromethane twice and the combined organics were dried over sodium sulfate, filtered and concentrated under reduced pressure to give 1,4-dioxaspiro[4.5]decane-8-methyl-8-(methylene(4-methylbenzene sulfonate)) (53c) (5.73 g, 16.35 mmol, 100%) as a colorless oil after purification by flash chromatography on silica gel (cyclohexane/ethyl acetate 50/50).

$^1$H NMR (400 MHz, CDCl$_3$) δ 0.95 (s, 3H), 1.38-1.63 (m, 8H), 2.45 (s, 3H), 3.75 (s, 2H), 3.90 (s, 4H), 7.33 (d, J=8.0 Hz, 2H), 7.77 (d, J=8.0 Hz, 2H).

MS m/z ([M+H]$^+$) 341.

Step 4: preparation of intermediate 8-fluoromethyl-8-methyl-1,4-dioxa-spiro[4.5]decane (53d)

To a 250 mL round-bottomed flask was added 1,4-dioxaspiro[4.5]decane-8-methyl-8-(methylene(4-methylbenzenesulfonate)) (53c) (5.73 g, 16.35 mmol). tetra-n-Butylammonium fluoride (1.0M in THF, 84 mL, 84.19 mmol) was added and the resulting solution was refluxed for 7 days. The reaction was cooled, diluted with diethyl ether and washed with water (×3) (Caution, gas formation). The organics were dried over sodium sulfate, filtered and concentrated under reduced pressure to give 8-fluoromethyl-8-methyl-1,4-dioxa-spiro[4.5]decane (53d) (1.47 g, 7.83 mmol, 47%) as a yellow oil after purification by flash chromatography on silica gel (cyclohexane/ethyl acetate 80/20).

$^1$H NMR (400 MHz, CDCl$_3$) δ 1.00 (d, J=1.5 Hz, 3H), 1.38-1.51 (m, 4H), 1.54-1.68 (m, 4H), 3.94 (s, 4H), 4.14 (d, J=47.9 Hz, 2H).

$^{19}$F NMR (282 MHz, CDCl$_3$): δ −100.0 (s, 1F).

Step 5: preparation of 4-(fluoromethyl)-4-methylcyclohexanone (53e)

To a 250 mL round-bottomed flask was added 8-fluoromethyl-8-methyl-1,4-dioxa-spiro[4.5]decane (53d) (1.84 g, 9.76 mmol) and 80% aqueous acetic acid (100 mL). The reaction was heated at 65° C. for 3 hours, cooled down and concentrated under reduced pressure to give 4-(fluoromethyl)-4-methylcyclohexanone (53e) (840 mg, 5.83 mmol, 60%) as a yellow oil after purification by flash chromatography on silica gel (cyclohexane/ethyl acetate 80/20).

$^1$H NMR (300 MHz, CDCl$_3$) δ 1.15 (s, 3H), 1.67-1.73 (m, 2H), 1.79-1.87 (m, 2H), 2.32-2.45 (m, 4H), 4.24 (d, J=47.9 Hz, 2H).

Step 6: preparation of 3-(Fluoromethyl)-3-methyl-cyclohex-1-en-2-yl trifluoromethanesulfonate (53f)

To a stirred solution of 4-(fluoromethyl)-4-methylcyclohexanone (53e) (738 mg, 5.12 mmol) and N-phenyltrifluoromethanesulfonimide (2.40 g, 6.65 mmol) in tetrahydrofuran (51 mL) under argon at −78° C. was added potassium bis-trimethylsilylamide (0.5M in toluene, 13.3 mL, 6.65 mmol). The reaction was stirred for 4 hours, then quenched with water and extracted with diethyl ether. The combined ether extract layers were washed with brine, dried over sodium sulfate, filtered and concentrated under reduced pressure to give 3-(fluoromethyl)-3-methylcyclohex-1-en-2-yl trifluoromethanesulfonate (53f) (1.50 g, 5.42 mmol, 82%) as a yellow oil after purification by flash chromatography on silica gel (cyclohexane/ethyl acetate 80/20).

$^1$H NMR (400 MHz, CDCl$_3$) δ 1.02 (s, 3H), 1.56-1.61 (m, 1H), 1.72-1.79 (m, 1H), 1.92-1.97 (m, 1H), 2.18-2.23 (m, 1H), 2.32-2.43 (m, 2H), 4.16 (ddd, J=47.9 Hz, J=8.8 Hz, J=16.8 Hz, 2H), 5.70 (s, 1H).

Step 7: preparation of 2-(4-fluoromethyl-4-methyl-cyclohex-1-enyl)-4,4,5,5-tetramethyl-[1,3,2]dioxaborolane (53g)

Under argon atmosphere, 3-(fluoromethyl)-3-methylcyclohex-1-en-2-yl trifluoromethanesulfonate (53f) (1.50 g, 5.42 mmol), bis(pinacolato)diboron (2.06 g, 8.13 mmol) and potassium acetate (1.60 g, 16.26 mmol) were dissolved in dioxane (36 mL). The solution was degassed with argon for 10 min and [1,1'-bis(diphenylphosphino)ferrocene]dichloropalladium(II) (397 mg, 0.54 mmol) was added. The reaction was heated and shaken at 85° C. for 21 hours. The reaction was cooled to room temperature diluted with ethyl acetate and filtered through Celite®. The filtrate was concentrated under reduced pressure and the residue was dissolved with AcOEt and water and was extracted with AcOEt. Then the combined organic layers were washed with brine, dried over sodium sulfate and concentrated under reduced pressure to give 2-(4-fluoromethyl-4-methylcyclohex-1-enyl)-4,4,5,5-tetramethyl-[1,3,2]dioxaborolane (53g) (1.00 g, 3.93 mmol, 73%) as a white solid after purification by flash chromatography on silica gel (cyclohexane/ethyl acetate 90/10).

$^1$H NMR (400 MHz, CDCl$_3$) δ 0.95 (d, J=1.6 Hz, 3H), 1.26 (s, 12H), 1.37-1.40 (m, 1H), 1.48-1.53 (m, 1H), 1.79-1.88 (m, 1H), 2.01-2.10 (m, 1H), 2.12-2.19 (m, 2H), 4.11 (ddd, J=47.9 Hz, J=12.1 Hz, J=8.6 Hz, 2H), 6.45-6.52 (m, 1H).

MS m/z ([M+H]$^+$) 255.

Step 8: preparation of [4-(4-fluoromethyl-4-methyl-cyclohex-1-enyl)-5-chloro-2-methyl-thiophen-3-yl]-tert-butoxy-acetic acid ethyl ester (53h)

Using the procedure described in example 39, step 6, ethyl 2-(4-bromo-5-chloro-2-methylthiophen-3-yl)-2-(tert-butoxy)acetate (1d) (200 mg, 0.54 mmol) is converted by reaction with 2-(4-fluoromethyl-4-methylcyclohex-1-enyl)-4,4,5,5-tetramethyl-[1,3,2]dioxaborolane (53g) (192 mg, 0.76 mmol) into [4-(4-fluoromethyl-4-methylcyclohex-1-enyl)-5-chloro-2-methyl-thiophen-3-yl]-tert-butoxy-acetic acid ethyl ester (53h) (228 mg, 0.54 mmol, 100%) as a colorless oil after purification by preparative TLC (cyclohexane/ethyl acetate 90/10).

$^1$H NMR (300 MHz, CDCl$_3$) δ 1.21 (s, 12H), 1.63-1.78 (m, 2H), 1.86-2.00 (m, 2H), 2.07-2.25 (m, 1H), 2.29-2.44 (m, 1H), 2.47 (d, J=0.4 Hz, 3H), 2.51 (s, 3H), 4.06-4.39 (m, 4H), 5.22 (s, 1H), 5.52-5.60 (m, 1H).

Step 9: preparation of [4-(4-fluoromethyl-4-methyl-cyclohex-1-enyl)-2-methyl-5-pyridin-4-yl-thiophen-3-yl]-tert-butoxy-acetic acid ethyl ester (53i)

Using the procedure described in example 1, step 6, [4-(4-fluoromethyl-4-methylcyclohex-1-enyl)-5-chloro-2-methyl-thiophen-3-yl]-tert-butoxy-acetic acid ethyl ester (53h) (134 mg, 0.32 mmol) is converted by reaction with 4-pyridine boronic acid pinacol ester (170 mg, 0.80 mmol) into [4-(4-fluoromethyl-4-methylcyclohex-1-enyl)-2-methyl-5-pyridin-4-yl-thiophen-3-yl]-tert-butoxy-acetic acid ethyl ester (53i) (10 mg, 0.022 mmol, 7%) after purification by preparative TLC (cyclohexane/ethyl acetate 50/50).

$^1$H NMR (300 MHz, CDCl$_3$) δ 1.20 (s, 9H), 1.24 (t, J=7.2 Hz, 3H), 1.37-1.52 (m, 2H), 1.62-1.82 (m, 2H), 1.86-2.01 (m, 1H), 2.12-2.29 (m, 1H), 2.51 (s, 3H), 2.61 (d, J=1.6 Hz, 3H), 4.09-4.20 (m, 4H), 4.75 (s, 1H), 5.49-5.90 (m, 1H), 7.40 (d, J=5.2 Hz, 2H), 8.52 (d, J=5.2 Hz, 2H).

MS m/z ([M+H]$^+$) 460.

Step 10: preparation of [4-(4-fluoromethyl-4-methylcyclohex-1-enyl)-2-methyl-5-pyridin-4-yl-thiophen-3-yl]-tert-butoxy-acetic acid (example 53)

Using the procedure described in example 3, step 2, [4-(4-fluoromethyl-4-methylcyclohex-1-enyl)-2-methyl-5-pyridin-4-yl-thiophen-3-yl]-tert-butoxy-acetic acid ethyl ester (53i) (10 mg, 0.022 mmol) is converted into [4-(4-fluoromethyl-4-methylcyclohex-1-enyl)-2-methyl-5-pyridin-4-yl-thiophen-3-yl]-tert-butoxy-acetic acid (example 53) (2.65 mg, 0.006 mmol, 28%) as a colorless oil after purification by preparative TLC (dichloromethane/methanol 90/10).

$^1$H NMR (400 MHz, CDCl$_3$) δ 1.03 (d, J=10.0 Hz, 3H), 1.24 (s, 9H), 1.50-1.67 (m, 2H), 1.85-2.03 (m, 2H), 2.13-2.39 (m, 2H), 2.54 (s, 3H), 4.08-4.31 (m, 2H), 5.16 (s, 1H), 5.50-6.38 (bs, 1H), 7.40 (d, J=5.6 Hz, 2H), 8.54 (d, J=5.6 Hz, 2H).

MS m/z ([M+H]$^+$) 432.
MS m/z ([M−H]$^-$) 430.

Example 54

Synthesis of 2-(tert-butoxy)-2-{2-methyl-4-[4,4-dimethylcyclohex-1-en-1-yl]-5-(thiazol-4-yl)thiophen-3-yl}acetic acid

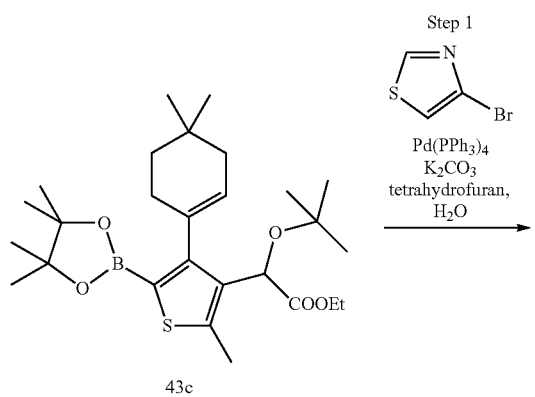

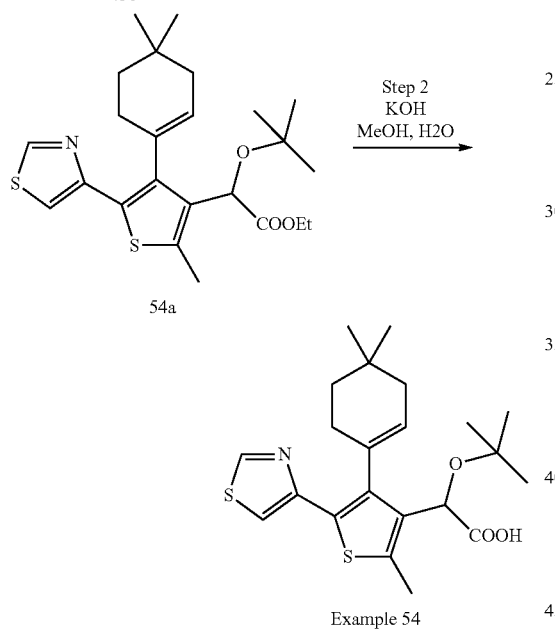

Example 54

Step 1: preparation of intermediate ethyl 2-(tert-butoxy)-2-[4-(4,4-dimethylcyclohex-1-en-1-yl)-2-methyl-5-(thiazol-4-yl)thiophen-3-yl]acetate (54a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 4-bromothiazole (42 mg, 0.25 mmol) into ethyl 2-(tert-butoxy)-2-[4-(4,4-dimethylcyclohex-1-en-1-yl)-2-methyl-5-(thiazol-4-yl)thiophen-3-yl]acetate (54a) (61 mg, 0.14 mmol, 69%) after purification by preparative TLC (cyclohexane/ethyl acetate 90/10).

$^1$H NMR (400 MHz, CDCl$_3$) δ 1.06 (s, 3H), 1.09 (s, 3H), 1.20 (s, 9H), 1.20 (t, J=7.2 Hz, 3H), 1.45-1.55 (m, 2H), 1.92-2.13 (m, 3H), 2.25-2.46 (m, 1H), 2.59 (s, 3H), 4.03-4.20 (m, 2H), 5.08 (s, 1H), 5.63-5.78 (bs, 1H), 7.32 (d, J=2.0 Hz, 1H), 8.75 (d, J=2.0 Hz, 1H).

MS m/z ([M+H]$^+$) 448.

Step 2: preparation of 2-(tert-butoxy)-2-{2-methyl-4-[4,4-dimethylcyclohex-1-en-1-yl]-5-(thiazol-4-yl)thiophen-3-yl}acetic acid (example 54)

Using the procedure described in example 3, step 2, ethyl 2-(tert-butoxy)-2-[4-(4,4-dimethylcyclohex-1-en-1-yl)-2-methyl-5-(thiazol-4-yl)thiophen-3-yl]acetate (54a) (61 mg, 0.14 mmol) is converted into 2-(tert-butoxy)-2-{2-methyl-4-[4,4-dimethylcyclohex-1-en-1-yl]-5-(thiazol-4-yl)thiophen-3-yl}acetic acid (example 54) (46 mg, 0.11 mmol, 80%) after purification by preparative TLC (dichloromethane/methanol 95/5).

$^1$H NMR (400 MHz, CDCl$_3$) δ 1.03 (s, 3H), 1.04 (s, 3H), 1.23 (s, 9H), 1.41-1.55 (m, 2H), 1.92-2.13 (m, 3H), 2.25-2.47 (m, 1H), 2.50 (s, 3H), 5.12 (s, 1H), 5.48-6.21 (bs, 1H), 7.34 (d, J=2.0 Hz, 1H), 8.76 (d, J=2.0 Hz, 1H).

MS m/z ([M+H]$^+$) 420.

MS m/z ([M−H]$^-$) 418.

Example 55

Synthesis of 2-(tert-butoxy)-2-{2-methyl-4-[4,4-dimethylcyclohex-1-en-1-yl]-5-(carboxamidephen-2-yl)thiophen-3-yl}acetic acid

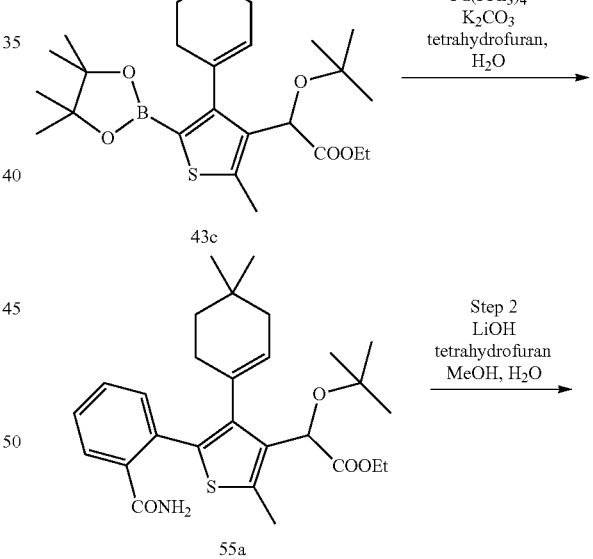

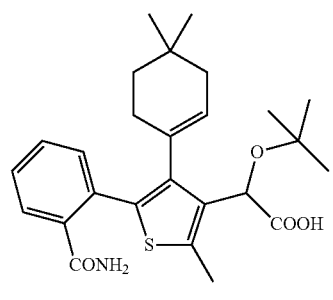

Example 55

Step 1: preparation of intermediate ethyl 2-(tert-butoxy)-2-[4-(4,4-dimethylcyclohex-1-en-1-yl)-2-methyl-5-(carboxamidephen-2-yl)thiophen-3-yl]acetate (55a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 2-bromobenzamide (50 mg, 0.25 mmol) into ethyl 2-(tert-butoxy)-2-[4-(4,4-dimethylcyclohex-1-en-1-yl)-2-methyl-5-(carboxamidephen-2-yl)thiophen-3-yl]acetate (55a) (46 mg, 0.10 mmol, 46%) after purification by preparative TLC (cyclohexane/ethyl acetate 50/50).

$^1$H NMR (400 MHz, CDCl$_3$) δ 0.74 (s, 3H), 0.80 (s, 3H), 1.14-1.19 (m, 2H), 1.19 (s, 9H), 1.21 (t, J=7.2 Hz, 3H), 1.67-1.77 (m, 1H), 1.82-1.88 (m, 2H), 1.94-2.00 (m, 1H), 2.58 (s, 3H), 4.09-4.18 (m, 2H), 5.10 (s, 1H), 5.53 (bs, 1H), 5.61 (bs, 1H), 5.68 (bs, 1H), 7.30-7.32 (m, 1H), 7.38-7.43 (m, 2H), 7.91-7.94 (m, 1H).

Step 2: preparation of 2-(tert-butoxy)-2-{2-methyl-4-[4,4-dimethylcyclohex-1-en-1-yl]-5-(carboxamidephen-2-yl)thiophen-3-yl}acetic acid (example 55)

Using the procedure described in example 15, step 2, 2-(tert-butoxy)-2-[4-(4,4-dimethylcyclohex-1-en-1-yl)-2-methyl-5-(carboxamidephen-2-yl)thiophen-3-yl]acetate (55a) (46 mg, 0.10 mmol) is converted into 2-(tert-butoxy)-2-{2-methyl-4-[4,4-dimethylcyclohex-1-en-1-yl]-5-(carboxamidephen-2-yl)thiophen-3-yl}acetic acid (example 55) (18 mg, 0.04 mmol, 42%) after purification by preparative TLC (dichloromethane/methanol 90/10).

$^1$H NMR (400 MHz, CDCl$_3$) δ 0.76 (s, 3H), 0.79 (s, 3H), 1.14-1.21 (m, 2H), 1.21 (s, 9H), 1.67-1.90 (m, 4H), 2.52 (s, 3H), 5.13 (s, 1H), 5.58 (bs, 1H), 5.66 (bs, 1H), 6.84-7.22 (bs, 1H), 7.35 (dd, J=1.2 Hz, J=6.8 Hz, 1H), 7.43 (m, 2H), 7.90 (dd, J=1.2 Hz, J=7.2 Hz, 1H), 11.07-12.67 (bs, 1H).
MS m/z ([M+H]$^+$) 456.
MS m/z ([M−H]$^−$) 454.

Example 56

Synthesis of 2-(tert-butoxy)-2-{2-methyl-4-[4,4-dimethylcyclohex-1-en-1-yl]-5-(N-methylbenzamide-2-yl)thiophen-3-yl}acetic acid

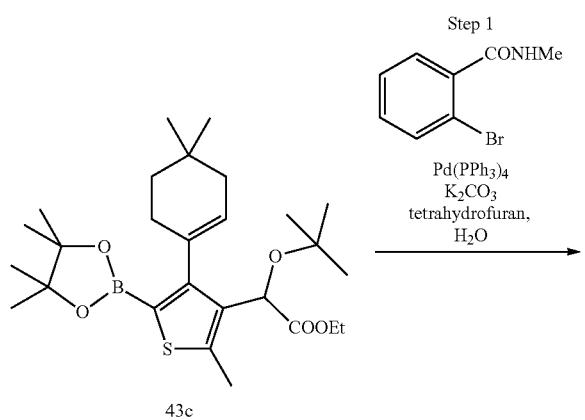

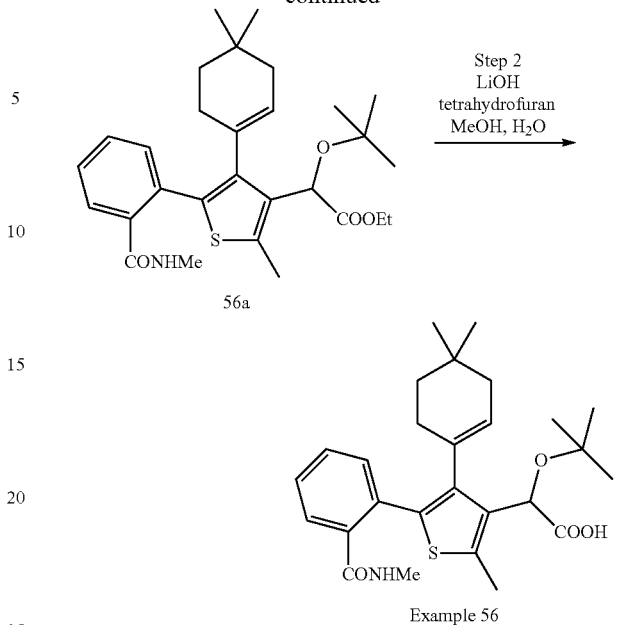

Example 56

Step 1: preparation of intermediate ethyl 2-(tert-butoxy)-2-[4-(4,4-dimethylcyclohex-1-en-1-yl)-2-methyl-5-(N-methylbenzamide-2-yl)thiophen-3-yl]acetate (56a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 2-bromo-N-methylbenzamide (52 mg, 0.25 mmol) into ethyl 2-(tert-butoxy)-2-[4-(4,4-dimethylcyclohex-1-en-1-yl)-2-methyl-5-(N-methylbenzamide-2-yl)thiophen-3-yl]acetate (56a) (67 mg, 0.13 mmol, 63%) after purification by preparative TLC (cyclohexane/ethyl acetate 50/50).

$^1$H NMR (400 MHz, CDCl$_3$) δ 0.76 (s, 3H), 0.81 (s, 3H), 1.18 (s, 9H), 1.20-1.26 (m, 5H), 1.64-1.74 (m, 1H), 1.81-1.99 (m, 3H), 2.57 (s, 3H), 2.71 (d, J=4.8 Hz, 3H), 4.08-4.19 (m, 2H), 5.10 (s, 1H), 5.53 (bs, 1H), 5.62 (bs, 1H), 7.29-7.31 (m, 1H), 7.36-7.38 (m, 2H), 7.82-7.85 (m, 1H).
MS m/z ([M+H]$^+$) 498.

Step 2: preparation of 2-(tert-butoxy)-2-{2-methyl-4-[4,4-dimethylcyclohex-1-en-1-yl]-5-(N-methylbenzamide-2-yl)thiophen-3-yl}acetic acid (example 56)

Using the procedure described in example 15, step 2, ethyl 2-(tert-butoxy)-2-[4-(4,4-dimethylcyclohex-1-en-1-yl)-2-methyl-5-(N-methylbenzamide-2-yl)thiophen-3-yl]acetate (56a) (67 mg, 0.13 mmol) is converted into 2-(tert-butoxy)-2-{2-methyl-4-[4,4-dimethylcyclohex-1-en-1-yl]-5-(N-methylbenzamide-2-yl)thiophen-3-yl}acetic acid (example 56) (18 mg, 0.04 mmol, 18%) after purification by preparative TLC (dichloromethane/methanol 90/10).

$^1$H NMR (400 MHz, CDCl$_3$) δ 0.73 (s, 3H), 0.80 (s, 3H), 1.14-1.23 (m, 2H), 1.23 (s, 9H), 1.65-1.97 (m, 4H), 2.49 (s, 3H), 2.72 (d, J=5.1 Hz, 3H), 5.19 (s, 1H), 5.58 (d, J=5.1 Hz, 1H), 5.66 (bs, 1H), 7.29-7.33 (m, 1H), 7.37-7.40 (m, 2H), 7.83-7.86 (m, 1H), 9.00-10.72 (bs, 1H).
MS m/z ([M+H]$^+$) 470.
MS m/z ([M−H]$^−$) 468.

Example 57

Synthesis of 2-(tert-butoxy)-2-[4-(4,4-dimethylcyclohex-1-en-1-yl)-5-(cyclohexen-1-yl)-2-methylthiophen-3-yl]acetic acid

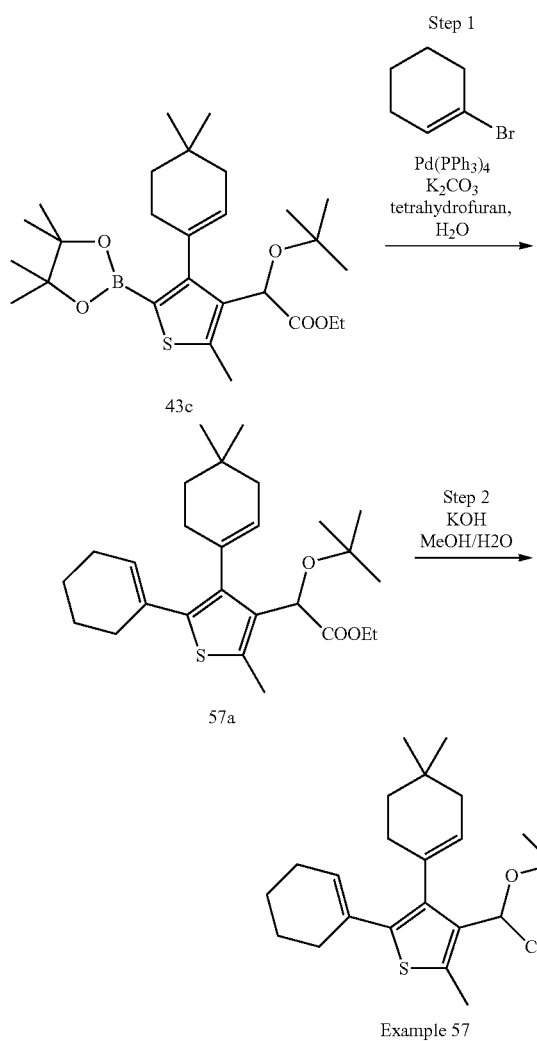

Example 57

Step 1: preparation of intermediate ethyl 2-(tert-butoxy)-2-[4-(4,4-dimethylcyclohex-1-en-1-yl)-2-methyl-5-(cyclohexen-1-yl)thiophen-3-yl]acetate (57a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 1-bromocyclohex-1-ene (39 mg, 0.25 mmol) into ethyl 2-(tert-butoxy)-2-[4-(4,4-dimethylcyclohex-1-en-1-yl)-2-methyl-5-(cyclohexen-1-yl)thiophen-3-yl]acetate (57a) (55 mg, 0.11 mmol, 58%) after purification by preparative TLC (cyclohexane/ethyl acetate 95/5).

$^1$H NMR (400 MHz, CDCl$_3$) δ 1.00 (s, 3H), 1.02 (s, 3H), 1.17 (s, 9H), 1.20 (d, J=7.2 Hz, 3H), 1.36-1.51 (m, 3H), 1.53-1.74 (m, 5H), 1.92-1.99 (m, 2H), 2.05-2.16 (m, 2H), 2.20-2.32 (m, 2H), 2.51 (s, 3H), 4.00-4.20 (m, 2H), 5.07 (s, 1H), 5.57 (bs, 1H), 5.94 (m, 1H).

MS m/z ([M+H]$^+$) 445.

Step 2: preparation of 2-(tert-butoxy)-2-{2-methyl-4-[4,4-dimethylcyclohex-1-en-1-yl]-5-(cyclohexen-1-yl)thiophen-3-yl}acetic acid (example 57)

Using the procedure described in example 3, step 2, ethyl 2-(tert-butoxy)-2-[4-(4,4-dimethylcyclohex-1-en-1-yl)-2-methyl-5-(cyclohexen-1-yl)thiophen-3-yl]acetate (57a) (55 mg, 0.11 mmol) is converted into 2-(tert-butoxy)-2-{2-methyl-4-[4,4-dimethylcyclohex-1-en-1-yl]-5-(cyclohexen-1-yl)thiophen-3-yl}acetic acid (example 57) (21 mg, 0.05 mmol, 41%) after purification by preparative TLC (dichloromethane/methanol 95/5).

$^1$H NMR (400 MHz, CDCl$_3$) δ 0.97 (s, 3H), 0.98 (s, 3H), 1.20 (s, 9H), 1.33-1.48 (m, 3H), 1.53-1.75 (m, 5H), 1.90-1.97 (m, 2H), 2.06-2.16 (m, 2H), 2.17-2.29 (m, 2H), 2.41 (s, 3H), 5.13 (s, 1H), 5.52-5.78 (bs, 1H), 5.93 (m, 1H), 9.66-10.14 (bs, 1H).

MS m/z ([M+H]$^+$) 417.
MS m/z ([M−H]$^−$) 415.

Example 58

Synthesis of 2-(tert-butoxy)-2-{2-methyl-4-[4,4-dimethylcyclohex-1-en-1-yl]-5-(isothiazol-3-yl)thiophen-3-yl}acetic acid

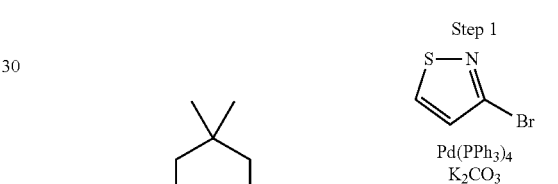

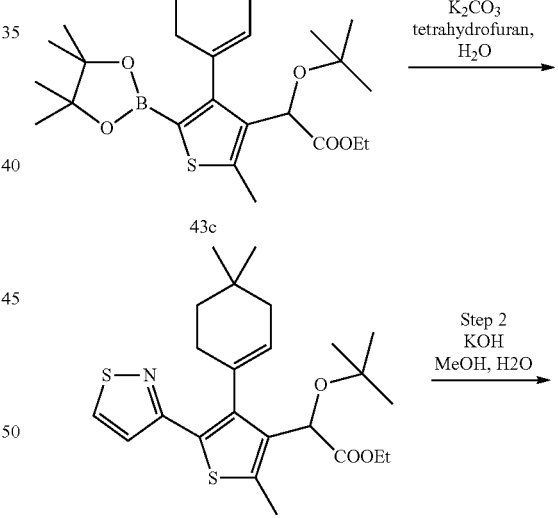

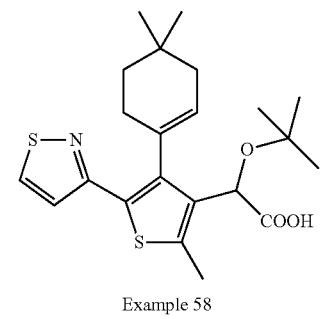

Example 58

Step 1: preparation of intermediate ethyl 2-(tert-butoxy)-2-[4-(4,4-dimethylcyclohex-1-en-1-yl)-2-methyl-5-(isothiazol-3-yl)thiophen-3-yl]acetate (58a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 3-bromoisothiazole (37 mg, 0.25 mmol) into ethyl 2-(tert-butoxy)-2-[4-(4,4-dimethylcyclohex-1-en-1-yl)-2-methyl-5-(isothiazol-3-yl)thiophen-3-yl]acetate (58a) (27 mg, 0.06 mmol, 29%) after purification by preparative TLC (cyclohexane/ethyl acetate 90/10).

$^1$H NMR (400 MHz, CDCl$_3$) δ 1.06 (s, 3H), 1.08 (s, 3H), 1.19 (s, 12H), 1.47-1.52 (m, 2H), 1.90-2.14 (m, 4H), 2.59 (s, 3H), 4.02-4.21 (m, 2H), 5.08 (s, 1H), 5.63-5.74 (bs, 1H), 7.46 (d, J=4.8 Hz, 1H), 8.59 (d, J=4.8 Hz, 1H).

MS m/z ([M+H]$^+$) 448.

Step 2: preparation of 2-(tert-butoxy)-2-{2-methyl-4-[4,4-dimethylcyclohex-1-en-1-yl]-5-(isothiazol-3-yl)thiophen-3-yl}acetic acid (example 58)

Using the procedure described in example 3, step 2, ethyl 2-(tert-butoxy)-2-[4-(4,4-dimethylcyclohex-1-en-1-yl)-2-methyl-5-(isothiazol-3-yl)thiophen-3-yl]acetate (58a) (27 mg, 0.06 mmol) is converted into 2-(tert-butoxy)-2-{2-methyl-4-[4,4-dimethylcyclohex-1-en-1-yl]-5-(isothiazol-3-yl)thiophen-3-yl}acetic acid (example 58) (4.6 mg, 0.01 mmol, 18%) after purification by preparative TLC (dichloromethane/methanol 90/10).

$^1$H NMR (400 MHz, CDCl$_3$) δ 1.03 (s, 6H), 1.23 (s, 9H), 1.42-1.53 (m, 2H), 1.92-2.13 (m, 4H), 2.50 (s, 3H), 5.13 (s, 1H), 5.47-5.83 (bs, 1H), 7.45 (d, J=4.8 Hz, 1H), 8.60 (d, J=4.8 Hz, 1H), 9.43-10.33 (bs, 1H).

MS m/z ([M+H]$^+$) 420.
MS m/z ([M−H]$^-$) 418.

Example 59

Synthesis of 2-(tert-butoxy)-2-[4-(4,4-dimethylcyclohex-1-en-1-yl)-5-(cyclopenten-1-yl)-2-methylthiophen-3-yl]acetic acid

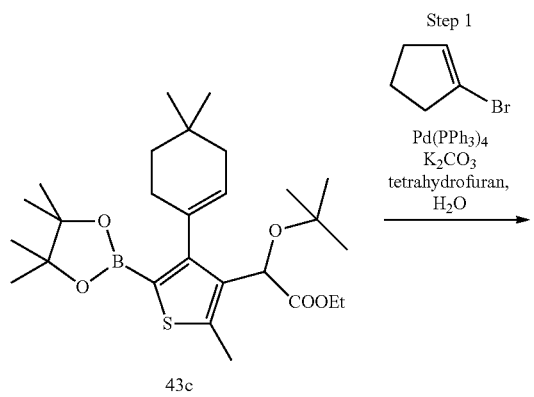

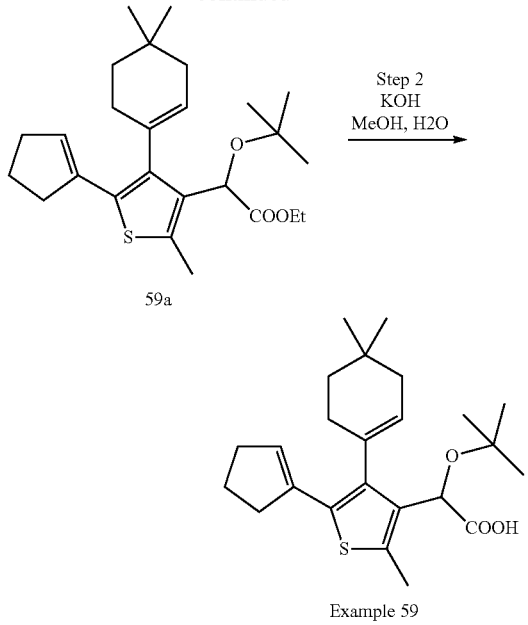

Example 59

Step 1: preparation of intermediate ethyl 2-(tert-butoxy)-2-[4-(4,4-dimethylcyclohex-1-en-1-yl)-2-methyl-5-(cyclopenten-1-yl)thiophen-3-yl]acetate (59a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 1-bromocyclopent-1-ene (35 mg, 0.25 mmol) into ethyl 2-(tert-butoxy)-2-[4-(4,4-dimethylcyclopent-1-en-1-yl)-2-methyl-5-(cyclopenten-1-yl)thiophen-3-yl]acetate (59a) (43 mg, 0.10 mmol, 46%) after purification by preparative TLC (cyclohexane/ethyl acetate 95/5).

$^1$H NMR (400 MHz, CDCl$_3$) δ 1.03 (s, 3H), 1.05 (s, 3H), 1.18 (s, 12H), 1.43-1.51 (m, 2H), 1.86-1.93 (m, 2H), 1.95-2.01 (m, 2H), 2.39-2.48 (m, 3H), 2.53 (s, 3H), 2.56-2.65 (m, 3H), 3.99-4.20 (m, 2H), 5.04 (s, 1H), 5.50-5.59 (m, 1H), 5.89-5.92 (m, 1H).

MS m/z ([M+H]$^+$) 431.

Step 2: preparation of 2-(tert-butoxy)-2-{2-methyl-4-[4,4-dimethylcyclohex-1-en-1-yl]-5-(cyclopenten-1-yl)thiophen-3-yl}acetic acid (example 59)

Using the procedure described in example 3, step 2, ethyl 2-(tert-butoxy)-2-[4-(4,4-dimethylcyclopent-1-en-1-yl)-2-methyl-5-(cyclohexen-1-yl)thiophen-3-yl]acetate (59a) (43 mg, 0.10 mmol) is converted into 2-(tert-butoxy)-2-{2-methyl-4-[4,4-dimethylcyclohex-1-en-1-yl]-5-(cyclopenten-1-yl)thiophen-3-yl}acetic acid (example 59) (9.6 mg, 0.02 mmol, 24%) after purification by preparative TLC (dichloromethane/methanol 95/5).

$^1$H NMR (400 MHz, CDCl$_3$) δ 1.00 (s, 6H), 1.22 (s, 9H), 1.24-1.27 (m, 2H), 1.41-1.48 (m, 2H), 1.82-1.99 (m, 4H), 2.42 (s, 3H), 2.43-2.47 (m, 2H), 2.54-2.68 (m, 2H), 5.08 (s, 1H), 5.43-5.62 (bs, 1H), 5.92 (m, 1H), 9.47-9.99 (bs, 1H).

MS m/z ([M+H]$^+$) 403.
MS m/z ([M−H]$^-$) 401.

Example 60

Synthesis of 2-(tert-butoxy)-2-[4-(3,4-dihydro-2H-1-benzopyran-6-yl)-5-phenyl-2-(trifluoromethyl)thiophen-3-yl]acetic acid

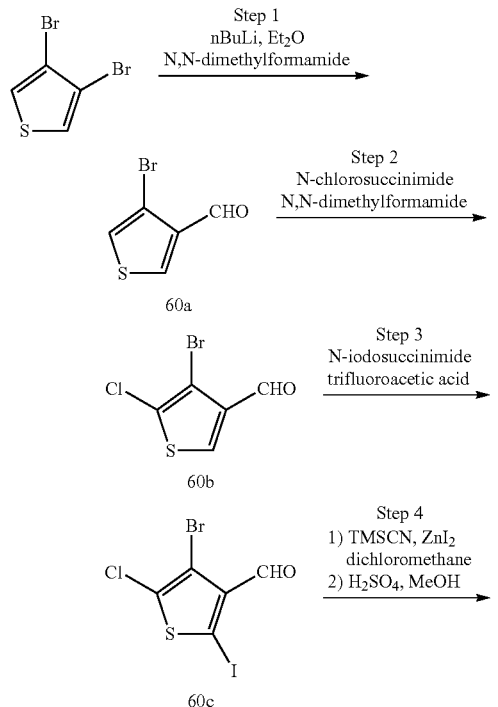

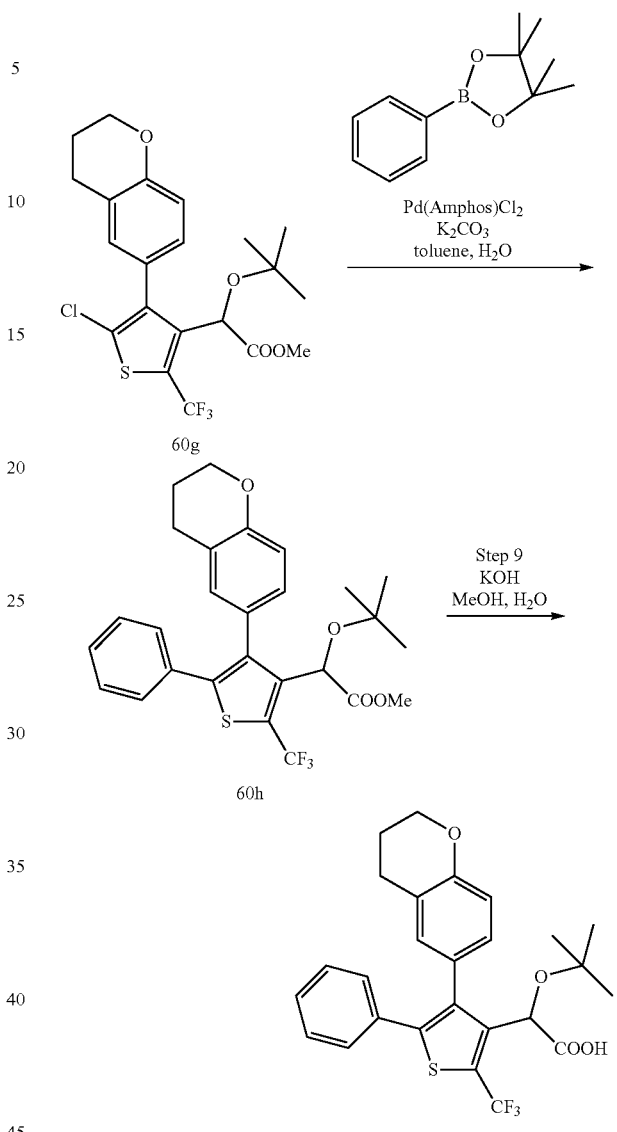

Step 1: preparation of intermediate 4-bromothiophene-3-carbaldehyde (60a)

Under an argon atmosphere and at −78° C., a solution of n-butyllithium (1.6M, 7.87 mL, 12.6 mmol) was added to a solution of 3,4-dibromothiophene (2.77 g, 11.45 mmol) in anhydrous diethyl ether (11 mL). After 45 minutes, anhydrous N,N-dimethylformamide (0.975 mL, 12.6 mmol) was added. The reaction mixture was stirred for additional 30 minutes at −78° C., quenched with water and extracted with ethyl acetate twice. The organic extract was washed with brine twice, dried over sodium sulfate, filtered and concentrated to provide 4-bromothiophene-3-carbaldehyde (60a) (1.88 g, 9.84 mmol, 86%) after purification by flash chromatography on silica gel (cyclohexane/ethyl acetate 97/3).

$^1$H NMR (400 MHz, CDCl$_3$) δ 7.37 (d, J=3.3 Hz, 1H), 8.16 (d, J=3.3 Hz, 1H), 9.95 (s, 1H).

MS m/z ([M+H]$^+$) 191/193.

Step 2: preparation of intermediate 4-bromo-5-chlorothiophene-3-carbaldehyde (60b)

N-chlorosuccinimide (2.76 g, 20.6 mmol) was added at room temperature per portion to a solution of 4-bromothiophene-3-carbaldehyde (60a) (1.88 g, 9.84 mmol) in N,N-dimethylformamide (16 mL) in an amber round bottom flask. After 2 hour at room temperature, water was then added and the mixture was extracted with ethyl acetate. The organic layer was washed with brine, dried over sodium sulfate, filtered, and evaporated under reduced pressure. The residue was purified by flash chromatography on silica gel (cyclohexane/dichloromethane 70/30) to afford the 4-bromo-5-chlorothiophene-3-carbaldehyde (60b) as white solid (1.8 g, 7.98 mmol, 81%).

$^1$H NMR (400 MHz, CDCl$_3$) δ 8.02 (s, 1H), 9.85 (s, 1H).

Step 3: preparation of intermediate 4-bromo-5-chloro-2-iodothiophene-3-carbaldehyde (60c)

N-iodosuccinimide (1.45 g, 6.43 mmol) was added at room temperature per portion to a solution of 4-bromo-5-chlorothiophene-3-carbaldehyde (60b) (1.45 g, 6.43 mmol) in trifluoroacetic acid (7 mL). After 3 hours of stirring at room temperature, the reaction mixture was solidified. Ethyl acetate was then added and the organic layer was washed with aqueous sodium hydroxide solution (2N), brine, dried over sodium sulfate, filtered, and evaporated under reduced pressure. The residue was taken up in cyclohexane, the organic layer was washed with water, with brine, dried over sodium sulfate, filtered and evaporated under reduced pressure to afford the 4-bromo-5-chloro-2-iodothiophene-3-carbaldehyde (60c) as yellow solid (2.15 g, 6.11 mmol, 95%).

$^1$H NMR (400 MHz, CDCl$_3$) δ 9.78 (s, 1H).

Step 4: preparation of intermediate methyl 2-(4-bromo-5-chloro-2-iodothiophen-3-yl)-2-hydroxyacetate (60d)

To a solution of 4-bromo-5-chloro-2-iodothiophene-3-carbaldehyde (60c) (1.6 g, 4.55 mmol) in anhydrous dichloromethane (30 mL) at 0° C. under nitrogen atmosphere, were successively added zinc iodide (145 mg, 0.455 mmol) and trimethylsilylcyanide (0.684 mL, 5.46 mmol). The reaction mixture was allowed to warm to room temperature and stirred overnight before adding a saturated solution of sodium hydrogenocarbonate (100 mL). The layers were separated. The aqueous layer was extracted with dichloromethane (100 mL). The combined organic layers were dried over sodium sulfate and concentrated in vacuo. The residue was taken up in anhydrous methanol (30 mL) at 0° C. under nitrogen atmosphere and sulfuric acid (10 mL) was dropwise added. The mixture was refluxed overnight then cooled at room temperature and poured in water (150 mL). The aqueous layer was extracted with dichloromethane (3×80 mL). The combined organic layers were washed with a saturated solution of sodium hydrogenocarbonate (100 mL), brine (100 mL), dried over sodium sulfate and concentrated in vacuo to provide methyl 2-(4-bromo-5-chloro-2-iodothiophen-3-yl)-2-hydroxyacetate (60d) (1.59 g, 3.87 mmol, 85%) after purification by flash chromatography on silica gel (dichloromethane).

$^1$H NMR (400 MHz, CDCl$_3$) δ 3.56 (d, J=4.6 Hz, 1H), 3.82 (s, 3H), 5.28 (d, J=4.6 Hz, 1H).

Step 5: preparation of intermediate methyl 2-[4-bromo-5-chloro-2-(trifluoromethyl)thiophen-3-yl]-2-hydroxyacetate (60e)

In a vial equipped with a stir bar, trifluoromethyl(1,10-phenanthroline)copper (296 mg, 0.948 mmol) was added to a solution of methyl 2-(4-bromo-5-chloro-2-iodothiophen-3-yl)-2-hydroxyacetate (60d) (300 mg, 0.729 mmol) in anhydrous N,N-dimethylformamide (3 mL). The reaction mixture was stirred at room temperature overnight before being diluted with ethyl acetate and filtered through a pad of Celite®. The Celite pad was washed with ethyl acetate. The combined filtrates were washed with 1M aqueous hydrochloric acid solution, saturated aqueous sodium hydrogenocarbonate solution and brine. The organic layer was dried over sodium sulfate and concentrated in vacuo to provide methyl 2-[4-bromo-5-chloro-2-(trifluoromethyl)thiophen-3-yl]-2-hydroxyacetate (60e) (209 mg, 0.590 mmol, 81%).

$^1$H NMR (400 MHz, CDCl$_3$) δ 3.60 (bs, 1H), 3.82 (s, 3H), 5.44 (bs, 1H).

Step 6: preparation of intermediate methyl 2-[4-bromo-5-chloro-2(trifluoromethyl)thiophen-3-yl]-2-(tert-butoxy)acetate (60f)

To a suspension of methyl 2-[4-bromo-5-chloro-2-(trifluoromethyl)thiophen-3-yl]-2-hydroxyacetate (60e) (203 mg, 0.574 mmol) in tert-butyl acetate (6 mL) at 0° C. was added sulfuric acid (0.122 mL, 2.30 mmol). The mixture was stirred at room temperature for 4 hours. The mixture was diluted with ethyl acetate (20 mL), washed with a saturated solution of sodium hydrogenocarbonate (20 mL), dried over sodium sulfate and concentrated in vacuo. The residue was purified by flash chromatography on silica gel (cyclohexane/dichloromethane 50/50) to provide methyl 2-[4-bromo-5-chloro-2(trifluoromethyl)thiophen-3-yl]-2-(tertbutoxy)acetate (60f) (122 mg, 0.298 mmol, 81%).

$^1$H NMR (400 MHz, CDCl$_3$) δ 1.21 (s, 9H), 3.72 (s, 3H), 5.34 (s, 1H).

Step 7: preparation of intermediate methyl 2-(tert-butoxy)-2-[5-chloro-4-(3,4-dihydro-2H-1-benzopyran-6-yl)-2-(trifluoromethyl)thiophen-3-yl]acetate (60g)

Using the procedure described in example 39, step 6, methyl 2-[4-bromo-5-chloro-2(trifluoromethyl)thiophen-3-yl]-2-(tertbutoxy)acetate (60f) (120 mg, 0.293 mmol) is converted by reaction with 6-(4,4,5,5-tetramethyl-1,3,2-dioxaborolan-2-yl)chroman (99 mg, 0.381 mmol) into methyl 2-(tert-butoxy)-2-[5-chloro-4-(3,4-dihydro-2H-1-benzopyran-6-yl)-2-(trifluoromethyl)thiophen-3-yl]acetate (60g) (62 mg, 0.134 mmol, 46%) as a yellow oil after purification by preparative TLC (cyclohexane/ethyl acetate 90/10).

$^1$H NMR (400 MHz, CDCl$_3$) δ 1.02 (s, 9H), 1.98-2.10 (m, 2H), 2.75-2.85 (m, 2H), 3.68 (s, 3H), 4.20-4.28 (m, 2H), 4.96 (s, 1H), 6.84 (d, J=8.9 Hz, 1H), 6.96-7.03 (m, 2H).

MS m/z ([M+Na]$^+$) 485.

Step 8: preparation of intermediate methyl 2-(tert-butoxy)-2-[4-(3,4-dihydro-2H-1-benzopyran-6-yl)-5-phenyl-2-(trifluoromethyl)thiophen-3-yl]acetate (60h)

Using the procedure described in example 1, step 6, methyl 2-(tert-butoxy)-2-[5-chloro-4-(3,4-dihydro-2H-1-benzopyran-6-yl)-2-(trifluoromethyl)thiophen-3-yl]acetate (60g) (60 mg, 0.13 mmol) is converted by reaction with 4,4,5,5-tetramethyl-2-phenyl-1,3,2-dioxaborolane (40 mg, 0.194 mmol) into methyl 2-(tert-butoxy)-2-[4-(3,4-dihydro-2H-1-benzopyran-6-yl)-5-phenyl-2-(trifluoromethyl)thiophen-3-yl]acetate (60h) (40 mg, 0.079 mmol, 61%) after purification by preparative TLC cyclohexane/ethyl acetate 90/10).

$^1$H NMR (400 MHz, CDCl$_3$) δ 1.03 (s, 9H), 1.94-2.08 (m, 2H), 2.63-2.84 (m, 2H), 3.69 (s, 3H), 4.17-4.26 (m, 2H), 5.02 (s, 1H), 6.72 (d, J=8.2 Hz, 1H), 6.81-6.98 (m, 2H), 7.15-7.25 (m, 5H).

MS m/z ([M+Na]$^+$) 527.

Step 8: preparation of 2-(tert-butoxy)-2-[4-(3,4-dihydro-2H-1-benzopyran-6-yl)-5-phenyl-2-(trifluoromethyl)thiophen-3-yl]acetic acid (example 60)

Using the procedure described in example 3, step 2, methyl 2-(tert-butoxy)-2-[4-(3,4-dihydro-2H-1-benzopyran-6-yl)-5-phenyl-2-(trifluoromethyl)thiophen-3-yl]acetate (60h) (32 mg, 0.063 mmol) is converted into 2-(tert-butoxy)-2-[4-(3,4-dihydro-2H-1-benzopyran-6-yl)-5-phenyl-2-(trifluoromethyl)thiophen-3-yl]acetic acid (example 60) (22 mg, 0.045 mmol, 71%).

$^1$H NMR (400 MHz, CDCl$_3$) δ 1.04 (s, 9H), 1.93-2.06 (m, 2H), 2.53-2.90 (m, 2H), 4.17-4.27 (m, 2H), 5.06 (bs, 1H), 6.55-6.90 (m, 3H), 7.15-7.25 (m, 5H).

MS m/z ([M–H]$^-$) 489.

Example 61

Synthesis of 2-(tert-butoxy)-2-[2-methyl-4-(2,3-dihydropyrano[4,3,2-de]quinolin-7-yl)-5-phenyl-thiophen-3-yl]acetic acid

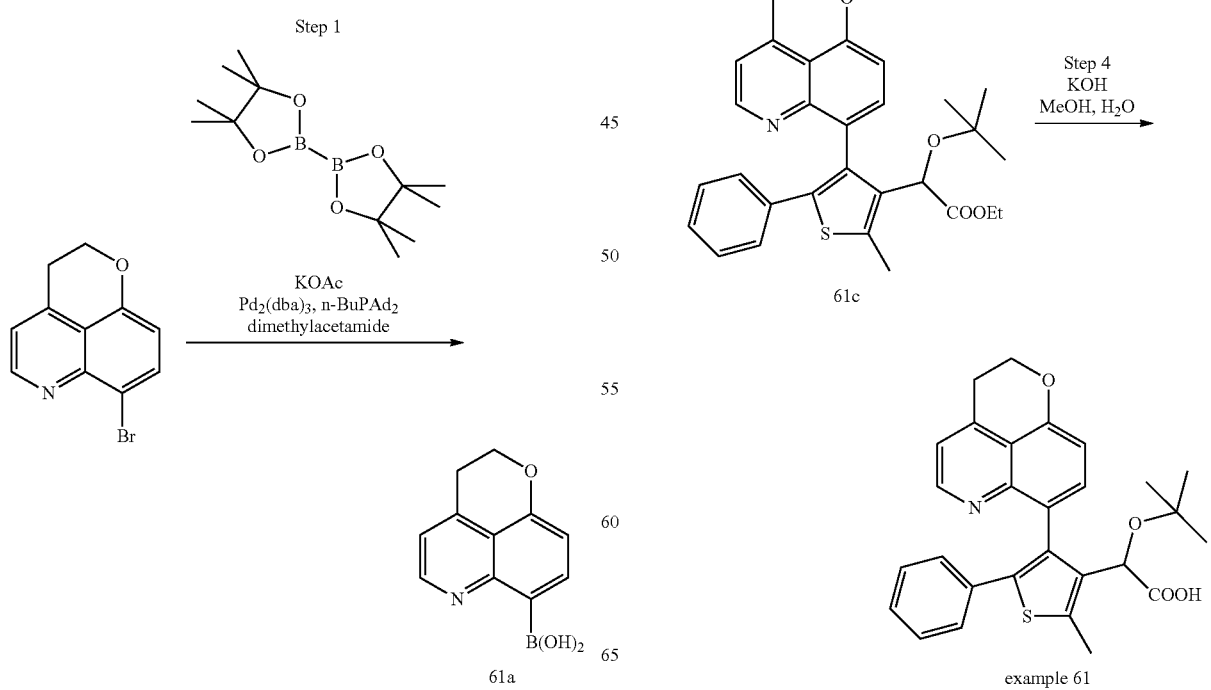

Step 1: preparation of intermediate (2,3-dihydropyrano[4,3,2-de]quinolin-7-yl)-boronic acid (61a)

A vial containing the 7-bromo-2,3-dihydro-1-oxa-6-azaphenalene (600 mg, 2.40 mmol, prepared according to WO2009/062289), tris(dibenzylidene acetone)dipalladium (0) (22 mg, 0.024 mmol), di(1-adamantyl)-n-butylphosphine (25.8 mg, 0.072 mmol), bis[pinacolato]diboron (731 mg, 2.88 mmol) and potassium acetate (706 mg, 7.20 mmol) was purged with argon for 10 minutes and then degassed anhydrous dimethylacetamide (2 mL) was added. The resulting mixture was stirred at 90° C. for 4 hours. The mixture was cooled to room temperature and water was added slowly (40 mL). The precipitate was filtered, washed with water (20 mL) and toluene (10 mL), dried in vacuo and triturated in diethyl ether. The powder was dissolved in acetonitrile and the solution was then filtered on Millipore and the filtrate concentrated in vacuo to provide (2,3-dihydropyrano[4,3,2-de]quinolin-7-yl)boronic acid (61a) (301 mg, 1.39 mmol, 58%).

$^1$H NMR (400 MHz, DMSO-$d_6$+$D_2O$) □ 3.27 (t, 2H, J=5.8 Hz), 4.44 (t, 2H, J=5.8 Hz), 7.03 (d, J=7.8 Hz, 1H), 7.35 (d, J=4.5 Hz, 1H), 8.16 (d, J=7.8 Hz, 1H), 8.83 (d, J=4.5 Hz, 1H).

Step 2: preparation of intermediate ethyl 2-(tert-butoxy)-2-[5-chloro-2-methyl-4-(2,3-dihydropyrano[4,3,2-de]quinolin-7-yl)thiophen-3-yl]acetate (61 b)

Using the procedure described in example 39, step 6, ethyl 2-(4-bromo-5-chloro-2-methylthiophen-3-yl)-2-(tert-butoxy)acetate (1d) (500 mg, 1.35 mmol) is converted by reaction with (2,3-dihydropyrano[4,3,2-de]quinolin-7-yl)-boronic acid (61a) (305 mg, 1.42 mmol) into ethyl 2-(tert-butoxy)-2-[5-chloro-2-methyl-4-(2,3-dihydropyrano[4,3,2-de]quinolin-7-yl)thiophen-3-yl]acetate (61b) (214 mg, 0.47 mmol, 35%) as a atropisomers mixture after purification by flash chromatography (cyclohexane/ethyl acetate 70/30).

$^1$H NMR (400 MHz, CDCl$_3$) δ 0.91 and 0.95 (s, 9H), 1.03 and 1.18 (t, J=7.2 Hz, 3H), 2.58 and 2.61 (s, 3H), 3.26-3.31 (m, 2H), 3.90-3.98 and 4.02-4.10 (m, 2H), 4.50-4.54 (m, 2H), 4.66 and 5.30 (s, 1H), 7.05 and 7.06 (d, J=8.0 Hz, 1H), 7.08 and 7.10 (d, J=4.4 Hz, 1H), 7.51 and 7.56 (d, J=8.0 Hz, 1H), 8.76 and 8.81 (d, J=4.4 Hz, 1H).

MS m/z [M+H]$^+$ 460/462

Step 3: preparation of intermediate ethyl 2-(tert-butoxy)-2-[2-methyl-4-(2,3-dihydropyrano[4,3,2-de]quinolin-7-yl)-5-phenylthiophen-3-yl]acetate (61c)

Using the procedure described in example 1, step 6, ethyl 2-(tert-butoxy)-2-[5-chloro-2-methyl-4-(2,3-dihydropyrano[4,3,2-de]quinolin-7-yl)thiophen-3-yl]acetate (61 b) (150 mg, 0.33 mmol) is converted by reaction with phenylboronic acid pinacol ester (100 mg, 0.49 mmol) into ethyl 2-(tert-butoxy)-2-[2-methyl-4-(2,3-dihydropyrano[4,3,2-de]quinolin-7-yl)-5-phenylthiophen-3-yl]acetate (61c) (75 mg, 0.15 mmol, 45%) as a atropisomers mixture after purification by flash chromatography (cyclohexane/ethyl acetate 80/20).

$^1$H NMR (400 MHz, CDCl$_3$) δ 0.92 and 0.93 (s, 9H), 1.06 and 1.15 (t, J=7.2 Hz, 3H), 2.70 and 2.71 (s, 3H), 3.26-3.31 (m, 2H), 3.90-4.15 (m, 2H), 4.48-4.52 (m, 2H), 4.63 and 5.30 (s, 1H), 6.88 and 6.94 (d, J=8.0 Hz, 1H), 6.98-7.04 (m, 5H), 7.05 and 7.08 (d, J=4.4 Hz, 1H), 7.32 and 7.42 (d, J=8.0 Hz, 1H), 8.77 and 8.78 (d, J=4.4 Hz, 1H).

MS m/z [M+H]$^+$ 502

Step 4: preparation of 2-(tert-butoxy)-2-[2-methyl-4-(2,3-dihydropyrano[4,3,2-de]quinolin-7-yl)-5-phenylthiophen-3-yl]acetic acid (example 61)

Potassium hydroxide (25 mg, 0.45 mmol) was added to a solution of ethyl 2-(tert-butoxy)-2-[5-chloro-2-methyl-4-(2,3-dihydropyrano[4,3,2-de]quinolin-7-yl)thiophen-3-yl]acetate (61 b) (75 mg, 0.15 mmol) in a mixture of methanol (1.2 mL) and water (1.4 mL). It was heated at 100° C. for 40 hours with two additions of potassium hydroxide (twice 15 mg, 0.26 mmol) after 5 hours and 24 hours of reaction. The mixture was concentrated under reduced pressure. Water was added and the aqueous layer was acidified to pH 4-5 with 1N hydrochloric acid solution and extracted three times with ethyl acetate. The organic layer was washed with brine, dried over sodium sulfate, filtered and concentrated under reduced pressure. The crude material was purified by preparative TLC (dichloromethane/methanol 95/5) to give 2-(tert-butoxy)-2-[2-methyl-4-(2,3-dihydropyrano[4,3,2-de]quinolin-7-yl)-5-phenylthiophen-3-yl]acetic acid (example 61) (31 mg, 0.06 mmol, 44%) as a atropisomers mixture.

$^1$H NMR (400 MHz, CDCl$_3$) δ 0.69 and 0.88 (s, 9H), 2.56 and 2.63 (s, 3H), 3.21-3.48 (m, 2H), 4.37-4.59 (m, 2H), 4.73 and 5.15 (s, 1H), 6.82 and 6.88 (d, J=8.0 Hz, 1H), 6.80-6.87 (m, 2H), 7.00-7.09 (m, 3H), 7.18 and 7.31 (d, J=4.4 Hz, 1H), 7.21 and 7.28 (d, J=8.0 Hz, 1H), 8.76 and 8.78 (d, J=4.4 Hz, 1H).

MS m/z [M−H]$^−$ 472

Example 62

Synthesis of 2-(tert-butoxy)-2-{2-methyl-4-[4,4-dimethylcyclohex-1-en-1-yl]-5-(5-chloro-4-methylisothiazol-3-yl)thiophen-3-yl}acetic acid

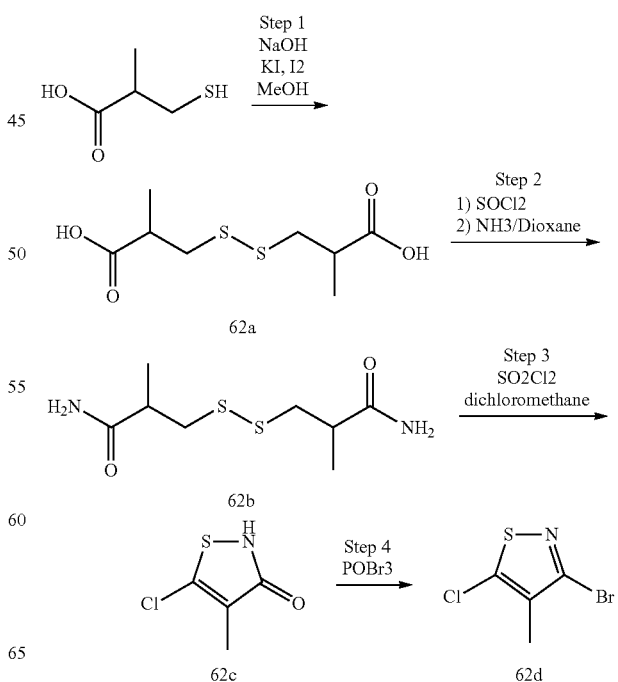

-continued

Step 5

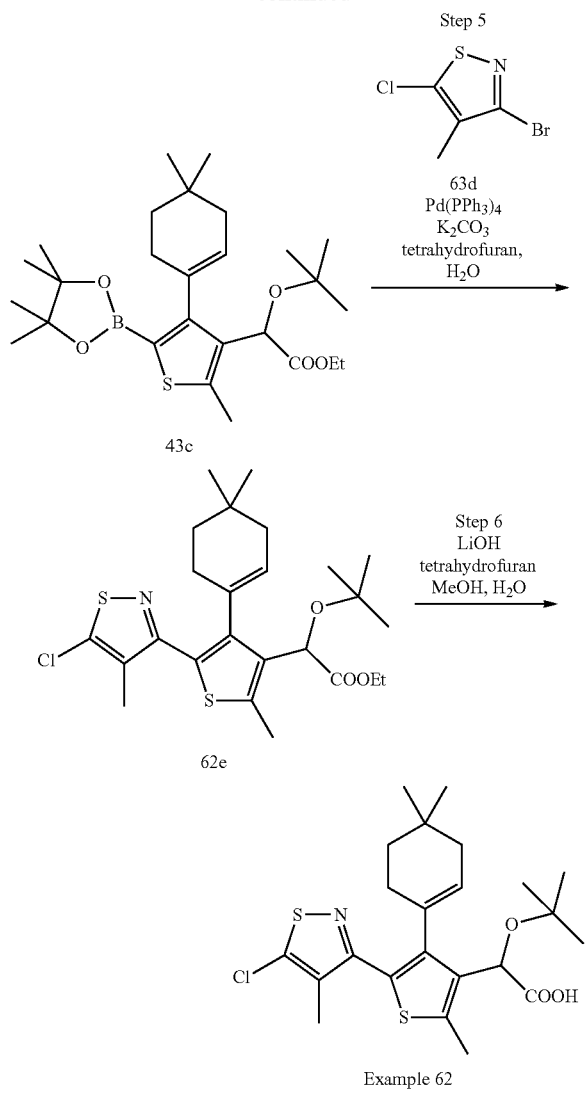

Step 1: preparation of intermediate 2,2'-dimethyl-4,4'-dithiodipropanoic acid (62a)

To a solution of 3-mercaptoisobutyric acid (2.402 g, 20.00 mmol) in methanol (100 mL) were added sodium hydroxyde (800 mg, 20.00 mmol) and potassium iodide (995 mg, 6.00 mmol). After complete dissolution, iodine (2.537 g, 10.00 mmol) was added portionwise until the yellow color persisted and then sodium sulfite solid was added until complete decoloring of the solution occurred. The solvent was evaporated, hydrochloric acid (1M) was added to reach pH 2 and the aqueous phase was extracted with ethyl acetate. The combined organic phases were dried over sodium sulphate and concentrated under reduced pressure to give 2,2'-dimethyl-4,4'-dithiodipropanoic acid (62a) (2.452 g, 10.00 mmol, 100%) as a white solid without further purification.

$^1$H NMR (300 MHz, DMSO-$d_6$) δ 1.16 (d, J=6.9 Hz, 6H), 2.66-2.80 (m, 4H), 2.93-3.00 (m, 2H), 12.40 (s, 2H).

MS m/z ([M−H]$^-$) 237.

Step 2: preparation of intermediate 2,2'-dimethyl-4,4'-dithiodipropanamide (62b)

Thionyl chloride (7.5 mL, 12.24 mmol) was added to neat 2,2'-dimethyl-4,4'-dithiodipropanoic acid (62a) (2.452 g, 10.00 mmol) and the mixture was stirred for 17 hours at room temperature to give an amber solution. The excess of thionyl chloride was removed under reduced pressure and the crude acid chloride was transferred via syringe into a dioxane solution of ammonia (0.5M, 103 mL, 51.44 mmol) at 0° C. The mixture was then stirred at room temperature for 30 minutes. The resulting precipitate was filtered off and washed with cold ethyl acetate (to eliminate the remaining diacide traces) twice to give 2,2'-dimethyl-4,4'-dithiodipropanamide (62b) (2.451 g, 10.00 mmol, 100%) as a white powder after precipitation in water.

$^1$H NMR (300 MHz, DMSO-$d_6$) δ 1.08 (d, J=6.9 Hz, 6H), 2.52-2.68 (m, 4H), 2.89-2.96 (m, 2H), 6.86 (bs, 2H), 7.41 (bs, 2H).

MS m/z ([M+H]$^+$) 237.

Step 3: preparation of intermediate 5-chloro-4-methylisothiazol-3(2H)-one (62c)

2,2'-Dimethyl-4,4'-dithiodipropanamide (62b) (201 mg, 0.85 mmol) was suspended in dichloromethane and sulfuryl chloride (0.42 mL, 5.10 mmol) was added dropwise (spontaneous solubilization and re-precipitation). The reaction was stirred at room temperature for 2 hours when water (10 mL) was added cautiously. The aqueous layer was basified with sodium hydroxide (1M) to pH 6-7, extracted with ethyl acetate and concentrated under reduced pressure to give 5-chloro-4-methylisothiazol-3(2H)-one (62c) (117 mg, 0.78 mmol, 46%) as white needles after purification by preparative TLC (cyclohexane/ethyl acetate 70/30).

$^1$H NMR (300 MHz, CDCl$_3$) (52.07 (s, 3H).
MS m/z ([M+H]$^+$) 150.
MS m/z ([M−H]$^-$) 148.

Step 4: preparation of intermediate 3-bromo-5-chloro-4-methylisothiazole (62d)

A stirred mixture of 5-chloro-4-methylisothiazol-3(2H)-one (62c) (70 mg, 0.47 mmol) and phosphorus oxybromide (5.366 g, 18.72 mmol), protected with a calcium chloride drying tube, was heated to 100° C. for 24 hours. The reaction mixture was cooled to room temperature, diluted with water and extracted with dichloromethane. The organic extracts were combined, dried and concentrated under reduced pressure to give 3-bromo-5-chloro-4-methylisothiazole (62d) (43 mg, 0.20 mmol, 43%) as a yellow liquid after purification by preparative TLC (cyclohexane/ethyl acetate 90/10).

$^1$H NMR (300 MHz, CDCl$_3$) (52.22 (s, 3H).
MS m/z ([M+H]$^+$) 212.

Step 5: preparation of intermediate ethyl 2-(tert-butoxy)-2-[4-(4,4-dimethylcyclohex-1-en-1-yl)-2-methyl-5-(5-chloro-4-methyl-isothiazol-3-yl)thiophen-3-yl]acetate (62e)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (105 mg, 0.21 mmol) is converted by reaction with 3-bromo-5-chloro-4-methylisothiazole (62d) (55 mg, 0.26 mmol) into ethyl 2-(tert-butoxy)-2-[4-(4,4-dimethylcyclohex-1-en-1-yl)-2-methyl-5-(5-chloro-4- methyl-isothiazol-3-yl)thiophen-3-yl]acetate (62e) (73 mg, 0.15 mmol, 40%, atropisomers mixture) as a yellow oil after purification by preparative TLC (cyclohexane/ethyl acetate 90/10).

$^1$H NMR (400 MHz, CDCl$_3$) δ 0.88, 0.91, 0.99 and 1.01 (s, 6H), 1.15 and 1.18 (s, 9H), 1.21 (t, J=7.2 Hz, 3H), 1.46-1.51 (m, 2H), 1.85-2.00 (m, 4H), 2.15 and 2.51 (s, 3H), 2.54 and 2.59 (s, 3H), 4.04-4.23 (m, 2H), 5.14 and 5.18 (s, 1H), 5.57-5.64 and 5.65-5.69 (bs, 1H).

MS m/z ([M+H]$^+$) 496/498.

Step 6: preparation of 2-(tert-butoxy)-2-{2-methyl-4-[4,4-dimethylcyclohex-1-en-1-yl]-5-(5-chloro-4-methyl-isothiazol-3-yl)thiophen-3-yl}acetic acid (example 62)

Using the procedure described in example 15, step 2, ethyl 2-(tert-butoxy)-2-[4-(4,4-dimethylcyclohex-1-en-1-yl)-2-methyl-5-(5-chloro-4-methyl-isothiazol-3-yl)thiophen-3-yl]acetate (62e) (73 mg, 0.15 mmol) is converted into 2-(tert-butoxy)-2-{2-methyl-4-[4,4-dimethylcyclohex-1-en-1-yl]-5-(5-chloro-4-methyl-isothiazol-3-yl)thiophen-3-yl}acetic acid (example 62) (13 mg, 0.03 mmol, 19%, atropisomers mixture) as a white solid after purification by preparative TLC (dichloromethane/methanol 95/5).

$^1$H NMR (400 MHz, CDCl$_3$) δ 0.84, 0.88 and 0.92 (s, 6H), 1.19 and 1.21 (s, 9H), 1.24-1.29 (m, 2H), 1.85-1.98 (m, 4H), 2.06 and 2.12 (s, 3H), 2.42 and 2.50 (s, 3H), 5.13 and 5.21 (s, 1H), 5.58-5.78 (bs, 1H), 9.15-10.63 (bs, 1H).

MS m/z ([M+H]$^+$) 468.
MS m/z ([M−H]$^-$) 466.

Example 63

Synthesis of 2-(tert-butoxy)-2-{2-methyl-4-[4,4-dimethylcyclohex-1-en-1-yl]-5-(isothiazol-5-yl)thiophen-3-yl}acetic acid

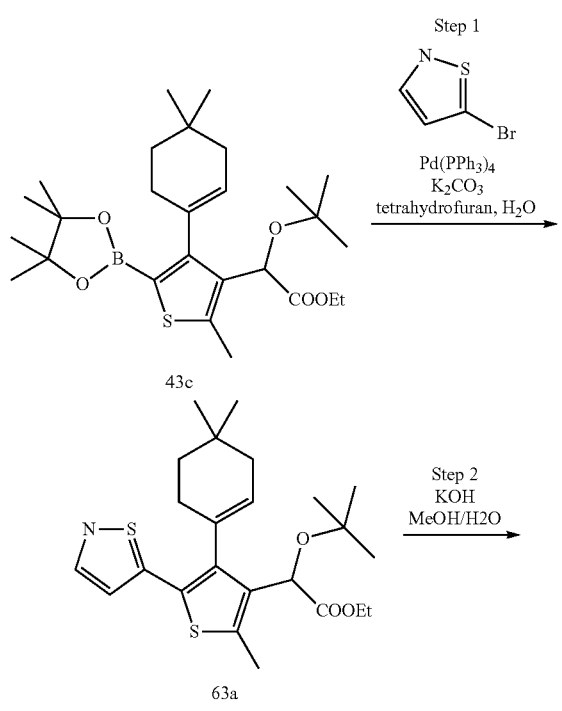

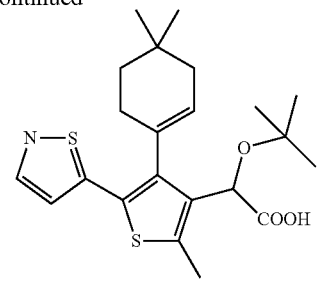

Example 63

Step 1: preparation of intermediate ethyl 2-(tert-butoxy)-2-[4-(4,4-dimethylcyclohex-1-en-1-yl)-2-methyl-5-(isothiazol-5-yl)thiophen-3-yl]acetate (63a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (108 mg, 0.22 mmol) is converted by reaction with 5-bromoisothiazole (54 mg, 0.33 mmol) into ethyl 2-(tert-butoxy)-2-[4-(4,4-dimethylcyclohex-1-en-1-yl)-2-methyl-5-(isothiazol-5-yl)thiophen-3-yl]acetate (63a) (30 mg, 0.07 mmol, 30%, atropisomers mixture) as a yellow oil after purification by preparative TLC (cyclohexane/ethyl acetate 90/10).

$^1$H NMR (300 MHz, CDCl$_3$) δ 0.78, 0.89, 0.95 and 0.98 (s, 6H), 1.17 and 1.19 (s, 9H), 1.24 (t, J=7.2 Hz, 3H), 1.33-1.42 (m, 2H), 1.79-2.01 (m, 4H), 2.52 and 2.59 (s, 3H), 4.03-4.25 (m, 2H), 5.00 and 5.19 (s, 1H), 5.57-5.63 and 5.68-5.77 (bs, 1H), 7.21 (d, J=6.6 Hz, 1H), 8.31 and 8.43 (s, 1H).

MS m/z ([M+H]$^+$) 448.

Step 2: preparation of 2-(tert-butoxy)-2-{2-methyl-4-[4,4-dimethylcyclohex-1-en-1-yl]-5-(isothiazol-3-yl)thiophen-5-yl}acetic acid (example 63)

Using the procedure described in example 3, step 2, ethyl 2-(tert-butoxy)-2-[4-(4,4-dimethylcyclohex-1-en-1-yl)-2-methyl-5-(isothiazol-5-yl)thiophen-3-yl]acetate (63a) (30 mg, 0.07 mmol) is converted into 2-(tert-butoxy)-2-{2-methyl-4-[4,4-dimethylcyclohex-1-en-1-yl]-5-(isothiazol-5-yl)thiophen-3-yl}acetic acid (example 63) (19 mg, 0.05 mmol, 68%, atropisomers mixture) as a white solid after purification by preparative TLC (dichloromethane/methanol 90/10).

$^1$H NMR (300 MHz, CDCl$_3$) δ 0.86, 0.88, 1.03 and 1.05 (s, 6H), 1.17 and 1.21 (s, 9H), 1.23-1.28 (m, 2H), 1.78-2.12 (m, 4H), 2.48 and 2.49 (s, 3H), 5.03 and 5.20 (s, 1H), 5.59-5.90 (bs, 1H), 7.19 and 7.22 (d, J=1.8 Hz, 1H), 8.32 and 8.43 (d, J=1.8 Hz, 1H).

MS m/z ([M+H]$^+$) 420.
MS m/z ([M−H]$^-$) 418.

Example 64

Synthesis of 2-[4-(4,4-dimethylcyclohex-1-en-1-yl)-2-methyl-5-(pyridin-4-yl)thiophen-3-yl]-2-ethoxyacetic acid

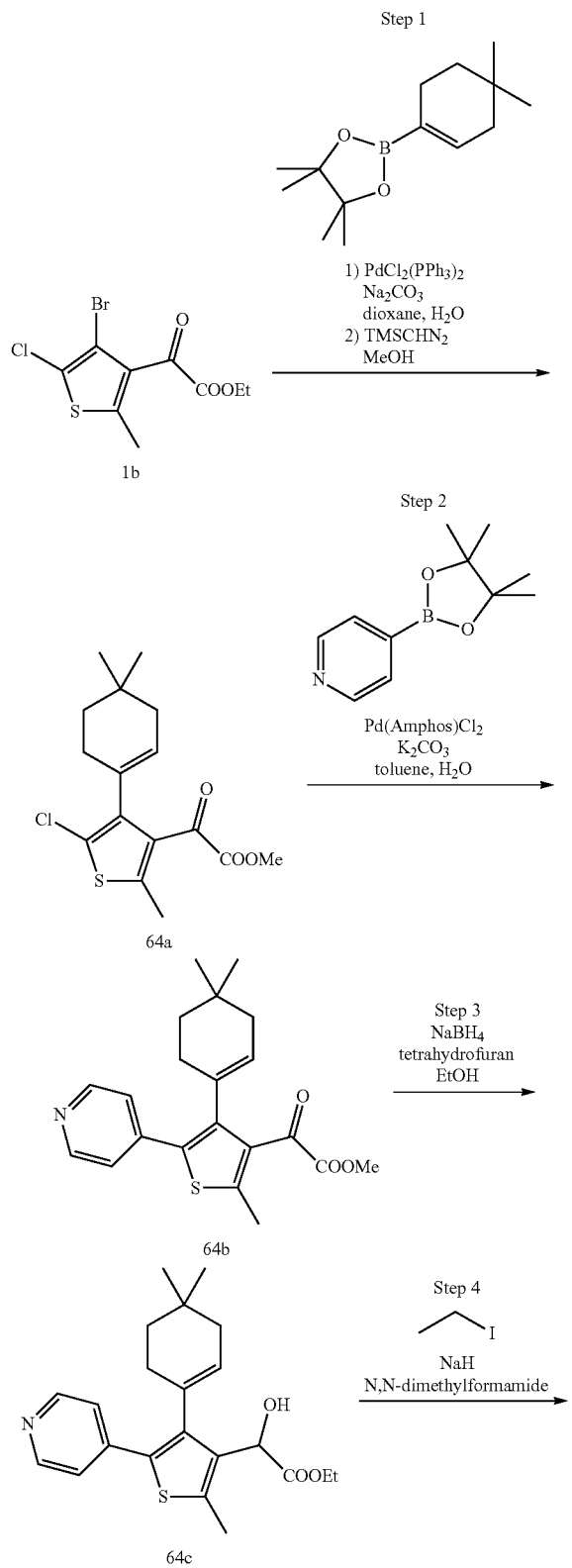

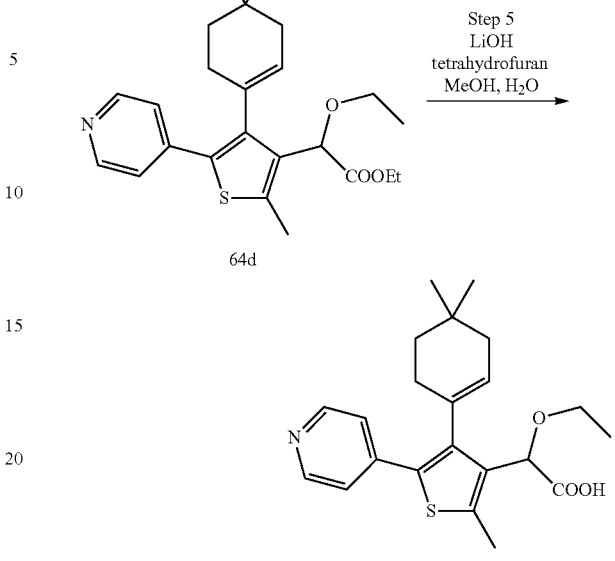

Step 1: preparation of intermediate methyl 2-[5-chloro-4-(4,4-dimethylcyclohex-1-en-1-yl)-2-methylthiophen-3-yl]-2-oxoacetate (64a)

Under argon atmosphere, ethyl 2-(4-bromo-5-chloro-2-methylthiophen-3-yl)-2-oxoacetate (1b) (317 mg, 1.02 mmol), 4,4-(dimethylcyclohexene-1-yl)boronic acid pinacol ester (312 mg, 1.32 mmol), potassium carbonate (422 mg, 3.05 mmol) were dissolved in tetrahydrofuran (8.5 mL) and water (1.7 mL). The solution was degassed under argon for 10 minutes before tetrakis(triphenylphosphine)palladium (0) (118 mg, 0.10 mmol) was added. The reaction was heated at 95° C. for 15 hours. After cooling down to room temperature, the mixture was partitioned between ethyl acetate and water and the aqueous layer was acidified to pH 7 with 1N hydrochloric acid solution. The organic layer was washed with brine, dried over sodium sulphate, filtered and concentrated under reduced pressure. Under argon, at 0° C., the crude carboxylic acid (318 mg, 1.02 mmol) was dissolved in methanol (3.4 mL), (trimethylsilyl) diazomethane solution (2M in diethylether, 2.0 mL, 4.07 mmol) was added dropwisely and the reaction mixture was stirred at room temperature for 3h. Few drops of acetic acid were added to quench the (trimethylsilyl)diazomethane and the reacting mixture was concentrated under reduced pressure. The residue was purified by preparative TLC (cyclohexane/ethyl acetate 90/10) to give methyl 2-[5-chloro-4-(4,4-dimethylcyclohex-1-en-1-yl)-2-methylthiophen-3-yl]-2-oxoacetate (64a) (229 mg, 0.70 mmol, 69% over 2 steps) as a yellow oil.

$^1$H NMR (300 MHz, CDCl$_3$) δ 0.98 (s, 6H), 1.40-1.45 (m, 2H), 1.86-1.89 (m, 2H), 2.31-2.36 (m, 2H), 2.56 (s, 3H), 3.84 (s, 3H), 5.49-5.52 (m, 1H).

MS m/z [M+H]$^+$ 327

Step 2: preparation of intermediate methyl 2-[4-(4,4-dimethylcyclohex-1-en-1-yl)-2-methyl-5-(pyridin-4-yl)thiophen-3-yl]-2-oxoacetate (64b)

Using the procedure described in example 1, step 6, methyl 2-[5-chloro-4-(4,4-dimethylcyclohex-1-en-1-yl)-2- methylthiophen-3-yl]-2-oxoacetate (64a) (229 mg, 0.70 mmol) is converted by reaction with 4-pyridine boronic acid pinacol ester (359 mg, 1.75 mmol) into methyl 2-[4-(4,4-dimethylcyclohex-1-en-1-yl)-2-methyl-5-(pyridin-4-yl)thiophen-3-yl]-2-oxoacetate (64b) (167 mg, 0.45 mmol, 64%) as a pale yellow solid after purification by preparative TLC (cyclohexane/ethyl acetate 70/30).

$^1$H NMR (400 MHz, CDCl$_3$) δ 0.92 (s, 6H), 1.31 (dd, J=6.0 Hz, J=6.0 Hz, 2H), 1.91-1.96 (m, 4H), 2.63 (s, 3H), 3.86 (s, 3H), 5.67-5.70 (m, 1H), 7.35 (dd, J=4.4 Hz, J=1.6 Hz, 2H), 8.58 (dd, J=4.4 Hz, J=1.6 Hz, 2H).

Step 3: preparation of intermediate ethyl 2-[4-(4,4-dimethylcyclohex-1-en-1-yl)-2-methyl-5-(pyridin-4-yl)thiophen-3-yl]-2-hydroxyacetate (64c)

To a solution of methyl 2-[4-(4,4-dimethylcyclohex-1-en-1-yl)-2-methyl-5-(pyridin-4-yl)thiophen-3-yl]-2-oxoacetate (64b) (161 mg, 0.44 mmol) in a mixture of tetrahydrofuran (2.8 mL) and ethanol (0.7 mL) was added sodium tetraborohydride (15 mg, 0.39 mmol) at 0° C. The mixture was stirred at 0° C. for 2 hours. The mixture was quenched with 1N hydrochloric acid solution and extracted with ethyl acetate twice. The organic extract was washed with brine twice, dried over sodium sulfate, filtered and concentrated under reduced pressure. The crude product was purified by preparative TLC (cyclohexane/ethyl acetate 70/30) to afford the transesterified product ethyl 2-[4-(4,4-dimethylcyclohex-1-en-1-yl)-2-methyl-5-(pyridin-4-yl)thiophen-3-yl]-2-hydroxyacetate (64c) (80 mg, 0.21 mmol, 47%) as a white solid.

$^1$H NMR (400 MHz, CDCl$_3$): δ 0.96 (s, 3H), 0.97 (s, 3H), 1.25 (t, J=7.2 Hz, 3H), 1.38 (dd, J=6.0 Hz, J=6.0 Hz, 2H), 1.86-2.17 (m, 4H), 2.46 (s, 3H), 3.32 (d, J=2.8 Hz, 1H), 4.14-4.22 (m, 1H), 4.27-4.35 (m, 1H), 5.20 (d, J=2.8 Hz, 1H), 5.68-5.78 (m, 1H), 7.43 (dd, J=4.4 Hz, J=1.6 Hz, 2H), 8.52 (dd, J=4.4 Hz, J=1.6 Hz, 2H).

MS m/z [M+H]$^+$ 386

Step 4: preparation of intermediate ethyl 2-[4-(4,4-dimethylcyclohex-1-en-1-yl)-2-methyl-5-(pyridin-4-yl)thiophen-3-yl]-2-ethoxyacetate (64d)

A mixture of ethyl 2-[4-(4,4-dimethylcyclohex-1-en-1-yl)-2-methyl-5-(pyridin-4-yl)thiophen-3-yl]-2-hydroxyacetate (64c) (40 mg, 0.10 mmol) in dry N,N-dimethylformamide (2 mL) was cooled at 0° C. and sodium hydride (60% dispersion in mineral oil, 4.35 mg, 0.11 mmol) was added. The mixture was stirred 20 minutes at 0° C. then 5 minutes at room temperature. Ethyl iodide (9 μL, 0.11 mmol) was added to the mixture at 0° C., the reacting mixture was stirred for 2 hours at 0° C. and then the ice-bath was removed and the mixture was allowed to warm up to room temperature for 20 hours. After cooling down to 0° C., the mixture was quenched with a saturated sodium hydrogenocarbonate aqueous solution and extracted with ethyl acetate twice. The organic layer was washed with brine, dried over sodium sulfate, filtered and concentrated under reduced pressure. The residue was purified by preparative TLC (cyclohexane/methanol 70/30) to give ethyl 2-[4-(4,4-dimethylcyclohex-1-en-1-yl)-2-methyl-5-(pyridin-4-yl)thiophen-3-yl]-2-ethoxyacetate (64d) (19 mg, 0.04 mmol, 46%).

$^1$H NMR (400 MHz, CDCl$_3$) δ 0.99 (s, 3H), 1.00 (s, 3H), 1.23 (t, J=7.2 Hz, 3H), 1.24 (t, J=7.2 Hz, 3H), 1.39-1.43 (m, 2H), 1.83-2.19 (m, 4H), 2.53 (s, 3H), 3.40-3.49 (m, 1H), 3.53-3.60 (m, 1H), 4.09-4.17 (m, 1H), 4.22-4.31 (m, 1H), 4.97 (s, 1H), 5.65-5.81 (m, 1H), 7.43 (dd, J=4.8 Hz, J=1.6 Hz, 2H), 8.52 (dd, J=4.8 Hz, J=1.6 Hz, 2H).

MS m/z [M+H]$^+$ 414

Step 5: preparation of 2-[4-(4,4-dimethylcyclohex-1-en-1-yl)-2-methyl-5-(pyridin-4-yl)thiophen-3-yl]-2-ethoxyacetic acid (example 64)

Using the procedure described in example 15, step 2, ethyl 2-[4-(4,4-dimethylcyclohex-1-en-1-yl)-2-methyl-5-(pyridin-4-yl)thiophen-3-yl]-2-ethoxyacetate (64d) (19 mg, 0.05 mmol) is converted into 2-[4-(4,4-dimethylcyclohex-1-en-1-yl)-2-methyl-5-(pyridin-4-yl)thiophen-3-yl]-2-ethoxyacetic acid (example 64) (8 mg, 0.02 mmol, 41%) as a white powder after purification by preparative TLC (dichloromethane/methanol 95/5).

$^1$H NMR (400 MHz, CDCl$_3$) δ 0.97 (s, 3H), 0.98 (s, 3H), 1.25 (t, J=7.2 Hz, 3H), 1.34-1.44 (m, 2H), 1.81-2.06 (m, 4H), 2.53 (s, 3H), 3.39-3.52 (m, 1H), 3.53-3.63 (m, 1H), 4.99 (s, 1H), 5.65-5.95 (m, 1H), 7.48 (m, 2H), 8.54 (m, 2H).

MS m/z [M−H]$^-$ 384

Example 65

Synthesis of 2-(tert-butoxy)-2-[4-(3,4-dihydro-2H-1-benzopyran-6-yl)-5-propyl)-2-methylthiophen-3-yl]acetic acid acid

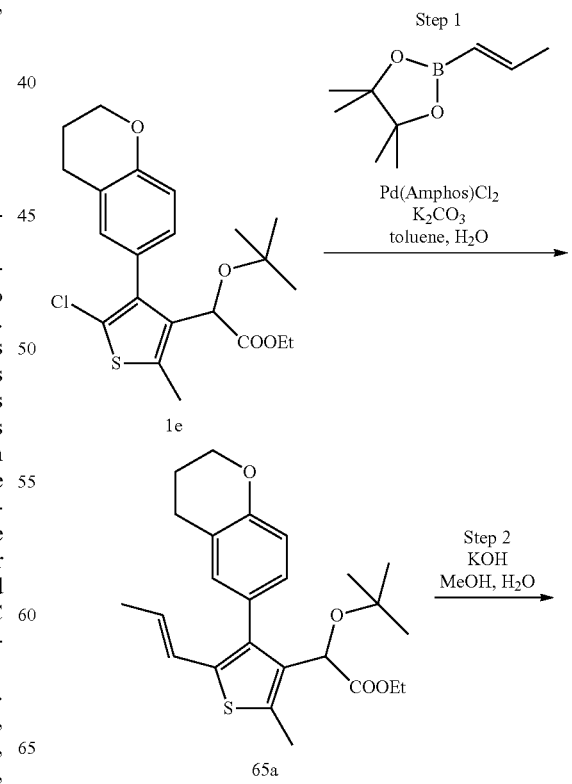

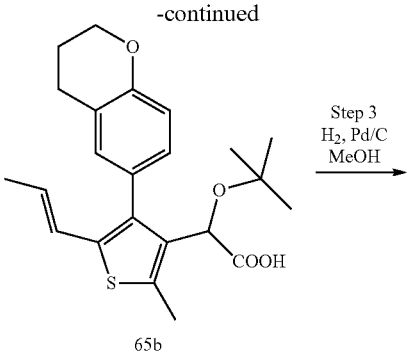

Step 3
H₂, Pd/C
MeOH

65b

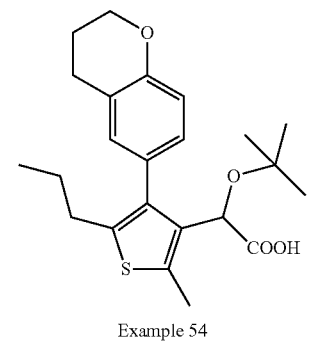

Example 54

Step 1: Preparation of intermediate ethyl 2-(tert-butoxy)-2-[4-(3,4-dihydro-2H-1-benzopyran-6-yl)-5-((E)-propenyl)-2-methylthiophen-3-yl]acetate (65a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (225 mg, 0.53 mmol) is converted by reaction with trans-propenylboronic acid pinacol ester (406 µL, 2.13 mmol) into ethyl 2-(tert-butoxy)-2-[4-(3,4-dihydro-2H-1-benzopyran-6-yl)-5-((E)-propenyl)-2-methylthiophen-3-yl]acetate (65a) (107 mg, 0.18 mmol, 33%) after purification by preparative TLC (cyclohexane/ethyl acetate 95/5).

¹H NMR (400 MHz, CDCl₃) δ 0.99 (s, 9H), 1.22-1.24 (m, 3H), 1.54-1.57 (m, 1H), 1.72-1.74 (m, 2H), 2.04-2.07 (m, 2H), 2.51 (s, 2H), 2.57 (s, 1H), 2.08-2.81 (m, 2H), 4.11-4.15 (m, 2H), 4.23-4.24 (m, 2H), 4.78 (s, 1H), 5.90 (dt, J=6.6 Hz, J=15.6 Hz, 1H), 6.18 (dd, J=1.6 Hz, J=15.6 Hz, 1H), 6.81-6.82 (m, 1H), 6.97 (bs, 2H).

MS m/z ([M+Na]⁺) 451

Step 2: Preparation of intermediate 2-(tert-butoxy)-2-[4-(3,4-dihydro-2H-1-benzopyran-6-yl)-5-((E)-propenyl)-2-methylthiophen-3-yl]acetic acid (65b)

Using the procedure described in example 1, step 7, ethyl 2-(tert-butoxy)-2-[4-(3,4-dihydro-2H-1-benzopyran-6-yl)-5-((E)-propenyl)-2-methylthiophen-3-yl]acetate (65a) (107 mg, 0.25 mmol) is converted, after purification by preparative TLC (dichloromethane/methanol 95/5) into 2-(tert-butoxy)-2-[4-(3,4-dihydro-2H-1-benzopyran-6-yl)-5-((E)-propenyl)-2-methylthiophen-3-yl]acetic acid (65b) (12.6 mg, 0.03 mmol, 12%).

MS m/z ([M-(OtBu)+H]⁺ 327

Step 3: Preparation of 2-(tert-butoxy)-2-[4-(3,4-dihydro-2H-1-benzopyran-6-yl)-5-propyl)-2-methyl-thiophen-3-yl]acetic acid (example 65)

A mixture of 2-(tert-butoxy)-2-[4-(3,4-dihydro-2H-1-benzopyran-6-yl)-5-((E)-propenyl)-2-methylthiophen-3-yl] acetic acid (65b) (12.6 mg, 0.03 mmol) and palladium on carbon (4 mg) in methanol (1.6 mL) was stirred under hydrogen atmosphere overnight. The mixture was filtered over Millipore and the filtrate was concentrated in vacuo to provide, after purification by preparative TLC (dichloromethane/methanol: 95/5), 2-(tert-butoxy)-2-[4-(3,4-dihydro-2H-1-benzopyran-6-yl)-5-propyl)-2-methylthiophen-3-yl]acetic acid (example 65) (3.1 mg, 0.0077 mmol, 24%) as a white solid.

¹H NMR (400 MHz, CDCl₃) δ 0.86 (t, J=7.3 Hz, 3H), 1.01 (bs, 9H), 1.23 (d, J=6.6 Hz, 1H), 1.51-1.56 (m, 2H), 2.00-2.04 (m, 2H), 2.41 (s, 3H), 2.52 (t, J=7.4 Hz, 1H), 2.79 (bs, 2H), 4.22 (t, J=5.0 Hz, 2H), 4.88 (bs, 1H), 6.78-6.87 (m, 2H), 7.15 (bs, 1H), 9.62 (bs, 1H).

MS m/z ([M-H]⁻) 401

Example 66

Synthesis of 2-(tert-butoxy)-2-{2-methyl-4-[4,4-dimethylcyclohex-1-en-1-yl]-5-(cyclopropyl)thiophen-3-yl}acetic acid

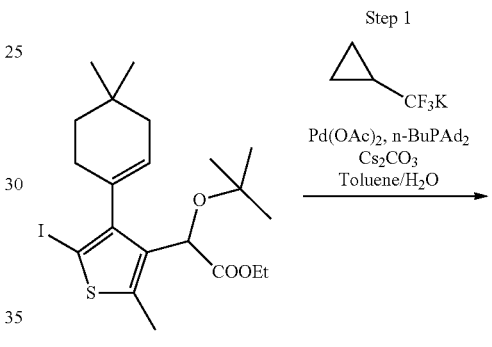

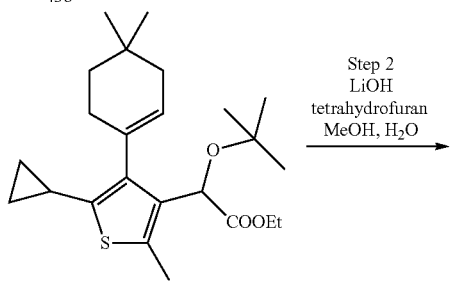

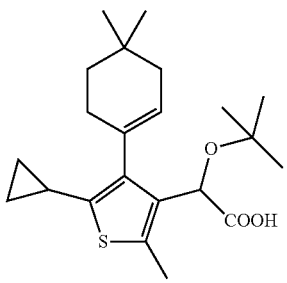

Example 66

Step 1: preparation of intermediate ethyl 2-(tert-butoxy)-2-[4-(4,4-dimethylcyclohex-1-en-1-yl)-2-methyl-5-(cyclopropyl)thiophen-3-yl]acetate (66a)

To a sealed and degassed vial under argon atmosphere charged with 2-(tert-butoxy)-2-[4-(4,4-dimethylcyclohex-1- en-1-yl)-2-methyl-5-iodothiophen-3-yl]acetate (43b), (105 mg, 0.21 mmol), potassium cyclopropyltrifluoroborate (32 mg, 0.22 mmol), cesium carbonate (209 mg, 0.64 mmol), and di(1-adamantyl)-n-butylphosphine (2 mg, 0.006 mmol) in a mixture toluene (1.9 mL)/water (0.2 mL) was added Palladium(II) acetate (1 mg, 0.004 mmol) and the reaction was heated at 100° C. for 24 hours. After cooling down at room temperature, the mixture was diluted with water extracted with ethyl acetate, dried over sodium sulfate and concentrated under reduced pressure to afford ethyl 2-(tert-butoxy)-2-[4-(4,4-dimethylcyclohex-1-en-1-yl)-2-methyl-5-(cyclopropyl)thiophen-3-yl]acetate (66a) (70 mg, 0.17 mmol, 78%, atropisomers mixture) as a yellow oil after purification by preparative TLC (cyclohexane/ethyl acetate 95/5).

$^1$H NMR (400 MHz, CDCl$_3$) δ 0.59-0.64 (m, 1H), 0.82-0.89 (m, 1H), 0.91-1.01 (m, 2H), 1.02, 1.04 and 1.06 (s, 6H), 1.17 (s, 9H), 1.21 (t, J=7.2 Hz, 3H), 1.46-1.52 (m, 2H), 1.94-2.40 (m, 4H), 2.47 and 2.53 (s, 3H), 2.52-2.54 (m, 1H), 4.02-4.18 (m, 2H), 4.99 and 5.01 (s, 1H), 5.51 and 5.55 (bs, 1H).

Step 2: preparation of 2-(tert-butoxy)-2-{2-methyl-4-[4,4-dimethylcyclohex-1-en-1-yl]-5-(cyclopropyl)thiophen-3-yl}acetic acid (example 66)

Using the procedure described in example 15, step 2, ethyl 2-(tert-butoxy)-2-[4-(4,4-dimethylcyclohex-1-en-1-yl)-2-methyl-5-(cyclopropyl)thiophen-3-yl]acetate (66a) (59 mg, 0.15 mmol) is converted into 2-(tert-butoxy)-2-{2-methyl-4-[4,4-dimethylcyclohex-1-en-1-yl]-5-(cyclo propyl)thiophen-3-yl}acetic acid (example 66) (42 mg, 0.11 mmol, 76%, atropisomers mixture) as a white solid after purification by preparative TLC (dichloromethane/methanol 95/5).

$^1$H NMR (400 MHz, CDCl$_3$) δ 0.61-0.63 (m, 1H), 0.85-0.88 (m, 1H), 0.91-0.99 (m, 2H), 1.00, 1.01, 1.02 and 1.05 (s, 6H), 1.21 (s, 9H), 1.45-1.50 (m, 2H), 1.85-1.99 (m, 3H), 2.09-2.23 (m, 1H), 2.38 and 2.45 (s, 3H), 2.42-2.48 (m, 1H), 5.04 and 5.06 (s, 1H), 5.47 and 5.58 (bs, 1H), 9.06-10.89 (bs, 1H).

MS m/z ([M−H]$^-$) 375.

Example 67

Synthesis of 2-(tert-butoxy)-2-[4-(5,5-dimethyl-5,6-dihydroquinolin-8-yl)-2-methyl-5-phenylthiophen-3-yl]acetic acid

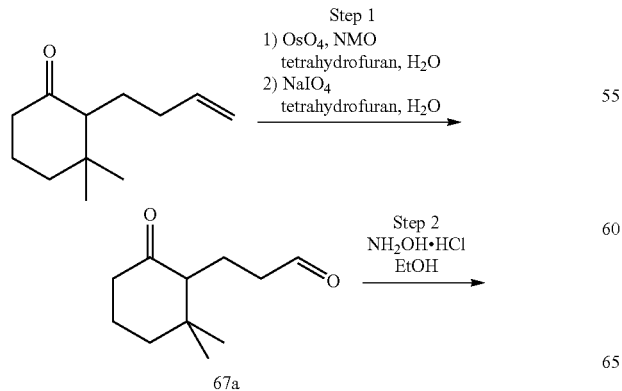

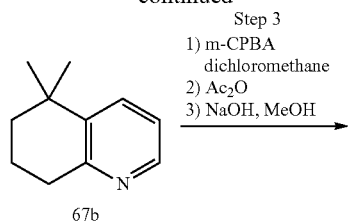

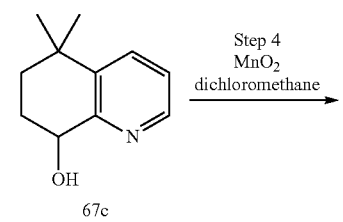

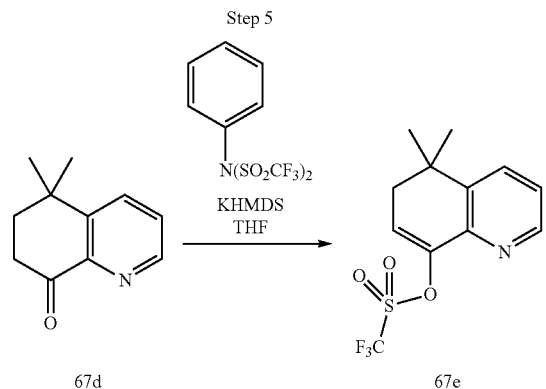

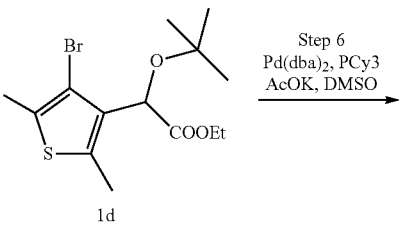

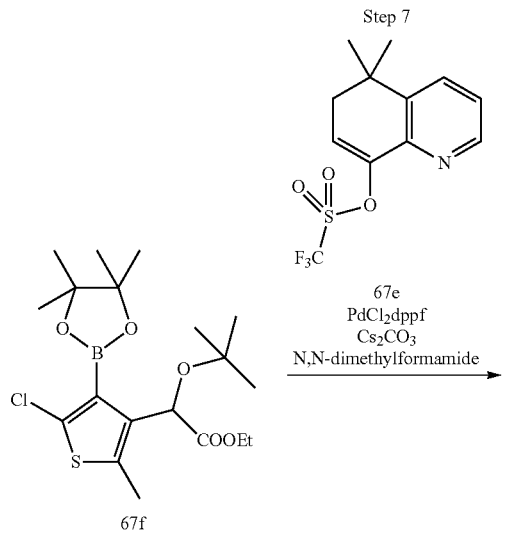

201

-continued

Step 8

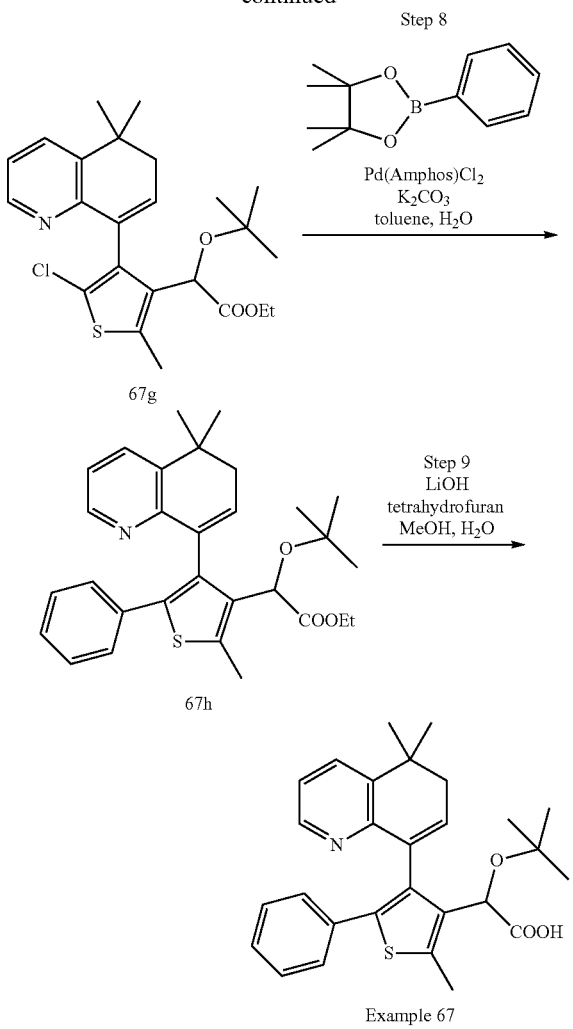

Example 67

Step 1: preparation of intermediate 3-(2,2-dimethyl-6-oxocyclohexyl)propanal (67a)

In an amber round bottom flask, under argon atmosphere, osmium tetroxide (solution 4% wt in water, 4.44 mL, 0.70 mmol) and N-methylmorpholino-N-oxide (3.25 g, 27.96 mmol) were added to a stirred solution of 2-(but-3-en-1-yl)-3,3-dimethylcyclohexan-1-one (prepared in three steps according to the literature: J.A.C.S, 2012, 134, 6528-6531) (2.52 g, 13.98 mmol) in a mixture of tetrahydrofuran (210 mL) and water (70 mL). After stirring at room temperature for 3 hours, the reaction was quenched with sodium thiosulfate saturated aqueous solution. It was extracted three times with diethylether and the combined organics were washed with saturated sodium bicarbonate solution and saturated brine, dried over sodium sulfate and concentrated under reduced pressure. The resultant oil was dissolved in a mixture of tetrahydrofuran (210 mL) and water (70 mL) and sodium periodate (5.98 g, 27.96 mmol) was added. After 16 hours at room temperature, the mixture was diluted with water and diethylether. The layers were separated and the aqueous phase extracted twice with diethylether. Then, the combined organic layers were washed with saturated sodium bicarbonate solution and saturated brine, dried over sodium sulfate and concentrated under reduced pressure to afford

202

3-(2,2-dimethyl-6-oxocyclohexyl)propanal (67a) (1.45 g, 7.96 mmol, 57%) without further purification.

$^1$H NMR (400 MHz, CDCl$_3$) δ 0.78 (s, 3H), 1.10 (s, 3H), 1.62-1.95 (m, 6H), 2.13-2.16 (m, 1H), 2.24-2.36 (m, 3H), 2.53-2.61 (m, 1H), 9.74-9.75 (m, 1H).

Step 2: preparation of intermediate 5,5-dimethyl-5,6,7,8-tetrahydroquinoline (67b)

3-(2,2-dimethyl-6-oxocyclohexyl)propanal (67a) (1.45 g, 7.96 mmol) and hydroxylamine hydrochloride (558 mg, 8.04 mmol) in ethanol (2.5 mL) were heated at 75° C. for 15 hours. After cooling down to room temperature, the mixture was quenched with saturated sodium carbonate solution and extracted twice with diethylether. Then, the combined organic layers were washed with a 1N hydrochloric acid aqueous solution and saturated brine, dried over sodium sulfate and concentrated under reduced pressure to afford 5,5-dimethyl-5,6,7,8-tetrahydroquinoline (67b) (775 mg, 4.80 mmol, 60%) as a brown oil without further purification.

$^1$H NMR (400 MHz, CDCl$_3$) δ 1.27 (s, 6H), 1.66-1.69 (m, 2H), 1.87-1.93 (m, 2H), 2.92 (t, J=6.5 Hz, 2H), 7.07 (dd, J=7.9 Hz, J=4.7 Hz, 1H), 7.60 (dd, J=7.9 Hz, J=1.7 Hz, 1H), 8.33 (dd, J=4.7 Hz, J=1.7 Hz, 1H).

MS m/z ([M+H]$^+$) 162

Step 3: preparation of intermediate 5,5-dimethyl-5,6,7,8-tetrahydroquinolin-8-ol (67c)

Under argon atmosphere, meta-chloroperbenzoic acid (1.50 g, 6.72 mmol) was added at 0° C. to a mixture of 5,5-dimethyl-5,6,7,8-tetrahydroquinoline (67b) (774 mg, 4.80 mmol) in dichloromethane (19.5 mL). The mixture was stirred for 10 min and warmed up to room temperature for 18 hours. Then, the mixture was quenched with a 3N sodium hydroxide aqueous solution and extracted three times with dichloromethane. The combined organic layers were washed with saturated sodium bicarbonate solution and saturated brine, dried over sodium sulfate and concentrated under reduced pressure to afford the corresponding N-oxide. The crude N-oxide was then acylated in acetic anhydride (14 mL). The mixture was stirred and heated at 100° C. for 5 hours. The reacting mixture was quenched with saturated sodium bicarbonate solution and extracted three times with ethyl acetate. The combined organic layers were washed with saturated brine, dried over sodium sulfate and concentrated under reduced pressure to afford the corresponding acetate.

Subsequently, a mixture of this crude product in methanol (8.3 mL) and sodium hydroxide 3N (69 mL) was stirred at room temperature for 30 min, then stirred at 80° C. for 3 hours. After cooling down to room temperature, it was extracted three times with dichloromethane. The combined organic layers were washed with saturated ammonium chloride solution and brine, dried over sodium sulfate and concentrated under reduced pressure to afford 5,5-dimethyl-5,6,7,8-tetrahydroquinolin-8-ol (67c) (332 mg, 1.87 mmol, 39% over three steps) without further purification $^1$H NMR (400 MHz, CDCl$_3$) δ 1.27 (s, 3H), 1.32 (s, 3H), 1.74-1.91 (m, 3H), 2.22-2.29 (m, 1H), 4.24-4.25 (m, 1H), 4.63 (dd, J=9.8 Hz, J=5.7 Hz, 1H), 7.17 (dd, J=7.9 Hz, J=4.7 Hz, 1H), 7.61 (dd, J=7.9 Hz, J=1.6 Hz, 1H), 8.40 (dd, J=4.7 Hz, J=1.6 Hz, 1H).

MS m/z ([M+H]$^+$) 178

Step 4: preparation of intermediate 5,5-dimethyl-5,6,7,8-tetrahydroquinolin-8-one (67d)

Under argon atmosphere, manganese (IV) oxide (1.62 g, 18.70 mmol) was added to the mixture of 5,5-dimethyl-5, 6,7,8-tetrahydroquinolin-8-ol (67c) (332 mg, 1.87 mmol) in dichloromethane (12.9 mL) at room temperature. After 15 hours, the mixture was filtered through Celite®, rinsed with methanol and concentrated under reduced pressure to afford 5,5-dimethyl-5,6,7,8-tetrahydroquinolin-8-one (67d) (275 mg, 1.57 mmol, 83%) without further purification.

$^1$H NMR (400 MHz, CDCl$_3$) δ 1.42 (s, 6H), 2.09 (dd, J=6.8 Hz, J=6.8 Hz, 2H), 2.88 (dd, J=6.8 Hz, J=6.8 Hz, 2H), 7.44 (dd, J=8.1 Hz, J=4.5 Hz, 1H), 7.82 (dd, J=8.1 Hz, J=1.6 Hz, 1H), 8.70 (dd, J=4.5 Hz, J=1.6 Hz, 1H).

MS m/z ([M+H]$^+$) 176

Step 5: preparation of intermediate 5,5-dimethyl-5,6-dihydroquinolin-8-yl trifluoromethanesulfonate (67e)

Under argon atmosphere, potassium bis(trimethylsilyl)amide solution (1M in THF, 2.03 mL, 2.03 mmol) was added to a solution of 5,5-dimethyl-5,6,7,8-tetrahydroquinolin-8-one (67d) (273 mg, 1.56 mmol) and N-phenyltrifluoromethanesulfonimide (724 mg, 2.03 mmol) in tetrahydrofuran (15.6 mL) at −78° C. The solution was stirred at −78° C. for 3.5 hours. Then, the mixture was quenched with water at −78° C., warmed up to room temperature and extracted three times with diethylether. The ether layer was washed with saturated sodium bicarbonate solution and brine, dried over sodium sulfate and concentrated under reduced pressure. The crude material was purified by flash chromatography (from cyclohexane to 90/10 cyclohexane/ethyl acetate) to provide 5,5-dimethyl-5,6-dihydroquinolin-8-yl trifluoromethanesulfonate (67e) (258 mg, 0.84 mmol, 54%).

$^1$H NMR (400 MHz, CDCl$_3$) δ 1.34 (s, 6H), 2.49 (d, J=4.8 Hz, 2H), 6.18 (t, J=4.8 Hz, 1H), 7.23 (dd, J=7.8 Hz, J=4.8 Hz, 1H), 7.58 (dd, J=7.8 Hz, J=1.5 Hz, 1H), 8.49 (dd, J=4.8 Hz, J=1.5 Hz, 1H).

MS m/z ([M+H]$^+$) 308

Step 6: preparation of intermediate ethyl 2-(tert-butoxy)-2-[5-chloro-2-methyl-4-(tetramethyl-1,3,2-dioxaborolan-2-yl)thiophen-3-yl]acetate (67f)

Under argon atmosphere, a mixture of bis(dibenzylideneacetone)palladium (9.3 mg, 0.02 mmol) and tricyclohexylphosphine (10.9 mg, 0.04 mmol) in dimethylsulfoxide (3.5 mL) was stirred for 10 minutes at room temperature. Then, potassium acetate (159 mg, 1.62 mmol), bis(pinacolo)diboron (179 mg, 0.70 mmol) and a solution of (1d) (200 mg, 0.54 mmol) in dimethylsulfoxide (1.5 mL) were successively added. The mixture was stirred at 95° C. for 22 hours. The reaction was cooled down to room temperature, diluted with ethyl acetate and filtered through Celite® (rinsed with ethyl acetate). The filtrate was concentrated under reduced pressure. The mixture was diluted with ethyl acetate and washed with water, brine, dried over sodium sulfate, filtered and concentrated under reduced pressure. The residue was purified by three preparative TLC (cyclohexane/ethyl acetate 90/10) to give ethyl 2-(tert-butoxy)-2-[5-chloro-2-methyl-4-(tetramethyl-1,3,2-dioxaborolan-2-yl)thiophen-3-yl]acetate (67f) (44 mg, 0.11 mmol, 20%).

$^1$H NMR (400 MHz, CDCl$_3$) δ 1.18-1.20 (m, 12H), 1.35-1.37 (m, 12H), 2.45 (s, 3H), 4.00-4.10 (m, 2H), 5.66 (s, 1H).

Step 7: preparation of intermediate ethyl 2-(tert-butoxy)-2-[5-chloro-4-(5,5-dimethyl-5,6-dihydroquinolin-8-yl)-2-methylthiophen-3-yl]acetate (67g)

Under argon atmosphere, ethyl 2-(tert-butoxy)-2-[5-chloro-2-methyl-4-(tetramethyl-1,3,2-dioxaborolan-2-yl)thiophen-3-yl]acetate (67f) (20 mg, 0.05 mmol), 5,5-dimethyl-5,6-dihydroquinolin-8-yl trifluoromethanesulfonate (67e) (19.2 mg, 0.06 mmol) and cesium carbonate (49 mg, 0.15 mmol) were dissolved in dry N,N-dimethylformamide (300 µL). The solution was degassed under argon and [1,1'-Bis(diphenylphosphino)ferrocene]dichloropalladium (II) (2.4 mg, 0.003 mmol) was added. The reaction was heated and shaken at 85° C. for 22 hours. The mixture was filtered through Celite®, rinsed with ethyl acetate and dichloromethane. The solution was concentrated under reduced pressure and then partitioned between ethyl acetate and water. The organic layer was washed with brine, dried over sodium sulfate, filtered and concentrated under reduced pressure. The crude material was purified by preparative TLC (cyclohexane/ethyl acetate 80/20) to provide ethyl 2-(tert-butoxy)-2-[5-chloro-4-(5,5-dimethyl-5,6-dihydroguinolin-8-yl)-2-methylthiophen-3-yl]acetate (67g) (10 mg, 0.02 mmol, 45%) as a mixture of atropoisomers.

$^1$H NMR (400 MHz, CDCl$_3$) δ 0.98 and 1.02 (s, 9H), 1.01 and 1.20 (t, J=7.2 Hz, 3H), 1.41-1.43 (m, 6H), 2.36-2.51 (m, 2H), 2.55 and 2.56 (s, 3H), 3.81-3.89 and 4.01-4.12 (m, 2H), 4.80 and 4.86 (s, 1H), 6.14 and 6.25 (t, J=5.0 Hz, 1H), 7.04-7.08 (m, 1H), 7.56-7.60 (m, 1H), 8.30 and 8.34 (dd, J=4.8 Hz, J=1.6 Hz, 1H).

MS m/z ([M+H]$^+$) 448/450

Step 8: preparation of intermediate ethyl 2-(tert-butoxy)-2-[4-(5,5-dimethyl-5,6-dihydroguinolin-8-yl)-2-methyl-5-phenylthiophen-3-yl]acetate (67h)

Using the procedure described in example 1, step 6, ethyl 2-(tert-butoxy)-2-[5-chloro-4-(5,5-dimethyl-5,6-dihydroguinolin-8-yl)-2-methylthiophen-3-yl]acetate (67g) (38 mg, 0.09 mmol) is converted by reaction with phenylboronic acid pinacol ester (26 mg, 0.13 mmol) into ethyl 2-(tert-butoxy)-2-[4-(5,5-dimethyl-5,6-dihydroguinolin-8-yl)-2-methyl-5-phenylthiophen-3-yl]acetate (67h) (42 mg, 0.08 mmol, 60%, atropisomers mixture) after purification by preparative TLC (ethyl acetate/acetone 95/5).

$^1$H NMR (400 MHz, CDCl$_3$) δ 0.95 and 0.99 (s, 9H), 1.11 and 1.18 (t, J=7.1 Hz, 3H), 1.41-1.42 (m, 6H), 2.27-2.29 and 2.40-2.41 (m, 2H), 2.64 and 2.67 (s, 3H), 3.93-4.13 (m, 2H), 4.77 and 4.85 (s, 1H), 5.99-6.01 and 6.21-6.23 (m, 1H), 6.93-7.18 (m, 4H), 7.28-7.33 (m, 1H), 7.57-7.61 (m, 1H), 7.70-7.75 (m, 1H), 8.32 and 8.39 (dd, J=4.8 Hz, J=1.6 Hz, 1H).

MS m/z ([M+H]$^+$) 490

Step 9: preparation of 2-(tert-butoxy)-2-[4-(5,5-dimethyl-5,6-dihydroguinolin-8-yl)-2-methyl-5-phenylthiophen-3-yl]acetic acid (example 67)

Using the procedure described in example 15, step 2, ethyl 2-(tert-butoxy)-2-[4-(5,5-dimethyl-5,6-dihydroguinolin-8-yl)-2-methyl-5-phenylthiophen-3-yl]acetate (67h) (45 mg, 0.09 mmol) is converted into 2-(tert-butoxy)-2-[4-(5,5-dimethyl-5,6-dihydroguinolin-8-yl)-2-methyl-5-phenylthiophen-3-yl]acetic acid (example 67) (7 mg, 0.02 mmol, 17%) after purification by preparative TLC (cyclohexane/ethyl acetate 50/50).

$^1$H NMR (400 MHz, CDCl$_3$) δ 0.95 (s, 3H), 1.14 (s, 9H), 1.41 (s, 3H), 2.13 (dd, J=17.5 Hz, J=6.6 Hz, 1H), 2.40 (dd, J=17.5 Hz, J=2.8 Hz, 1H), 2.58 (s, 3H), 4.80 (s, 1H), 6.11 (dd, J=6.6 Hz, J=2.8 Hz, 1H), 7.05-7.07 (m, 2H), 7.18-7.20 (m, 3H), 7.30 (dd, J=7.8 Hz, J=5.0 Hz, 1H), 7.78 (dd, J=7.8 Hz, J=1.6 Hz, 1H), 8.29 (dd, J=5.0 Hz, J=1.6 Hz, 1H).

MS m/z ([M+H]$^+$) 462
MS m/z ([M−H]$^-$) 460

Example 68

Synthesis of 2-(tert-butoxy)-2-{2-methyl-4-[4,4-dimethylcyclohex-1-en-1-yl]-5-(N-pyrrolidinone)thiophen-3-yl}acetic acid

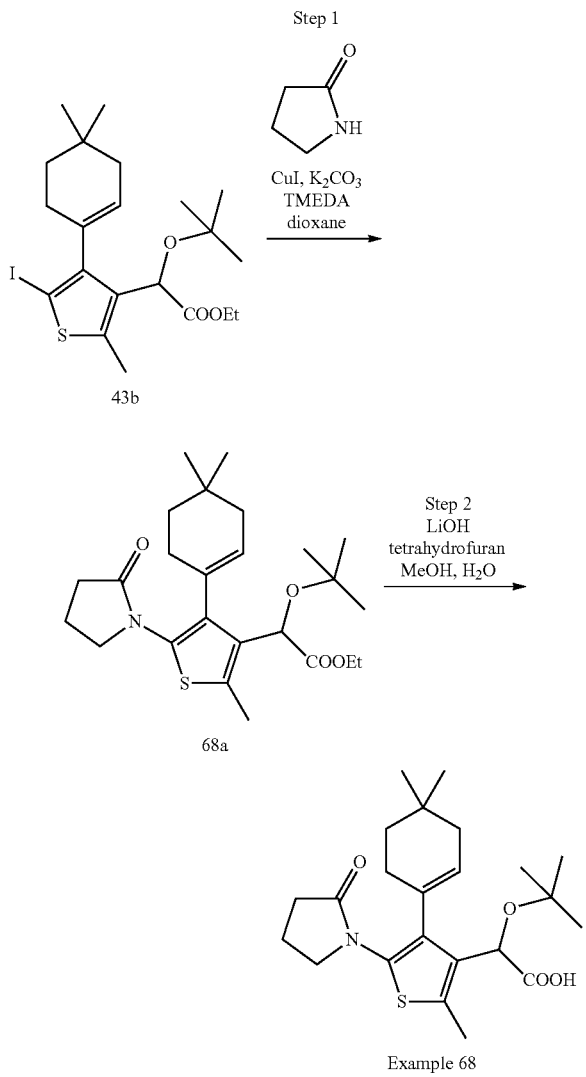

Example 68

Step 1: preparation of intermediate ethyl 2-(tert-butoxy)-2-[4-(4,4-dimethylcyclohex-1-en-1-yl)-2-methyl-5-(N-pyrrolidinone)thiophen-3-yl]acetate (68a)

To a degassed solution of ethyl 2-(tert-butoxy)-2-[4-(4,4-dimethylcyclohex-1-en-1-yl)-2-methyl-5-iodothiophen-3-yl]acetate (43b), (100 mg, 0.20 mmol), potassium carbonate (122 mg, 0.88 mmol), N,N,N',N'-tetramethylethylenediamine (1 drop, 0.02 mmol) and 2-pyrrolidinone (21 mg, 0.25 mmol) in dioxane (1.0 mL). Copper(I) iodide (4 mg, 0.02 mmol) was added and the reaction was heated at 110° C. for 5 days. After cooling down at room temperature, the mixture was diluted in ethyl acetate, filtered over a pad of silica gel and concentrated under reduced pressure to afford ethyl 2-(tert-butoxy)-2-[4-(4,4-dimethylcyclohex-1-en-1-yl)-2-methyl-5-(N-pyrrolidinone)thiophen-3-yl]acetate (68a) (41 mg, 0.09 mmol, 45%) as a yellow oil after purification by preparative TLC (cyclohexane/ethyl acetate 50/50).

$^1$H NMR (400 MHz, CDCl$_3$) δ 0.98 (s, 3H), 1.01 (s, 3H), 1.16 (s, 9H), 1.21 (t, J=7.2 Hz, 3H), 1.38-1.50 (m, 2H), 1.91-1.96 (m, 2H), 2.05-2.12 (m, 3H), 2.27-2.39 (m, 1H), 2.47 (dd, J=8.0 Hz, J=8.4 Hz, 2H), 2.51 (s, 3H), 3.65 (dd, J=2.1 Hz, J=2.4 Hz, 2H), 4.01-4.19 (m, 2H), 4.97 (s, 1H), 5.57 (bs, 1H).

MS m/z ([M+H]$^+$) 448.

Step 2: preparation of 2-(tert-butoxy)-2-{2-methyl-4-[4,4-dimethylcyclohex-1-en-1-yl]-5-(N-pyrrolidinone)thiophen-3-yl}acetic acid (example 68)

Using the procedure described in example 15, step 2, ethyl 2-(tert-butoxy)-2-[4-(4,4-dimethylcyclohex-1-en-1-yl)-2-methyl-5-(N-pyrrolidinone)thiophen-3-yl]acetate (68a) (41 mg, 0.09 mmol) is converted into 2-(tert-butoxy)-2-{2-methyl-4-[4,4-dimethylcyclohex-1-en-1-yl]-5-(N-pyrrolidinone)thiophen-3-yl}acetic acid (example 68) (32 mg, 0.08 mmol, 83%) as a colorless oil after purification by preparative TLC (dichloromethane/methanol 90/10).

$^1$H NMR (400 MHz, CDCl$_3$) δ 0.96 (s, 3H), 0.98 (s, 3H), 1.20 (s, 9H), 1.36-1.48 (m, 2H), 1.89-1.95 (m, 2H), 2.05-2.12 (m, 3H), 2.29-2.40 (m, 1H), 2.42 (s, 3H), 2.48 (dd, J=7.6 Hz, J=8.4 Hz, 2H), 3.59-3.70 (m, 2H), 5.05 (s, 1H), 5.65 (bs, 1H).

MS m/z ([M+H]$^+$) 420.
MS m/z ([M−H]$^−$) 418.

Example 69

Synthesis of 2-(tert-butoxy)-2-[4-(4,4-dimethylcyclohex-1-en-1-yl)-2-methyl-5-(1-methyl-5-oxo-2,5-dihydro-1H-pyrrol-3-yl)thiophen-3-yl]acetic acid

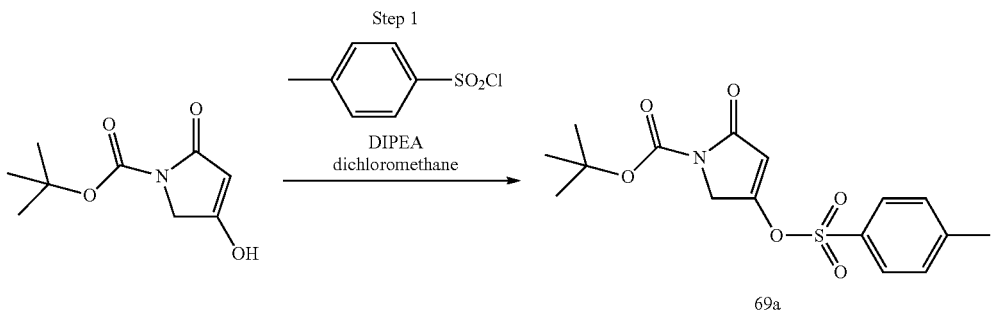

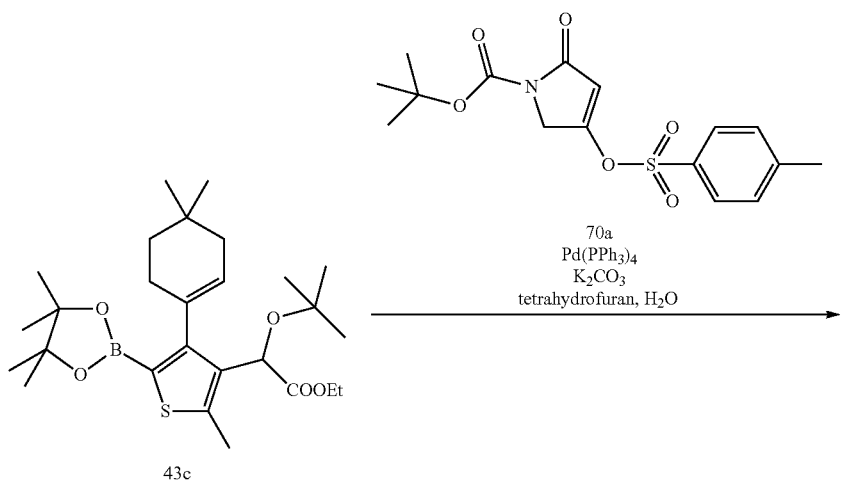

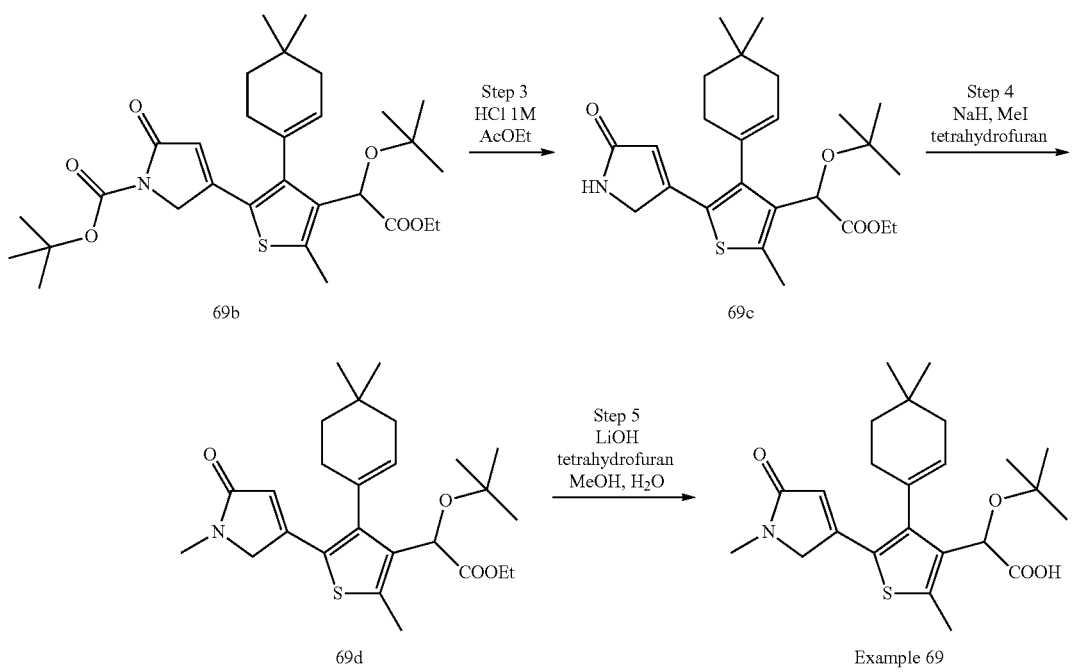

Step 1: preparation of intermediate tert-butyl-4-{[(4-methylbenzene)sulfonyl]oxy}-2-oxo-2,5-dihydro-1H-pyrrole-1-carboxylate (69a)

Under argon atmosphere, tert-butyl-4-hydroxy-2-oxo-2,5-dihydro-1H-pyrrole-1-carboxylate (679 mg, 3.41 mmol) was dissolved in dichloromethane (35 mL) and p-toluenesulfonyl chloride (650 mg, 3.41 mmol) and DIPEA (1.2 mL, 6.82 mmol) were added at 0° C. The resulting mixture was stirred for 18 hours at room temperature. The reaction was washed with 1N hydrochloric acid solution, saturated sodium bicarbonate solution and brine, dried over sodium sulfate, filtered and concentrated under reduced pressure. The crude material was purified by flash chromatography on silica gel (cyclohexane/ethyl acetate 80/20) to give tert-butyl-4-{[(4-methylbenzene)sulfonyl]oxy}-2-oxo-2,5-dihydro-1H-pyrrole-1-carboxylate (69a) (983 mg, 2.78 mmol, 82%).

$^1$H NMR (400 MHz, CDCl$_3$) δ 1.51 (s, 9H), 2.49 (s, 3H), 4.21 (s, 2H), 5.74 (s, 1H), 7.41 (d, J=8.4 Hz, 2H), 7.85 (d, J=8.4 Hz, 2H).
MS m/z ([M+H]$^+$) 354

Step 2: preparation of intermediate tert-butyl-4-{4-[1-(tert-butoxy)-2-ethoxy-2-oxoethyl]-3-(4,4-dimethylcyclohex-1-en-1-yl)-5-methylthiophen-2-yl}-2-oxo-2,5-dihydro-1H-pyrrole-1-carboxylate (69b)

Under argon atmosphere, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (652 mg, 1.33 mmol), tert-butyl-4-{[(4-methylbenzene)sulfonyl]oxy}-2-oxo-2,5-dihydro-1H-pyrrole-1-carboxylate (69a) (470 mg, 1.33 mmol) and potassium carbonate (552 mg, 4.00 mmol) were dissolved in tetrahydrofuran (10.8 mL) and water (2.2 mL). The solution was degassed under argon for 10 minutes and tetrakis(triphenylphosphine)palladium (0) (154 mg, 0.13 mmol) was added. The reaction was shaken at room temperature for 2 h and then heated at 70° C. for 18 hours more. After cooling down to room temperature, water was added and the mixture was extracted twice with ethyl acetate. The organic layer was washed with brine, dried over sodium sulfate, filtered and concentrated under reduced pressure. The crude material was purified by flash chromatography on silica gel (cyclohexane/ethyl acetate 95/5) to give tert-butyl-4-{4-[1-(tert-butoxy)-2-ethoxy-2-oxoethyl]-3-(4,4-dimethylcyclohex-1-en-1-yl)-5-methylthiophen-2-yl}-2-oxo-2,5-dihydro-1H-pyrrole-1-carboxylate (69b) (116 mg, 0.21 mmol, 16%).

$^1$H NMR (400 MHz, CDCl$_3$) δ 1.05 (s, 3H), 1.08 (s, 3H), 1.18-1.28 (m, 12H), 1.54-1.62 (m, 11H), 1.91-2.15 (m, 4H), 2.60 (s, 3H), 4.05-4.16 (m, 2H), 4.45-4.62 (m, 2H), 4.96-5.04 (m, 1H), 5.60-5.67 (m, 1H), 6.10 (s, 1H).

MS m/z ([M+H]$^+$) 546

Step 3: preparation of intermediate ethyl 2-(tert-butoxy)-2-[4-(4,4-dimethylcyclohex-1-en-1-yl)-2-methyl-5-(5-oxo-2,5-dihydro-1H-pyrrol-3-yl)thiophen-3-yl]acetate (69c)

Under an argon atmosphere, tert-butyl-4-{4-[1-(tert-butoxy)-2-ethoxy-2-oxoethyl]-3-(4,4-dimethylcyclohex-1-en-1-yl)-5-methylthiophen-2-yl}-2-oxo-2,5-dihydro-1H-pyrrole-1-carboxylate (69b) (93 mg, 0.17 mmol) was dissolved in ethyl acetate (1 mL). The mixture was cooled at 0° C. and a solution 1M hydrochloric acid solution in ethyl acetate (870 μL, 0.87 mmol) was added. After 2 hours at 0° C., the reaction was warmed up to room temperature for 1 hour more. All the start material wasn't consumed, so it will be recycled during the purification. The mixture was quenched with saturated aqueous solution of sodium carbonate and extracted twice with ethyl acetate. The organic layer was washed with brine, dried over sodium sulfate, filtered and concentrated under reduced pressure. The crude material was purified by preparative TLC (cyclohexane/ethyl acetate 40/60) to give ethyl 2-(tert-butoxy)-2-[4-(4,4-dimethylcyclohex-1-en-1-yl)-2-methyl-5-(5-oxo-2,5-dihydro-1H-pyrrol-3-yl)thiophen-3-yl]acetate (69c) (40 mg, 0.09 mmol, 53%).

$^1$H NMR (400 MHz, CDCl$_3$) δ 1.05 (s, 3H), 1.07 (s, 3H), 1.18-1.23 (m, 12H), 1.53-1.54 (m, 2H), 1.89-2.16 (m, 4H), 2.59 (s, 3H), 4.05-4.18 (m, 2H), 4.21-4.33 (m, 2H), 4.97-5.04 (m, 1H), 5.59-5.66 (m, 1H), 6.13 (s, 1H), 6.42 (bs, 1H).

MS m/z ([M+H]$^+$) 446

Step 4: preparation of intermediate ethyl 2-(tert-butoxy)-2-[4-(4,4-dimethylcyclohex-1-en-1-yl)-2-methyl-5-(1-methyl-5-oxo-2,5-dihydro-1H-pyrrol-3-yl)thiophen-3-yl]acetate (69d)

A mixture of ethyl 2-(tert-butoxy)-2-[4-(4,4-dimethylcyclohex-1-en-1-yl)-2-methyl-5-(5-oxo-2,5-dihydro-1H-pyrrol-3-yl)thiophen-3-yl]acetate (69c) (66 mg, 0.15 mmol) in dry tetrahydrofuran (4 mL) was cooled at 0° C. and sodium hydride (60% dispersion in mineral oil, 6 mg, 0.15 mmol) was added. The mixture was stirred for 20 minutes at 0° C. before methyl iodide (10 μL, 0.16 mmol) was added. After 2 hours at 0° C., the mixture was quenched with a saturated sodium hydrogenocarbonate solution and extracted with ethyl acetate twice. The organic layer was washed with brine, dried over sodium sulfate, filtered and concentrated under reduced pressure. The residue was purified by preparative TLC (cyclohexane/ethyl acetate 40/60) to give ethyl 2-(tert-butoxy)-2-[4-(4,4-dimethylcyclohex-1-en-1-yl)-2-methyl-5-(1-methyl-5-oxo-2,5-dihydro-1H-pyrrol-3-yl)thiophen-3-yl]acetate (69d) (18 mg, 0.04 mmol, 26%).

$^1$H NMR (400 MHz, CDCl$_3$) δ 1.03 (s, 3H), 1.05 (s, 3H), 1.19 (s, 9H), 1.22 (t, J=7.2 Hz, 3H), 1.24-1.26 (m, 2H), 1.94-2.04 (m, 4H), 2.05 (dd, J=1.6 Hz, J=1.6 Hz, 3H), 2.61 (s, 3H), 4.05-4.21 (m, 4H), 5.04 (s, 1H), 5.57-5.63 (m, 1H), 5.84-5.90 (m, 1H).

MS m/z ([M+H]$^+$) 460.

Step 5: preparation of 2-(tert-butoxy)-2-[4-(4,4-dimethylcyclohex-1-en-1-yl)-2-methyl-5-(1-methyl-5-oxo-2,5-dihydro-1H-pyrrol-3-yl)thiophen-3-yl]acetic acid (example 69)

Using the procedure described in example 15, step 2, ethyl 2-(tert-butoxy)-2-[4-(4,4-dimethylcyclohex-1-en-1-yl)-2-methyl-5-(1-methyl-5-oxo-2,5-dihydro-1H-pyrrol-3-yl)thiophen-3-yl]acetate (69d) (34 mg, 0.07 mmol) is converted into 2-(tert-butoxy)-2-[4-(4,4-dimethylcyclohex-1-en-1-yl)-2-methyl-5-(1-methyl-5-oxo-2,5-dihydro-1H-pyrrol-3-yl)thiophen-3-yl]acetic acid (example 69) (8 mg, 0.02 mmol, 25%) after purification by preparative TLC (cyclohexane/ethyl acetate 40/60).

$^1$H NMR (400 MHz, CDCl$_3$) δ 0.98-1.04 (m, 6H), 1.22 (s, 9H), 1.24-1.26 (m, 2H), 1.91-2.02 (m, 4H), 2.03 (s, 3H), 2.52 (s, 3H), 4.07-4.23 (m, 2H), 5.10 (s, 1H), 5.55-5.80 (m, 1H), 6.87-6.98 (m, 1H).

MS m/z ([M−H]$^−$) 430

Example 70

Synthesis of 2-(tert-butoxy)-2-{2-methyl-4-[4,4-dimethylcyclohex-1-en-1-yl]-5-(phenylethyl)thiophen-3-yl}acetic acid

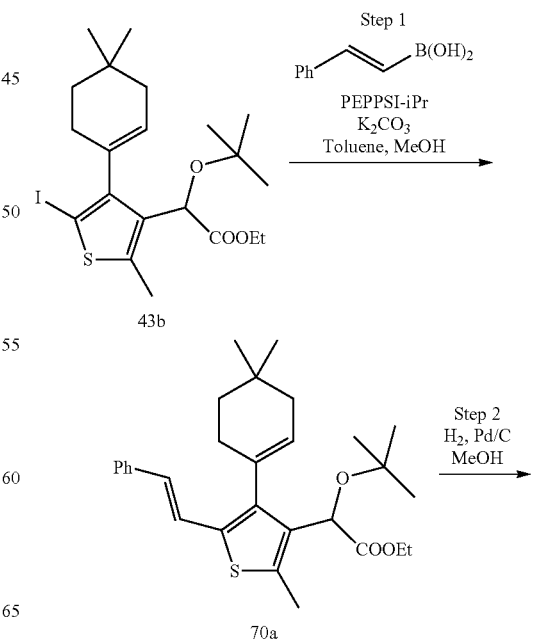

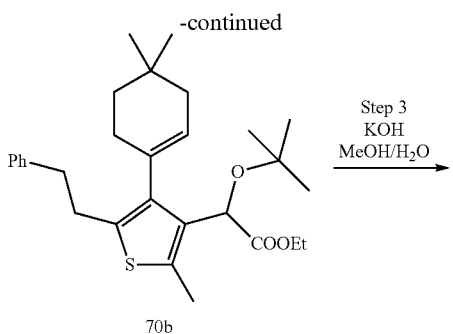

70b

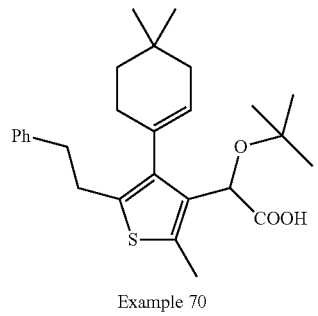

Example 70

Step 1: preparation of intermediate ethyl 2-(tert-butoxy)-2-[4-(4,4-dimethylcyclohex-1-en-1-yl)-2-methyl-5-(trans-phenylvinyl)thiophen-3-yl]acetate (70a)

Under argon atmosphere, ethyl 2-(tert-butoxy)-2-[4-(4,4-dimethylcyclohex-1-en-1-yl)-2-methyl-5-iodothiophen-3-yl]acetate (43b), (100 mg, 0.20 mmol), trans-2-phenylvinyl boronic acid (78 mg, 0.51 mmol) and potassium carbonate (57 mg, 0.41 mmol) were dissolved in a mixture toluene/water (1.8 mL/0.2 mL). The solution was degassed with argon for 10 minutes and [1,3-bis(2,6-diisopropylphenyl)imidazol-2-ylidene](3-chloropyridyl) palladium(II) dichloride (PEPPSI-IPr), (14 mg, 0.02 mmol) was added. The reaction was heated at 90° C. for 16 hours. After cooling down to room temperature, the solution was partitioned between ethyl acetate and water. The organic layer was washed with brine, dried over sodium sulfate, filtered, and concentrated under reduced pressure to afford ethyl 2-(tert-butoxy)-2-[4-(4,4-dimethylcyclohex-1-en-1-yl)-2-methyl-5-(trans-phenylvinyl)thiophen-3-yl]acetate (70a) (74 mg, 0.16 mmol, 75%) as a yellow oil after purification by preparative TLC (cyclohexane/ethyl acetate 95/5).

$^1$H NMR (400 MHz, CDCl$_3$) δ 1.09 (s, 6H), 1.19 (s, 9H), 1.22 (t, J=7.2 Hz, 3H), 1.53-1.56 (m, 2H), 1.94-2.20 (m, 3H), 2.29-2.46 (m, 1H), 2.56 (s, 3H), 4.05-4.20 (m, 2H), 5.01 (s, 1H), 5.54-5.64 (bs, 1H), 6.73 (d, J=16.4 Hz, 1H), 7.05 (d, J=16.4 Hz, 1H), 7.20 (dd, J=7.2 Hz, J=7.2 Hz, 1H), 7.31 (dd, J=7.6 Hz, J=7.6 Hz, 2H), 7.38 (d, J=7.2 Hz, 2H).

Step 2: preparation of intermediate ethyl 2-(tert-butoxy)-2-[4-(4,4-dimethylcyclohex-1-en-1-yl)-2-methyl-5-(phenylethyl)thiophen-3-yl]acetate (70b)

Palladium on active carbon (2 mg, 0.02 mmol) was added to a solution of ethyl 2-(tert-butoxy)-2-[4-(4,4-dimethylcyclohex-1-en-1-yl)-2-methyl-5-(trans-phenylvinyl)thiophen-3-yl]acetate (70a) (74 mg, 0.16 mmol) in methanol (1.6 mL). The mixture was stirred vigorously for 15 hours under H$_2$ atmosphere. After completion of the reaction, the mixture was filtered over Celite® and concentrated under reduced pressure to afford ethyl 2-(tert-butoxy)-2-[4-(4,4-dimethylcyclohex-1-en-1-yl)-2-methyl-5-(phenylethyl)thiophen-3-yl]acetate (70b) (62 mg, 0.13 mmol, 83%) as a colorless oil after purification by preparative TLC (cyclohexane/ethyl acetate 95/5).

$^1$H NMR (400 MHz, CDCl$_3$) δ 1.01 (s, 3H), 1.02 (s, 3H), 1.17 (s, 9H), 1.18-1.22 (m, 5H), 1.41-1.47 (m, 2H), 1.82-2.02 (m, 3H), 2.25-2.43 (m, 1H), 2.52 (s, 3H), 2.86 (m, 2H), 4.03-4.18 (m, 2H), 4.94 (s, 1H), 5.23-5.37 (bs, 1H), 7.13-7.30 (m, 5H).

Step 3: preparation of 2-(tert-butoxy)-2-{2-methyl-4-[4,4-dimethylcyclohex-1-en-1-yl]-5-(phenylethyl)thiophen-3-yl}acetic acid (example 70)

Using the procedure described in example 3, step 2, ethyl 2-(tert-butoxy)-2-[4-(4,4-dimethylcyclohex-1-en-1-yl)-2-methyl-5-(phenylethyl)thiophen-3-yl]acetate (70b) (62 mg, 0.13 mmol) is converted into 2-(tert-butoxy)-2-{2-methyl-4-[4,4-dimethylcyclohex-1-en-1-yl]-5-(phenyl ethyl)thiophen-3-yl}acetic acid (example 70) (46 mg, 0.10 mmol, 79%) as a yellow oil after purification by preparative TLC (dichloromethane/methanol 95/5).

$^1$H NMR (400 MHz, CDCl$_3$) δ 0.98 (s, 6H), 1.20 (s, 9H), 1.40-1.43 (m, 2H), 1.82-1.99 (m, 3H), 2.23-2.38 (m, 1H), 2.43 (s, 3H), 2.84-2.88 (m, 4H), 4.99 (s, 1H), 5.12-5.27 (bs, 1H), 7.11-7.13 (m, 2H), 7.16-7.20 (m, 1H), 7.22-7.27 (m, 2H), 9.56-10.35 (bs, 1H).

MS m/z ([M–H]$^-$) 439.

Example 71

Synthesis of 2-(tert-butoxy)-2-{2-methyl-4-[4,4-dimethylcyclohex-1-en-1-yl]-5-(4-(n-propyl)pyridin-2-yl)thiophen-3-yl}acetic acid

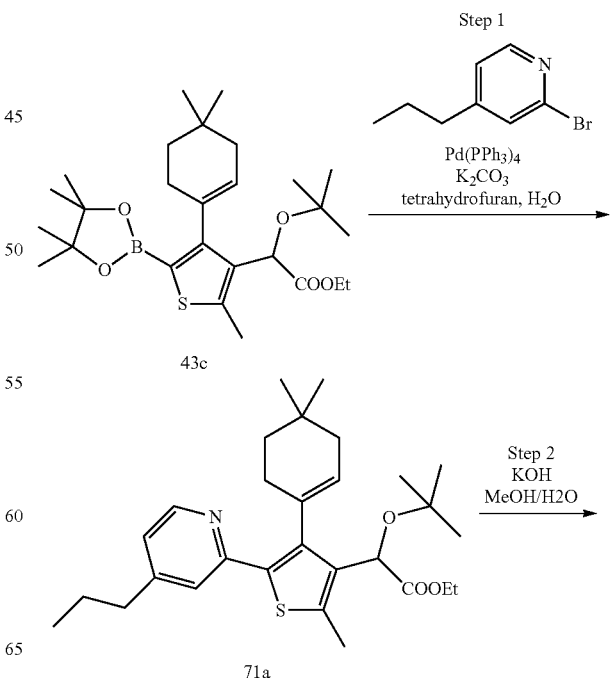

43c

71a

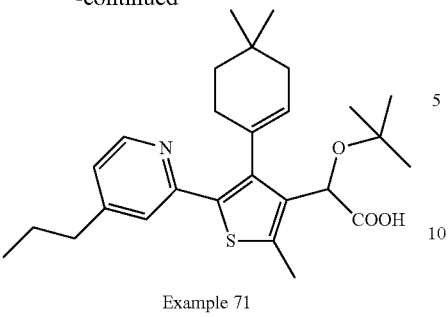

Example 71

Step 1: preparation of intermediate ethyl 2-(tert-butoxy)-2-[4-(4,4-dimethylcyclohex-1-en-1-yl)-2-methyl-5-(4-(n-propyl)pyridin-2-yl)thiophen-3-yl] acetate (71a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 2-bromo-4-(n-propyl)pyridine (52 mg, 0.25 mmol) into ethyl 2-(tert-butoxy)-2-[4-(4,4-dimethylcyclohex-1-en-1-yl)-2-methyl-5-(4-(n-propyl)pyridin-2-yl)thiophen-3-yl]acetate (71a) (87 mg, 0.18 mmol, 88%) after purification by preparative TLC (cyclohexane/ethyl acetate 85/15).

$^1$H NMR (400 MHz, CDCl$_3$) δ 0.94 (t, J=7.2 Hz, 3H), 1.06 (s, 3H), 1.08 (s, 3H), 1.19 (s, 9H), 1.23 (t, J=7.2 Hz, 3H), 1.42-1.54 (m, 2H), 1.60-1.69 (m, 2H), 1.94-2.11 (m, 4H), 2.55 (t, J=7.6 Hz, 2H), 2.58 (s, 3H), 4.11 (q, J=7.2 Hz, 2H), 5.09 (s, 1H), 5.56-5.84 (bs, 1H), 6.88 (d, J=5.2 Hz, 1H), 7.51 (s, 1H), 8.38 (d, J=5.2 Hz, 1H).

MS m/z ([M+H]$^+$) 484.

Step 2: preparation of 2-(tert-butoxy)-2-{2-methyl-4-[4,4-dimethylcyclohex-1-en-1-yl]-5-(4-(n-propyl)pyridin-2-yl)thiophen-3-yl}acetic acid (example 71)

Using the procedure described in example 3, step 2, ethyl 2-(tert-butoxy)-2-[4-(4,4-dimethylcyclohex-1-en-1-yl)-2-methyl-5-(4-(n-propyl)pyridin-2-yl)thiophen-3-yl]acetate (71a) (87 mg, 0.18 mmol) is converted into 2-(tert-butoxy)-2-{2-methyl-4-[4,4-dimethylcyclohex-1-en-1-yl]-5-(4-(n-propyl)pyridin-2-yl)thiophen-3-yl}acetic acid (example 71) (34 mg, 0.07 mmol, 42%) after purification by preparative TLC (dichloromethane/methanol 95/5).

$^1$H NMR (400 MHz, CDCl$_3$) δ 0.93 (t, J=7.2 Hz, 3H), 1.02 (s, 3H), 1.03 (s, 3H), 1.22 (s, 9H), 1.39-1.51 (m, 2H), 1.60-1.69 (m, 2H), 1.92-2.13 (m, 4H), 2.49 (s, 3H), 2.53 (t, J=7.6 Hz, 2H), 5.11 (s, 1H), 5.53-6.25 (bs, 1H), 6.92 (d, J=5.2 Hz, 1H), 7.49 (s, 1H), 8.40 (d, J=5.2 Hz, 1H), 9.63-10.29 (bs, 1H).

MS m/z ([M+H]$^+$) 456.
MS m/z ([M–H]$^-$) 454.

Example 72

Synthesis of 2-(tert-butoxy)-2-{2-methyl-4-[4,4-dimethylcyclohex-1-en-1-yl]-5-(4-methylpyridin-2-yl)thiophen-3-yl}acetic acid

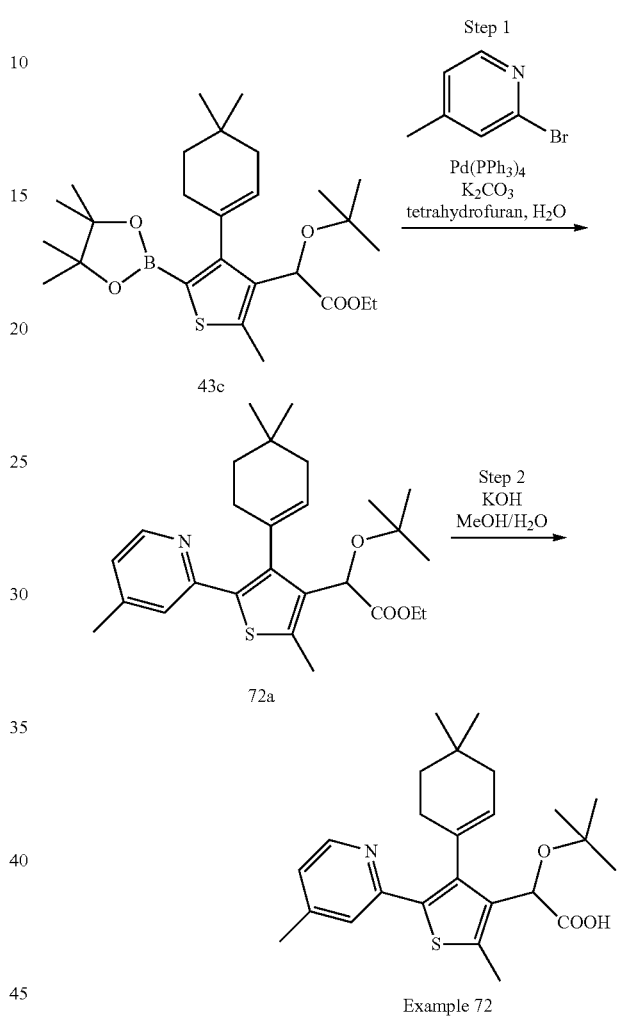

Example 72

Step 1: preparation of intermediate ethyl 2-(tert-butoxy)-2-[4-(4,4-dimethylcyclohex-1-en-1-yl)-2-methyl-5-(4-methylpyridin-2-yl)thiophen-3-yl]acetate (72a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 2-bromo-4-methylpyridine (43 mg, 0.25 mmol) into ethyl 2-(tert-butoxy)-2-[4-(4,4-dimethylcyclohex-1-en-1-yl)-2-methyl-5-(4-methylpyridin-2-yl)thiophen-3-yl]acetate (72a) (59 mg, 0.13 mmol, 62%) after purification by preparative TLC (cyclohexane/ethyl acetate 80/20).

$^1$H NMR (400 MHz, CDCl$_3$) δ 1.06 (s, 3H), 1.08 (s, 3H), 1.19 (s, 12H), 1.43-1.59 (m, 2H), 1.96-2.16 (m, 4H), 2.31 (s, 3H), 2.59 (s, 3H), 4.03-4.19 (m, 2H), 5.10 (s, 1H), 5.61-5.84 (bs, 1H), 6.89 (d, J=5.2 Hz, 1H), 7.51 (s, 1H), 8.37 (d, J=5.2 Hz, 1H).

MS m/z ([M+H]$^+$) 456.

Step 2: preparation of 2-(tert-butoxy)-2-{2-methyl-4-[4,4-dimethylcyclohex-1-en-1-yl]-5-(4-methylpyridin-2-yl)thiophen-3-yl}acetic acid (example 72)

Using the procedure described in example 3, step 2, ethyl 2-(tert-butoxy)-2-[4-(4,4-dimethylcyclohex-1-en-1-yl)-2-methyl-5-(4-methylpyridin-2-yl)thiophen-3-yl]acetate (72a) (59 mg, 0.13 mmol) is converted into 2-(tert-butoxy)-2-{2-methyl-4-[4,4-dimethylcyclohex-1-en-1-yl]-5-(4-methylpyridin-2-yl)thiophen-3-yl}acetic acid (example 72) (51 mg, 0.12 mmol, 92%) after purification by preparative TLC (dichloromethane/methanol 95/5).

$^1$H NMR (400 MHz, CDCl$_3$) δ 1.01 (s, 3H), 1.02 (s, 3H), 1.21 (s, 9H), 1.37-1.52 (m, 2H), 1.94-2.08 (m, 4H), 2.31 (s, 3H), 2.50 (s, 3H), 5.12 (s, 1H), 5.48-6.28 (bs, 1H), 6.93 (d, J=4.8 Hz, 1H), 7.49 (s, 1H), 8.39 (d, J=4.8 Hz, 1H).

MS m/z ([M+H]$^+$) 428.
MS m/z ([M−H]$^-$) 426.

Example 73

Synthesis of 2-(tert-butoxy)-2-{2-methyl-4-[4,4-dimethylcyclohex-1-en-1-yl]-5-(6-methylpyridin-2-yl)thiophen-3-yl}acetic acid Step 1: preparation of intermediate ethyl 2-(tert-butoxy)-2-[4-(4,4-dimethylcyclohex-1-en-1-yl)-2-methyl-5-(6-methylpyridin-2-yl)thiophen-3-yl]acetate (73a)

Using the procedure described in example 43, step 4, ethyl 2-(tert-butoxy)-2-[4-(4,4-dimethylcyclohex-1-en-1-yl)-2-methyl-5-(tetramethyl-1,3,2-dioxaborolan-2-yl)thiophen-3-yl]acetate (43c) (100 mg, 0.20 mmol) is converted by reaction with 2-bromo-6-methylpyridine (43 mg, 0.25 mmol) into ethyl 2-(tert-butoxy)-2-[4-(4,4-dimethylcyclohex-1-en-1-yl)-2-methyl-5-(6-methylpyridin-2-yl)thiophen-3-yl]acetate (73a) (66 mg, 0.14 mmol, 68%) after purification by preparative TLC (cyclohexane/ethyl acetate 80/20).

$^1$H NMR (400 MHz, CDCl$_3$) δ 1.04 (s, 3H), 1.06 (s, 3H), 1.19 (s, 9H), 1.21 (t, J=6.8 Hz, 3H), 1.41-1.52 (m, 2H), 1.91-2.12 (m, 4H), 2.53 (s, 3H), 2.59 (s, 3H), 4.06-4.18 (m, 2H), 5.10 (s, 1H), 5.60-5.80 (bs, 1H), 6.93 (d, J=8.0 Hz, 1H), 7.43 (d, J=7.2 Hz, 1H), 7.47 (dd, J=7.2 Hz, J=8.0 Hz, 1H).

MS m/z ([M+H]$^+$) 456.

Step 2: preparation of 2-(tert-butoxy)-2-{2-methyl-4-[4,4-dimethylcyclohex-1-en-1-yl]-5-(6-methylpyridin-2-yl)thiophen-3-yl}acetic acid (example 73)

Using the procedure described in example 3, step 2, ethyl 2-(tert-butoxy)-2-[4-(4,4-dimethylcyclohex-1-en-1-yl)-2-methyl-5-(6-methylpyridin-2-yl)thiophen-3-yl]acetate (73a) (66 mg, 0.14 mmol) is converted into 2-(tert-butoxy)-2-{2-methyl-4-[4,4-dimethylcyclohex-1-en-1-yl]-5-(6-methylpyridin-2-yl)thiophen-3-yl}acetic acid (example 73) (51 mg, 0.12 mmol, 82%) after purification by preparative TLC (dichloromethane/methanol 95/5).

$^1$H NMR (400 MHz, CDCl$_3$) δ 1.00 (s, 3H), 1.01 (s, 3H), 1.21 (s, 9H), 1.37-1.48 (m, 2H), 1.88-2.07 (m, 4H), 2.50 (s, 3H), 2.54 (s, 3H), 5.11 (s, 1H), 5.46-6.25 (bs, 1H), 6.96 (d, J=7.6 Hz, 1H), 7.43 (d, J=7.6 Hz, 1H), 7.49 (dd, J=7.6 Hz, J=7.6 Hz, 1H).

MS m/z ([M+H]$^+$) 428.
MS m/z ([M−H]$^-$) 426.

Example 74

Synthesis of 2-(tert-butoxy)-2-(2-methyl-4-(2,3-dihydropyrano[4,3,2-de]quinolin-7-yl)-5-(pyridin-4-yl)thiophen-3-yl)acetic acid

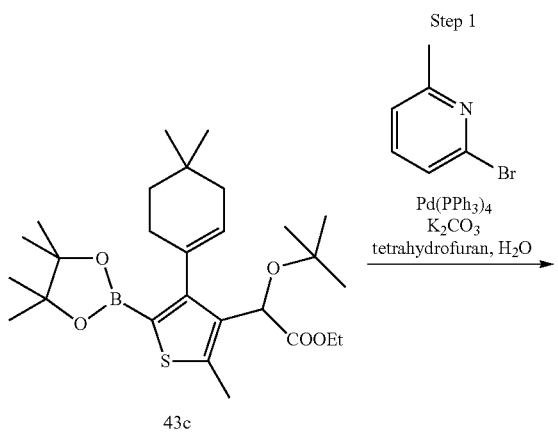

43c

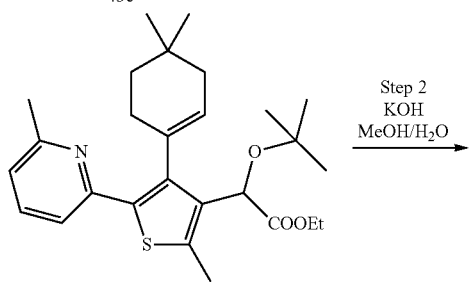

73a

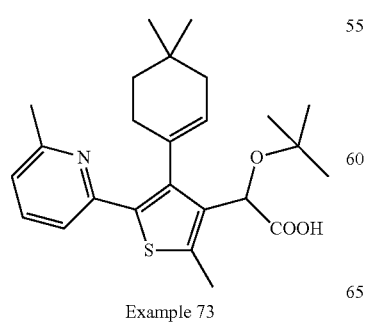

Example 73

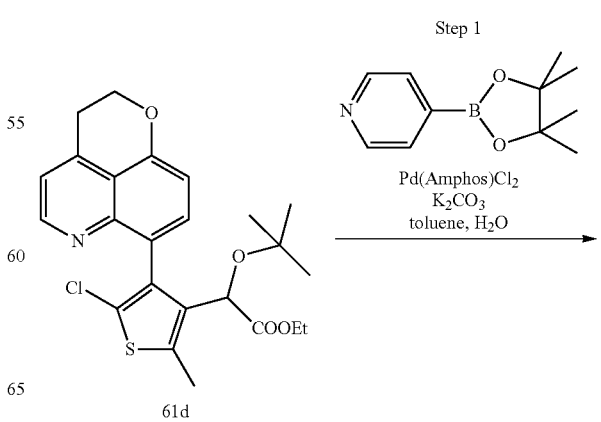

61d

1H), 6.95-7.19 (m, 2H), 7.28-7.62 (m, 2H), 8.14-8.21 and 8.23-8.32 (m, 2H), 8.62 and 8.79 (d, J=4.2 Hz, 1H).
MS m/z [M−H]⁻ 473.

Example 75

Synthesis of 2-[4,5-bis(8-fluoro-3,4-dihydro-2H-1-benzopyran-6-yl)-2-methylthiophen-3-yl]-2-(tert-butoxy)acetic acid

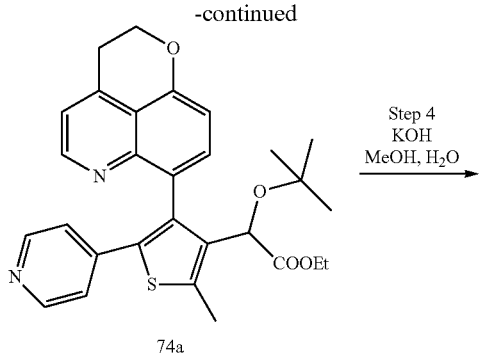

74a

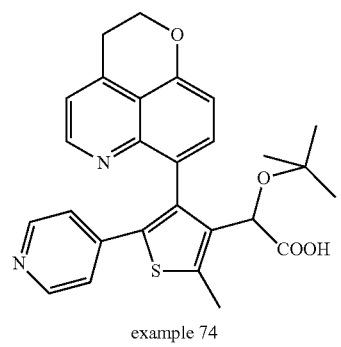

example 74

Step 1: preparation of intermediate ethyl 2-(tert-butoxy)-2-(2-methyl-4-(2,3-dihydropyrano[4,3,2-de]quinolin-7-yl)-5-(pyridin-4-yl)thiophen-3-yl)acetate (74a)

Using the procedure described in example 1, step 6, ethyl 2-(tert-butoxy)-2-[5-chloro-2-methyl-4-(2,3-dihydropyrano[4,3,2-de]quinolin-7-yl)thiophen-3-yl]acetate (61 b) (120 mg, 0.26 mmol) is converted by reaction with 4-pyridine boronic acid pinacol ester (64 mg, 0.31 mmol) into ethyl 2-(tert-butoxy)-2-(2-methyl-4-(2,3-dihydropyrano[4,3,2-de]quinolin-7-yl)-5-(pyridin-4-yl)thiophen-3-yl)acetate (74a) (53 mg, 0.11 mmol, 40%, atropisomers mixture) after purification by preparative TLC (ethyl acetate/acetone 95/5).

¹H NMR (400 MHz, CDCl₃) δ 0.88 and 0.96 (s, 9H), 1.01 and 1.20 (t, J=7.2 Hz, 3H), 2.72 and 2.76 (s, 3H), 3.29-3.34 (m, 2H), 3.85-3.93 and 4.02-4.10 (m, 2H), 4.54 (dd, J=5.6 Hz, J=5.6 Hz, 2H), 4.56 and 4.68 (s, 1H), 6.97 (d, J=6.4 Hz, 2H), 6.98 and 7.04 (d, J=8.0 Hz, 1H), 7.07 and 7.11 (d, J=4.0 Hz, 1H), 7.37 and 7.56 (d, J=8.0 Hz, 1H), 8.16 and 8.19 (dd, J=6.4 Hz, J=1.6 Hz, 2H), 8.67 and 8.72 (d, J=4.0 Hz, 1H).
MS m/z [M+H]⁺ 503.

Step 2: preparation of 2-(tert-butoxy)-2-(2-methyl-4-(2,3-dihydropyrano[4,3,2-de]quinolin-7-yl)-5-(pyridin-4-yl)thiophen-3-yl)acetic acid (example 74)

Using the procedure described in example 3, step 2, ethyl 2-(tert-butoxy)-2-(2-methyl-4-(2,3-dihydropyrano[4,3,2-de]quinolin-7-yl)-5-(pyridin-4-yl)thiophen-3-yl)acetate (74a) (53 mg, 0.11 mmol) is converted into 2-(tert-butoxy)-2-(2-methyl-4-(2,3-dihydropyrano[4,3,2-de]quinolin-7-yl)-5-(pyridin-4-yl)thiophen-3-yl)acetic acid (example 74) (23 mg, 0.05 mmol, 46%, atropisomers mixture) after purification by preparative TLC (dichloromethane/methanol 90/10).

¹H NMR (400 MHz, CDCl₃) δ 0.79 and 0.88 (s, 9H), 2.63 and 2.68 (s, 3H), 3.29-3.34 and 3.41-3.46 (m, 2H), 4.49-4.55 and 4.57-4.62 (m, 2H), 4.73 and 5.04 (s, 1H), 6.76-6.82 (m,

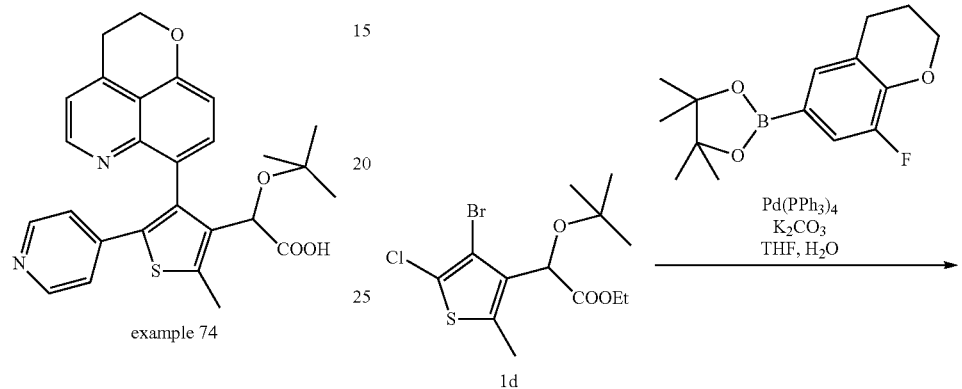

75a

Example 75

Step 1: preparation of intermediate ethyl 2-[4,5-bis(8-fluoro-3,4-dihydro-2H-1-benzopyran-6-yl)-2-methylthiophen-3-yl]-2-(tert-butoxy)acetate (75a)

Using the procedure described in example 39, step 6, ethyl 2-(4-bromo-5-chloro-2-methylthiophen-3-yl)-2-(tert-butoxy)acetate (1d) (200 mg, 0.54 mmol) is converted by reaction with 2-(8-fluoro-3,4-dihydro-2H-1-benzopyran-6-yl)-4,4,5,5-tetramethyl-1,3,2-dioxaborolane (196 mg, 0.70 mmol) into ethyl 2-[4,5-bis(8-fluoro-3,4-dihydro-2H-1-benzopyran-6-yl)-2-methylthiophen-3-yl]-2-(tert-butoxy)acetate (75a) (60 mg, 0.11 mmol, 20%) after purification by preparative TLC (cyclohexane/ethyl acetate 90/10).

$^{1}$H NMR (400 MHz, CDCl$_3$) δ 1.03 (s, 9H), 1.26 (t, J=7.2 Hz, 3H), 1.96-2.03 (m, 2H), 2.04-2.09 (m, 2H), 2.57 (s, 3H), 2.66-2.71 (m, 2H), 2.72-2.79 (m, 2H), 4.09-4.18 (m, 2H), 4.22 (dd, J=5.2 Hz, J=5.2 Hz, 2H), 4.31 (dd, J=5.2 Hz, J=5.2 Hz, 2H), 4.80 (s, 1H), 6.61 (d, J=12.4 Hz, 1H), 6.66-6.69 (m, 1H), 6.70-6.90 (m, 2H).

Step 2: preparation of 2-[4,5-bis(8-fluoro-3,4-dihydro-2H-1-benzopyran-6-yl)-2-methylthiophen-3-yl]-2-(tert-butoxy)acetic acid (example 75)

Using the procedure described in example 3, step 2, ethyl 2-[4,5-bis(8-fluoro-3,4-dihydro-2H-1-benzopyran-6-yl)-2-methylthiophen-3-yl]-2-(tert-butoxy)acetate (75a) (56 mg, 0.10 mmol) is converted into 2-[4,5-bis(8-fluoro-3,4-dihydro-2H-1-benzopyran-6-yl)-2-methylthiophen-3-yl]-2-(tert-butoxy)acetic acid (example 75) (40 mg, 0.07 mmol, 78%).

$^{1}$H NMR (400 MHz, CDCl$_3$) δ 1.06 (s, 9H), 1.97-2.03 (m, 2H), 2.04-2.09 (m, 2H), 2.48 (s, 3H), 2.64-2.73 (m, 2H), 2.74-2.86 (m, 2H), 4.23 (dd, J=5.2 Hz, J=5.2 Hz, 2H), 4.30 (dd, J=5.2 Hz, J=5.2 Hz, 2H), 4.96 (s, 1H), 6.61 (dd, J=12.4 Hz, J=1.6 Hz, 1H), 6.64-6.67 (m, 1H), 6.70-7.10 (m, 2H). MS m/z [M−H]$^-$ 527

Example 76

Synthesis of 2-(tert-butoxy)-2-[4-(4,4-dimethylcyclohex-1-en-1-yl)-2-methyl-5-(dimethylcarboamidophen-4-yl)thiophen-3-yl]]acetic acid

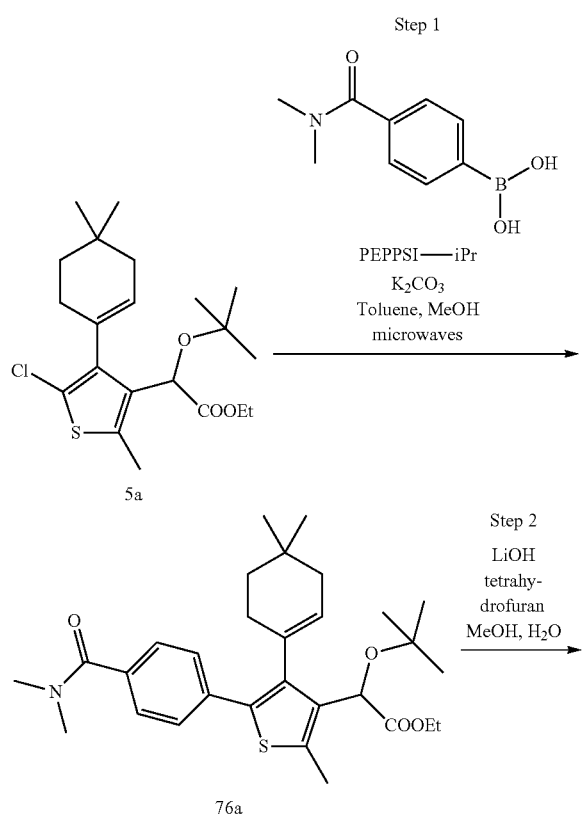

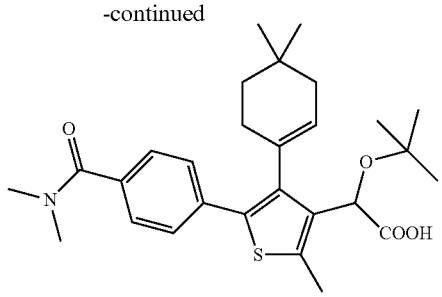

Example 76

Step 1: preparation of intermediate ethyl 2-(tert-butoxy)-2-[4-(4,4-dimethylcyclohex-1-en-1-yl)-2-methyl-5-(dimethylcarboamidophen-4-yl)thiophen-3-yl]acetate (76a)

Using the procedure described in example 14, step 1, ethyl 2-(tert-butoxy)-2-[5-chloro-4-(4,4-dimethylcyclohex-1-en-1-yl)-2-methylthiophen-3-yl]acetate (5a) (150 mg, 0.336 mmol) is converted by reaction with 4-dimethylcarboamidophenyl boronic acid (138 mg, 0.672 mmol) into ethyl 2-(tert-butoxy)-2-[4-(4,4-dimethylcyclohex-1-en-1-yl)-2-methyl-5-(dimethylcarboamidophen-4-yl)thiophen-3-yl]acetate (76a) (107 mg, 0.209 mmol, 62%) after purification by preparative TLC (cyclohexane/ethyl acetate 50/50).

$^{1}$H NMR (400 MHz, CDCl$_3$) δ 0.95 (s, 3H), 0.98 (s, 3H), 1.19 (s, 9H), 1.21 (t, J=6.8 Hz, 3H), 1.26-1.40 (m, 2H), 1.84-2.24 (m, 4H), 2.59 (s, 3H), 3.00 (bs, 3H), 3.09 (bs, 3H), 4.04-4.20 (m, 2H), 5.11 (s, 1H), 5.59-5.77 (bs, 1H), 7.36 (d, J=8.4 Hz, 2H), 7.53 (d, J=8.4 Hz, 2H).

MS m/z ([M+H]$^+$) 512.

Step 2: preparation of 2-(tert-butoxy)-2-[4-(4,4-dimethylcyclohex-1-en-1-yl)-2-methyl-5-(dimethylcarboamidophen-4-yl)thiophen-3-yl]acetic acid (example 76)

Using the procedure described in example 15, step 2, ethyl 2-(tert-butoxy)-2-[4-(4,4-dimethylcyclohex-1-en-1-yl)-2-methyl-5-(dimethylcarboamidophen-4-yl)thiophen-3-yl]acetate (76a) (107 mg, 0.209 mmol) is converted into 2-(tert-butoxy)-2-[4-(4,4-dimethylcyclohex-1-en-1-yl)-2-methyl-5-(dimethylcarboamidophen-4-yl)thiophen-3-yl]acetic acid (example 76) (65 mg, 0.134 mmol, 64%) after purification by preparative TLC (dichloromethane/methanol 95/5).

$^{1}$H NMR (400 MHz, CDCl$_3$) δ 0.91 (s, 3H), 0.93 (s, 3H), 1.21 (s, 9H), 1.29-1.36 (m, 2H), 1.81-1.95 (m, 4H), 2.49 (s, 3H), 2.98 (bs, 3H), 3.09 (bs, 3H), 5.16 (s, 1H), 5.43-6.12 (bs, 1H), 7.35 (d, J=7.2 Hz, 2H), 7.50 (d, J=7.2 Hz, 2H).

MS m/z ([M+H]$^+$) 484.

MS m/z ([M−H]$^-$) 482.

Example 77

Synthesis of 2-(tert-butoxy)-2-[4-(4,4-dimethylcyclohex-1-en-1-yl)-5-[4-(dimethylsulfamoyl)phenyl]-2-methylthiophen-3-yl]acetic acid

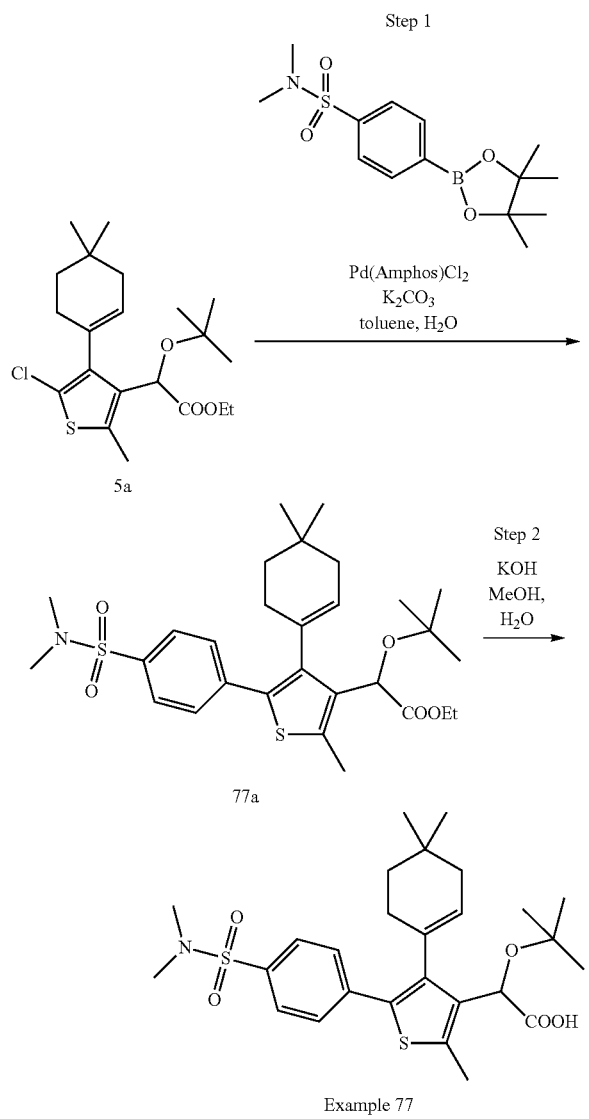

Step 1: preparation of intermediate ethyl 2-(tert-butoxy)-2-[4-(4,4-dimethylcyclohex-1-en-1-yl)-5-[4-(dimethylsulfamoyl)phenyl]-2-methylthiophen-3-yl] acetate (77a)

Using the procedure described in example 1, step 6, ethyl 2-(tert-butoxy)-2-[5-chloro-4-(4,4-dimethylcyclohex-1-en-1-yl)-2-methylthiophen-3-yl]acetate (5a) (80 mg, 0.20 mmol) is converted by reaction with N,N-dimethyl-4-(tetramethyl-1,3,2-dioxaborolan-2-yl)benzene-1-sulfonamide (75 mg, 0.24 mmol) into ethyl 2-(tert-butoxy)-2-[4-(4,4-dimethylcyclohex-1-en-1-yl)-5-[4-(dimethylsulfamoyl)phenyl]-2-methylthiophen-3-yl]acetate (77a) (85 mg, 0.16 mmol, 78%) after purification by preparative TLC (cyclohexane/ethyl acetate 70/30).

$^1$H NMR (400 MHz, CDCl$_3$) δ 0.98-1.00 (m, 6H), 1.20 (s, 9H), 1.23 (t, J=7.2 Hz, 3H), 1.33-1.43 (m, 2H), 1.82-2.02 (m, 4H), 2.61 (s, 3H), 2.71 (s, 6H), 4.08-4.20 (m, 2H), 5.12 (s, 1H), 5.71-5.74 (m, 1H), 7.67 (d, J=8.8 Hz, 2H), 7.70 (d, J=8.4 Hz, 2H).
MS m/z ([M+H])$^+$ 548

Step 2: preparation of 2-(tert-butoxy)-2-[4-(4,4-dimethylcyclohex-1-en-1-yl)-5-[4-(dimethylsulfamoyl)phenyl]-2-methylthiophen-3-yl]acetic acid (example 77)

Using the procedure described in example 3, step 2, ethyl 2-(tert-butoxy)-2-[4-(4,4-dimethylcyclohex-1-en-1-yl)-5-[4-(dimethylsulfamoyl)phenyl]-2-methylthiophen-3-yl]acetate (77a) (83 mg, 0.15 mmol) is converted into 2-(tert-butoxy)-2-[4-(4,4-dimethylcyclohex-1-en-1-yl)-5-[4-(dimethylsulfamoyl)phenyl]-2-methylthiophen-3-yl]acetic acid (example 77) (29 mg, 0.06 mmol, 37%) after purification by preparative TLC (dichloromethane/methanol 90/10).

$^1$H NMR (400 MHz, CDCl$_3$) δ 0.93-0.96 (m, 6H), 1.21 (s, 9H), 1.30-1.39 (m, 2H), 1.53-1.98 (m, 4H), 2.51 (s, 3H), 2.72 (s, 6H), 5.18 (s, 1H), 5.63-5.75 (m, 1H), 7.65 (d, J=8.4 Hz, 2H), 7.71 (d, J=8.4 Hz, 2H).
MS m/z ([M−H])$^-$ 518

Example 78

Synthesis of 2-(tert-butoxy)-2-[4-(3,4-dihydro-2H-1-benzopyran-6-yl)-5-(3,6-dihydro-2H-pyran-4-yl)-2-methylthiophen-3-yl]acetic acid

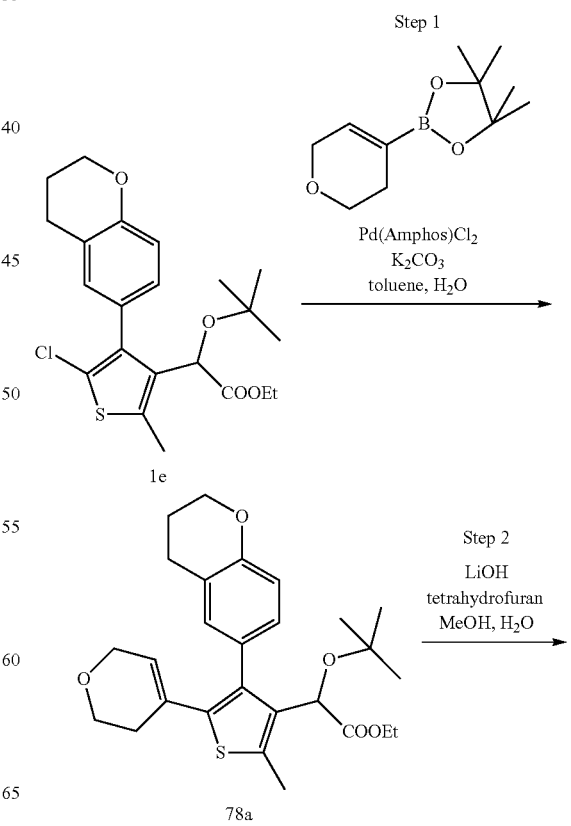

Example 78

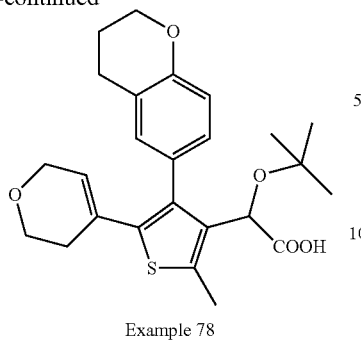

Example 78

Step 1: preparation of intermediate ethyl 2-(tert-butoxy)-2-[4-(3,4-dihydro-2H-1-benzopyran-6-yl)-5-(3,6-dihydro-2H-pyran-4-yl)-2-methylthiophen-3-yl]acetate (78a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (110 mg, 0.26 mmol) is converted by reaction with 4-(4,4,5,5-tetramethyl-1,3,2-dioxaborolan-2-yl)-3,6-dihydro-2H-pyran (66 mg, 0.31 mmol), into ethyl 2-(tert-butoxy)-2-[4-(3,4-dihydro-2H-1-benzopyran-6-yl)-5-(3,6-dihydro-2H-pyran-4-yl)-2-methylthiophen-3-yl]acetate (78a) (88 mg, 0.19 mmol, 65%) after purification by flash chromatography on silica gel (cyclohexane/ethyl acetate 95/5).

MS m/z ([M+Na]$^+$) 493.

Step 2: preparation of 2-(tert-butoxy)-2-[4-(3,4-dihydro-2H-1-benzopyran-6-yl)-5-(3,6-dihydro-2H-pyran-4-yl)-2-methylthiophen-3-yl]acetic acid (example 78)

Using the procedure described in example 15, step 2, ethyl 2-(tert-butoxy)-2-[4-(3,4-dihydro-2H-1-benzopyran-6-yl)-5-(3,6-dihydro-2H-pyran-4-yl)-2-methylthiophen-3-yl]acetate (78a) (88 mg, 0.19 mmol) is converted by reaction with lithium hydroxide (1N, 1.9 mL, 1.9 mmol) into 2-(tert-butoxy)-2-[4-(3,4-dihydro-2H-1-benzopyran-6-yl)-5-(3,6-dihydro-2H-pyran-4-yl)-2-methylthiophen-3-yl]acetic acid (example 78) (83 mg, 0.18 mmol, 99%).

$^1$H NMR (400 MHz, DMSO-$d_6$) δ 0.90 (s, 9H), 1.83-1.99 (m, 4H), 2.42 (s, 3H), 2.72 (t, J=6.3 Hz, 2H), 3.46-3.60 (m, 2H), 4.01-4.07 (m, 2H), 4.17 (t, J=5.1 Hz, 2H), 4.68 (s, 1H), 5.69-5.72 (m, 1H), 5.77 (d, J=8.4 Hz, 1H), 6.90-7.01 (m, 2H), 12.51 (bs, 1H).

MS m/z ([M−H]$^-$) 441.

Example 79

Synthesis of 2-(tert-butoxy)-2-[4-(3,4-dihydro-2H-1-benzopyran-6-yl)-5-(6-methoxypyridin-3-yl)-2-methylthiophen-3-yl]acetic acid

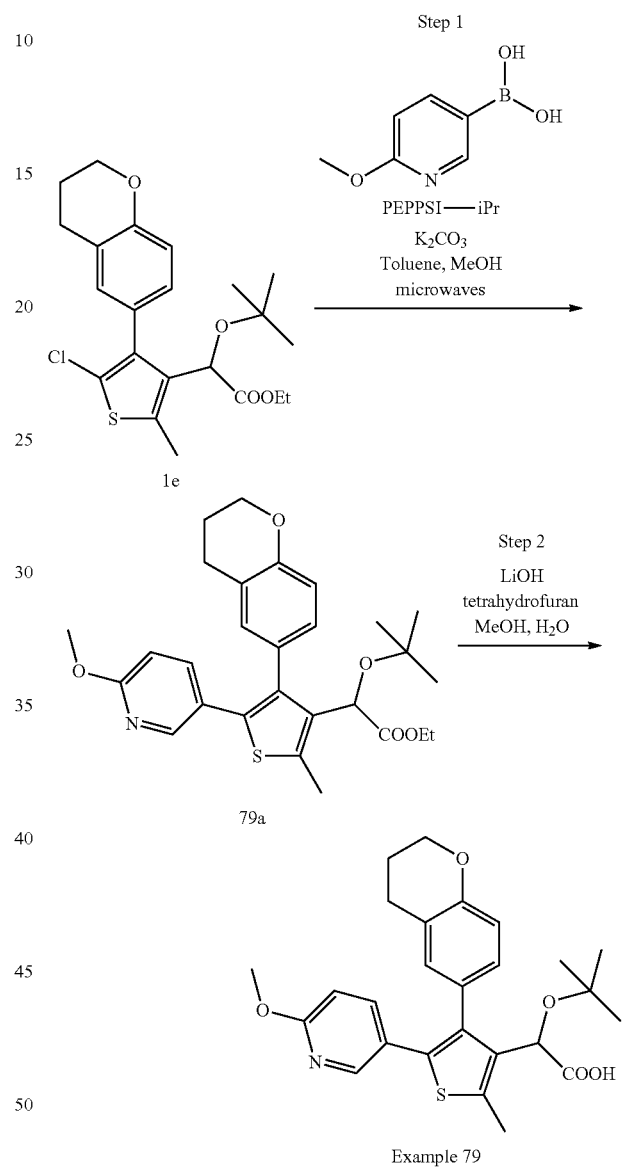

Example 79

Step 1: preparation of intermediate ethyl 2-(tert-butoxy)-2-[4-(3,4-dihydro-2H-1-benzopyran-6-yl)-5-(6-methoxypyridin-3-yl)-2-methylthiophen-3-yl]acetate (79a)

Using the procedure described in example 14, step 1, ethyl 2-(tert-butoxy)-2-[5-chloro-4-(3,4-dihydro-2H-1-benzopyran-6-yl)-2-methylthiophen-3-yl]acetate (1e) (105 mg, 0.25 mmol) is converted by reaction with 2-methoxy-5-pyridinylboronic acid (76 mg, 0.50 mmol) into ethyl 2-(tert-butoxy)-2-[4-(3,4-dihydro-2H-1-benzopyran-6-yl)-5-(6-methoxypyridin-3-yl)-2-methylthiophen-3-yl]acetate (79a)

(100 mg, 0.20 mmol, 73%) after purification by flash chromatography on silica gel (cyclohexane/ethyl acetate 80/20).

MS m/z ([M+H]$^+$) 496.

Step 2: preparation of 2-(tert-butoxy)-2-[4-(3,4-dihydro-2H-1-benzopyran-6-yl)-5-(6-methoxypyridin-3-yl)-2-methylthiophen-3-yl]acetic acid (example 79)

Using the procedure described in example 15, step 2, ethyl 2-(tert-butoxy)-2-[4-(3,4-dihydro-2H-1-benzopyran-6-yl)-5-(6-methoxypyridin-3-yl)-2-methylthiophen-3-yl]acetate (79a) (100 mg, 0.20 mmol) is converted into 2-(tert-butoxy)-2-[4-(3,4-dihydro-2H-1-benzopyran-6-yl)-5-(6-methoxypyridin-3-yl)-2-methylthiophen-3-yl]acetic acid (example 79) (65 mg, 0.14 mmol, 69%) after purification by flash chromatography on silica gel (dichloromethane/methanol 98/2).

$^1$H NMR (400 MHz, DMSO-d$_6$) δ 0.92 (s, 9H), 1.86-1.95 (m, 2H), 2.49 (s, 3H), 2.63-2.72 (m, 2H), 3.79 (s, 3H), 4.16 (t, J=5.0 Hz, 2H), 4.73 (s, 1H), 6.69 (d, J=8.6 Hz, 1H), 6.70-6.76 (m, 1H), 6.79-7.06 (m, 2H), 7.37 (dd, J=2.5 Hz, J=8.6 Hz, 1H), 7.91 (d, J=2.5 Hz, 1H), 12.60 (bs, 1H).

MS m/z ([M−H]$^-$) 466.

Example 80

Synthesis of 2-[5-(1-benzyl-1H-pyrazol-4-yl)-4-(3,4-dihydro-2H-1-benzopyran-6-yl)-2-methylthiophen-3-yl]-2-(tert-butoxy)acetic acid

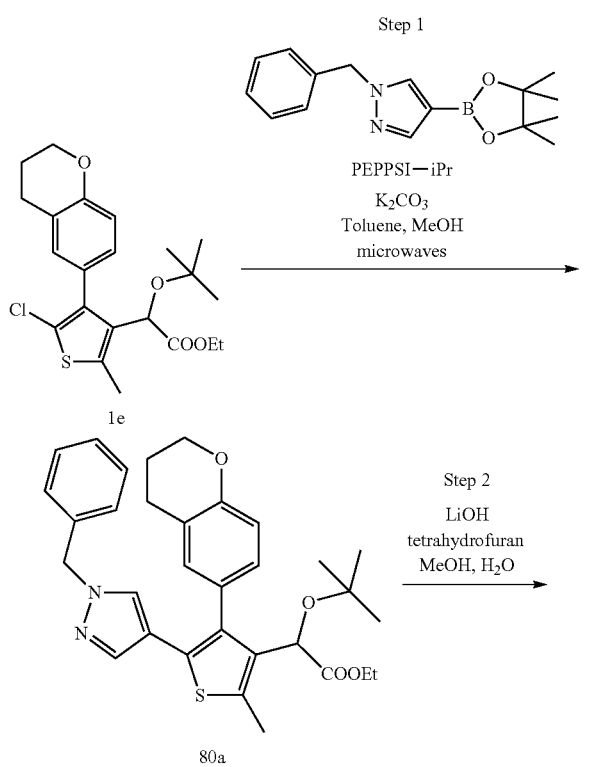

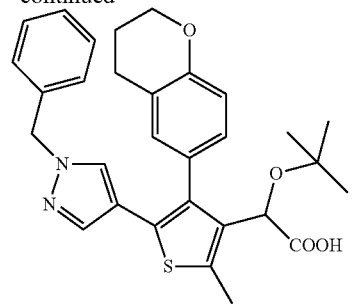

Example 80

Step 1: preparation of intermediate ethyl 2-[5-(1-benzyl-1H-pyrazol-4-yl)-4-(3,4-dihydro-2H-1-benzopyran-6-yl)-2-methylthiophen-3-yl]-2-(tert-butoxy)acetate (80a)

Using the procedure described in example 14, step 1, ethyl 2-(tert-butoxy)-2-[5-chloro-4-(3,4-dihydro-2H-1-benzopyran-6-yl)-2-methylthiophen-3-yl]acetate (1e) (110 mg, 0.26 mmol) is converted by reaction with 1-Benzyl-4-(4,4,5,5-tetramethyl-1,3,2-dioxaborolan-2-yl)-1H-pyrazole (148 mg, 0.52 mmol) into ethyl 2-[5-(1-benzyl-1H-pyrazol-4-yl)-4-(3,4-dihydro-2H-1-benzopyran-6-yl)-2-methylthiophen-3-yl]-2-(tert-butoxy)acetate (80a) (42 mg, 0.078 mmol, 30%) after purification by flash chromatography on silica gel (cyclohexane/ethyl acetate 80/20).

MS m/z ([M+H]$^+$) 545.

Step 2: preparation of 2-[5-(1-benzyl-1H-pyrazol-4-yl)-4-(3,4-dihydro-2H-1-benzopyran-6-yl)-2-methylthiophen-3-yl]-2-(tert-butoxy)acetic acid (example 80)

Using the procedure described in example 15, step 2, ethyl 2-[5-(1-benzyl-1H-pyrazol-4-yl)-4-(3,4-dihydro-2H-1-benzopyran-6-yl)-2-methylthiophen-3-yl]-2-(tert-butoxy)acetate (80a) (55 mg, 0.1 mmol) is converted into 2-[5-(1-benzyl-1H-pyrazol-4-yl)-4-(3,4-dihydro-2H-1-benzopyran-6-yl)-2-methylthiophen-3-yl]-2-(tert-butoxy)acetic acid (example 80) (40 mg, 0.077 mmol, 77%) after purification by flash chromatography on silica gel (dichloromethane/methanol 98/2).

$^1$H NMR (400 MHz, DMSO-d$_6$) δ 0.93 (s, 9H), 1.87-1.96 (m, 2H), 2.44 (s, 3H), 2.61-2.69 (m, 2H), 4.16 (t, J=5.1 Hz, 2H), 4.64 (s, 1H), 5.20 (s, 2H), 6.75 (d, J=8.3 Hz, 1H), 6.86-6.98 (m, 2H), 7.01 (s, 1H), 7.12 (dd, J=1.6 Hz, J=7.9 Hz, 2H), 7.25-7.34 (m, 3H), 7.44 (s, 1H), 12.50 (bs, 1H).

MS m/z ([M−H]$^-$) 515.

Example 81

Synthesis of 2-(tert-butoxy)-2-[4-(3,4-dihydro-2H-1-benzopyran-6-yl)-2-methyl-5-(1-methyl-1H-pyrrol-2-yl)thiophen-3-yl]acetic acid

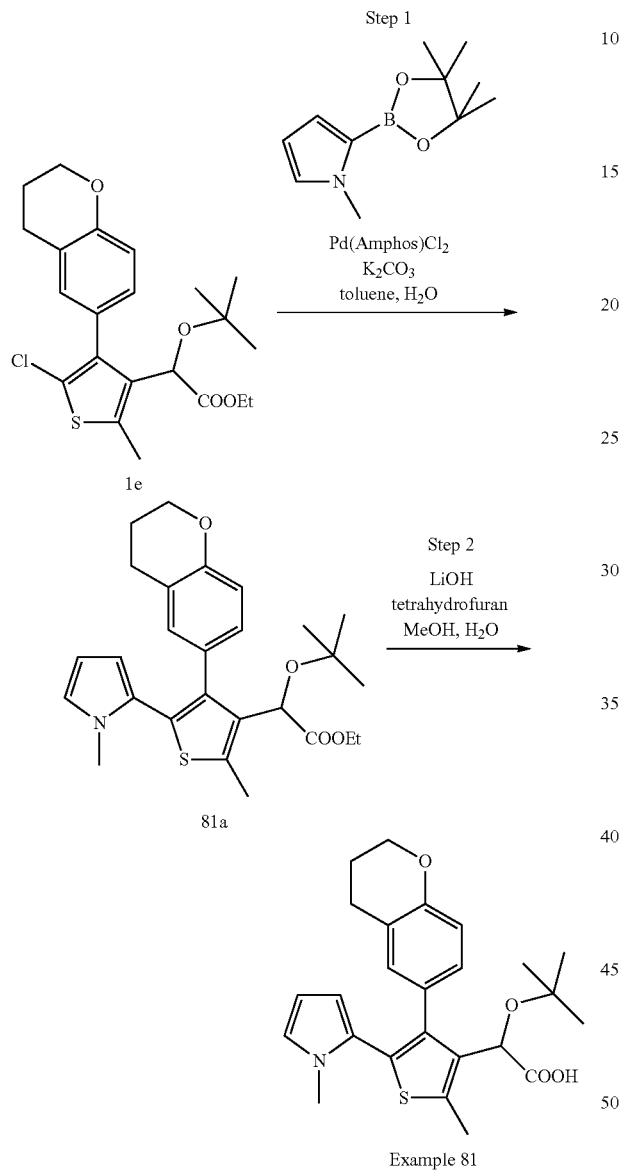

Step 1: preparation of intermediate ethyl 2-(tert-butoxy)-2-[4-(3,4-dihydro-2H-1-benzopyran-6-yl)-2-methyl-5-(1-methyl-1H-pyrrol-2-yl)thiophen-3-yl]acetate (81a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (158 mg, 0.37 mmol) is converted by reaction with 1-Methyl-2-(4,4,5,5-tetramethyl-1,3,2-dioxaborolan-2-yl)-1H-pyrrole (93 mg, 0.45 mmol) into ethyl 2-(tert-butoxy)-2-[4-(3,4-dihydro-2H-1-benzopyran-6-yl)-2-methyl-5-(1-methyl-1H-pyrrol-2-yl)thiophen-3-yl]acetate (81a) (100 mg, 0.18 mmol, 48%) after purification by flash chromatography on silica gel (cyclohexane/ethyl acetate 95/5).

MS m/z ([M+H]$^+$) 468.

Step 2: preparation of intermediate 2-(tert-butoxy)-2-[4-(3,4-dihydro-2H-1-benzopyran-6-yl)-2-methyl-5-(1-methyl-1H-pyrrol-2-yl)thiophen-3-yl]acetic acid (example 81)

Using the procedure described in example 15, step 2, ethyl 2-(tert-butoxy)-2-[4-(3,4-dihydro-2H-1-benzopyran-6-yl)-2-methyl-5-(1-methyl-1H-pyrrol-2-yl)thiophen-3-yl]acetate (81a) (50 mg, 0.1 mmol) is converted into 2-(tert-butoxy)-2-[4-(3,4-dihydro-2H-1-benzopyran-6-yl)-2-methyl-5-(1-methyl-1H-pyrrol-2-yl)thiophen-3-yl]acetic acid (example 81) (23 mg, 0.052 mmol, 52%) after purification by flash chromatography on silica gel (dichloromethane/methanol 95/5).

$^1$H NMR (400 MHz, DMSO-d$_6$) δ 0.91 (s, 9H), 1.86-1.91 (m, 2H), 2.48 (s, 3H), 2.59-2.68 (m, 2H), 3.11 (s, 3H), 4.13 (dd, J=4.8 Hz, J=5.2 Hz, 2H), 4.85 (s, 1H), 5.94 (dd, J=2.7 Hz, J=3.5 Hz, 1H), 5.98 (dd, J=1.8 Hz, J=3.5 Hz, 1H), 6.65-6.68 (m, 2H), 6.89 (d, J=8.0 Hz, 1H), 6.94 (bs, 1H), 12.64 (bs, 1H).

MS m/z ([M−H]$^−$) 438.

Example 82

Synthesis of 2-(tert-butoxy)-2-[4-(4-methoxy-4-methylcyclohex-1-en-1-yl)-2-methyl-5-{2H,3H,4H-pyrano[2,3-b]pyridin-6-yl}thiophen-3-yl]acetic acid

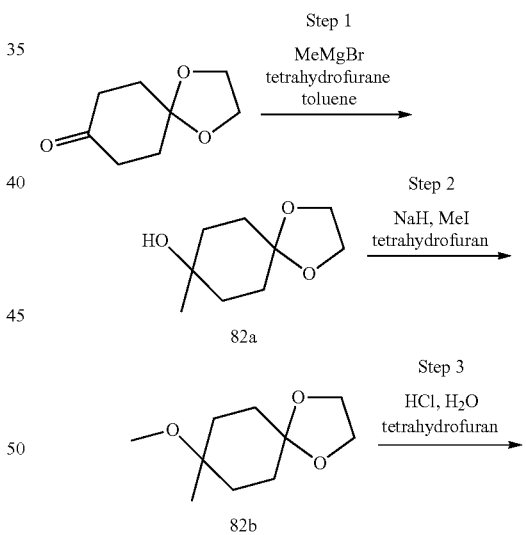

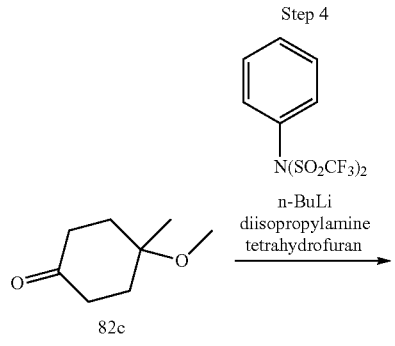

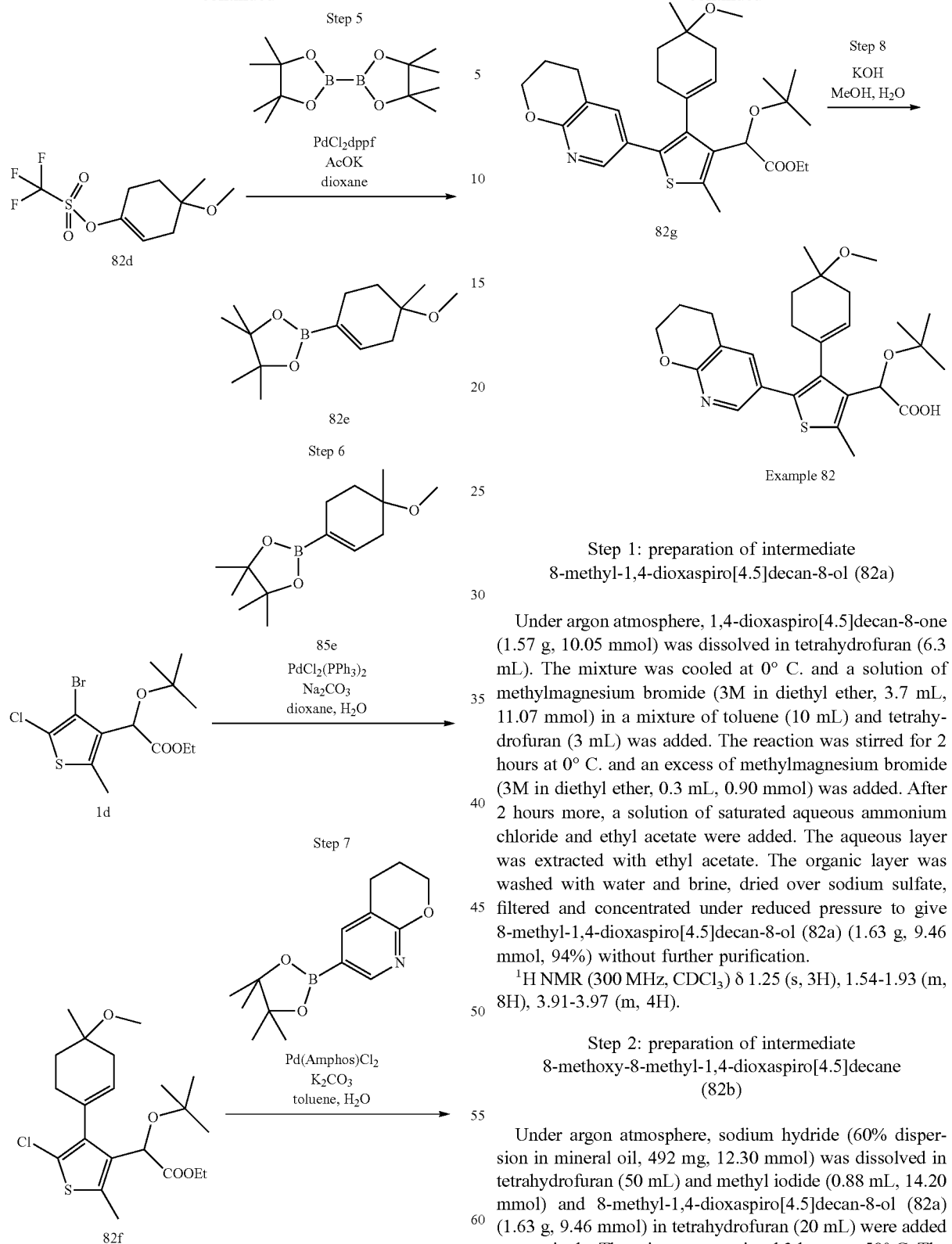

Step 1: preparation of intermediate 8-methyl-1,4-dioxaspiro[4.5]decan-8-ol (82a)

Under argon atmosphere, 1,4-dioxaspiro[4.5]decan-8-one (1.57 g, 10.05 mmol) was dissolved in tetrahydrofuran (6.3 mL). The mixture was cooled at 0° C. and a solution of methylmagnesium bromide (3M in diethyl ether, 3.7 mL, 11.07 mmol) in a mixture of toluene (10 mL) and tetrahydrofuran (3 mL) was added. The reaction was stirred for 2 hours at 0° C. and an excess of methylmagnesium bromide (3M in diethyl ether, 0.3 mL, 0.90 mmol) was added. After 2 hours more, a solution of saturated aqueous ammonium chloride and ethyl acetate were added. The aqueous layer was extracted with ethyl acetate. The organic layer was washed with water and brine, dried over sodium sulfate, filtered and concentrated under reduced pressure to give 8-methyl-1,4-dioxaspiro[4.5]decan-8-ol (82a) (1.63 g, 9.46 mmol, 94%) without further purification.

$^1$H NMR (300 MHz, CDCl$_3$) δ 1.25 (s, 3H), 1.54-1.93 (m, 8H), 3.91-3.97 (m, 4H).

Step 2: preparation of intermediate 8-methoxy-8-methyl-1,4-dioxaspiro[4.5]decane (82b)

Under argon atmosphere, sodium hydride (60% dispersion in mineral oil, 492 mg, 12.30 mmol) was dissolved in tetrahydrofuran (50 mL) and methyl iodide (0.88 mL, 14.20 mmol) and 8-methyl-1,4-dioxaspiro[4.5]decan-8-ol (82a) (1.63 g, 9.46 mmol) in tetrahydrofuran (20 mL) were added successively. The mixture was stirred 3 hours at 50° C. The mixture was cooled down to room temperature, quenched with water and extracted with diethyl ether twice. The organic layer was washed with brine, dried over sodium sulfate, filtered and concentrated under reduced pressure. The residue was purified by flash chromatography on silica gel (cyclohexane/ethyl acetate 80/20) to give 8-methoxy-8-methyl-1,4-dioxaspiro[4.5]decane (82b) (1.17 g, 6.28 mmol, 66%).

$^1$H NMR (400 MHz, CDCl$_3$) δ 1.13 (s, 3H), 1.50-1.83 (m, 8H), 3.18 (s, 3H), 3.93-3.96 (m, 4H).

Step 3: preparation of intermediate 4-methoxy-4-methylcyclohexan-1-one (82c)

8-Methoxy-8-methyl-1,4-dioxaspiro[4.5]decane (82b) (1.17 g, 6.28 mmol) was dissolved in a mixture of tetrahydrofuran (6.5 mL) and water (9 mL) and concentrated hydrochloric acid (1.2 mL) was added. The mixture was stirred at room temperature for 1 hour and then neutralized with 2M aqueous sodium hydroxide solution. The mixture was concentrated and extracted with diethyl ether twice. The organic layer was washed with water and brine, dried over sodium sulfate, filtered and concentrated under reduced pressure to give 4-methoxy-4-methylcyclohexan-1-one (82c) (775 mg, 5.45 mmol, 86%) without further purification.

$^1$H NMR (300 MHz, CDCl$_3$) δ 1.23 (s, 3H), 1.64-1.75 (m, 2H), 2.08-2.21 (m, 4H), 2.52-2.64 (m, 2H), 3.28 (s, 3H).

Step 4: preparation of intermediate 4-methoxy-4-methylcyclohex-1-en-1-yl trifluoromethanesulfonate (82d)

Using the procedure described in example 6, step 1,4-methoxy-4-methylcyclohexan-1-one (82c) (775 mg, 5.42 mmol) is converted into 4-methoxy-4-methylcyclohex-1-en-1-yl trifluoromethanesulfonate (82d) (860 mg, 3.13 mmol, 58%) after purification by preparative TLC (cyclohexane/ethyl acetate from 100/0 to 95/5).

$^1$H NMR (400 MHz, CDCl$_3$) δ 1.23 (s, 3H), 1.69-1.76 (m, 1H), 1.92-1.98 (m, 1H), 2.12-2.53 (m, 4H), 3.22 (s, 3H), 5.61-5.63 (m, 1H).

Step 5: preparation of intermediate 2-(4-methoxy-4-methylcyclohex-1-en-1-yl)-4,4,5,5-tetramethyl-1,3,2-dioxaborolane (82e)

Using the procedure described in example 6, step 2,4-methoxy-4-methylcyclohex-1-en-1-yl trifluoromethanesulfonate (82d) (740 mg, 2.70 mmol) is converted into 2-(4-methoxy-4-methylcyclohex-1-en-1-yl)-4,4,5,5-tetramethyl-1,3,2-dioxaborolane (82e) (518 mg, 2.05 mmol, 76%) after purification by flash chromatography on silica gel (cyclohexane/ethyl acetate from 100/0 to 95/5).

$^1$H NMR (400 MHz, CDCl$_3$) δ 1.15 (s, 3H), 1.26 (s, 12H), 1.70-1.76 (m, 2H), 2.04-2.12 (m, 2H), 2.23-2.29 (m, 2H), 3.22 (s, 3H), 6.44 (s, 1H).

Step 6: preparation of intermediate ethyl 2-(tert-butoxy)-2-[5-chloro-4-(4-methoxy-4-methylcyclohex-1-en-1-yl)-2-methylthiophen-3-yl]acetate (82f)

Using the procedure described in example 1, step 5, ethyl 2-(4-bromo-5-chloro-2-methylthiophen-3-yl)-2-(tert-butoxy)acetate (82e) (80 mg, 0.22 mmol) is converted by reaction with 2-(4-methoxy-4-methylcyclohex-1-en-1-yl)-4, 4,5,5-tetramethyl-1,3,2-dioxaborolane (82d) (71 mg, 0.28 mmol) into ethyl 2-(tert-butoxy)-2-[5-chloro-4-(4-methoxy-4-methylcyclohex-1-en-1-yl)-2-methylthiophen-3-yl]acetate (82f) (46 mg, 0.11 mmol, 51%) as a mixture of diastereoisomers (1/1) after purification by preparative TLC (cyclohexane/ethyl acetate 90/10).

$^1$H NMR (300 MHz, CDCl$_3$) δ 1.17 (s, 9H), 1.23 (t, J=7.2 Hz, 3H), 1.30 (s, 3H), 1.71-1.77 (m, 1H), 1.84-1.89 (m, 1H), 2.13-2.38 (m, 4H), 2.47 (s, 3H), 3.27 & 3.29 (s, 3H), 4.06-4.18 (m, 2H), 4.97 & 4.99 (s, 1H), 5.52-5.56 (m, 1H).

Step 7: preparation of intermediate ethyl 2-(tert-butoxy)-2-[4-(4-methoxy-4-methylcyclohex-1-en-1-yl)-2-methyl-5-{2H,3H,4H-pyrano[2,3-b]pyridin-6-yl}thiophen-3-yl]acetate (82g)

Using the procedure described in example 1, step 6, ethyl 2-(tert-butoxy)-2-[5-chloro-4-(4-methoxy-4-methylcyclohex-1-en-1-yl)-2-methylthiophen-3-yl]acetate (82f) (45 mg, 0.11 mmol) is converted by reaction with 6-(tetramethyl-1, 3,2-dioxaborolan-2-yl)-2H,3H,4H-pyrano[2,3-b]pyridine (57 mg, 0.22 mmol) into ethyl 2-(tert-butoxy)-2-[4-(4-methoxy-4-methylcyclohex-1-en-1-yl)-2-methyl-5-{2H,3H, 4H-pyrano[2,3-b]pyridin-6-yl}thiophen-3-yl]acetate (82g) (35 mg, 0.07 mmol, 63%) as a mixture of diastereoisomers after purification by preparative TLC (cyclohexane/ethyl acetate 50/50).

$^1$H NMR (300 MHz, CDCl$_3$) δ 1.20 (s, 9H), 1.22 (t, J=7.2 Hz, 3H), 1.24 (s, 3H), 1.90-1.97 (m, 2H), 1.99-2.05 (m, 2H), 2.14-2.21 (m, 2H), 2.26-2.48 (m, 2H), 2.57 (s, 3H), 2.80 (dd, J=6.4 Hz, J=6.4 Hz, 2H), 3.23 & 3.25 (m, 3H), 4.06-4.22 (m, 2H), 4.36 (dd, J=5.2 Hz, J=5.2 Hz, 2H), 5.08 & 5.11 (s, 1H), 5.61-5.68 (m, 1H), 7.51 (d, J=15.6 Hz, 1H), 8.20 (d, J=15.6 Hz, 1H).

MS m/z [M+H]$^+$ 514

Step 8: preparation of 2-(tert-butoxy)-2-[4-(4-methoxy-4-methylcyclohex-1-en-1-yl)-2-methyl-5-{2H,3H,4H-pyrano[2,3-b]pyridin-6-yl}thiophen-3-yl]acetic acid (example 82)

Using the procedure described in example 3, step 2, ethyl 2-(tert-butoxy)-2-[4-(4-methoxy-4-methylcyclohex-1-en-1-yl)-2-methyl-5-{2H,3H,4H-pyrano[2,3-b]pyridin-6-yl}thiophen-3-yl]acetate (82g) (35 mg, 0.07 mmol) is converted into 2-(tert-butoxy)-2-[4-(4-methoxy-4-methylcyclohex-1-en-1-yl)-2-methyl-5-{2H,3H,4H-pyrano[2,3-b]pyridin-6-yl}thiophen-3-yl]acetic acid (example 82) (16 mg, 0.03 mmol, 47%) after purification by preparative TLC (dichloromethane/methanol 90/10).

$^1$H NMR (400 MHz, CDCl$_3$) δ 1.19-1.24 (m, 12H), 1.71-1.96 (m, 2H), 1.98-2.08 (m, 2H), 2.10-2.21 (m, 2H), 2.25-2.42 (m, 2H), 2.47 & 2.49 (s, 3H), 2.80 (dd, J=5.2 Hz, J=5.2 Hz, 2H), 3.20 & 3.23 (s, 3H), 4.36 (dd, J=5.2 Hz, J=5.2 Hz, 2H), 5.12-5.15 (m, 1H), 5.55-5.68 (m, 1H), 7.47-7.55 (m, 1H), 8.18-8.21 (m, 1H).

MS m/z [M−H]$^-$ 484

Example 83

Synthesis of 2-(tert-butoxy)-2-[4-(3,4-dihydro-2H-1-benzopyran-6-yl)-2-methyl-5-[1-methyl-3-(trifluoromethyl)-1H-pyrazol-5-yl]thiophen-3-yl]acetic acid

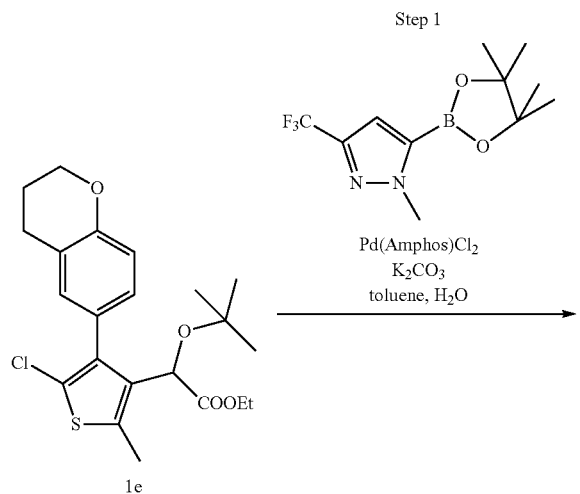

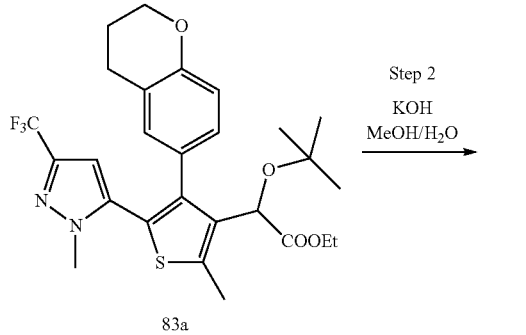

Step 1: preparation of intermediate ethyl 2-(tert-butoxy)-2-[4-(3,4-dihydro-2H-1-benzopyran-6-yl)-2-methyl-5-[1-methyl-3-(trifluoromethyl)-1H-pyrazol-5-yl]thiophen-3-yl]acetate (83a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (150 mg, 0.35 mmol) is converted by reaction with 1-Methyl-5-(4,4,5,5-tetramethyl-1,3,2-dioxaborolan-2-yl)-3-trifluoromethyl-1H-pyrazole (118 mg, 0.43 mmol) into ethyl 2-(tert-butoxy)-2-[4-(3,4-dihydro-2H-1-benzopyran-6-yl)-2-methyl-5-[1-methyl-3-trifluoro methyl)-1H-pyrazol-5-yl]thiophen-3-yl]acetate (83a) (150 mg, 0.2 mmol, 59%) after purification by flash chromatography on silica gel (cyclohexane/ethyl acetate 95/5).

MS m/z ([M+H]$^+$) 537.

Step 2: preparation of intermediate 2-(tert-butoxy)-2-[4-(3,4-dihydro-2H-1-benzopyran-6-yl)-2-methyl-5-[1-methyl-3-(trifluoromethyl)-1H-pyrazol-5-yl]thiophen-3-yl]acetic acid (example 83)

Using the procedure described in example 3, step 2, ethyl 2-(tert-butoxy)-2-[4-(3,4-dihydro-2H-1-benzopyran-6-yl)-2-methyl-5-[1-methyl-3-trifluoro methyl)-1H-pyrazol-5-yl]thiophen-3-yl]acetate (83a) (150 mg, 0.2 mmol) is converted into 2-(tert-butoxy)-2-[4-(3,4-dihydro-2H-1-benzopyran-6-yl)-2-methyl-5-[1-methyl-3-(trifluoromethyl)-1H-pyrazol-5-yl]thiophen-3-yl]acetic acid (example 83) (50 mg, 0.098 mmol, 35%) after purification by flash chromatography (dichloromethane/methanol 98/2).

$^1$H NMR (400 MHz, DMSO-d$_6$) δ 0.93 (s, 9H), 1.85-1.93 (m, 2H), 2.54 (s, 3H), 2.62-2.67 (m, 2H), 3.42 (s, 3H), 4.14 (t, J=4.9 Hz, 2H), 4.87 (s, 1H), 6.73 (d, J=8.4 Hz, 1H), 6.75 (s, 1H), 6.86-6.97 (m, 2H), 12.73 (bs, 1H).

MS m/z ([M−H]$^-$) 507.

Example 84

Synthesis of 2-(tert-butoxy)-2-[4-(3,4-dihydro-2H-1-benzopyran-6-yl)-5-(2-methoxy-pyridin-4-yl)-2-methylthiophen-3-yl]acetic acid

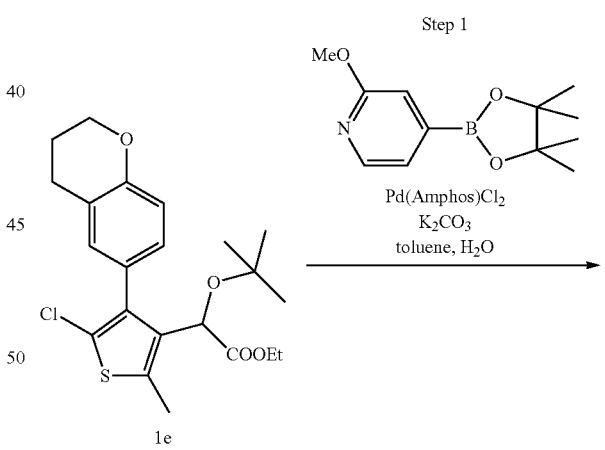

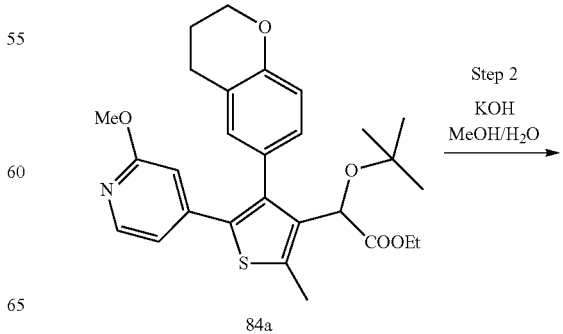

235
-continued

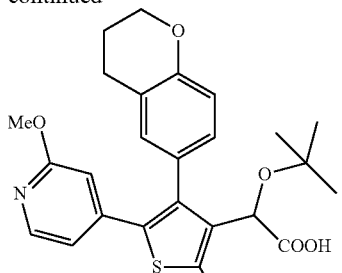

Example 84

Step 1: preparation of intermediate ethyl 2-(tert-butoxy)-2-[4-(3,4-dihydro-2H-1-benzopyran-6-yl)-5-(2-methoxy-pyridin-4-yl)-2-methylthiophen-3-yl] acetate (84a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (168 mg, 0.40 mmol) is converted by reaction with 2-fluoro-4-(4,4,5,5-Tetramethyl-1,3,2-dioxaborolan-2-yl)-pyridine (106 mg, 0.48 mmol) into ethyl 2-(tert-butoxy)-2-[4-(3,4-dihydro-2H-1-benzopyran-6-yl)-5-(2-methoxy-pyridin-4-yl)-2-methyl-thiophen-3-yl]acetate (84a) (58 mg, 0.11 mmol, 28%) after purification by flash chromatography on silica gel (cyclohexane/ethyl acetate 90/10).

MS m/z ([M+H]$^+$) 484.

Step 2: preparation of 2-(tert-butoxy)-2-[4-(3,4-dihydro-2H-1-benzopyran-6-yl)-5-(2-methoxy-pyridin-4-yl)-2-methylthiophen-3-yl]acetic acid (example 84)

Using the procedure described in example 3, step 2, ethyl 2-(tert-butoxy)-2-[4-(3,4-dihydro-2H-1-benzopyran-6-yl)-5-(2-methoxy-pyridin-4-yl)-2-methylthiophen-3-yl]acetate (84a) (42 mg, 0.086 mmol) is converted into 2-(tert-butoxy)-2-[4-(3,4-dihydro-2H-1-benzopyran-6-yl)-5-(2-methoxy-pyridin-4-yl)-2-methylthiophen-3-yl]acetic acid (example 84) (25 mg, 0.053 mmol, 62%) after purification by flash chromatography (dichloromethane/methanol 95/5).

$^1$H NMR (400 MHz, DMSO-d$_6$) δ 0.92 (s, 9H), 1.88-1.97 (m, 2H), 2.51 (s, 3H), 2.63-2.74 (m, 2H), 3.76 (s, 3H), 4.14-4.21 (m, 2H), 4.72 (s, 1H), 6.43 (d, J=1.5 Hz, 1H), 6.62 (dd, J=1.5 Hz, J=5.4 Hz, 1H), 6.72-6.81 (m, 1H), 6.82-7.06 (m, 2H), 7.97 (d, J=5.4 Hz, 1H), 12.63 (bs, 1H).

MS m/z ([M−H]$^−$) 466.

236
Example 85

Synthesis of 2-(tert-butoxy)-2-[4-(3,4-dihydro-2H-1-benzopyran-6-yl)-2-methyl-5-(1H-pyrazol-1-yl) thiophen-3-yl]acetic acid

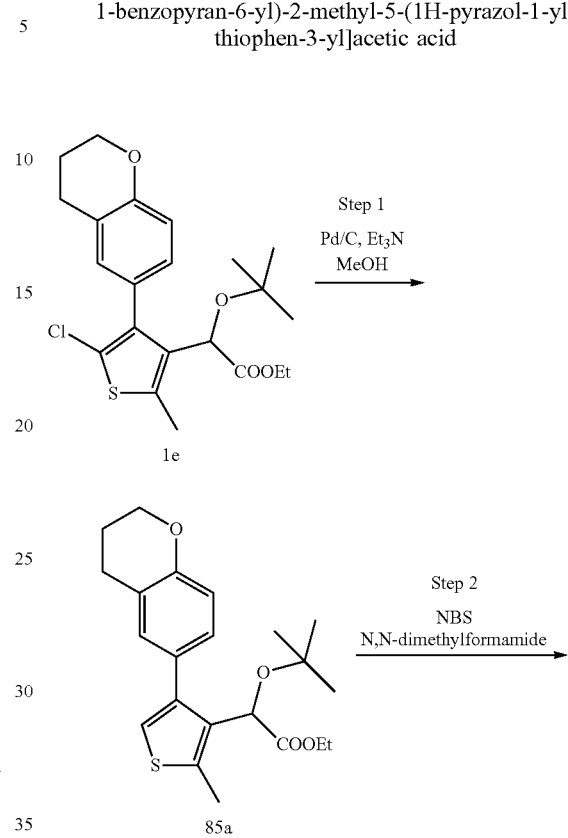

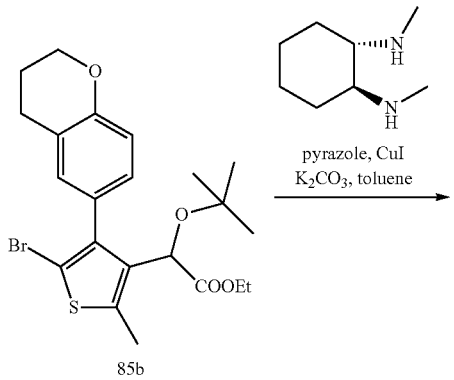

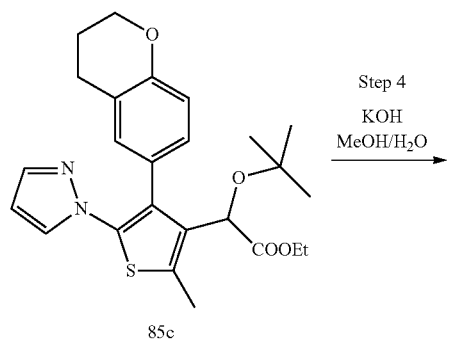

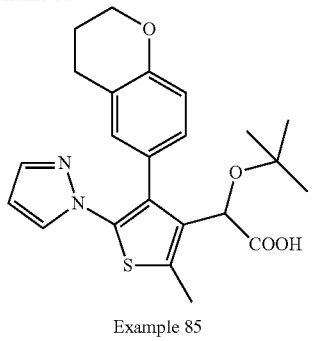 [SMILES: Cc1sc(-n2cccn2)c(-c2ccc3c(c2)CCCO3)c1C(OC(C)(C)C)C(=O)O]

Example 85

Step 1: preparation of intermediate ethyl 2-(tert-butoxy)-2-[4-(3,4-dihydro-2H-1-benzopyran-6-yl)-2-methylthiophen-3-yl]acetate (85a)

Using the procedure described in example 43, step 1, ethyl 2-(tert-butoxy)-2-[5-chloro-4-(3,4-dihydro-2H-1-benzopyran-6-yl)-2-methylthiophen-3-yl]acetate (1e) (1 g, 2.36 mmol) is converted into ethyl 2-(tert-butoxy)-2-[4-(3,4-dihydro-2H-1-benzopyran-6-yl)-2-methylthiophen-3-yl]acetate (85a) (1.04 g, 2.68 mmol, 100%) without further purification.

$^{1}$H NMR (400 MHz, CDCl$_{3}$) δ 1.04 (s, 9H), 1.27 (t, J=7.2 Hz, 3H), 2.05-2.11 (m, 2H), 2.61 (s, 3H), 2.83-2.87 (m, 2H), 4.15-4.20 (m, 2H), 4.21-4.28 (m, 2H), 5.09 (s, 1H), 6.83-6.85 (m, 2H), 7.17-7.20 (m, 2H).

MS m/z ([M+H]$^{+}$ 389

Step 2: preparation of intermediate ethyl 2-[5-bromo-4-(3,4-dihydro-2H-1-benzopyran-6-yl)-2-methylthiophen-3-yl]-2-(tert-butoxy)acetate (85b)

Under nitrogen atmosphere, N-bromosuccinimide (463 mg, 2.60 mmol) in N,N-dimethylformamide (12 mL) was added at 0° C. to a solution of ethyl 2-(tert-butoxy)-2-[4-(3,4-dihydro-2H-1-benzopyran-6-yl)-2-methylthiophen-3-yl]acetate (85a) (1 g, 2.60 mmol) in N,N-dimethylformamide (35 mL) in an amber round bottom flask. After 30 minutes at 0° C., the reaction mixture was warmed up to room temperature for 5 hours. At 0° C., water was added and the mixture was diluted with ethyl acetate and layers were separated. The organic layer was washed with a saturated aqueous solution of sodium bicarbonate, a solution of sodium thiosulfate and brine, dried over sodium sulfate, filtered and evaporated under reduced pressure. Ethyl 2-[5-bromo-4-(3,4-dihydro-2H-1-benzopyran-6-yl)-2-methylthiophen-3-yl]-2-(tert-butoxy)acetate (85b) (1.18 g, 2.52 mmol, 97%) was obtained as an oil without purification.

$^{1}$H NMR (400 MHz, CDCl$_{3}$) δ 1.00 (s, 9H), 1.24 (t, J=7.2 Hz, 3H), 2.04-2.07 (m, 2H), 2.50 (s, 3H), 2.79-2.84 (m, 2H), 4.09-4.18 (m, 2H), 4.24 (dd, J=5.2 Hz, J=5.2 Hz, 2H), 4.80 (s, 1H), 6.84 (d, J=8.4 Hz, 1H), 7.02-7.04 (m, 2H).

Step 3: preparation of intermediate ethyl 2-(tert-butoxy)-2-[4-(3,4-dihydro-2H-1-benzopyran-6-yl)-2-methyl-5-(1H-pyrazol-1-yl)thiophen-3-yl]acetate (85c)

Under argon atmosphere, ethyl 2-[5-bromo-4-(3,4-dihydro-2H-1-benzopyran-6-yl)-2-methylthiophen-3-yl]-2-(tert-butoxy)acetate (85b) (50 mg, 0.11 mmol), pyrazole (11 mg, 0.16 mmol), potassium carbonate (31 mg, 0.22 mmol) were dissolved in toluene (0.3 mL). The solution was degassed under argon for 10 minutes before adding CuI (1 mg, 0.01 mmol) and trans-N,N'-dimethyl-1,2-cyclohexanediamine (3 µL, 0.02 mmol). The reaction was shaken at room temperature for 15 minutes, then it was heated at 110° C. for 20 h. After cooling down to room temperature, the mixture was filtered through Celite® and rinsed with methanol. The solution was concentrated under reduced pressure and partitioned between ethyl acetate and water. The organic layer was washed with brine, dried over sodium sulfate, filtered and concentrated under reduced pressure. Ethyl 2-(tert-butoxy)-2-[4-(3,4-dihydro-2H-1-benzopyran-6-yl)-2-methyl-5-(1H-pyrazol-1-yl)thiophen-3-yl]acetate (85c) (17 mg, 0.04 mmol, 35%) was obtained after purification by preparative TLC (cyclohexane/ethyl acetate 80/20).

$^{1}$H NMR (400 MHz, CDCl$_{3}$) δ 1.02 (s, 9H), 1.24 (t, J=7.2 Hz, 3H), 2.01-2.03 (m, 2H), 2.56 (s, 3H), 2.72-2.75 (m, 2H), 4.08-4.18 (m, 2H), 4.22 (dd, J=5.2 Hz, J=5.2 Hz, 2H), 4.82 (s, 1H), 6.14 (dd, J=2.4 Hz, J=1.6 Hz, 1H), 6.78 (d, J=8.4 Hz, 1H), 6.97-6.98 (m, 2H), 7.05 (d, J=2.4 Hz, 1H), 7.55 (d, J=1.6 Hz, 1H).

MS m/z ([M+H]$^{+}$) 455

Step 4: preparation of 2-(tert-butoxy)-2-[4-(3,4-dihydro-2H-1-benzopyran-6-yl)-2-methyl-5-(1H-pyrazol-1-yl)thiophen-3-yl]acetic acid (example 85)

Using the procedure described in example 3, step 2, ethyl 2-(tert-butoxy)-2-[4-(3,4-dihydro-2H-1-benzopyran-6-yl)-2-methyl-5-(1H-pyrazol-1-yl)thiophen-3-yl]acetate (88c) (17 mg, 0.04 mmol) is converted into 2-(tert-butoxy)-2-[4-(3,4-dihydro-2H-1-benzopyran-6-yl)-2-methyl-5-(1H-pyrazol-1-yl)thiophen-3-yl]acetic acid (example 85) (8 mg, 0.02 mmol, 49%) after purification by preparative TLC (dichloromethane/methanol 95/5).

$^{1}$H NMR (400 MHz, CDCl$_{3}$): δ 1.05 (s, 9H), 1.99-2.04 (m, 2H), 2.48 (s, 3H), 2.72-2.77 (m, 2H), 4.21 (dd, J=5.2 Hz, J=5.2 Hz, 2H), 4.99 (s, 1H), 6.16 (dd, J=2.4 Hz, J=1.6 Hz, 1H), 6.76-6.78 (m, 1H), 6.96-7.03 (m, 2H), 7.04 (d, J=2.4 Hz, 1H), 7.57 (d, J=1.6 Hz, 1H).

MS m/z ([M−H])$^{−}$ 425

Example 86

Synthesis of 2-(tert-butoxy)-2-[4-(3,4-dihydro-2H-1-benzopyran-6-yl)-2-methyl-5-(1,2-thiazol-3-yl)thiophen-3-yl]acetic acid

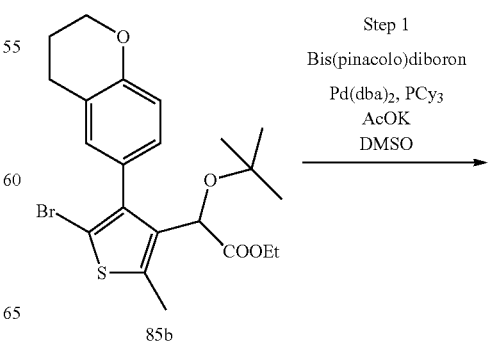

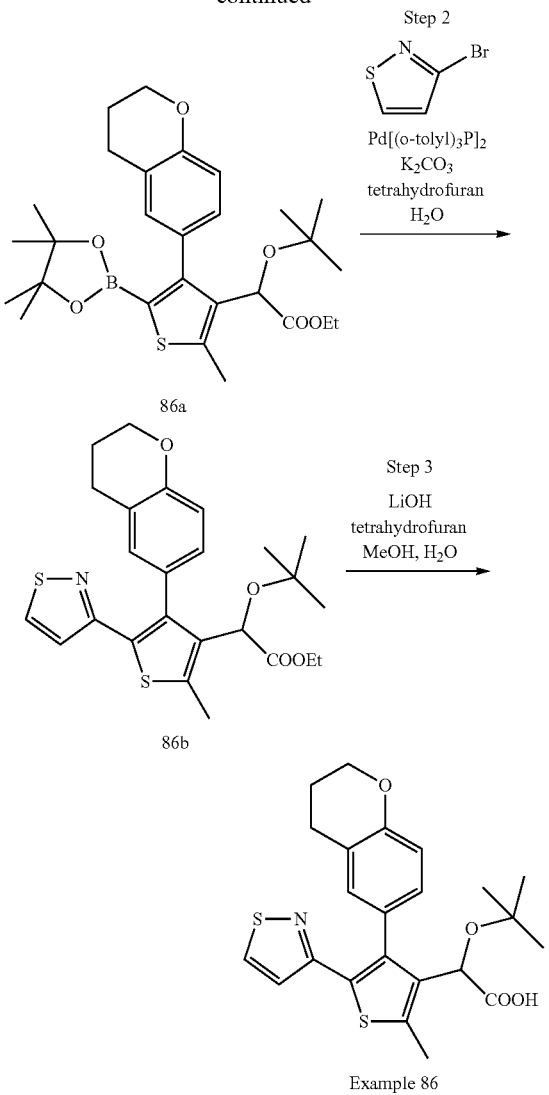

Example 86

Step 1: preparation of intermediate ethyl 2-(tert-butoxy)-2-[4-(3,4-dihydro-2H-1-benzopyran-6-yl)-2-methyl-5-(tetramethyl-1,3,2-dioxaborolan-2-yl)thiophen-3-yl]acetate (86a)

Under argon atmosphere, a mixture of bis(dibenzylideneacetone)palladium (4 mg, 0.01 mmol) and tricyclohexylphosphine (4.2 mg, 0.02 mmol) in dimethylsulfoxide (1.0 mL) was stirred for 20 minutes at room temperature. Then potassium acetate (62 mg, 0.63 mmol), bis(pinacolo)diboron (82 mg, 0.32 mmol) and a solution of ethyl 2-[5-bromo-4-(3,4-dihydro-2H-1-benzopyran-6-yl)-2-methylthiophen-3-yl]-2-(tert-butoxy)acetate (85b) (100 mg, 0.21 mmol) in dimethylsulfoxide (0.8 mL) was added successively. The mixture was stirred at 110° C. for 6 hours. The reaction was cooled down to room temperature, diluted with ethyl acetate and filtered through Celite® (with ethyl acetate washings). The filtrate was concentrated under reduced pressure diluted in ethyl acetate and washed with a saturated aqueous solution of sodium bicarbonate, water and brine, dried over sodium sulfate, filtered and concentrated under reduced pressure. The residue was purified by preparative TLC (cyclohexane/ethyl acetate 95/5) to afford ethyl 2-(tert-butoxy)-2-[4-(3,4-dihydro-2H-1-benzopyran-6-yl)-2-methyl-5-(tetramethyl-1,3,2-dioxaborolan-2-yl)thiophen-3-yl]acetate (86a) (30 mg, 0.06 mmol, 28%).

$^1$H NMR (400 MHz, CDCl$_3$) δ 0.95 (s, 9H), 1.19 (s, 12H), 1.23 (t, J=7.2 Hz, 3H), 2.02-2.07 (m, 2H), 2.58 (s, 3H), 2.78 (dd, J=6.4 Hz, J=6.4 Hz, 2H), 4.08-4.19 (m, 2H), 4.24 (dd, J=5.2 Hz, J=5.2 Hz, 2H), 4.98 (s, 1H), 6.76 (d, J=8.4 Hz, 1H), 7.03-7.06 (m, 1H), 7.07-7.11 (m, 1H).

MS m/z [M+H]$^+$ 515

Step 2: preparation of intermediate ethyl 2-(tert-butoxy)-2-[4-(3,4-dihydro-2H-1-benzopyran-6-yl)-2-methyl-5-(1,2-thiazol-3-yl)thiophen-3-yl]acetate (86b)

Under argon atmosphere, ethyl 2-(tert-butoxy)-2-[4-(3,4-dihydro-2H-1-benzopyran-6-yl)-2-methyl-5-(tetramethyl-1,3,2-dioxaborolan-2-yl)thiophen-3-yl]acetate (86a) (50 mg, 0.10 mmol), 3-bromo-1,2-thiazole (19 mg, 0.12 mmol), potassium carbonate (40 mg, 0.29 mmol) were dissolved in tetrahydrofuran (0.8 mL) and water (0.2 mL). The solution was degassed under argon for 10 minutes before bis[tris(2-methylphenyl)phosphine]palladium (7 mg, 0.01 mmol) was added. The reaction was heated and shaken at 60° C. for 19 hours. After cooling down to room temperature, water was added and the mixture was extracted twice with ethyl acetate. The organic layer was washed with brine, dried over sodium sulfate, filtered and concentrated under reduced pressure. The crude material was purified by preparative TLC (cyclohexane/ethyl acetate 90/10) to give ethyl 2-(tert-butoxy)-2-[4-(3,4-dihydro-2H-1-benzopyran-6-yl)-2-methyl-5-(1,2-thiazol-3-yl)thiophen-3-yl]acetate (86b) (8 mg, 0.02 mmol, 18%).

$^1$H NMR (400 MHz, CDCl$_3$) δ 1.03 (s, 9H), 1.23 (t, J=7.2 Hz, 3H), 2.00-2.13 (m, 2H), 2.60 (s, 3H), 2.65-2.88 (m, 2H), 4.06-4.19 (m, 2H), 4.27 (dd, J=5.2 Hz, J=5.2 Hz, 2H), 4.78 (s, 1H), 6.37 (d, J=4.8 Hz, 1H), 6.74-7.22 (m, 3H), 8.32 (d, J=4.8 Hz, 1H).

MS m/z [M+H]$^+$ 472

Step 3: preparation of 2-(tert-butoxy)-2-[4-(3,4-dihydro-2H-1-benzopyran-6-yl)-2-methyl-5-(1,2-thiazol-3-yl)thiophen-3-yl]acetic acid (example 86)

Using the procedure described in example 15, step 2, ethyl 2-(tert-butoxy)-2-[4-(3,4-dihydro-2H-1-benzopyran-6-yl)-2-methyl-5-(1,2-thiazol-3-yl)thiophen-3-yl]acetate (86b) (8 mg, 0.02 mmol) is converted into 2-(tert-butoxy)-2-[4-(3,4-dihydro-2H-1-benzopyran-6-yl)-2-methyl-5-(1,2-thiazol-3-yl)thiophen-3-yl]acetic acid (example 86) (3 mg, 0.01 mmol, 40%) after purification by preparative TLC (dichloromethane/methanol 95/5).

$^1$H NMR (400 MHz, CDCl$_3$) δ 1.04 (s, 9H), 1.98-2.09 (m, 2H), 2.51 (s, 3H), 2.63-2.89 (m, 2H), 4.21-4.30 (m, 2H), 4.92 (s, 1H), 6.40 (d, J=4.8 Hz, 1H), 6.72-6.95 (m, 2H), 7.25-7.36 (m, 1H), 8.34 (d, J=4.8 Hz, 1H).

MS m/z [M−H]$^−$ 442

Example 87

Synthesis of 2-[5-(3-amino-3-methylbut-1-yn-1-yl)-4-(3,4-dihydro-2H-1-benzopyran-6-yl)-2-methylthiophen-3-yl]-2-(tert-butoxy)acetic acid

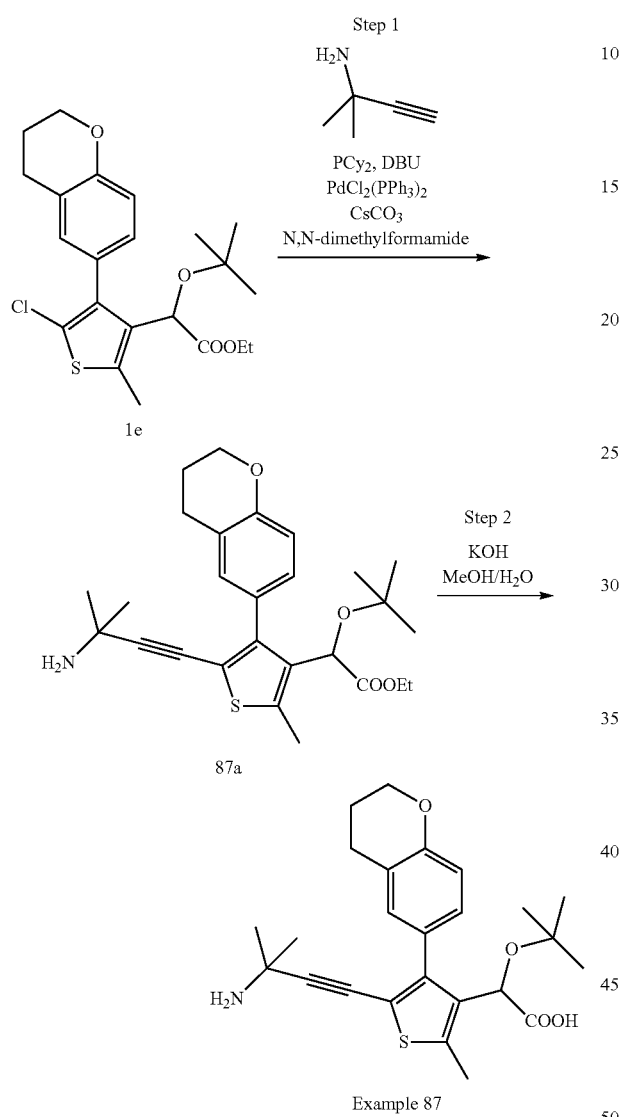

Example 87

Step 1: preparation of intermediate ethyl 2-[5-(3-amino-3-methylbut-1-yn-1-yl)-4-(3,4-dihydro-2H-1-benzopyran-6-yl)-2-methylthiophen-3-yl]-2-(tert-butoxy)acetate (87a)

Under argon atmosphere, (1e) (100 mg, 0.24 mmol), 2-methyl-3-butyn-2-amine (39 mg, 0.47 mmol) and cesium carbonate (77 mg, 0.24 mmol) were dissolved in N,N-dimethylformamide (1.6 mL). The solution was degassed under argon for 10 min before $PdCl_2(PPh_3)_2$ (3 mg, 0.05 mmol), tricyclohexylphosphine (3 mg, 0.01 mmol) and 1,8-Diazabicyclo[5.4.0]undec-7-ene (4 μL, 0.02 mmol) were added. The vial was sealed and the reaction was then heated under microwaves at 150° C. for 2 hours. After the reaction was cooled to room temperature, the crude reaction mixture was diluted with ethyl acetate and then filtered through Celite®. The Celite® pad was washed with methanol and ethyl acetate and the filtrate was concentrated under reduced pressure. This crude material was then dissolved in ethyl acetate, washed with water and brine, dried over sodium sulfate, filtered, and concentrated under reduced pressure. The crude material was purified by preparative TLC (dichloromethane/methanol 95/5) to give ethyl 2-[5-(3-amino-3-methylbut-1-yn-1-yl)-4-(3,4-dihydro-2H-1-benzopyran-6-yl)-2-methylthiophen-3-yl]-2-(tert-butoxy)acetate (87a) (42 mg, 0.09 mmol, 37%).

$^1$H NMR (400 MHz, $CDCl_3$): δ 0.97 (s, 9H), 1.23-1.28 (m, 3H), 1.47-1.48 (m, 6H), 2.00-2.06 (m, 2H), 2.53 (s, 3H), 2.81-2.84 (m, 2H), 4.12-4.25 (m, 4H), 4.97 (s, 1H), 6.82 (dd, J=8.8 Hz, J=1.2 Hz, 1H), 7.17-7.20 (m, 2H).

MS m/z $[M+H]^+$ 470

Step 2: preparation of 2-[5-(3-amino-3-methylbut-1-yn-1-yl)-4-(3,4-dihydro-2H-1-benzopyran-6-yl)-2-methylthiophen-3-yl]-2-(tert-butoxy)acetic acid (example 87)

Using the procedure described in example 3, step 2, ethyl 2-[5-(3-amino-3-methylbut-1-yn-1-yl)-4-(3,4-dihydro-2H-1-benzopyran-6-yl)-2-methylthiophen-3-yl]-2-(tert-butoxy)acetate (87a) (55 mg, 0.12 mmol) is converted into 2-[5-(3-amino-3-methylbut-1-yn-1-yl)-4-(3,4-dihydro-2H-1-benzopyran-6-yl)-2-methylthiophen-3-yl]-2-(tert-butoxy)acetic acid (example 87) (7 mg, 0.02 mmol, 12%).

$^1$H NMR (400 MHz, $CDCl_3$): δ 0.97 (s, 9H), 1.50-1.60 (m, 6H), 1.99-2.02 (m, 2H), 2.43 (s, 3H), 2.79-2.83 (m, 2H), 4.19-4.23 (m, 2H), 5.07 (s, 1H), 6.81-6.83 (d, J=8.0 Hz, 1H), 7.23-7.26 (m, 2H).

MS m/z $[M-H]^-$ 440

Example 88

Synthesis of 2-(tert-butoxy)-2-[4-(3,4-dihydro-2H-1-benzopyran-6-yl)-2-methyl-5-(1-methyl-1H-pyrazol-4-yl)thiophen-3-yl]acetic acid

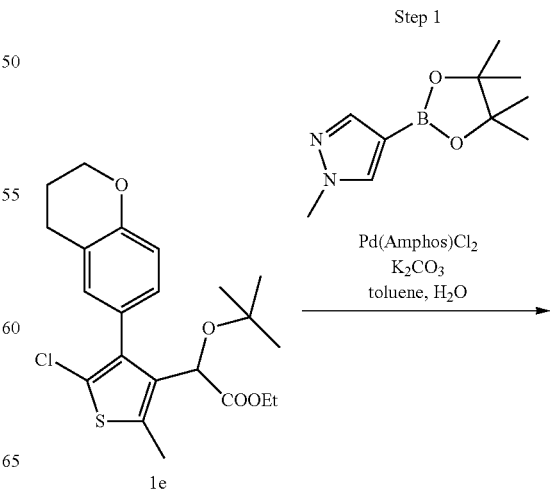

243

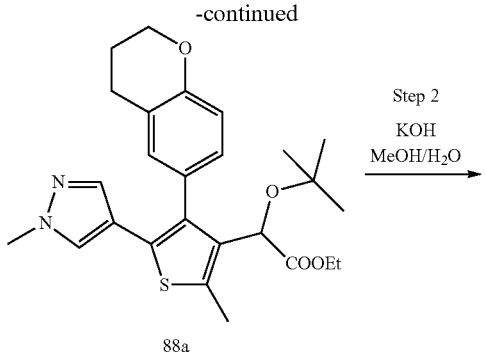

88a

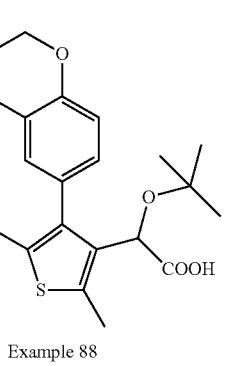

Example 88

Step 1: preparation of intermediate ethyl 2-(tert-butoxy)-2-[4-(3,4-dihydro-2H-1-benzopyran-6-yl)-2-methyl-5-(1-methyl-1H-pyrazol-4-yl)thiophen-3-yl]acetate (88a)

Using the procedure described in example 1, step 6, ethyl 2-(tert-butoxy)-2-[5-chloro-4-(3,4-dihydro-2H-1-benzopyran-6-yl)-2-methylthiophen-3-yl]acetate (1e) (70 mg, 0.165 mmol) is converted by reaction with 1-Methylpyrazole-4-boronic acid pinacol ester (41.3 mg, 0.20 mmol) into ethyl 2-(tert-butoxy)-2-[4-(3,4-dihydro-2H-1-benzopyran-6-yl)-2-methyl-5-(1-methyl-1H-pyrazol-4-yl)thiophen-3-yl]acetate (88a) (48 mg, 0.10 mmol, 62%) after purification by preparative TLC (cyclohexane/ethyl acetate 70/30).

$^1$H NMR (400 MHz, CDCl$_3$) δ 1.04 (s, 9H), 1.21-1.25 (m, 3H), 2.02-2.08 (m, 2H), 2.55 (s, 3H), 2.77 (m, 2H), 3.76 (s, 3H), 4.07-4.16 (m, 2H), 4.23-4.26 (m, 2H), 4.75 (s, 1H), 6.80-7.0 (m, 4H), 7.14 (s, 1H).

MS m/z ([M+H]$^+$) 469.

Step 2: preparation of 2-(tert-butoxy)-2-[4-(3,4-dihydro-2H-1-benzopyran-6-yl)-2-methyl-5-(1-methyl-1H-pyrazol-4-yl)thiophen-3-yl]acetic acid (example 88)

Using the procedure described in example 3, step 2, ethyl 2-(tert-butoxy)-2-[4-(3,4-dihydro-2H-1-benzopyran-6-yl)-2-methyl-5-(1-methyl-1H-pyrazol-4-yl)thiophen-3-yl]acetate (88a) (48 mg, 0.1 mmol) is converted into 2-(tert-butoxy)-2-[4-(3,4-dihydro-2H-1-benzopyran-6-yl)-2-methyl-5-(1-methyl-1H-pyrazol-4-yl)thiophen-3-yl]acetic acid (example 88) (16 mg, 0.04 mmol, 36%) after purification by preparative TLC (dichloromethane/methanol 90/10).

$^1$H NMR (400 MHz, CDCl$_3$) δ 1.08-1.12 (m, 9H), 2.02-2.05 (m, 2H), 2.47 (s, 3H), 2.74-2.82 (m, 2H), 3.80 (s, 3H), 4.22-4.25 (m, 2H), 4.89-4.91 (m, 1H), 6.78-6.90 (m, 2H), 6.95 (s, 1H), 7.15-7.20 (m, 2H).

MS m/z ([M−H]$^−$) 439.

244

Example 89

Synthesis of 2-(tert-butoxy)-2-{2-methyl-4-[4,4-dimethylcyclohex-1-en-1-yl]-5-(4-methylisothiazol-3-yl)thiophen-3-yl}acetic acid

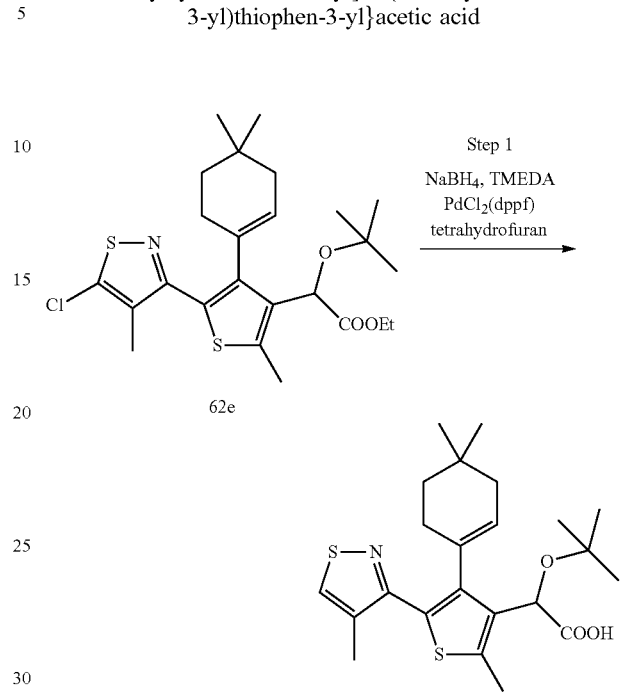

Step 1: preparation of intermediate ethyl 2-(tert-butoxy)-2-[4-(4,4-dimethylcyclohex-1-en-1-yl)-2-methyl-5-(4-methylisothiazol-3-yl)thiophen-3-yl] acetate (example 89)

A solution of ethyl 2-(tert-butoxy)-2-[4-(4,4-dimethylcyclohex-1-en-1-yl)-2-methyl-5-(5-chloro-4-methylisothiazol-3-yl)thiophen-3-yl]acetate (62e) (202 mg, 0.407 mmol) in anhydrous tetrahydrofuran (8.1 mL) was degassed by bubbling argon for a few minutes. Then, [1,1'-bis(diphenylphosphino)ferrocene]dichloro palladium(II) (17 mg, 0.020 mmol), N,N,N',N'-tetramethylethylenediamine (0.21 mL, 1.384 mmol) and finally sodium tetraborohydride (52 mg, 1.384 mmol) were introduced in sequence. The mixture was stirred at 65° C. for 16 hours. After cooling down to room temperature, the reaction mixture was quenched with water and the pH of the aqueous phase was adjusted to 4-5 with hydrochloric acid (1.0M). The residue was taken up in brine and extracted with ethyl acetate. The organic phase was separated, dried over sodium sulphate and the solvent was evaporated under reduced pressure to give 2-(tert-butoxy)-2-{2-methyl-4-[4,4-dimethylcyclohex-1-en-1-yl]-5-(4-methyl isothiazol-3-yl)thiophen-3-yl}acetic acid (example 89) (20 mg, 0.046 mmol, 11%, atropisomers mixture) as a brown solid after two purifications by preparative TLC (dichloromethane/methanol 90/10).

$^1$H NMR (300 MHz, CDCl$_3$) δ 0.82, 086, 0.96 and 0.98 (s, 3H), 1.21 and 1.23 (s, 9H), 1.39-1.50 (m, 2H), 1.83-2.01 (m, 4H), 2.20 (d, J=0.6 Hz, 3H) and 2.36 (s, 3H), 2.50 (s, 3H), 5.21 and 5.22 (s, 1H), 5.67-5.79 (m, 1H), 8.20 (s, 1H) and 8.26 (d, J=0.6 Hz, 1H).

MS m/z ([M+H]$^+$) 434.
MS m/z ([M−H]$^−$) 432.

Example 90

Synthesis of 2-(tert-butoxy)-2-{2-methyl-4-[4,4-dimethylcyclohex-1-en-1-yl]-5-(2-propenyl)thiophen-3-yl}acetic acid

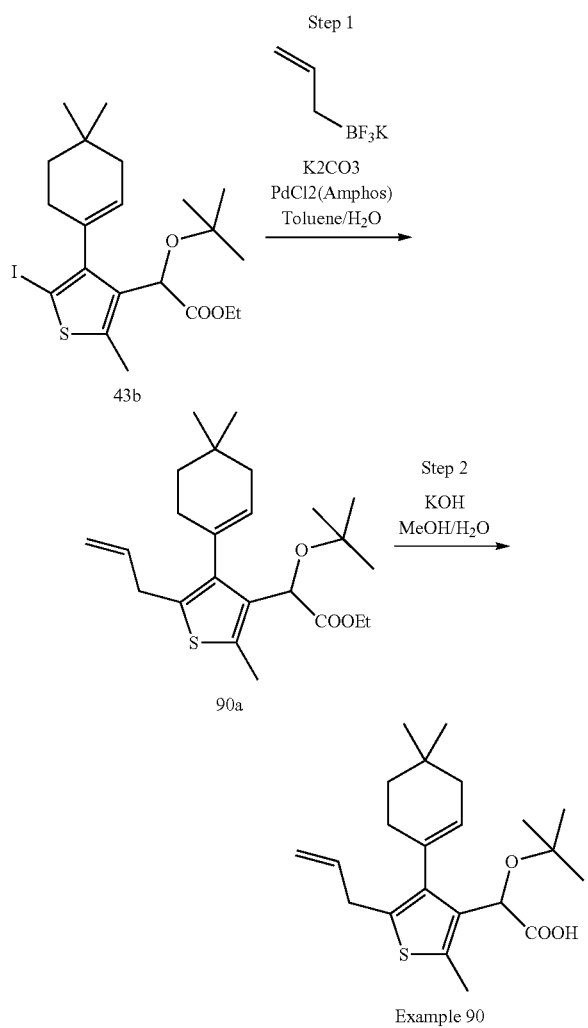

Step 1: preparation of intermediate ethyl 2-(tert-butoxy)-2-[4-(4,4-dimethylcyclohex-1-en-1-yl)-2-methyl-5-(2-propenyl)thiophen-3-yl]acetate (90a)

Using the procedure described in example 1, step 6, 2-(tert-butoxy)-2-[4-(4,4-dimethylcyclohex-1-en-1-yl)-2-methyl-5-iodothiophen-3-yl]acetate (43b) (100 mg, 0.20 mmol) is converted by reaction with potassium allyltrifluoroborate (75 mg, 0.51 mmol) into ethyl 2-(tert-butoxy)-2-[4-(4,4-dimethylcyclohex-1-en-1-yl)-2-methyl-5-(2-propenyl)thiophen-3-yl]acetate (90a) (52 mg, 0.13 mmol, 63%, atropisomers mixture) as a yellow oil after purification by preparative TLC (cyclohexane/ethyl acetate 95/5).

$^1$H NMR (300 MHz, CDCl$_3$) δ 0.94, 0.98, 1.01 a 1.03 (s, 6H), 1.17 (m, 9H), 1.20 and 1.21 (t, J=7.2 Hz, 3H), 1.47 (ddd, J=6.6 Hz, J=6.6 Hz, J=1.8 Hz, 2H), 1.91-2.08 (m, 4H), 2.43 and 2.50 (s, 3H), 3.33 and 3.60 (dd, J=6.6 Hz, J=1.8 Hz, 2H), 4.01-4.19 (m, 2H), 4.95 (s, 1H), 5.02-5.04 (m, 1H), 5.07-5.10 (m, 1H), 5.43-5.52 (m, 1H), 5.82-5.98 (m, 1H).

Step 2: preparation of 2-(tert-butoxy)-2-{2-methyl-4-[4,4-dimethylcyclohex-1-en-1-yl]-5-(2-propenyl)thiophen-3-yl}acetic acid (example 90)

Using the procedure described in example 3, step 2, ethyl 2-(tert-butoxy)-2-[4-(4,4-dimethylcyclohex-1-en-1-yl)-2-methyl-5-(2-propenyl)thiophen-3-yl]acetate (90a) (52 mg, 0.13 mmol) is converted into 2-(tert-butoxy)-2-{2-methyl-4-[4,4-dimethylcyclohex-1-en-1-yl]-5-(2-propenyl)thiophen-3-yl}acetic acid (example 90) (28 mg, 0.07 mmol, 58%, atropisomers mixture) as a colourless oil after purification by preparative TLC (dichloromethane/methanol 95/5).

$^1$H NMR (400 MHz, CDCl$_3$) δ 0.98, 0.99 and 1.01 (s, 6H), 1.21 and 1.22 (s, 9H), 1.45-1.49 (m, 2H), 1.80 (dd, J=6.6 Hz, J=1.8 Hz, 2H), 1.91-2.04 (m, 4H), 2.41 and 2.43 (s, 3H), 4.98-5.00 and 5.21-5.24 (m, 1H), 5.01 and 5.08 (s, 1H), 5.37-5.74 (m, 1H), 5.85 and 5.90 (ddd, J=15.6 Hz, J=13.5 Hz, J=6.6 Hz, 1H), 6.29 and 6.35 (ddd, J=15.6 Hz, J=3.0 Hz, J=1.8 Hz, 1H).

MS m/z ([M+H]$^+$) 377.
MS m/z ([M−H]$^−$) 375.

Antiviral Activity

The antiviral activity, particularly against HIV, of compounds according to the invention is evaluated by the protocol described below.

Preparation of Virus Stock of the NL4-3 Strain of HIV-1 (Adachi et al, J Virol, 1986, 59(2):284-91).

The virus was prepared as described in Lopez et al (Lopez et al, Proc Natl Acad Sci USA., 2006, 103(40):14947-52, by transfecting 2×10$^6$ 293 T cells (CRL-1573, ATCC) with following modifications: 6 μg of NL4-3 proviral DNA molecular clone were mixed with Fugene 6 transfection reagent from Roche, and used according to manufacturer's instructions. Forty eight hours later, transfected cell supernatants were harvested, filtered through 0.45-μm-pore-size filters, quantified for HIV-1 p24 antigen by using a Innotest HIV antigen mAb assay (Ingen) according to manufacturer's instructions, and used in infection experiments.

Preparation of Compounds:

Serial dilutions of compounds to be tested were prepared in complete RPMI medium from 10 mM DMSO stock solutions, and distributed in a volume of 20 □l in 96 well Falcon 353072 Microtest™ tissue culture plate, in order to get 0.5% DMSO final concentration in each well, after the addition of infected cells. Control wells contained also 0.5% DMSO final concentration but no compound.

Infection of Cells:

MT4 cells (from the NIH AIDS Research and Reference Reagent Program) in RPMI complete medium were counted (10×10$^6$ cells per well in Falcon 353047 Multiwell™ 24 well) and infected for 2 hours at 37°, at a multiplicity of infection (moi) of 0.0001-0.00001. Cells were then centrifuged 3 min at 3000 rpm, and washed two times in 1 ml PBS to remove viruses that have not entered in cells. Infected cells were resuspended in complete RPMI at 1.25×10$^6$ cells/ml, and 80 □l of infected cells were distributed in each well containing compounds to be tested or control wells. The plates were then incubated at 37° for 5 days.

Assay Used to Measure the Inhibition of HIV Replication by the Compounds
(according to Gregg S. Jones et al., Antimicrobial Agents and Chemotherapy, 2009, 53 (3): 1194-1203).

After 5 days of incubation, 50l of CellTiter-Glo reagent (Promega Biosciences, Inc., Madison Wis., USA) were added to each well. Cell lysis was carried out at room temperature during 10 min, 150 µl of lysates were transferred in Packard Optiplate 96 well, and luminescence was read on a Fluoroskan (Thermo Scientific).

The EC50, or effective concentration 50, is the concentration of compound leading to 50% of cyto-protection in a Cell-Titer-Glo® viability assay based on MT4 cells infected with NL4-3 virus (table 1).

TABLE 1

| Example number | EC50 (µM) |
| --- | --- |
| 1 | 0.26 |
| 2 | 0.19 |
| 3 | 0.10 |
| 4 | 0.18 |
| 5 | 0.041 |
| 6 | 0.16 |
| 7 | 0.081 |
| 8 | 0.27 |
| 9 | 0.62 |
| 10 | 0.14 |
| 11 | 0.032 |
| 12 | 0.13 |
| 13 | 0.15 |
| 14 | 0.48 |
| 15 | 0.41 |
| 16 | 0.82 |
| 17 | 0.65 |
| 18 | 0.26 |
| 19 | 0.43 |
| 20 | 0.22 |
| 21 | 0.58 |
| 22 | 0.30 |
| 23 | 0.17 |
| 24 | 0.31 |
| 25 | 0.19 |
| 26 | 0.83 |
| 27 | 0.09 |
| 28 | 0.75 |
| 29 | 0.09 |
| 30 | 0.07 |
| 31 | 0.04 |
| 32 | 0.43 |
| 33 | 0.23 |
| 34 | 0.75 |
| 35 | 0.34 |
| 36 | 0.10 |
| 37 | 0.32 |
| 38 | 2.30 |
| 39 | 0.73 |
| 40 | 0.36 |
| 41 | 0.05 |
| 42 | 0.04 |
| 43 | 0.44 |
| 44 | 0.23 |
| 45 | 0.44 |
| 46 | 0.45 |
| 47 | 0.51 |
| 48 | 0.13 |
| 49 | 0.99 |
| 50 | 0.77 |
| 51 | 0.27 |
| 52 | 0.93 |
| 53 | 0.07 |
| 54 | 0.47 |
| 55 | 0.09 |
| 56 | 0.12 |
| 57 | 1.20 |
| 58 | 0.11 |
| 59 | 0.67 |
| 60 | 0.50 |
| 61 | 0.21 |
| 62 | 0.82 |
| 63 | 0.95 |
| 64 | 0.71 |

TABLE 1-continued

| Example number | EC50 (µM) |
| --- | --- |
| 65 | 1.40 |
| 66 | 1.10 |
| 67 | 2.30 |
| 68 | 1.90 |
| 71 | 1.10 |
| 72 | 2.30 |
| 73 | 6.90 |
| 74 | 6.80 |
| 75 | 2.40 |
| 76 | 3.30 |
| 77 | 4.40 |
| 78 | 4.30 |
| 79 | 1.50 |
| 80 | 6.20 |
| 81 | 2.50 |
| 82 | 1.00 |
| 83 | 1.70 |
| 84 | 1.50 |
| 85 | 1.90 |
| 86 | 0.27 |
| 88 | 1.60 |
| 89 | 0.86 |

The results show that the compounds according to the invention can inhibit the HIV replication and thus can be used as anti-HIV compounds.

The invention claimed is:

1. A compound of formula (I):

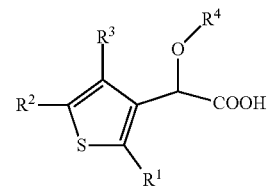

(I)

wherein:

$R^1$, identical or different, independently represent a halogen atom; —$CF_3$; a linear or branched $C_1$-$C_6$ alkyl; a linear or branched $C_2$-$C_6$ alkenyl; a linear or branched $C_2$-$C_6$ alkynyl; a linear or branched fluoroalkyl; a $C_3$-$C_6$ cycloalkyl, —$CH_2OH$; or —$CH_2$—O—$CH_3$;

$R^2$, non-substituted or substituted by at least one $T^1$, represents a linear or branched $C_2$-$C_8$ alkyl; a linear or branched $C_2$-$C_8$ alkenyl; a linear or branched $C_2$-$C_8$ alkynyl; a saturated, partially or totally unsaturated or aromatic 3-, 4-, 5-, 6- or 7-membered carbocycle; a saturated, partially or totally unsaturated or aromatic 4-, 5-, 6- or 7-membered heterocycle; a saturated, partially or totally unsaturated or aromatic 3-, 4-, 5-, 6- or 7-membered carbocycle fused with a saturated, partially or totally unsaturated 3-, 4-, 5-, 6- or 7-membered carbocycle; a saturated, partially or totally unsaturated or aromatic 3-, 4-, 5-, 6- or 7-membered carbocycle fused with a saturated, partially or totally unsaturated 4-, 5-, 6- or 7-membered heterocycle; a saturated, partially or totally unsaturated or aromatic 4-, 5-, 6- or 7-membered heterocycle fused with a saturated, partially or totally unsaturated 3-, 4-, 5-, 6- or 7-membered carbocycle; a saturated, partially or totally unsaturated or aromatic 4-, 5-, 6- or 7-membered heterocycle fused with a saturated, partially or totally unsaturated 4-, 5-, 6- or 7-membered heterocycle; a $C_1$-$C_8$ alkyl-(saturated, partially or totally unsaturated or aromatic $C_3$-$C_7$ carbocycle); a $C_1$-$C_8$ alkyl-(saturated, partially or totally unsaturated or aromatic $C_4$-$C_7$ heterocycle); a bicyclo [2.2.1]heptane; a bicyclo [2.2.1]heptene; a bicyclo [2.2.2]octane; or a bicyclo [2.2.1]octane;

$R^3$, non-substituted or substituted by at least one $T^2$, represents an aryl; an aryl fused with a saturated, partially or totally unsaturated or aromatic 3-, 4-, 5-, 6- or 7-membered carbocycle; an aryl fused with a saturated, partially or totally unsaturated or aromatic 4-, 5-, 6- or 7-membered heterocycle; an aryl fused with a saturated, partially or totally unsaturated or aromatic 4-, 5-, 6- or 7-membered heterocycle and further fused with a saturated, partially or totally unsaturated or aromatic 4-, 5-, 6- or 7-membered heterocycle; a heteroaryl; a heteroaryl fused with a saturated, partially or totally unsaturated or aromatic 3-, 4-, 5-, 6- or 7-membered carbocycle; a heteroaryl fused with a saturated, partially or totally unsaturated or aromatic 4-, 5-, 6- or 7-membered heterocycle; a $C_5$-$C_7$ cycloalkenyl; a $C_5$-$C_7$ cycloalkenyl fused with a saturated, partially or totally unsaturated or aromatic 4-, 5-, 6- or 7-membered heterocycle; or a saturated, partially or totally unsaturated or aromatic 5-, 6- or 7-membered heterocycle;

$R^4$, substituted or non-substituted by at least one $T^5$, represents a linear or branched $C_2$-$C_6$ alkyl; a linear or branched $C_1$-$C_6$ fluoroalkyl; or a $C_3$-$C_6$ cycloalkyl;

$T^1$ independently represents a hydrogen atom; a halogen atom; an alkyl; -$(X)_a$-$C_1$-$C_6$ alkyl; a linear or branched fluoroalkyl; a linear or branched —O—$C_1$-$C_3$ fluoroalkyl; —$(X)_a$-$C_3$-$C_6$ cycloalkyl; -$(X)_a$—$(CT^5T^6)_b$-$C_3$-$C_6$ cycloalkyl; —$(X)_a$—$(CT^5T^6)_b$-aryl; —$(X)_a$—$(CT^5T^6)_b$CN; —$(X)_a$—$(CT^5T^6)_b$OT$^3$; —$(X)_a$—$(CT^5T^6)_b$ST$^3$; —$(X)_a$—$(CT^5T^6)_b$S(O)T$^3$; —$(X)_a$—$(CT^5T^6)_b$S(O)$_2$T$^3$; —$(X)_a$—$(CT^5T^6)_b$NT$^3$T$^4$; —$(X)_a$—$(CT^5T^6)_b$C(O)T$^3$; —$(X)_a$—$(CT^5T^6)_b$C(O)OT$^3$; —$(X)_a$—$(CT^5T^6)_b$C(O)NT$^3$T$^4$; —$(X)_a$—$(CT^5T^6)_b$NT$^3$C(O)NT$^3$T$^4$; —$(X)_a$—$(CT^5T^6)_b$NT$^3$C(O)T$^4$; —$(X)_a$—$(CT^5T^6)_b$NT$^3$C(O)OT$^4$; —$(X)_a$—$(CT^5T^6)_b$OC(O)NT$^3$T$^4$; —$(X)_a$—$(CT^5T^6)_b$ S(O)$_2$NT$^3$T$^4$ or —$(X)_a$—$(CT^5T^6)_b$NT$^3$S(O)$_2$T$^4$;

$T^2$ independently represents a hydrogen atom; a halogen atom; a linear or branched —O—$C_1$-$C_3$ alkyl; a linear or branched $C_1$-$C_3$ fluoroalkyl; a linear or branched —O—$C_1$-$C_3$ fluoroalkyl; a linear or branched $C_1$-$C_3$ alkyl; or —CN; optionally two geminal $T^2$ form with the carbon atom to which they are bonded, a $C_3$-$C_7$ cycloalkyl;

X independently represents an oxygen atom; a sulphur atom; NT$^3$; S═O or S(O)$_2$;

$T^3$ and $T^4$, identical or different, independently represent a hydrogen atom; a branched or linear $C_1$-$C_6$ alkyl or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom or a linear or branched $C_1$-$C_3$ alkyl or a $C_3$-$C_6$ cycloalkyl; optionally $T^5$, $T^6$ and the carbon atom to which they are bonded form a cyclopropyl;

a independently represents 0 or 1;

b independently represents 0, 1, 2 or 3; and wherein one or two heteroatoms are present in each hetercycle or heteroaryl, and wherein the heteroatoms are either O, N or S;

or a racemate, enantiomer, tautomer, atropisomer, diastereoisomer or a pharmaceutically acceptable salt thereof.

2. The compound according to claim 1 wherein $R^4$ represents tBu.

3. The compound according to claim 1, wherein:

$R^2$, non-substituted or substituted by at least one $T^1$, represents a linear or branched $C_2$-$C_8$ alkyl; a linear or branched $C_2$-$C_8$ alkenyl; a linear or branched $C_2$-$C_8$ alkynyl; a $C_1$-$C_8$ alkyl-(saturated, partially or totally unsaturated or aromatic $C_3$-$C_7$ carbocycle); a saturated, partially or totally unsaturated or aromatic 3-, 4-, 5-, 6- or 7-membered carbocycle; a saturated, partially or totally unsaturated or aromatic 3-, 4-, 5-, 6- or 7-membered carbocycle fused with a saturated, partially or totally unsaturated or aromatic 4-, 5-, 6- or 7-membered heterocycle; a saturated, partially or totally unsaturated or aromatic 4-, 5-, 6- or 7-membered heterocycle; a saturated, partially or totally unsaturated or aromatic 4-, 5-, 6- or 7-membered heterocycle fused with a saturated, partially or totally unsaturated 3-, 4-, 5-, 6- or 7-membered carbocycle; or a saturated, partially or totally unsaturated or aromatic 4-, 5-, 6- or 7-membered heterocycle fused with a saturated, partially or totally unsaturated 4-, 5-, 6- or 7-membered heterocycle;

$T^1$ represents a hydrogen atom; a halogen atom; —CH$_3$; —CH$_2$—CH$_3$; —CH—(CH$_3$)$_2$; —CH$_2$—CH$_2$—CH$_3$; —CH$_2$F; —CHF$_2$; —CF$_3$; —OCH$_3$; —OCH$_2$F; —OCHF$_2$; —OCF$_3$; —$(X)_a$—$C_1$-$C_6$ cycloalkyl; —$(X)_a$—$(CT^5T^6)_b$—$(C1$-$C_6$cycloalkyl); —$(X)_a$—$(CT^5T^6)_b$-aryl; —$(X)_a$—$(CT^5T^6)_b$CN; —$(X)_a$—$(CT^5T^6)_b$OT$^3$; —$(X)_a$—$(CT^5T^6)_b$ST$^3$; —$(X)_a$—$(CT^5T^6)_b$S(O)T$^3$; —$(X)_a$—$(CT^5T^6)_b$S(O)$_2$T$^3$; —$(X)_a$—$(CT^5T^6)_b$NT$^3$T$^4$; —$(X)_a$—$(CT^5T^6)_b$C(O)T$^3$; —$(X)_a$—$(CT^5T^6)_b$C(O)OT$^3$; —$(X)_a$—$(CT^5T^6)_b$C(O)NT$^3$T$^4$; —$(X)_a$—$(CT^5T^6)_b$NT$^3$C(O)NT$^3$T$^4$; —$(X)_a$—$(CT^5T^6)_b$NT$^3$C(O)T$^4$; —$(X)_a$—$(CT^5T^6)_b$NT$^3$C(O)OT$^4$; —$(X)_a$—$(CT^5T^6)_b$OC(O)NT$^3$T$^4$; —$(X)_a$—$(CT^5T^6)_b$—S(O)$_2$NT$^3$T$^4$ or —$(X)_a$—$(CT^5T^6)_b$NT$^3$S(O)$_2$T$^4$;

X independently represents an oxygen atom; a sulphur atom; NT$^3$; S═O; or S(O)$_2$;

$T^3$ and $T^4$, identical or different, independently represent a hydrogen atom; a branched or linear $C_1$-$C_6$ alkyl; or a $C_3$-$C_6$ cycloalkyl; optionally $T^3$, $T^4$ and the nitrogen atom to which they are bonded form a $C_4$-$C_6$ heterocycloalkyl;

$T^5$ and $T^6$, identical or different, independently represent a hydrogen atom; a fluorine atom;or methyl;

a independently represents 0 or 1; and b independently represents 0, 1, 2 or 3.

4. The compound according to claim 1 of formula (A), (B), (C) or (D)

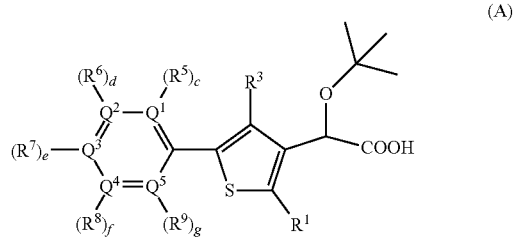

(A)

-continued

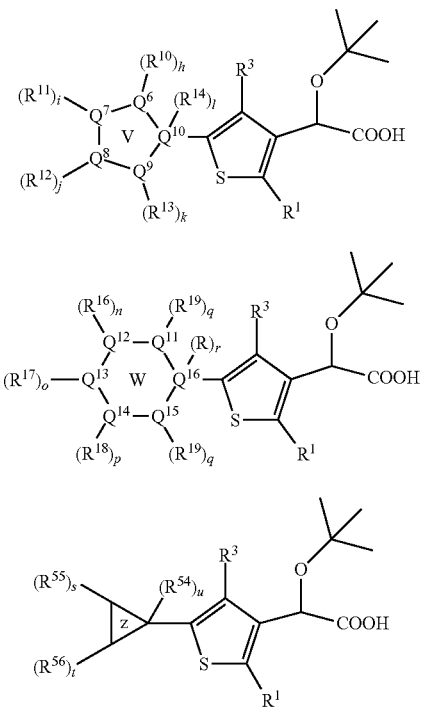

wherein
h, i, j, k, m, n, o, p, q, s and t independently represent 0, 1 or 2;
c, d, e, f, g, l, r and u independently represents 0 or 1;
V represents a substituted or non-substituted, saturated, partially or totally unsaturated carbocycle or a saturated, partially or totally unsaturated or aromatic heterocycle;
W represents a substituted or non-substituted, saturated, partially unsaturated carbocycle- or a saturated, partially unsaturated heterocycle;
Z represents a substituted or non-substituted, cyclopropyl;
$Q^1$ represents $CR^5$ or N;
$Q^2$ represents $CR^6$ or N;
$Q^3$ represents $CR^7$ or N;
$Q^4$ represents $CR^8$ or N;
$Q^5$ represents $CR^9$ or N;
$Q^6$ represents $CR^{10}$, C=O, N, $NR^{10}$, O, S, S=O or $S(O)_2$;
$Q^7$ represents $CR^{11}$, C=O, N, $NR^{11}$, O, S, S=O or $S(O)_2$;
$Q^8$ represents $CR^{12}$, C=O, N, $NR^{12}$, O, S, S=O or $S(O)_2$;
$Q^9$ represents $CR^{13}$, C=O, N, $NR^{13}$, O, S, S=O or $S(O)_2$;
$Q^{10}$ represents C, $CR^{14}$ or N;
$Q^{11}$ represents C, $CR^{15}$, C=O, N, $NR^{15}$, O, S, S=O or $S(O)_2$;
$Q^{12}$ represents C, $CR^{16}$, C=O, N, $NR^{16}$, O, S, S=O or $S(O)_2$;
$Q^{13}$ represents C, $CR^{17}$, C=O, N, $NR^{17}$, O, S, S=O or $S(O)_2$;
$Q^{14}$ represents C, $CR^{18}$, C=O, N, $NR^{18}$, O, S, S=O or $S(O)_2$;
$Q^{15}$ represents C, $CR^{19}$, C=O, N, $NR^{19}$, O, S, S=O or $S(O)_2$;
$Q^{16}$ represents C, CR or N;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{54}$, $R^{55}$, $R^{56}$ and R identical or different, independently represent a hydrogen atom; a halogen atom; —$CH_3$; —$CH_2$—$CH_3$; —CH—$(CH_3)_2$; —$CH_2$—$CH_2$—$CH_3$; —$CH_2F$; —$CHF_2$; —$CF_3$; —$OCH_3$; —$OCH_2F$; —$OCHF_2$; —$OCF_3$; —$(X)_a$—$C_1$-$C_6$ cycloalkyl; —$(X)_a$—$(CT^5T^6)_b$—($C_3$-$C_6$ cycloalkyl); —$(X)_a$—$(CT^5T^6)_b$-aryl; —$(X)_a$—$(CT^5T^6)_b$CN; —$(X)_a$—$(CT^5T^6)_bOT^3$; —$(X)_a$—$(CT^5T^6)_bST^3$; —$(X)_a$—$(CT^5T^6)_bS(O)T^3$; —$(X)_a$—$(CT^5T^6)_bS(O)_2T^3$; —$(X)_a$—$(CT^5T^6)_bNT^3T^4$; —$(X)_a$—$(CT^5T^6)_bC(O)T^3$; —$(X)_a$—$(CT^5T^6)_bC(O)OT^3$; —$(X)_a$—$(CT^5T^6)_bC(O)NT^3T^4$; —$(X)_a$—$(CT^5T^6)_bNT^3C(O)NT^3T^4$; —$(X)_a$—$(CT^5T^6)_bNT^3C(O)T^4$; —$(X)_a$—$(CT^5T^6)_bNT^3C(O)OT^4$; —$(X)_a$—$(CT^5T^6)_bOC(O)NT^3T^4$; —$(X)_a$—$(CT^5T^6)_b$ $S(O)_2NT^3T^4$ or —$(X)_a$—$(CT^5T^6)_bNT^3S(O)_2T^4$;

$T^2$ independently represents a hydrogen atom; a halogen atom; methyl; —$CH_2F$; —$CHF_2$; —$CF_3$; —OMe; —$OCH_2F$; —$OCHF_2$; —$OCF_3$; or —CN; optionally two geminal $T^2$ form with the carbon atom to which they are bonded, a cyclopropyl; and $R^1$, $R^3$, X, a, b and $T^3$ to $T^6$ are independently defined as for the compounds as defined in claim 1.

5. The compound according to claim 1 wherein $R^1$ represents:
a linear or branched $C_1$-$C_3$ alkyl;
a linear or branched $C_1$-$C_3$ fluoroalkyl;
a $C_3$-$C_6$ cycloalkyl; or
—$CH_2OH$.

6. A compound according to claim 1, wherein $R^2$, non-substituted or substituted by at least one $T^1$, represents a linear or branched $C_2$-$C_8$ alkyl; a linear or branched $C_2$-$C_8$ alkenyl; a linear or branched $C_2$-$C_8$ alkynyl; a saturated, partially or totally unsaturated or aromatic 3-, 4-, 5- or 6-membered carbocycle; a saturated, partially or totally unsaturated or aromatic 5- or 6-membered heterocycle; an aromatic 6-membered heterocycle fused with a totally unsaturated 6-membered carbocycle; an aromatic 6-membered heterocycle fused with a partially or totally unsaturated 6-membered heterocycle; an aromatic 6-membered carbocyle fused with a partially or totally unsaturated 6-memebered heterocycle; or a $C_1$-$C_8$ alkyl-(aromatic $C_6$ carbocycle).

7. A compound according to claim 1, wherein $R^3$, non-substituted or substituted by at least one $T^2$, represents an aryl; an aryl fused with a saturated, partially or totally unsaturated or aromatic 5-, 6- or 7-membered heterocycle; an aryl fused with a saturated, partially or totally unsaturated or aromatic 5-, 6- or 7-membered heterocycle and further fused with a saturated, partially or totally unsaturated or aromatic 5-, 6- or 7-membered heterocycle; a $C_5$-$C_7$ cycloalkenyl; or a $C_5$-$C_7$ cycloalkenyl fused with a saturated, partially or totally unsaturated or aromatic 5-, 6- or 7-membered heterocycle.

8. A compound according to claim 1, wherein:
$T^1$ independently represents a hydrogen atom; a halogen atom; an alkyl; a linear or branched fluoroalkyl; —$(X)_a$—$C_1$-$C_6$ alkyl; —$(X)_a$—$C_1$-$C_6$ cycloalkyl; —$(X)_a$—$(CT^5T^6)_b$—($C_1$-$C_6$cycloalkyl); —$(X)_a$—$(CT^5T^6)_b$-aryl; —$(X)_a$—$(CT^5T^6)_bNT^3T^4$; —$(X)_a$—$(CT^5T^6)_bNT^3C(O)T^4$; —$(X)_a$—$(CT^5T^6)_bC(O)NT^3T^4$; —$(X)_a$—$(CT^5T^6)_b$ $S(O)_2NT^3T^4$;
$T^2$ independently represents a hydrogen atom; a halogen atom; a linear or branched —O—$C_1$-$C_3$ alkyl; a linear or branched $C_1$-$C_3$ fluoroalkyl; a linear or branched C₁-C₃ alkyl; or; optionally two geminal T² form with the carbon atom to which they are bonded, a cyclopropyl;

X independently represents an oxygen atom;

T³ and T⁴, identical or different, independently represent a hydrogen atom; or a branched or linear C₁-C₆ alkyl;

T⁵ and T⁶, identical or different, independently represent a hydrogen atom; a fluorine atom; or a linear or branched C₁-C₃ alkyl;

a independently represents 0 or 1; and b independently represents 0, 1, 2 or 3.

9. A compound according to claim 1 selected from the group consisting of:

2-(tert-butoxy)-2-[4-(4,4-dimethylcyclohex-1-en-1-yl)-2-methyl-5-(benzene sulfonamide-4-yl)thiophen-3-yl]acetic acid;

2-(tert-butoxy)-2-[5-(4-carbamoylphenyl)-4-(4,4-dimethylcyclohex-1-en-1-yl)-2-methylthiophen-3-yl]acetic acid;

2-(tert-butoxy)-2-[4-(4,4-dimethylcyclohex-1-en-1-yl)-2-methyl-5-(N-methyl-4-aminocarbonylphenyl)thiophen-3-yl]acetic acid;

2-(tert-butoxy)-2-[4-(4,4-dimethylcyclohex-1-en-1-yl)-2-methyl-5-(aminocarbonylphen-3-yl)thiophen-3-yl]acetic acid;

2-(tert-butoxy)-2-[4-(4,4-dimethylcyclohex-1-en-1-yl)-2-methyl-5-(methylaminocarbonylphen-3-yl)thiophen-3-yl]acetic acid;

2-(tert-butoxy)-2-[4-(4,4-dimethylcyclohex-1-en-1-yl)-2-methyl-5-[3-(propylcarbamoyl)phenyl]thiophen-3-yl]acetic acid;

2-(tert-butoxy)-2-[4-(4,4-dimethylcyclohex-1-en-1-yl)-2-methyl-5-phenylthiophen-3-yl]acetic acid;

2-(tert-butoxy)-2-{2-methyl-4-[4,4-dimethylcyclohex-1-en-1-yl]-5-(carboxamidephen-2-yl)thiophen-3-yl}acetic acid;

2-(tert-butoxy)-2-[4-(4,4-dimethylcyclohex-1-en-1-yl)-2-methyl-5-(dimethylcarboamidophen-4-yl)thiophen-3-yl]acetic acid;

2-(tert-butoxy)-2-[4-(4,4-dimethylcyclohex-1-en-1-yl)-5-[4-(dimethylsulfamoyl)phenyl]-2-methylthiophen-3-yl]acetic acid;

2-(tert-butoxy)-2-[4-(4,4-dimethylcyclohex-1-en-1-yl)-2-methyl-5-(acetamidophen-4-yl)thiophen-3-yl]acetic acid;

2-(tert-butoxy)-2-[4-(3,4-dihydro-2H-1-benzopyran-6-yl)-2-methyl-5-phenylthiophen-3-yl]acetic acid;

2-(tert-butoxy)-2-[4-(3,4-dihydro-2H-1-benzopyran-6-yl)-5-(4-fluorophenyl)-2-methylthiophen-3-yl]acetic acid;

2-(tert-butoxy)-2-[4-(3,4-dihydro-2H-1-benzopyran-6-yl)-5-(4-methoxyphenyl)-2-methylthiophen-3-yl]acetic acid;

2-(tert-butoxy)-2-[4-(3,4-dihydro-2H-1-benzopyran-6-yl)-5-[4-(acetamidomethyl)phenyl]-2-methylthiophen-3-yl]acetic acid;

2-(tert-butoxy)-2-[5-(4-carbamoylphenyl)-4-(3,4-dihydro-2H-1-benzopyran-6-yl)-2-methylthiophen-3-yl]acetic acid;

2-[4,5-bis(8-fluoro-3,4-dihydro-2H-1-benzopyran-6-yl)-2-methylthiophen-3-yl]-2-(tert-butoxy)acetic acid;

2-(tert-butoxy)-2-[4-(3,4-dihydro-2H-1-benzopyran-6-yl)-5-phenyl-2-(trifluoromethyl)thiophen-3-yl]acetic acid;

2-(tert-butoxy)-2-[2-methyl-4-(2,3-dihydropyrano[4,3,2-de]quinolin-7-yl)-5-phenyl-thiophen-3-yl]acetic acid;

2-(tert-butoxy)-2-[4-(5,5-dimethyl-5,6-dihydroquinolin-8-yl)-2-methyl-5-phenylthiophen-3-yl]acetic acid;

2-(tert-butoxy)-2-[4-(4,4-dimethylcyclohex-1-en-1-yl)-2-methyl-5-(pyridin-2-yl)thiophen-3-yl]acetic acid;

2-(tert-butoxy)-2-[4-(4,4-dimethylcyclohex-1-en-1-yl)-2-methyl-5-(5-methylpyridin-2-yl)thiophen-3-yl]acetic acid;

2-(tert-butoxy)-2-[4-(4,4-dimethylcyclohex-1-en-1-yl)-2-methyl-5-(3-methylpyridin-2-yl)thiophen-3-yl]acetic acid;

2-(tert-butoxy)-2-{2-methyl-4-[4,4-dimethylcyclohex-1-en-1-yl]-5-(4-methylpyridin-2-yl)thiophen-3-yl}acetic acid;

2-(tert-butoxy)-2-{2-methyl-4-[4,4-dimethylcyclohex-1-en-1-yl]-5-(6-methylpyridin-2-yl)thiophen-3-yl}acetic acid;

2-(tert-butoxy)-2-{2-methyl-4-[4,4-dimethylcyclohex-1-en-1-yl]-5-(6-(n-propyl)pyridin-2-yl)thiophen-3-yl}acetic acid;

2-(tert-butoxy)-2-{2-methyl-4-[4,4-dimethylcyclohex-1-en-1-yl]-5-(5-(n-propyl)pyridin-2-yl)thiophen-3-yl}acetic acid;

2-(tert-butoxy)-2-{2-methyl-4-[4,4-dimethylcyclohex-1-en-1-yl]-5-(4-(n-propyl)pyridin-2-yl)thiophen-3-yl}acetic acid;

2-(tert-butoxy)-2-[4-(3,4-dihydro-2H-1-benzopyran-6-yl)-2-methyl-5-{2H,3H,4H-pyrano[2,3-b]pyridin-6-yl}thiophen-3-yl]acetic acid;

2-(tert-butoxy)-2-[4-(4-methoxy-4-methylcyclohex-1-en-1-yl)-2-methyl-5-{2H,3H,4H-pyrano[2,3-b]pyridin-6-yl}thiophen-3-yl]acetic acid;

2-(tert-butoxy)[4-(3,4-dihydro-2H-1-benzopyran-6-yl)-2-methyl-5-{2H,3H,4H-pyrano[2,3-b]pyridin-6-yl}thiophen-3-yl]acetic acid;

2-(tert-butoxy)-2-[4-(3,4-dihydro-2H-1-benzopyran-6-yl)-2-methyl-5-(pyridin-3-yl)thiophen-3-yl]acetic acid;

2-(tert-butoxy)-2-[4-(3,4-dihydro-2H-1-benzopyran-6-yl)-5-(6-methoxypyridin-3-yl)-2-methylthiophen-3-yl]acetic acid;

2-(tert-butoxy)-2-[4-(4,4-dimethylcyclohex-1-en-1-yl)-2-methyl-5-(pyridin-4-yl)thiophen-3-yl]acetic acid;

2-(tert-butoxy)-2-{2-methyl-4-[4-(propan-2-yl)cyclohex-1-en-1-yl]-5-(pyridin-4-yl)thiophen-3-yl}acetic acid;

2-(tert-butoxy)-2-[2-methyl-4-(4-methylcyclohex-1-en-1-yl)-5-(pyridin-4-yl)thiophen-3-yl]acetic acid;

(2S)-2-(tert-butoxy)-2-[4-(4,4-dimethylcyclohex-1-en-1-yl)-2-methyl-5-(pyridin-4-yl)thiophen-3-yl]acetic acid;

2-(tert-butoxy)-2-[2-methyl-5-(pyridin-4-yl)-4-{spiro[2,5]oct-5-en-6-y'}thiophen-3-yl]acetic acid;

2-(tert-butoxy)-2-[2-methyl-4-(4,4-difluorocyclohex-1-en-1-yl)-5-(pyridin-4-yl)thiophen-3-yl]acetic acid;

[4-(4,4-bis-fluoromethyl-cyclohex-1-enyl)-2-methyl-5-pyridin-4-yl-thiophen-3-yl]-tert-butoxy-acetic acid;

[4-(4-fluoromethyl-4-methylcyclohex-1-enyl)-2-methyl-5-pyridin-4-yl-thiophen-3-yl]-tert-butoxy-acetic acid;

2-[4-(4,4-dimethylcyclohex-1-en-1-yl)-2-methyl-5-(pyridin-4-yl)thiophen-3-yl]-2-ethoxyacetic acid;

2-(tert-butoxy)-2-[4-(3,4-dihydro-2H-1-benzopyran-6-yl)-5-(2-fluoropyridin-4-yl)-2-methylthiophen-3-yl]acetic acid;

2-(tert-butoxy)-2-[4-(3,4-dihydro-2H-1-benzopyran-6-yl)-2-methyl-5-(pyridin-4-yl)thiophen-3-yl]acetic acid;

2-(tert-butoxy)-2-[4-(3,4-dihydro-2H-1-benzopyran-6-yl)-2-methyl-5-(2-methylpyridin-4-yl)thiophen-3-yl]acetic acid;

2-(tert-butoxy)-2-[4-(3,4-dihydro-2H-1-benzopyran-6-yl)-2-methyl-5-(quinolin-4-yl)thiophen-3-yl]acetic acid;
2-{5-[2-(benzyloxy)pyridin-4-yl]-4-(3,4-dihydro-2H-1-benzopyran-6-yl)-2-methylthiophen-3-yl}-2-(tert-butoxy)acetic acid;
2-(tert-butoxy)-2-[4-(3,4-dihydro-2H-1-benzopyran-6-yl)-5-(6-methoxypyridin-3-yl)-2-methylthiophen-3-yl]acetic acid;
2-(tert-butoxy)-2-[4-(3,4-dihydro-2H-1-benzopyran-6-yl)-2-(hydroxymethyl)-5-(pyridin-4-yl)thiophen-3-yl]acetic acid;
2-(tert-butoxy)-2-[4-(8-fluoro-5-methyl-3,4-dihydro-2H-1-benzopyran-6-yl)-2-methyl-5-(pyridin-4-yl)thiophen-3-yl]acetic acid;
2-(tert-butoxy)-2-[4-(8-fluoro-3,4-dihydro-2H-1-benzopyran-6-yl)-2-methyl-5-(pyridin-4-yl)thiophen-3-yl]acetic acid;
2-(tert-butoxy)-2-(2-methyl-4-(2,3-dihydropyrano[4,3,2-de]quinolin-7-yl)-5-(pyridin-4-yl)thiophen-3-yl)acetic acid;
2-(tert-butoxy)-2-{2-methyl-4-[4,4-dimethylcyclohex-1-en-1-yl]-5-(pyrimidin-2-yl)thiophen-3-yl}acetic acid;
2-(tert-butoxy)-2-[4-(4,4-dimethylcyclohex-1-en-1-yl)-2-methyl-5-(pyrimidin-5-yl)thiophen-3-yl]acetic acid;
2-(tert-butoxy)-2-[4-(3,4-dihydro-2H-1-benzopyran-6-yl)-2-methyl-5-(pyrimidin-5-yl)thiophen-3-yl]acetic acid;
2-(tert-butoxy)-2-[4-(3,4-dihydro-2H-1-benzopyran-6-yl)-2-methyl-5-(thiophen-2-yl)thiophen-3-yl]acetic acid;
2-(tert-butoxy)-2-[4-(3,4-dihydro-2H-1-benzopyran-6-yl)-2-methyl-5-(thiophen-3-yl)thiophen-3-yl]acetic acid;
2-(tert-butoxy)-2-[4-(3,4-dihydro-2H-1-benzopyran-6-yl)-5-(furan-3-yl)-2-methylthiophen-3-yl]acetic acid;
2-(tert-butoxy)-2-[4-(3,4-dihydro-2H-1-benzopyran-6-yl)-2-methyl-5-[1-methyl-3-(trifluoromethyl)-1H-pyrazol-5-yl]thiophen-3-yl]acetic acid 2-(tert-butoxy)-2-[4-(4,4-dimethylcyclohex-1-en-1-yl)-2-methyl-5-(N-methylpyrazol-4-yl)thiophen-3-yl]acetic acid;
2-(tert-butoxy)-2-{2-methyl-4-[4-(propan-2-yl)cyclohex-1-en-1-yl]-5-(N-methylpyrazol-4-yl)thiophen-3-yl}acetic acid;
2-(tert-butoxy)-2-[4-(3,4-dihydro-2H-1-benzopyran-6-yl)-2-methyl-5-(1-methyl-1H-pyrazol-4-yl)thiophen-3-yl]acetic acid;
2-[5-(1-benzyl-1H-pyrazol-4-yl)-4-(3,4-dihydro-2H-1-benzopyran-6-yl)-2-methylthiophen-3-yl]-2-(tert-butoxy)acetic acid;
2-(tert-butoxy)-2-[4-(4,4-dimethylcyclohex-1-en-1-yl)-2-methyl-5-(1H-pyrazol-1-yl)thiophen-3-yl]acetic acid;
2-(tert-butoxy)-2-[4-(3,4-dihydro-2H-1-benzopyran-6-yl)-2-methyl-5-(1H-pyrazol-1-yl)thiophen-3-yl]acetic acid;
2-(tert-butoxy)-2-[4-(3,4-dihydro-2H-1-benzopyran-6-yl)-2-methyl-5-(1-methyl-1H-pyrrol-2-yl)thiophen-3-yl]acetic acid;
2-(tert-butoxy)-2-[4-(4,4-dimethylcyclohex-1-en-1-yl)-2-methyl-5-(1,3-thiazol-2-yl)thiophen-3-yl]acetic acid;
2-(tert-butoxy)-2-{2-methyl-4-[4,4-dimethylcyclohex-1-en-1-yl]-5-(thiazol-4-yl)thiophen-3-yl}acetic acid;
2-(tert-butoxy)-2-{2-methyl-4-[4,4-dimethylcyclohex-1-en-1-yl]-5-(cyclopenten-1-yl)thiophen-3-yl}acetic acid;
2-(tert-butoxy)-2-{2-methyl-4-[4,4-dimethylcyclohex-1-en-1-yl]-5-(5-chloro-4-methyl-isothiazol-3-yl)thiophen-3-yl}acetic acid;
2-(tert-butoxy)-2-{2-methyl-4-[4,4-dimethylcyclohex-1-en-1-yl]-5-(4-methylisothiazol-3-yl)thiophen-3-yl}acetic acid;
2-(tert-butoxy)-2-[4-(3,4-dihydro-2H-1-benzopyran-6-yl)-2-methyl-5-(1,2-thiazol-3-yl)thiophen-3-yl]acetic acid;
2-(tert-butoxy)-2-{2-methyl-4-[4,4-dimethylcyclohex-1-en-1-yl]-5-(isothiazol-5-yl)thiophen-3-yl}acetic acid;
2-(tert-butoxy)-2-{2-methyl-4-[4,4-dimethylcyclohex-1-en-1-yl]-5-(isothiazol-3-yl)thiophen-3-yl}acetic acid;
2-(tert-butoxy)-2-[4-(4,4-dimethylcyclohex-1-en-1-yl)-2-methyl-5-(1-methyl-5-oxo-2,5-dihydro-1H-pyrrol-3-yl)thiophen-3-yl]acetic acid;
2-(tert-butoxy)-2-{2-methyl-4-[4,4-dimethylcyclohex-1-en-1-yl]-5-(N-pyrrolidinone)thiophen-3-yl}acetic acid;
2-(tert-butoxy)-2-{2-methyl-4-[4,4-dimethylcyclohex-1-en-1-yl]-5-(cyclopropyl)thiophen-3-yl}acetic acid;
2-(tert-butoxy)-2-[4-(4,4-dimethylcyclohex-1-en-1-yl)-2-methyl-5-(N-Methyl-1H-pyridin-2-one-4-yl)thiophen-3-yl]acetic acid;
2-(tert-butoxy)-2-[4-(4,4-dimethylcyclohex-1-en-1-yl)-2-methyl-5-(N-propyl-1H-pyridin-2-one-4-yl)thiophen-3-yl]acetic acid;
2-(tert-butoxy)-2-[4-(4,4-dimethylcyclohex-1-en-1-yl)-2-methyl-5-(N-benzyl-1H-pyridin-2-one-4-yl)thiophen-3-yl]acetic acid;
2-(tert-butoxy)-2-[4-(4,4-dimethylcyclohex-1-en-1-yl)-2-methyl-5-(N-(methylenecyclopropyl)-1H-pyridin-2-one-4-yl)thiophen-3-yl]acetic acid;
2-(tert-butoxy)-2-[4-(3,4-dihydro-2H-1-benzopyran-6-yl)-2-methyl-5-(1-methyl-6-oxo-1,6-dihydropyridin-3-yl)thiophen-3-yl]acetic acid;
2-(tert-butoxy)-2-[4-(3,4-dihydro-2H-1-benzopyran-6-yl)-5-(3,6-dihydro-2H-pyran-4-yl)-2-methylthiophen-3-yl]acetic acid;
2-(tert-butoxy)-2-[4-(4,4-dimethylcyclohex-1-en-1-yl)-5-(cyclohexen-1-yl)-2-methylthiophen-3-yl]acetic acid;
2-[5-(3-amino-3-methylbut-1-yn-1-yl)-4-(3,4-dihydro-2H-1-benzopyran-6-yl)-2-methylthiophen-3-yl]-2-(tert-butoxy)acetic acid;
2-(tert-butoxy)-2-{2-methyl-4-[4,4-dimethylcyclohex-1-en-1-yl]-5-(phenylethyl)thiophen-3-yl}acetic acid;
2-(tert-butoxy)-2-[4-(3,4-dihydro-2H-1-benzopyran-6-yl)-5-propyl)-2-methylthiophen-3-yl]acetic acid;
2-(tert-butoxy)-2-{2-methyl-4-[4,4-dimethylcyclohex-1-en-1-yl]-5-(2-propenyl)thiophen-3-yl}acetic acid;
2-(tert-butoxy)-2-[4-(4,4-dimethylcyclohex-1-en-1-yl)-2-methyl-5-[4-(propylcarbamoyl)phenyl]thiophen-3-yl]acetic acid; or
2-(tert-butoxy)-2-{2-methyl-4-[4,4-dimethylcyclohex-1-en-1-yl]-5-(N-methylbenzamide-2-yl)thiophen-3-yl}acetic acid.

10. A method for the treatment of HIV infection comprising administering to a patient in need thereof the compound according to claim 1.

11. A pharmaceutical composition comprising a compound according to claim 1 as an active ingredient and at least a pharmaceutically acceptable carrier.

12. A pharmaceutical composition according to claim 11 further comprising at least a further antiviral agent.

13. A method for the treatment of HIV comprising the administration of the pharmaceutical composition according to claim 11 to a patient in need thereof.

14. The method according to claim 13 wherein the patient is a mammal being infected by the HIV.

* * * * *